(12) United States Patent
Song

(10) Patent No.: US 11,939,622 B2
(45) Date of Patent: Mar. 26, 2024

(54) SINGLE CELL CHROMATIN IMMUNOPRECIPITATION SEQUENCING ASSAY

(71) Applicant: Becton, Dickinson and Company, Franklin Lakes, NJ (US)

(72) Inventor: Hye-Won Song, San Jose, CA (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 444 days.

(21) Appl. No.: 16/934,530

(22) Filed: Jul. 21, 2020

(65) Prior Publication Data

US 2021/0024977 A1    Jan. 28, 2021

Related U.S. Application Data

(60) Provisional application No. 62/876,922, filed on Jul. 22, 2019, provisional application No. 63/049,980, filed on Jul. 9, 2020.

(51) Int. Cl.
    *C12P 19/34*      (2006.01)
    *C12N 9/22*      (2006.01)
    (Continued)

(52) U.S. Cl.
    CPC ............ *C12Q 1/6806* (2013.01); *C12N 9/22* (2013.01); *C12Q 1/68* (2013.01); *C12Q 1/6874* (2013.01);
    (Continued)

(58) Field of Classification Search
    USPC ......... 435/6.1, 6.11, 6.12, 91.1, 91.2, 91.51; 436/94, 501; 536/23.1, 24.3, 24.33
    See application file for complete search history.

(56) References Cited

U.S. PATENT DOCUMENTS 4,510,244 A    4/1985   Parks et al.
4,725,536 A    2/1988   Fritsch et al.
(Continued)

FOREIGN PATENT DOCUMENTS

CA      2474509      2/2003
DE    102008025656    12/2009
(Continued)

OTHER PUBLICATIONS

"DNase I", "Restriction enzymes" and "Micrococcal Nuclease". Printed on Dec. 3, 2022.*

(Continued)

*Primary Examiner* — Frank W Lu
(74) *Attorney, Agent, or Firm* — Sheppard, Mullin, Richter & Hampton LLP

(57) ABSTRACT

Disclosed herein include systems, methods, kits, and compositions for labeling nuclear target-associated DNA in a cell. Some embodiments provide digestion compositions comprising a DNA digestion enzyme and a binding reagent capable of specifically binding to the nuclear target. Some embodiments provide conjugates comprising a transposome and a binding reagent capable of specifically binding to a nuclear target. The transposome can comprise a transposase (e.g., Tn5 transposase), a first adaptor having a first 5' overhang, and a second adaptor having a second 5' overhang. The methods can comprise contacting a permeabilized cell comprising a nuclear target associated with dsDNA, such as genomic DNA (gDNA), with the compositions provided herein to generate a plurality of nuclear target-associated dsDNA fragments (e.g., nuclear target-associated gDNA fragments) each comprising the one or two single-stranded overhangs.

17 Claims, 17 Drawing Sheets

Specification includes a Sequence Listing.

(51) Int. Cl.
    *C12Q 1/68*     (2018.01)
    *C12Q 1/6806*     (2018.01)
    *C12Q 1/6874*     (2018.01)

(52) U.S. Cl.
    CPC ............... *C12Q 2565/1025* (2013.01); *C12Q 2600/154* (2013.01)

(56) References Cited

U.S. PATENT DOCUMENTS

| | | |
|---|---|---|
| 5,124,246 A | 6/1992 | Urdea et al. |
| 5,149,625 A | 9/1992 | Church et al. |
| 5,200,314 A | 4/1993 | Urdea |
| 5,308,990 A | 5/1994 | Takahashi et al. |
| 5,424,186 A | 6/1995 | Fodor et al. |
| 5,424,413 A | 6/1995 | Hogan et al. |
| 5,445,934 A | 8/1995 | Fodor et al. |
| 5,604,097 A | 2/1997 | Brenner |
| 5,635,352 A | 6/1997 | Urdea et al. |
| 5,635,400 A | 6/1997 | Brenner |
| 5,648,245 A | 7/1997 | Fire et al. |
| 5,654,413 A | 8/1997 | Brenner |
| 5,656,731 A | 8/1997 | Urdea |
| 5,658,737 A | 8/1997 | Nelson et al. |
| 5,714,330 A | 2/1998 | Brenner et al. |
| 5,744,305 A | 4/1998 | Fodor et al. |
| 5,759,778 A | 6/1998 | Li et al. |
| 5,763,175 A | 6/1998 | Brenner |
| 5,800,992 A | 9/1998 | Fodor et al. |
| 5,830,712 A | 11/1998 | Rampersad et al. |
| 5,846,719 A | 12/1998 | Brenner et al. |
| 5,854,033 A | 12/1998 | Lizardi |
| 5,871,928 A | 2/1999 | Fodor et al. |
| 5,925,525 A | 7/1999 | Fodor et al. |
| 5,935,793 A | 8/1999 | Wong |
| 5,962,271 A | 10/1999 | Chenchik et al. |
| 5,962,272 A | 10/1999 | Chenchik et al. |
| 5,968,740 A | 10/1999 | Fodor et al. |
| 5,981,176 A | 11/1999 | Wallace |
| 5,981,179 A | 11/1999 | Lorinez et al. |
| 6,013,445 A | 1/2000 | Albrecht et al. |
| 6,040,138 A | 3/2000 | Lockhart et al. |
| 6,046,005 A | 4/2000 | Ju et al. |
| 6,060,596 A | 5/2000 | Lerner et al. |
| 6,064,755 A | 5/2000 | Some |
| 6,114,149 A | 9/2000 | Fry et al. |
| 6,117,631 A | 9/2000 | Nilsen |
| 6,124,092 A | 9/2000 | O'Neill et al. |
| 6,138,077 A | 10/2000 | Brenner |
| 6,140,489 A | 10/2000 | Brenner |
| 6,172,214 B1 | 1/2001 | Brenner |
| 6,197,506 B1 | 3/2001 | Fodor et al. |
| 6,197,554 B1 | 3/2001 | Lin et al. |
| 6,214,558 B1 | 4/2001 | Shuber et al. |
| 6,235,475 B1 | 5/2001 | Brenner et al. |
| 6,235,483 B1 | 5/2001 | Wolber et al. |
| 6,265,163 B1 | 7/2001 | Albrecht et al. |
| 6,268,152 B1 | 7/2001 | Fodor et al. |
| 6,284,460 B1 | 9/2001 | Fodor et al. |
| 6,284,485 B1 | 9/2001 | Boyle et al. |
| 6,309,822 B1 | 10/2001 | Fodor et al. |
| 6,309,823 B1 | 10/2001 | Cronin et al. |
| 6,326,148 B1 | 12/2001 | Pauletti et al. |
| 6,355,431 B1 | 3/2002 | Chee et al. |
| 6,355,432 B1 | 3/2002 | Fodor et al. |
| 6,372,813 B1 | 4/2002 | Johnson et al. |
| 6,395,491 B1 | 5/2002 | Fodor et al. |
| 6,406,848 B1 | 6/2002 | Bridgham et al. |
| 6,436,675 B1 | 8/2002 | Welch et al. |
| 6,440,667 B1 | 8/2002 | Fodor et al. |
| 6,440,706 B1 | 8/2002 | Vogelstein et al. |
| 6,451,536 B1 | 9/2002 | Fodor et al. |
| 6,458,530 B1 | 10/2002 | Morris et al. |
| 6,468,744 B1 | 10/2002 | Cronin et al. |
| 6,480,791 B1 | 11/2002 | Strathmann |
| 6,489,114 B2 | 12/2002 | Laayoun et al. |
| 6,489,116 B2 | 12/2002 | Wagner |
| 6,492,121 B2 | 12/2002 | Kurane et al. |
| 6,500,620 B2 | 12/2002 | Yu et al. |
| 6,512,105 B1 | 1/2003 | Hogan et al. |
| 6,514,699 B1 | 2/2003 | O'Neill et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,600,996 B2 | 7/2003 | Webster et al. |
| 6,629,040 B1 | 9/2003 | Goodlett et al. |
| 6,653,077 B1 | 11/2003 | Brenner |
| 6,753,147 B2 | 6/2004 | Vogelstein et al. |
| 6,787,308 B2 | 9/2004 | Balasubramanian et al. |
| 6,808,906 B2 | 10/2004 | Shen et al. |
| 6,849,404 B2 | 2/2005 | Park et al. |
| 6,852,488 B2 | 2/2005 | Fodor et al. |
| 6,858,412 B2 | 2/2005 | Willis et al. |
| 6,890,741 B2 | 5/2005 | Fan et al. |
| 6,946,251 B2 | 9/2005 | Kurn |
| 6,974,669 B2 | 12/2005 | Mirkin et al. |
| 7,022,479 B2 | 4/2006 | Wagner |
| 7,034,145 B2 | 4/2006 | Shen et al. |
| 7,155,050 B1 | 12/2006 | Sloge |
| 7,294,466 B2 | 11/2007 | McMillan |
| 7,323,309 B2 | 1/2008 | Mirkin et al. |
| 7,393,665 B2 | 7/2008 | Brenner |
| 7,407,757 B2 | 8/2008 | Brenner |
| 7,424,368 B2 | 9/2008 | Huang et al. |
| 7,432,055 B2 | 10/2008 | Pemov et al. |
| 7,470,515 B2 | 12/2008 | Rashtchian et al. |
| 7,473,767 B2 | 1/2009 | Dimitrov |
| 7,476,786 B2 | 1/2009 | Chan et al. |
| 7,537,897 B2 | 5/2009 | Brenner et al. |
| 7,544,473 B2 | 6/2009 | Brenner |
| 7,635,566 B2 | 12/2009 | Brenner |
| 7,638,612 B2 | 12/2009 | Rashtchian et al. |
| 7,718,403 B2 | 5/2010 | Kamberov et al. |
| 7,771,946 B2 | 8/2010 | Kurn |
| 7,822,555 B2 | 10/2010 | Huang et al. |
| 7,824,856 B2 | 11/2010 | Monforte |
| 7,824,889 B2 | 11/2010 | Vogelstein et al. |
| 7,915,015 B2 | 3/2011 | Vogelstein et al. |
| 7,985,546 B2 | 7/2011 | Church et al. |
| 8,071,311 B2 | 12/2011 | Kurn |
| 8,110,351 B2 | 2/2012 | Bosnes |
| 8,114,681 B2 | 2/2012 | Martin et al. |
| 8,148,068 B2 | 4/2012 | Brenner |
| 8,168,385 B2 | 5/2012 | Brenner |
| 8,206,913 B1 | 6/2012 | Kamberov et al. |
| 8,241,850 B2 | 8/2012 | Brenner |
| 8,298,767 B2 | 10/2012 | Brenner et al. |
| 8,318,433 B2 | 11/2012 | Brenner |
| 8,367,051 B2 | 2/2013 | Matyjaszewski et al. |
| 8,420,324 B2 | 4/2013 | Rashtchian et al. |
| 8,445,205 B2 | 5/2013 | Brenner |
| 8,470,996 B2 | 6/2013 | Brenner |
| 8,476,018 B2 | 7/2013 | Brenner |
| 8,481,292 B2 | 7/2013 | Casbon et al. |
| 8,535,889 B2 | 9/2013 | Larson et al. |
| 8,563,274 B2 | 10/2013 | Brenner et al. |
| 8,603,749 B2 | 12/2013 | Gillevet et al. |
| 8,679,756 B1 | 3/2014 | Brenner et al. |
| 8,685,678 B2 | 4/2014 | Casbon et al. |
| 8,685,753 B2 | 4/2014 | Martin et al. |
| 8,715,967 B2 | 5/2014 | Casbon et al. |
| 8,722,368 B2 | 5/2014 | Casbon et al. |
| 8,728,766 B2 | 5/2014 | Casbon et al. |
| 8,741,606 B2 | 6/2014 | Casbon et al. |
| 8,835,110 B2 | 9/2014 | Wang et al. |
| 8,841,071 B2 | 9/2014 | Link |
| 8,856,410 B2 | 10/2014 | Park |
| 9,150,852 B2 | 10/2015 | Samuels et al. |
| 9,181,582 B2 | 11/2015 | Kurn |
| 9,188,586 B2 | 11/2015 | Fan et al. |
| 9,228,229 B2 | 1/2016 | Olson et al. |
| 9,262,376 B2 | 2/2016 | Tsuto |
| 9,297,047 B2 | 3/2016 | Furchak et al. |
| 9,371,598 B2 | 6/2016 | Chee |
| 9,582,877 B2 | 2/2017 | Fu et al. |

(56) References Cited

U.S. PATENT DOCUMENTS

| | | |
|---|---|---|
| 9,593,365 B2 | 3/2017 | Frisen et al. |
| 9,644,204 B2 | 5/2017 | Hindson et al. |
| 9,689,024 B2 | 6/2017 | Hindson et al. |
| 9,695,468 B2 | 7/2017 | Hindson et al. |
| 9,787,810 B1 | 10/2017 | Chiang |
| 9,850,515 B2 | 12/2017 | McCoy et al. |
| 9,856,530 B2 | 1/2018 | Hindson et al. |
| 9,868,979 B2 | 1/2018 | Chee et al. |
| 9,879,313 B2 | 1/2018 | Chee et al. |
| 9,905,005 B2 | 2/2018 | Fu et al. |
| 9,938,523 B2 | 4/2018 | LaBaer |
| 9,951,386 B2 | 4/2018 | Hindson et al. |
| 9,988,660 B2 | 6/2018 | Rashtchian et al. |
| 10,002,316 B2 | 6/2018 | Fodor et al. |
| 10,011,872 B1 | 7/2018 | Belgrader et al. |
| 10,017,761 B2 | 7/2018 | Weissman et al. |
| 10,023,910 B2 | 7/2018 | Drmanac et al. |
| 10,030,267 B2 | 7/2018 | Hindson et al. |
| 10,041,116 B2 | 8/2018 | Hindson et al. |
| 10,131,958 B1 | 11/2018 | Fan et al. |
| 10,138,518 B2 | 11/2018 | Chun |
| 10,151,003 B2 | 12/2018 | Fan et al. |
| 10,208,343 B2 | 2/2019 | Hindson et al. |
| 10,227,648 B2 | 3/2019 | Hindson et al. |
| 10,246,703 B2 | 4/2019 | Church et al. |
| 10,253,364 B2 | 4/2019 | Hindson et al. |
| 10,266,874 B2 | 4/2019 | Weissleder et al. |
| 10,273,541 B2 | 4/2019 | Hindson et al. |
| 10,288,608 B2 | 5/2019 | Kozlov et al. |
| 10,294,511 B2 | 5/2019 | Sanches-Kuiper et al. |
| 10,308,982 B2 | 6/2019 | Chee |
| 10,323,278 B2 | 6/2019 | Belgrader et al. |
| 10,337,061 B2 | 7/2019 | Hindson et al. |
| 10,344,329 B2 | 7/2019 | Hindson et al. |
| 10,450,607 B2 | 10/2019 | Hindson et al. |
| 10,550,429 B2 | 2/2020 | Harada et al. |
| RE47,983 E | 5/2020 | Gao et al. |
| 11,092,607 B2 | 8/2021 | Gaublomme et al. |
| 11,460,468 B2 | 10/2022 | Fan et al. |
| 11,467,157 B2 | 10/2022 | Fan et al. |
| 11,535,882 B2 | 12/2022 | Fu et al. |
| 2001/0024784 A1 | 9/2001 | Wagner |
| 2001/0036632 A1 | 11/2001 | Yu et al. |
| 2002/0019005 A1 | 2/2002 | Kamb |
| 2002/0051986 A1 | 5/2002 | Baez et al. |
| 2002/0065609 A1 | 5/2002 | Ashby |
| 2002/0072058 A1 | 6/2002 | Voelker et al. |
| 2002/0094116 A1 | 7/2002 | Forst et al. |
| 2002/0106666 A1 | 8/2002 | Hayashizaki |
| 2002/0132241 A1 | 9/2002 | Fan et al. |
| 2002/0168665 A1 | 11/2002 | Okawa |
| 2002/0172953 A1 | 11/2002 | Mirkin et al. |
| 2002/0187480 A1 | 12/2002 | Brandon |
| 2002/0192687 A1 | 12/2002 | Mirkin et al. |
| 2003/0003490 A1 | 1/2003 | Fan et al. |
| 2003/0013091 A1 | 1/2003 | Dimitrov |
| 2003/0032049 A1 | 2/2003 | Wagner |
| 2003/0049616 A1 | 3/2003 | Brenner et al. |
| 2003/0077611 A1 | 4/2003 | Slepnev |
| 2003/0082818 A1 | 5/2003 | Bahnson et al. |
| 2003/0087242 A1 | 5/2003 | Mirkin et al. |
| 2003/0104436 A1 | 6/2003 | Morris et al. |
| 2003/0165935 A1 | 9/2003 | Vann et al. |
| 2003/0175908 A1 | 9/2003 | Linnarsson |
| 2003/0186251 A1 | 10/2003 | Dunn et al. |
| 2003/0207296 A1 | 11/2003 | Park et al. |
| 2003/0207300 A1 | 11/2003 | Matray et al. |
| 2004/0047769 A1 | 3/2004 | Tanaami |
| 2004/0091864 A1 | 5/2004 | French et al. |
| 2004/0096368 A1 | 5/2004 | Davis et al. |
| 2004/0096892 A1 | 5/2004 | Wang et al. |
| 2004/0121342 A1 | 6/2004 | Mckeown |
| 2004/0146901 A1 | 7/2004 | Morris et al. |
| 2004/0147435 A1 | 7/2004 | Hawiger et al. |
| 2004/0157243 A1 | 8/2004 | Huang et al. |
| 2004/0209298 A1 | 10/2004 | Kamberov et al. |
| 2004/0224325 A1 | 11/2004 | Knapp et al. |
| 2004/0259118 A1 | 12/2004 | Macevicz |
| 2005/0019776 A1 | 1/2005 | Callow et al. |
| 2005/0032110 A1 | 2/2005 | Shen et al. |
| 2005/0048500 A1 | 3/2005 | Lawton |
| 2005/0053952 A1 | 3/2005 | Hong et al. |
| 2005/0105077 A1 | 5/2005 | Padmanabhan et al. |
| 2005/0170373 A1 | 8/2005 | Monforte |
| 2005/0175993 A1 | 8/2005 | Wei |
| 2005/0196760 A1 | 9/2005 | Pemov et al. |
| 2005/0214825 A1 | 9/2005 | Stuelpnagel |
| 2005/0250146 A1 | 11/2005 | McMillan |
| 2005/0250147 A1 | 11/2005 | Macevicz |
| 2006/0002824 A1 | 1/2006 | Chang et al. |
| 2006/0035258 A1 | 2/2006 | Tadakamalla et al. |
| 2006/0040297 A1 | 2/2006 | Leamon et al. |
| 2006/0041385 A1 | 2/2006 | Bauer |
| 2006/0057634 A1 | 3/2006 | Rye |
| 2006/0073506 A1 | 4/2006 | Christians et al. |
| 2006/0211030 A1 | 9/2006 | Brenner |
| 2006/0257902 A1 | 11/2006 | Mendoza et al. |
| 2006/0263709 A1 | 11/2006 | Matsumura et al. |
| 2006/0263789 A1 | 11/2006 | Kincaid |
| 2006/0280352 A1 | 12/2006 | Muschler et al. |
| 2006/0281092 A1 | 12/2006 | Wille et al. |
| 2006/0286570 A1 | 12/2006 | Rowlen et al. |
| 2007/0020640 A1 | 1/2007 | McCloskey et al. |
| 2007/0031829 A1 | 2/2007 | Yasuno et al. |
| 2007/0042400 A1 | 2/2007 | Choi et al. |
| 2007/0042419 A1 | 2/2007 | Barany et al. |
| 2007/0065823 A1 | 3/2007 | Dressman et al. |
| 2007/0065844 A1 | 3/2007 | Golub et al. |
| 2007/0105090 A1 | 5/2007 | Cassidy et al. |
| 2007/0117121 A1 | 5/2007 | Hutchison et al. |
| 2007/0117134 A1 | 5/2007 | Kou |
| 2007/0117177 A1 | 5/2007 | Luo et al. |
| 2007/0133856 A1 | 6/2007 | Dutta-Choudhury |
| 2007/0172873 A1 | 7/2007 | Brenner et al. |
| 2007/0178478 A1 | 8/2007 | Dhallan et al. |
| 2007/0202523 A1 | 8/2007 | Becker et al. |
| 2007/0281317 A1 | 12/2007 | Becker et al. |
| 2008/0038727 A1 | 2/2008 | Spier |
| 2008/0070303 A1 | 3/2008 | West et al. |
| 2008/0119736 A1 | 5/2008 | Dentinger |
| 2008/0194414 A1 | 8/2008 | Albert et al. |
| 2008/0261204 A1 | 10/2008 | Lexow |
| 2008/0268508 A1 | 10/2008 | Sowlay |
| 2008/0269068 A1 | 10/2008 | Church et al. |
| 2008/0274458 A1 | 11/2008 | Latham et al. |
| 2008/0299609 A1 | 12/2008 | Kwon et al. |
| 2008/0318802 A1 | 12/2008 | Brenner |
| 2009/0053669 A1 | 2/2009 | Liu et al. |
| 2009/0061513 A1 | 3/2009 | Andersson Svahn et al. |
| 2009/0105959 A1 | 4/2009 | Braverman et al. |
| 2009/0131269 A1 | 5/2009 | Martin et al. |
| 2009/0137407 A1 | 5/2009 | Church et al. |
| 2009/0208936 A1 | 8/2009 | Tan et al. |
| 2009/0220385 A1 | 9/2009 | Brown et al. |
| 2009/0226891 A2 | 9/2009 | Nova et al. |
| 2009/0252414 A1 | 10/2009 | Suzuki |
| 2009/0253586 A1 | 10/2009 | Nelson et al. |
| 2009/0283676 A1 | 11/2009 | Skoglund |
| 2009/0290151 A1 | 11/2009 | Agrawal et al. |
| 2009/0298709 A1 | 12/2009 | Ma |
| 2009/0311694 A1 | 12/2009 | Gallagher et al. |
| 2010/0069250 A1 | 3/2010 | White, III |
| 2010/0105049 A1 | 4/2010 | Ehrich et al. |
| 2010/0105112 A1 | 4/2010 | Holtze et al. |
| 2010/0105886 A1 | 4/2010 | Woudenberg et al. |
| 2010/0120098 A1 | 5/2010 | Grunenwald et al. |
| 2010/0120630 A1 | 5/2010 | Huang et al. |
| 2010/0136544 A1 | 6/2010 | Agresti et al. |
| 2010/0159533 A1 | 6/2010 | Lipson et al. |
| 2010/0167354 A1 | 7/2010 | Kurn |
| 2010/0184076 A1 | 7/2010 | Lawton |
| 2010/0255471 A1 | 10/2010 | Clarke |
| 2010/0267028 A1 | 10/2010 | Pasche |
| 2010/0291666 A1 | 11/2010 | Collier et al. |

(56) References Cited

U.S. PATENT DOCUMENTS

| | | |
|---|---|---|
| 2010/0300895 A1 | 12/2010 | Nobile et al. |
| 2010/0323348 A1 | 12/2010 | Hamady et al. |
| 2010/0330574 A1 | 12/2010 | Whitman |
| 2011/0038507 A1 | 2/2011 | Hager |
| 2011/0059436 A1 | 3/2011 | Hardin et al. |
| 2011/0059556 A1 | 3/2011 | Strey |
| 2011/0070584 A1 | 3/2011 | Wohlgemuth et al. |
| 2011/0072889 A1 | 3/2011 | Albitar et al. |
| 2011/0160078 A1 | 6/2011 | Fodor et al. |
| 2011/0201507 A1 | 8/2011 | Rava et al. |
| 2011/0230358 A1 | 9/2011 | Rava |
| 2011/0244455 A1 | 10/2011 | Larson et al. |
| 2011/0245111 A1 | 10/2011 | Chee |
| 2011/0263457 A1 | 10/2011 | Krutzik et al. |
| 2011/0294689 A1 | 12/2011 | Namsaraev |
| 2011/0312511 A1 | 12/2011 | Winquist et al. |
| 2012/0004132 A1 | 1/2012 | Zhang et al. |
| 2012/0010091 A1 | 1/2012 | Linnarson |
| 2012/0014977 A1 | 1/2012 | Furihata et al. |
| 2012/0034607 A1 | 2/2012 | Rothberg et al. |
| 2012/0040843 A1 | 2/2012 | Ducree et al. |
| 2012/0045844 A1 | 2/2012 | Rothberg et al. |
| 2012/0058520 A1 | 3/2012 | Hayashida |
| 2012/0058902 A1 | 3/2012 | Livingston et al. |
| 2012/0065081 A1 | 3/2012 | Chee |
| 2012/0071331 A1 | 3/2012 | Casbon |
| 2012/0087862 A1 | 4/2012 | Hood et al. |
| 2012/0142018 A1 | 6/2012 | Jiang |
| 2012/0149603 A1 | 6/2012 | Cooney et al. |
| 2012/0156675 A1 | 6/2012 | Lueerssen et al. |
| 2012/0163681 A1 | 6/2012 | Lohse |
| 2012/0165219 A1 | 6/2012 | Van Der Zaag et al. |
| 2012/0173159 A1 | 7/2012 | Davey et al. |
| 2012/0190020 A1 | 7/2012 | Oliphant et al. |
| 2012/0202293 A1 | 8/2012 | Martin et al. |
| 2012/0220022 A1 | 8/2012 | Ehrlich et al. |
| 2012/0220494 A1 | 8/2012 | Samuels et al. |
| 2012/0231972 A1 | 9/2012 | Golyshin et al. |
| 2012/0252012 A1 | 10/2012 | Armougom et al. |
| 2012/0253689 A1 | 10/2012 | Rogan |
| 2012/0316074 A1 | 12/2012 | Saxonov |
| 2012/0322681 A1 | 12/2012 | Kung et al. |
| 2013/0005585 A1 | 1/2013 | Anderson et al. |
| 2013/0022977 A1 | 1/2013 | Lapidus et al. |
| 2013/0045994 A1 | 2/2013 | Shinozuka et al. |
| 2013/0116130 A1 | 5/2013 | Fu et al. |
| 2013/0190206 A1 | 7/2013 | Leonard |
| 2013/0203047 A1 | 8/2013 | Casbon et al. |
| 2013/0210643 A1 | 8/2013 | Casbon et al. |
| 2013/0210659 A1 | 8/2013 | Watson et al. |
| 2013/0224743 A1 | 8/2013 | Casbon et al. |
| 2013/0225418 A1 | 8/2013 | Watson |
| 2013/0225623 A1 | 8/2013 | Buxbaum et al. |
| 2013/0237458 A1 | 9/2013 | Casbon et al. |
| 2013/0267424 A1 | 10/2013 | Casbon et al. |
| 2013/0274117 A1 | 10/2013 | Church |
| 2013/0323732 A1 | 12/2013 | Anderson et al. |
| 2014/0004569 A1 | 1/2014 | Lambowitz et al. |
| 2014/0057799 A1 | 2/2014 | Johnson et al. |
| 2014/0066318 A1 | 3/2014 | Frisen et al. |
| 2014/0147860 A1 | 5/2014 | Kaduchak et al. |
| 2014/0155274 A1 | 6/2014 | Xie et al. |
| 2014/0155295 A1 | 6/2014 | Hindson et al. |
| 2014/0178438 A1 | 6/2014 | Sahin et al. |
| 2014/0194324 A1 | 7/2014 | Gormley et al. |
| 2014/0206079 A1 | 7/2014 | Malinoski et al. |
| 2014/0206547 A1 | 7/2014 | Wang |
| 2014/0216128 A1 | 8/2014 | Trotter et al. |
| 2014/0227684 A1 | 8/2014 | Hindson et al. |
| 2014/0227705 A1 | 8/2014 | Vogelstein et al. |
| 2014/0228239 A1 | 8/2014 | McCoy et al. |
| 2014/0228255 A1 | 8/2014 | Hindson et al. |
| 2014/0235506 A1 | 8/2014 | Hindson et al. |
| 2014/0243242 A1 | 8/2014 | Nicol et al. |
| 2014/0244742 A1 | 8/2014 | Yu et al. |
| 2014/0272952 A1 | 9/2014 | May et al. |
| 2014/0274811 A1 | 9/2014 | Arnold |
| 2014/0287963 A1 | 9/2014 | Hindson et al. |
| 2014/0303005 A1 | 10/2014 | Samuels et al. |
| 2014/0309945 A1 | 10/2014 | Park et al. |
| 2014/0315211 A1 | 10/2014 | Sugino et al. |
| 2014/0322716 A1 | 10/2014 | Robins |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0011396 A1 | 1/2015 | Schroeder et al. |
| 2015/0017654 A1 | 1/2015 | Gorfinkel et al. |
| 2015/0066385 A1 | 3/2015 | Schnall-Levin et al. |
| 2015/0072867 A1 | 3/2015 | Soldatov et al. |
| 2015/0072873 A1 | 3/2015 | Heinz et al. |
| 2015/0099661 A1 | 4/2015 | Fodor et al. |
| 2015/0099673 A1 | 4/2015 | Fodor et al. |
| 2015/0111256 A1 | 4/2015 | Church et al. |
| 2015/0118680 A1 | 4/2015 | Fodor et al. |
| 2015/0119255 A1 | 4/2015 | Fodor et al. |
| 2015/0119256 A1 | 4/2015 | Fodor et al. |
| 2015/0119257 A1 | 4/2015 | Fodor et al. |
| 2015/0119258 A1 | 4/2015 | Fodor et al. |
| 2015/0119290 A1 | 4/2015 | Fodor et al. |
| 2015/0133319 A1 | 5/2015 | Fu et al. |
| 2015/0141292 A1 | 5/2015 | Fodor et al. |
| 2015/0152409 A1 | 6/2015 | Seitz et al. |
| 2015/0203897 A1 | 7/2015 | Robons et al. |
| 2015/0211050 A1 | 7/2015 | Lafrate et al. |
| 2015/0218620 A1 | 8/2015 | Behlke et al. |
| 2015/0225777 A1 | 8/2015 | Hindson et al. |
| 2015/0225778 A1 | 8/2015 | Hindson et al. |
| 2015/0247182 A1 | 9/2015 | Faham et al. |
| 2015/0253237 A1 | 9/2015 | Castellarnau et al. |
| 2015/0259734 A1 | 9/2015 | Asbury et al. |
| 2015/0275295 A1 | 10/2015 | Wang et al. |
| 2015/0298091 A1 | 10/2015 | Weitz |
| 2015/0299784 A1 | 10/2015 | Fan et al. |
| 2015/0307874 A1 | 10/2015 | Jaitin |
| 2015/0329852 A1 | 11/2015 | Nolan |
| 2015/0360193 A1 | 12/2015 | Fan et al. |
| 2015/0376609 A1 | 12/2015 | Hindson et al. |
| 2016/0017320 A1 | 1/2016 | Wang et al. |
| 2016/0026758 A1 | 1/2016 | Jabara et al. |
| 2016/0053253 A1 | 2/2016 | Salathia et al. |
| 2016/0055632 A1 | 2/2016 | Fu et al. |
| 2016/0060621 A1 | 3/2016 | Agresti et al. |
| 2016/0060682 A1 | 3/2016 | Pregibon et al. |
| 2016/0068889 A1 | 3/2016 | Gole et al. |
| 2016/0122751 A1 | 5/2016 | LaBaer |
| 2016/0122753 A1 | 5/2016 | Mikkelsen et al. |
| 2016/0138091 A1 | 5/2016 | Chee et al. |
| 2016/0145677 A1 | 5/2016 | Chee et al. |
| 2016/0145683 A1 | 5/2016 | Fan et al. |
| 2016/0153973 A1 | 6/2016 | Smith |
| 2016/0201125 A1 | 7/2016 | Samuels et al. |
| 2016/0208322 A1 | 7/2016 | Anderson et al. |
| 2016/0222378 A1 | 8/2016 | Fodor et al. |
| 2016/0232291 A1 | 8/2016 | Kyriazopoulou-Panagiotopoulou et al. |
| 2016/0244742 A1 | 8/2016 | Linnarsson et al. |
| 2016/0244828 A1 | 8/2016 | Mason |
| 2016/0265027 A1 | 9/2016 | Sanches-Kuiper et al. |
| 2016/0265069 A1 | 9/2016 | Fan et al. |
| 2016/0266094 A1 | 9/2016 | Ankrum et al. |
| 2016/0289669 A1 | 10/2016 | Fan et al. |
| 2016/0289670 A1 | 10/2016 | Samuels et al. |
| 2016/0298180 A1 | 10/2016 | Chee |
| 2016/0312276 A1 | 10/2016 | Fu et al. |
| 2016/0320720 A1 | 11/2016 | Murata et al. |
| 2016/0355879 A1 | 12/2016 | Kamberov et al. |
| 2016/0362730 A1 | 12/2016 | Alexander et al. |
| 2017/0044525 A1 | 2/2017 | Kaper et al. |
| 2017/0136458 A1 | 5/2017 | Dunne et al. |
| 2017/0154421 A1 | 6/2017 | Fu et al. |

(56) References Cited

U.S. PATENT DOCUMENTS

| | | |
|---|---|---|
| 2017/0192013 A1 | 7/2017 | Agresti et al. |
| 2017/0260584 A1 | 9/2017 | Zheng et al. |
| 2017/0275669 A1 | 9/2017 | Weissleder et al. |
| 2017/0314067 A1 | 11/2017 | Shum et al. |
| 2017/0342405 A1 | 11/2017 | Fu et al. |
| 2017/0342465 A1 | 11/2017 | Shum et al. |
| 2017/0342484 A1 | 11/2017 | Shum et al. |
| 2017/0344866 A1 | 11/2017 | Fan et al. |
| 2018/0016634 A1 | 1/2018 | Hindson et al. |
| 2018/0024139 A1 | 1/2018 | Peikon et al. |
| 2018/0030522 A1 | 2/2018 | Kamberov et al. |
| 2018/0037942 A1 | 2/2018 | Fu et al. |
| 2018/0057873 A1 | 3/2018 | Zhou et al. |
| 2018/0088112 A1 | 3/2018 | Fan et al. |
| 2018/0094312 A1 | 4/2018 | Hindson et al. |
| 2018/0094314 A1 | 4/2018 | Hindson et al. |
| 2018/0094315 A1 | 4/2018 | Hindson et al. |
| 2018/0105808 A1 | 4/2018 | Mikkelsen et al. |
| 2018/0112266 A1 | 4/2018 | Hindson et al. |
| 2018/0127743 A1 | 5/2018 | Vigneault et al. |
| 2018/0142292 A1 | 5/2018 | Hindson et al. |
| 2018/0163201 A1 | 6/2018 | Larson |
| 2018/0179590 A1 | 6/2018 | Belgrader et al. |
| 2018/0179591 A1 | 6/2018 | Belgrader et al. |
| 2018/0201923 A1 | 7/2018 | LaBaer |
| 2018/0201980 A1 | 7/2018 | Chee et al. |
| 2018/0208975 A1 | 7/2018 | Peterson et al. |
| 2018/0216174 A1 | 8/2018 | Shum et al. |
| 2018/0230527 A1 | 8/2018 | Fang et al. |
| 2018/0251825 A1 | 9/2018 | Stoeckius et al. |
| 2018/0258482 A1 | 9/2018 | Hindson et al. |
| 2018/0276332 A1 | 9/2018 | Fan et al. |
| 2018/0282803 A1 | 10/2018 | Belgrader et al. |
| 2018/0002738 A1 | 11/2018 | Wang et al. |
| 2018/0320241 A1 | 11/2018 | Nolan et al. |
| 2018/0340170 A1 | 11/2018 | Belhocine et al. |
| 2018/0346969 A1 | 12/2018 | Chang et al. |
| 2018/0346970 A1 | 12/2018 | Chang et al. |
| 2018/0371536 A1 | 12/2018 | Fu et al. |
| 2019/0010552 A1 | 1/2019 | Xu et al. |
| 2019/0025304 A1 | 1/2019 | Vigneault et al. |
| 2019/0032129 A1 | 1/2019 | Hindson et al. |
| 2019/0095578 A1 | 3/2019 | Shum et al. |
| 2019/0119726 A1 | 4/2019 | Shum et al. |
| 2019/0136316 A1 | 5/2019 | Hindson et al. |
| 2019/0136317 A1 | 5/2019 | Hindson et al. |
| 2019/0136319 A1 | 5/2019 | Hindson et al. |
| 2019/0161743 A1 | 5/2019 | Church et al. |
| 2019/0177788 A1 | 6/2019 | Hindson et al. |
| 2019/0177800 A1 | 6/2019 | Boutet et al. |
| 2019/0203270 A1 | 7/2019 | Amit et al. |
| 2019/0203291 A1 | 7/2019 | Hindson et al. |
| 2019/0211395 A1 | 7/2019 | Tsao et al. |
| 2019/0218276 A1 | 7/2019 | Regev et al. |
| 2019/0218607 A1 | 7/2019 | Love et al. |
| 2019/0221287 A1 | 7/2019 | Tsujimoto |
| 2019/0221292 A1 | 7/2019 | Tsujimoto |
| 2019/0256888 A1 | 8/2019 | Weissleder et al. |
| 2019/0256907 A1 | 8/2019 | Ryan et al. |
| 2019/0292592 A1 | 9/2019 | Shum et al. |
| 2019/0338353 A1 | 11/2019 | Belgrader et al. |
| 2019/0338357 A1 | 11/2019 | Fan et al. |
| 2019/0390253 A1 | 12/2019 | Kennedy et al. |
| 2020/0102598 A1 | 4/2020 | Xie et al. |
| 2020/0109437 A1 | 4/2020 | Chang et al. |
| 2020/0115753 A1 | 4/2020 | Shalek et al. |
| 2020/0149037 A1 | 5/2020 | Shum |
| 2021/0039582 A1 | 2/2021 | Patton et al. |
| 2021/0123044 A1 | 4/2021 | Zhang et al. |
| 2021/0132078 A1 | 5/2021 | Peikon et al. |
| 2021/0198754 A1 | 7/2021 | Fan et al. |
| 2021/0213413 A1 | 7/2021 | Saligrama et al. |
| 2021/0214770 A1 | 7/2021 | Prosen et al. |
| 2021/0214784 A1 | 7/2021 | Prosen et al. |
| 2021/0222163 A1 | 7/2021 | Wu et al. |
| 2021/0222244 A1 | 7/2021 | Martin et al. |
| 2021/0230582 A1 | 7/2021 | Fu et al. |
| 2021/0230583 A1 | 7/2021 | Lam et al. |
| 2021/0230666 A1 | 7/2021 | Wu et al. |
| 2021/0246492 A1 | 8/2021 | Song et al. |
| 2021/0263019 A1 | 8/2021 | Martin et al. |
| 2021/0355484 A1 | 11/2021 | Jensen et al. |
| 2021/0371909 A1 | 12/2021 | Lazaruk |
| 2021/0371914 A1 | 12/2021 | Stoeckius et al. |
| 2022/0010361 A1 | 1/2022 | Song et al. |
| 2022/0010362 A1 | 1/2022 | Campbell |
| 2022/0033810 A1 | 2/2022 | Song et al. |
| 2022/0154288 A1 | 5/2022 | Mortimer |
| 2022/0162695 A1 | 5/2022 | Sakofsky et al. |
| 2022/0162773 A1 | 5/2022 | Sakofsky et al. |
| 2022/0178909 A1 | 6/2022 | Huang et al. |
| 2022/0214356 A1 | 7/2022 | Henikoff et al. |
| 2022/0219170 A1 | 7/2022 | Khurana et al. |
| 2022/0220549 A1 | 7/2022 | Shum et al. |
| 2022/0267759 A1 | 8/2022 | Sanjana et al. |
| 2022/0333185 A1 | 10/2022 | Fu et al. |
| 2022/0348904 A1 | 11/2022 | Shum et al. |
| 2023/0083422 A1 | 3/2023 | Fu et al. |
| 2023/0109336 A1 | 4/2023 | Shum et al. |
| 2023/0125113 A1 | 4/2023 | Fan et al. |
| 2023/0193372 A1 | 6/2023 | Shum et al. |

FOREIGN PATENT DOCUMENTS

| | | |
|---|---|---|
| EP | 1473080 | 11/2004 |
| EP | 1647600 | 4/2006 |
| EP | 1845160 | 10/2007 |
| EP | 2036989 | 3/2009 |
| EP | 1379693 | 5/2009 |
| EP | 2204456 | 7/2010 |
| EP | 2431465 | 3/2012 |
| EP | 2203749 | 8/2012 |
| EP | 2511708 | 10/2012 |
| EP | 2538220 | 12/2012 |
| EP | 2623613 | 8/2013 |
| EP | 1745155 | 10/2014 |
| EP | 2805769 | 11/2014 |
| EP | 2556171 | 9/2015 |
| EP | 2970958 | 12/2017 |
| EP | 3263715 | 1/2018 |
| EP | 2670863 B1 | 6/2018 |
| EP | 3136103 | 8/2018 |
| EP | 2954102 | 12/2018 |
| EP | 3428290 | 1/2019 |
| EP | 2970957 | 4/2019 |
| EP | 3058092 | 5/2019 |
| EP | 3256606 | 5/2019 |
| EP | 3327123 | 8/2019 |
| GB | 2293238 A | 3/1996 |
| JP | H04108385 | 4/1992 |
| JP | 2001078768 | 3/2001 |
| JP | 2005233974 | 9/2005 |
| JP | 2007504831 | 3/2007 |
| JP | 2008256428 | 10/2008 |
| JP | 2013039275 | 2/2013 |
| WO | WO1989001050 | 2/1989 |
| WO | WO1996024061 | 8/1996 |
| WO | WO1997010365 | 3/1997 |
| WO | WO1999015702 | 4/1999 |
| WO | WO1999028505 | 6/1999 |
| WO | WO2000058516 | 10/2000 |
| WO | WO2001048242 | 7/2001 |
| WO | WO2001053539 | 7/2001 |
| WO | WO2002018643 | 3/2002 |
| WO | WO2002046472 | 6/2002 |
| WO | WO2002056014 | 7/2002 |
| WO | WO2002059355 | 8/2002 |
| WO | WO2002070684 | 9/2002 |
| WO | WO2002072772 | 9/2002 |
| WO | WO2002079490 | 10/2002 |
| WO | WO2002083922 | 10/2002 |
| WO | WO2002101358 | 12/2002 |
| WO | WO2003031591 | 4/2003 |
| WO | WO2003035829 | 5/2003 |

(56) References Cited

FOREIGN PATENT DOCUMENTS

| | | |
|---|---|---|
| WO | WO2004017374 | 2/2004 |
| WO | WO2004021986 | 3/2004 |
| WO | WO2004033669 | 4/2004 |
| WO | WO2004066185 | 8/2004 |
| WO | WO2004081225 | 9/2004 |
| WO | WO2005017206 | 2/2005 |
| WO | WO2005021731 | 3/2005 |
| WO | WO2005042759 | 5/2005 |
| WO | WO2005071110 | 8/2005 |
| WO | WO2005080604 | 9/2005 |
| WO | WO2005111242 | 11/2005 |
| WO | WO2005111243 | 11/2005 |
| WO | WO2006026828 | 3/2006 |
| WO | WO2006071776 | 7/2006 |
| WO | WO2006102264 | 9/2006 |
| WO | WO2006137932 | 12/2006 |
| WO | WO2007087310 | 8/2007 |
| WO | WO2007087312 | 8/2007 |
| WO | WO2007147079 | 12/2007 |
| WO | WO2008047428 | 4/2008 |
| WO | WO2008051928 | 5/2008 |
| WO | WO2008057163 | 5/2008 |
| WO | WO2008096318 | 8/2008 |
| WO | WO2008104380 | 9/2008 |
| WO | WO2008147428 | 12/2008 |
| WO | WO2008150432 | 12/2008 |
| WO | WO2009048530 | 4/2009 |
| WO | WO2009148560 | 12/2009 |
| WO | WO2009152928 | 12/2009 |
| WO | WO2010048605 | 4/2010 |
| WO | WO2010059820 | 5/2010 |
| WO | WO2010117620 | 10/2010 |
| WO | WO2011091393 | 7/2011 |
| WO | WO2011106738 | 9/2011 |
| WO | WO2011123246 | 10/2011 |
| WO | WO2011127099 | 10/2011 |
| WO | WO2011143659 | 11/2011 |
| WO | WO2011155833 | 12/2011 |
| WO | WO2012038839 | 3/2012 |
| WO | WO2012041802 | 4/2012 |
| WO | WO2012042374 | 4/2012 |
| WO | WO2012047297 | 4/2012 |
| WO | WO2012048341 | 4/2012 |
| WO | WO2012083225 | 6/2012 |
| WO | WO2012099896 | 7/2012 |
| WO | WO2012103154 | 8/2012 |
| WO | WO2012108864 | 8/2012 |
| WO | WO2012112804 | 8/2012 |
| WO | WO2012129363 | 9/2012 |
| WO | WO2012140224 | 10/2012 |
| WO | WO2012142213 | 10/2012 |
| WO | WO2012148477 | 11/2012 |
| WO | WO2012148497 | 11/2012 |
| WO | WO2012149042 | 11/2012 |
| WO | WO2012156744 | 11/2012 |
| WO | WO2012162267 | 11/2012 |
| WO | WO2012177639 | 12/2012 |
| WO | WO2013019075 | 3/2013 |
| WO | WO2013070990 | 5/2013 |
| WO | WO2013096802 | 6/2013 |
| WO | WO2013117595 | 8/2013 |
| WO | WO2013130674 | 9/2013 |
| WO | WO2013148525 | 10/2013 |
| WO | WO2013173394 | 11/2013 |
| WO | WO2013176767 | 11/2013 |
| WO | WO2013177206 | 11/2013 |
| WO | WO2013188831 | 12/2013 |
| WO | WO2013188872 | 12/2013 |
| WO | WO2013191775 | 12/2013 |
| WO | WO2014015084 | 1/2014 |
| WO | WO2014015098 | 1/2014 |
| WO | WO2014018093 | 1/2014 |
| WO | WO2014018460 | 1/2014 |
| WO | WO2014028537 | 2/2014 |
| WO | WO2014031997 | 2/2014 |
| WO | WO2014065756 | 5/2014 |
| WO | WO2014093676 | 6/2014 |
| WO | WO2014108850 | 7/2014 |
| WO | WO2014124046 | 8/2014 |
| WO | WO2014124336 | 8/2014 |
| WO | WO2014124338 | 8/2014 |
| WO | WO2014126937 | 8/2014 |
| WO | WO2014144495 | 9/2014 |
| WO | WO2014145458 | 9/2014 |
| WO | WO2014176575 | 10/2014 |
| WO | WO2014200767 | 12/2014 |
| WO | WO2014201273 | 12/2014 |
| WO | WO2014204939 | 12/2014 |
| WO | WO2014210223 | 12/2014 |
| WO | WO2014210225 | 12/2014 |
| WO | WO2014210353 | 12/2014 |
| WO | WO2015002908 | 1/2015 |
| WO | WO2015031691 | 3/2015 |
| WO | WO2015035087 | 3/2015 |
| WO | WO2015044428 | 4/2015 |
| WO | WO2015047186 | 4/2015 |
| WO | WO2015057985 | 4/2015 |
| WO | WO2014071361 | 5/2015 |
| WO | WO2015061844 | 5/2015 |
| WO | WO2015103339 | 7/2015 |
| WO | WO2015117163 | 8/2015 |
| WO | WO2015134787 | 9/2015 |
| WO | WO2015160439 | 10/2015 |
| WO | WO2015168161 | 11/2015 |
| WO | WO2015179339 | 11/2015 |
| WO | WO2015200869 | 12/2015 |
| WO | WO2015200893 | 12/2015 |
| WO | WO2016044227 | 3/2016 |
| WO | WO2016049418 | 3/2016 |
| WO | WO2016061517 | 4/2016 |
| WO | WO2016100976 | 6/2016 |
| WO | WO2016118915 | 7/2016 |
| WO | WO2016126871 | 8/2016 |
| WO | WO2016130578 | 8/2016 |
| WO | WO2016160965 | 8/2016 |
| WO | WO2016138496 | 9/2016 |
| WO | WO2016138500 | 9/2016 |
| WO | WO2016145409 | 9/2016 |
| WO | WO2016149418 | 9/2016 |
| WO | WO2016160844 | 10/2016 |
| WO | WO2016168825 | 10/2016 |
| WO | WO2016172373 | 10/2016 |
| WO | WO2016190795 | 12/2016 |
| WO | WO2016191272 | 12/2016 |
| WO | WO2017032808 | 3/2017 |
| WO | WO2017040306 | 3/2017 |
| WO | WO2017044574 | 3/2017 |
| WO | WO2017053905 | 3/2017 |
| WO | WO2017079593 | 5/2017 |
| WO | WO2017087873 | 5/2017 |
| WO | WO2017096239 | 6/2017 |
| WO | WO2017097939 | 6/2017 |
| WO | WO2017117358 | 7/2017 |
| WO | WO2017125508 | 7/2017 |
| WO | WO2017139690 | 8/2017 |
| WO | WO2017164936 | 9/2017 |
| WO | WO2017173328 | 10/2017 |
| WO | WO2017205691 | 11/2017 |
| WO | WO2018017949 | 1/2018 |
| WO | WO2018018008 | 1/2018 |
| WO | WO2018020489 | 2/2018 |
| WO | WO2018031631 | 2/2018 |
| WO | WO2018058073 | 3/2018 |
| WO | WO2018064640 | 4/2018 |
| WO | WO2018075693 | 4/2018 |
| WO | WO2018111872 | 6/2018 |
| WO | WO2018115852 | 6/2018 |
| WO | WO2018119447 | 6/2018 |
| WO | WO2018132635 | 7/2018 |
| WO | WO2018140966 | 8/2018 |
| WO | WO2018144240 | 8/2018 |
| WO | WO2018144813 | 8/2018 |
| WO | WO2018174827 | 8/2018 |
| WO | WO2018217862 | 8/2018 |

(56) References Cited

FOREIGN PATENT DOCUMENTS

| WO | WO2018218222 | 11/2018 |
|---|---|---|
| WO | WO2018222548 | 12/2018 |
| WO | WO2018226293 | 12/2018 |
| WO | WO2019055852 | 3/2019 |
| WO | WO2019076768 | 4/2019 |
| WO | WO2019084046 | 5/2019 |
| WO | WO2019099906 | 5/2019 |
| WO | WO2019113457 | 6/2019 |
| WO | WO2019113499 | 6/2019 |
| WO | WO2019113506 | 6/2019 |
| WO | WO2019113533 | 6/2019 |
| WO | WO2019118355 | 6/2019 |
| WO | WO2019126789 | 6/2019 |
| WO | WO2019157529 | 8/2019 |
| WO | WO2013137737 | 9/2019 |
| WO | WO2019178164 | 9/2019 |
| WO | WO2019213237 | 11/2019 |
| WO | WO2019213294 | 11/2019 |
| WO | WO2019218101 | 11/2019 |
| WO | WO2020028266 | 2/2020 |
| WO | WO2020033164 | 2/2020 |
| WO | WO2020037065 | 2/2020 |
| WO | WO2020046833 | 3/2020 |
| WO | WO2020072380 | 4/2020 |
| WO | WO2020097315 | 5/2020 |
| WO | WO2020123384 | 6/2020 |
| WO | WO2020131699 | 6/2020 |
| WO | WO2020154247 | 7/2020 |
| WO | WO2020159757 | 8/2020 |
| WO | WO2020167920 | 8/2020 |
| WO | WO2020214642 | 10/2020 |
| WO | WO2020219721 | 10/2020 |
| WO | WO2020242377 | 12/2020 |
| WO | WO2021092386 | 5/2021 |
| WO | WO2021142233 | 7/2021 |
| WO | WO2021146207 | 7/2021 |
| WO | WO2021146219 | 7/2021 |
| WO | WO2021146636 | 7/2021 |
| WO | WO2021155057 | 8/2021 |
| WO | WO2021155284 | 8/2021 |
| WO | WO2021163374 | 8/2021 |
| WO | WO2021168015 | 8/2021 |
| WO | WO2021168261 | 8/2021 |
| WO | WO20210178199 | 9/2021 |
| WO | WO2021247593 | 12/2021 |
| WO | WO2022015667 | 1/2022 |
| WO | WO2022026909 | 2/2022 |
| WO | WO2022040453 | 2/2022 |
| WO | WO2022143221 | 7/2022 |
| WO | WO2022256324 | 12/2022 |
| WO | WO2023034739 | 3/2023 |
| WO | WO2023034789 | 3/2023 |
| WO | WO2023034790 | 3/2023 |
| WO | WO2023034794 | 3/2023 |
| WO | WO2023034872 | 3/2023 |
| WO | WO2023039433 | 3/2023 |

OTHER PUBLICATIONS

"DNase footprinting assay" and "Chromatin" from Wikipedia. Printed on May 24, 2023.*
Adey et al., "Rapid, low-input, low-bias construction of shotgun fragment libraries by high-density in vitro transposition," Genome Biology 2010, 11(R19), in 17 pages.
Ahern, "Biochemical, Reagent Kits Offer Scientists Good Return on Investment," The Scientist 1995, 9(15), in 5 pages.
Bolivar et al., "Targeted next-generation sequencing of endometrial cancer and matched circulating tumor DNA: identification of plasma-based, tumor-associated mutations in early stage patients," Modern Pathology 2019, 32(3), 405-414.
Brouilette et al., "A Simple and Novel Method for RNA-seq Library Preparation of Single Cell cDNA Analysis by Hyperactive Tn5 Transposase," Developmental Dynamics 2012, 241, 1584-1590.
Buenrosto et al., "Transposition of native chromatin for multimodal regulatory analysis and personal epigenomics," Nat Methods 2013, 10(12), 1213-1218.
Buenrosto et al., "ATAC-seq: A Method for Assaying Chromatin Accessibility Genome-Wide," Curr Protoc Mol Biol 2016, 109, 1-21.
Chang et al., "Single-cell protein and gene expression profiling of stem memory T cells by BD Ab-seq," Annual Joint Meeting of the American Society for Cell Biology and the European Molecular Biology Organization 2017, 28(26), P1896.
Chen et al., "High-throughput sequencing of the transcriptome and chromatin accessibility in the same cell," Nature Biotechnology 2019, 37, 1452-1457.
Dengl et al., "Engineered hapten-binding antibody derivatives for modulation of pharmacokinetic properties of small molecules and targeted payload delivery," Immunol Rev. 2016, 270, 165-177.
Examination Report dated Mar. 25, 2021 in European Patent Application No. 17781265.8.
Examination Report dated Oct. 8, 2021 in European Patent Application No. 18716877.8.
Examination Report dated Nov. 18, 2021 in European Patent Application No. 19724003.9.
Examination Report dated Nov. 24, 2021 in European Patent Application No. 19762517.1.
Examination Report dated Dec. 6, 2021 in European Patent Application No. 18703156.2.
Examination Report dated Dec. 9, 2021 in European Patent Application No. 19723988.2.
Examination Report dated Apr. 7, 2022 in Singapore Patent Application No. 10201806890V.
Examination Report dated Apr. 8, 2022 in Australian Patent Application No. 2018281745.
Extended European Search Report dated May 6, 2021 in European Patent Application No. 20207621.2.
Extended European Search Report dated May 28, 2021 in European Patent Application No. 20209777.0.
Final Office Action dated Feb. 11, 2021 in U.S. Appl. No. 15/134,967.
Final Office Action dated Mar. 16, 2021 in U.S. Appl. No. 15/715,028.
Final Office Action dated Mar. 25, 2021 in U.S. Appl. No. 16/374,626.
Final Office Action dated Jun. 15, 2021 in U.S. Appl. No. 15/084,307.
Final Office Action dated Jul. 15, 2021 in U.S. Appl. No. 16/836,750.
Final Office Action dated Aug. 10, 2021 in U.S. Appl. No. 16/012,584.
Final Office Action dated Aug. 27, 2021 in U.S. Appl. No. 15/055,407.
Final Office Action dated Sep. 24, 2021 in U.S. Appl. No. 16/788,743.
Final Office Action dated Oct. 1, 2021 in U.S. Appl. No. 16/677,012.
Final Office Action dated Nov. 2, 2021 in U.S. Appl. No. 16/789,311.
Final Office Action dated Jan. 18, 2022 in U.S. Appl. No. 16/588,405.
Final Office Action dated Feb. 23, 2022 in U.S. Appl. No. 16/707,780.
Final Office Action dated Mar. 15, 2022 in U.S. Appl. No. 16/374,626.
Final Office Action dated Mar. 25, 2022 in U.S. Appl. No. 16/551,620.
Final Office Action dated Apr. 12, 2022 in U.S. Appl. No. 15/084,307.
Final Office Action dated May 26, 2022 in U.S. Appl. No. 16/747,737.
Final Office Action dated Jun. 14, 2022 in U.S. Appl. No. 15/055,407.
Final Office Action dated Aug. 23, 2022 in U.S. Appl. No. 16/012,584.
Final Office Action dated Nov. 15, 2022 in U.S. Appl. No. 16/525,054.
Final Office Action dated Nov. 16, 2022 in U.S. Appl. No. 16/588,405.
Fitgerald and Grivel, "A Universal Nanoparticle Cell Secretion Capture Assay," Cytometry Part A 2012, 83A(2), 205-211.
Gertz et al., "Transposase mediated construction of RNA-seq libraries," Genome Research 2012, 22, 134-141.
Goodridge et al., "Synthesis of Albumin and Malic Enzyme in Wheat-Germ Lysates and Xenopus laevis Oocytes Programmed with Chicken-Liver Messenger RNA," Eur. J. Biochem. 1979, 96, 1-8.
Gratton et al., "Cell-permeable peptides improve cellular uptake and therapeutic gene delivery of replication-deficient viruses in cells and in vivo," Nature Medicine 2003, 9(3), 357-362.
International Search Report and Written Opinion dated Jan. 19, 2021 in PCT Application No. PCT/US2020/059419.
International Search Report and Written Opinion dated Apr. 9, 2021 in PCT Application No. PCT/US2021/013137.
International Search Report and Written Opinion dated Apr. 21, 2021 in PCT Application No. PCT/US2021/015571.

(56) References Cited

OTHER PUBLICATIONS

International Search Report and Written Opinion dated May 4, 2021 in PCT Application No. PCT/US2021/013109.
International Search Report and Written Opinion dated May 11, 2021 in PCT Application No. PCT/US2021/013748.
International Search Report and Written Opinion dated Jul. 15, 2021 in PCT Application No. PCT/US2021/019475.
International Search Report and Written Opinion dated Jul. 20, 2021 in PCT Application No. PCT/US2021/015898.
International Search Report and Written Opinion dated Aug. 31, 2021 in PCT Application No. PCT/US2021/035270.
International Search Report and Written Opinion dated Sep. 22, 2021, in PCT Application No. PCT/US2021/013747.
International Search Report and Written Opinion dated Sep. 27, 2021, in PCT Application No. PCT/US2021/013747.
International Search Report and Written Opinion dated Oct. 12, 2021, in PCT Application No. PCT/US2021/041327.
International Search Report and Written Opinion dated Oct. 29, 2021, in PCT Application No. PCT/US2021/032319.
International Search Report and Written Opinion dated Dec. 6, 2021, in PCT Application No. PCT/US2021/046750.
International Search Report and Written Opinion dated Nov. 12, 2021, in PCT Application No. PCT/US2021/044036.
International Search Report and Written Opinion dated Mar. 10, 2022, in PCT Application No. PCT/US2021/060206.
International Search Report and Written Opinion dated Apr. 12, 2022, in PCT Application No. PCT/US2021/059573.
International Search Report and Written Opinion dated Mar. 11, 2022, in PCT Application No. PCT/US2021/060197.
International Search Report and Written Opinion dated Apr. 5, 2022, in PCT Application No. PCT/US2021/062473.
International Search Report and Written Opinion dated Jun. 8, 2022, in PCT Application No. PCT/US2022/021015.
International Search Report and Written Opinion dated Jul. 29, 2022, in PCT Application No. PCT/US2022/029023.
International Search Report and Written Opinion dated Jul. 29, 2022, in PCT Application No. PCT/US2022/029057.
Invitation to Pay Fees dated May 25, 2021 in PCT Application No. PCT/US2021/01598.
Invitation to Pay Additional Search Fees dated Sep. 8, 2021 in PCT Application No. PCT/US2021/032319.
Invitation to Provide Informal Clarification dated Jun. 9, 2021 in PCT Application No. PCT/US2021/019475.
Jacobsen et al., "33rd Annual Meeting & Pre-Conference Programs of the Society for Immunotherapy of Cancer," Journal for Immunotherapy of Cancer 2018, 6(S1), 7-11.
Janeway et al., "Structural variation in immunoglobulin constant regions," Immunology: The Immune System in Health and Disease 1999, 101-103.
Lake et al., "Integrative single-cell analysis of transcriptional and epigenetic states in the human adult brain," Nature Biotechnology 2018, 36(1), 70-80.
Lan et al., "Droplet barcoding for massively parallel single-molecule deep sequencing," Nature Communications 2016, 7(11784), in 10 pages.
Livingstone, "rRNA depletion, poly(A) enrichment, or exonuclease treatment?" Tebu-Bio Blog 2015, in 1 page.
Lutz et al., "Isolation and analysis of high quality nuclear DNA with reduced organellar DNA for plant genome sequencing and resequencing," BMC Biotechnology 2011, 11(54), in 9 pages.
Mair et al., "A Targeted Multi-omic Analysis Approach Measures Protein Expression and Low-Abundance Transcripts on the Single-Cell Level", Cell Reports 2020, 31(1), 107499, in 20 pages.
Minnoye et al., "Chromatin accessibility profiling methods," Nature Reviews Method Primers 2021, 1-24.
Monneron, "One-step Isolation and Characterization of Nuclear Membranes, 1974 Electron Microscopy and Composition of Biological Membranes and Envelops," The Royal Publishing Society 1974, 268, 101-108.

Non-Final Office Action dated Jan. 19, 2021 in U.S. Appl. No. 16/836,750.
Non-Final Office Action dated Feb. 2, 2021 in U.S. Appl. No. 16/535,080.
Non-Final Office Action dated Feb. 25, 2021 in U.S. Appl. No. 15/055,407.
Non-Final Office Action dated Feb. 25, 2021 in U.S. Appl. No. 15/084,307.
Non-Final Office Action dated Mar. 29, 2021 in U.S. Appl. No. 16/789,358.
Non-Final Office Action dated Apr. 14, 2021 in U.S. Appl. No. 16/789,311.
Non-Final Office Action dated Apr. 20, 2021 in U.S. Appl. No. 15/875,816.
Non-Final Office Action dated May 18, 2021 in U.S. Appl. No. 16/535,080.
Non-Final Office Action dated Jun. 9, 2021 in U.S. Appl. No. 16/588,405.
Non-Final Office Action dated Aug. 17, 2021 in U.S. Appl. No. 16/551,620.
Non-Final Office Action dated Aug. 19, 2021 in U.S. Appl. No. 16/781,814.
Non-Final Office Action dated Aug. 31, 2021 in U.S. Appl. No. 15/715,028.
Non-Final Office Action dated Sep. 1, 2021 in U.S. Appl. No. 16/789,358.
Non-Final Office Action dated Sep. 14, 2021 in U.S. Appl. No. 16/707,780.
Non-Final Office Action dated Sep. 28, 2021 in U.S. Appl. No. 16/400,885.
Non-Final Office Action dated Sep. 30, 2021 in U.S. Appl. No. 16/374,626.
Non-Final Office Action dated Oct. 1, 2021 in U.S. Appl. No. 16/677,012.
Non-Final Office Action dated Oct. 8, 2021 in U.S. Appl. No. 16/400,866.
Non-Final Office Action dated Dec. 15, 2021 in U.S. Appl. No. 15/875,816.
Non-Final Office Action dated Dec. 21, 2021 in U.S. Appl. No. 15/055,407.
Non-Final Office Action dated Jan. 6, 2022 in U.S. Appl. No. 15/084,307.
Non-Final Office Action dated Feb. 2, 2022 in U.S. Appl. No. 16/747,737.
Non-Final Office Action dated Feb. 9, 2022 in U.S. Appl. No. 16/525,054.
Non-Final Office Action dated Apr. 5, 2022 in U.S. Appl. No. 16/400,885.
Non-Final Office Action dated Apr. 8, 2022 in U.S. Appl. No. 16/232,287.
Non-Final Office Action dated May 3, 2022 in U.S. Appl. No. 16/012,584.
Non-Final Office Action dated May 11, 2022 in U.S. Appl. No. 16/588,405.
Non-Final Office Action dated May 19, 2022 in U.S. Appl. No. 16/459,444.
Non-Final Office Action dated Jul. 7, 2022 in U.S. Appl. No. 16/788,743.
Non-Final Office Action dated Jul. 7, 2022 in U.S. Appl. No. 16/677,012.
Non-Final Office Action dated Jul. 18, 2022 in U.S. Appl. No. 16/551,620.
Non-Final Office Action dated Jul. 27, 2022 in U.S. Appl. No. 16/747,737.
Non-Final Office Action dated Oct. 13, 2022 in U.S. Appl. No. 17/147,272.
Non-Final Office Action dated Nov. 17, 2022 in U.S. Appl. No. 16/551,638.
Notice of Allowance dated Jan. 13, 2021 in U.S. Appl. No. 14/381,488.
Notice of Allowance dated Jan. 13, 2021 in U.S. Appl. No. 15/459,977.
Notice of Allowance dated Apr. 26, 2021 in Japanese Patent Application No. 2019-014564.

(56) References Cited

OTHER PUBLICATIONS

Notice of Allowance dated Aug. 16, 2021 in Japanese Patent Application No. 2018-512152.
Notice of Allowance dated Nov. 16, 2021 in U.S. Appl. No. 16/836,750.
Notice of Allowance dated Jan. 24, 2022 in Korean U.S. Appl. No. 16/836,750.
Notice of Allowance dated Feb. 9, 2022 in U.S. Appl. No. 16/781,814.
Notice of Allowance dated Feb. 11, 2022 in Chinese Patent Application No. 201680007351.2.
Notice of Allowance dated Feb. 16, 2022 in U.S. Appl. No. 15/875,816.
Notice of Allowance dated Feb. 21, 2022 in Korean Patent Application No. 10-2020-7033213.
Notice of Allowance dated Apr. 11, 2022 in U.S. Appl. No. 15/134,967.
Notice of Allowance dated Apr. 25, 2022 in Korean Patent Application No. 10-2018-7008560.
Notice of Allowance dated Apr. 27, 2022 in U.S. Appl. No. 16/400,886.
Notice of Allowance dated May 9, 2022 in Australian Patent Application No. 2018281745.
Notice of Allowance dated May 15, 2022 in Japanese Patent Application No. 2019-540515.
Notice of Allowance dated May 23, 2022 in U.S. Appl. No. 15/715,028.
Notice of Allowance dated May 26, 2022 in Korean Patent Application No. 10-2019-7038794.
Notice of Allowance dated Jun. 6, 2022 in U.S. Appl. No. 16/789,358.
Notice of Allowance dated Jul. 20, 2022 in U.S. Appl. No. 16/707,780.
Notice of Allowance dated Aug. 9, 2022 in U.S. Appl. No. 16/232,287.
Notice of Allowance dated Sep. 26, 2022, 2022 in U.S. Appl. No. 16/232,287.
Notice of Allowance dated Oct. 17, 2022, 2022 in U.S. Appl. No. 16/400,885.
Notice of Allowance dated Oct. 20, 2022 in Australian Patent Application No. 2019204928.
Notice of Allowance dated Oct. 21, 2022 in European Patent Application No. 19762517.1.
Notice of Allowance dated Oct. 24, 2022 in European Patent Application No. 20708266.0.
Notice of Allowance dated Oct. 25, 2022 in European Patent Application No. 19724003.9.
Notice of Allowance dated Nov. 7, 2022 in U.S. Appl. No. 16/012,584.
Novus Biologicals, "Fixation and Permeability in ICC IF," Novus Biologicals 2021, 1-3.
Nowak et al., "Does the KIR2DS5 gene protect from some human diseases?," PLoS One 2010, 5(8), in 6 pages.
Office Action dated Jan. 6, 2021 in Chinese Patent Application No. 201680052330.2.
Office Action dated Jan. 14, 2021 in Japanese Patent Application No. 2019-014564.
Office Action dated Jan. 15, 2021 in Korean Patent Application No. 10-2020-7033213.
Office Action dated Jan. 26, 2021 in Chinese Patent Application No. 201680007351.2.
Office Action dated Feb. 4, 2021 in Canadian Patent Application No. 2,865,575.
Office Action dated Feb. 20, 2021 in Chinese Patent Application No. 201680022865.5.
Office Action dated Mar. 1, 2021 in Chinese Patent Application No. 201680007652.5.
Office Action dated Mar. 2, 2021 in Chinese Patent Application No. 2016800157452.
Office Action dated Mar. 8, 2021 in Japanese Patent Application No. 2018-512152.
Office Action dated Mar. 16, 2021 in Chinese Patent Application No. 2018800377201.
Office Action dated May 10, 2021 in Japanese Patent Application No. 2019-566787.
Office Action dated May 21, 2021 in Chinese Patent Application No. 201680007351.2 .
Office Action dated Jul. 26, 2021 in Korean Patent Application No. 10-2019-7011635.
Office Action dated Jul. 28, 2021 in Korean Patent Application No. 10-2020-7033213.
Office Action dated Aug. 13, 2021 in Chinese Patent Application No. 2017800587991.
Office Action dated Aug. 27, 2021 in Chinese Patent Application No. 2016800076525.
Office Action dated Aug. 30, 2021 in Japanese Patent Application No. 2019-540515.
Office Action dated Aug. 31, 2021, in Korean Patent Application No. 10-2019-7038794.
Office Action dated Sep. 14, 2021, in Chinese Patent Application No. 2016800523302.
Office Action dated Oct. 21, 2021, in Chinese Patent Application No. 2016800073512 .
Office Action dated Nov. 2, 2021, in Japanese Patent Application No. 2017-549390.
Office Action dated Dec. 23, 2021, in Japanese Patent Application No. 2019-566787.
Office Action dated Dec. 17, 2021 in Korean Patent Application No. 10-2018-7008560.
Office Action dated Jan. 13, 2022 in Chinese Patent Application No. 2017800587991.
Office Action dated Feb. 9, 2022 in Japanese Patent Application No. 2019-540515.
Office Action dated Mar. 7, 2022 in Korean Patent Application No. 10-2022-7004715.
Office Action dated May 17, 2022 in Australian Patent Application No. 2019204928.
Office Action dated May 24, 2022 in European Patent Application No. 20708266.0.
Office Action dated Jun. 28, 2022 in European Patent Application No. 16719706.0.
Office Action dated Aug. 2, 2022 in European Patent Application No. 19765601.0.
Office Action dated Aug. 1, 2022 in Korean Patent Application No. 10-2022-7017261.
Prevette et al., "Polycation-Induced Cell Membrane Permeability Does Not Enhance Cellular Uptake or Expression Efficiency of Delivered DNA," Molecular Pharmaceutics 2010, 7(3), 870-883.
Pringle et al., "In Situ Hybridization Demonstration of Poly-Adenylated RNA Sequences in Formalin-Fixed Parafin Sections Using a Biotinylated Oligonucleotide Poly d(T) Probe," Journal of Pathology 1989, 158, 279-286.
Quail et al., "SASI-Seq: sample assurance Spike-Ins, and highly differentiating 384 barcoding for Illumina sequencing," BMC Genomics 2014, 15(110), in 13 pages.
Restriction Requirement dated Jun. 4, 2021 in U.S. Appl. No. 16/551,620.
Restriction Requirement dated Aug. 8, 2022 in U.S. Appl. No. 17/163,177.
Restriction Requirement dated Aug. 11, 2022 in U.S. Appl. No. 17/091,639.
Restriction Requirement dated Aug. 19, 2022 in U.S. Appl. No. 17/147,283.
Restriction Requirement dated Sep. 16, 2022 in U.S. Appl. No. 17/151,050.
Restriction Requirement dated Sep. 19, 2022 in U.S. Appl. No. 16/934,530.
Restriction Requirement dated Oct. 21, 2022 in U.S. Appl. No. 17/320,052.
Restriction Requirement dated Nov. 8, 2022 in U.S. Appl. No. 17/157,872.
Schouten et al., "Relative quantification of 40 nucleic acid sequences by multiplex ligation-dependent probe amplification," Nucleic Acids Research 2002, 30(12), e57.
Shapiro et al., "Single-cell sequencing-based technologies will revolutionize whole-organism science," Nature Reviews Genetics 2013, 14, 618-629.

(56) References Cited

OTHER PUBLICATIONS

Song et al., DNase-seq: a high-resolution technique for mapping active gene regulatory elements across the genome from mammalian cells, Cold Spring Harb Protoc 2010, 2, in 13 pages.
Sos et al., "Characterization of chromatin accessibility with a transposome hypersensitive sites sequencing (THS-seq) assay," Genome Biology 2016, 17(20), in 15 pages.
Stoeckius et al., "Cell Hashing with barcoded antibodies enables multiplexing and doublet detection for single cell genomics," Genome Biology 2018, 19(224), 1-12.
Takara Bio, "SMARTer Human BCR IgG IgM H/K/L Profiling Kit User Manual," Takara Bio USA Inc. 2019, 1-22.
TotalSeq™-A0251 anti-human Hashtag 1 Antibody, BioLegend ®, Jul. 2018, 1-10.
Trzupek et al., "Discovery of CD80 and CD86 as recent activation markers on regulatory T cells by protein-RNA single-cell analysis", Genome Medicine 2020, 12(1), in 22 pages.
Vestheim et al., "Application of Blocking Oligonucleotides to Improve Signal-to-Noise Ratio in a PCR," Methods in Molecular Biology 2011, 687, 265-274.
Wang et al., "Tagmentation-based whole-genome bisulfite sequencing," Nature Protocols 2013, 8(10), 2022-2032.
Yang & Zhao, "Quantitative Analysis of Nonoxynol-9 in Blood," Contraception 1991, 43(2), 161-166.
Zeberg et al., "The major genetic risk factor for severe COVID-19 is inherited from Neanderthals," Nature 2020, 587(7835), 1-13.
Zhang et al., "Immunoaffinity Purification of Plasma Membrane with Secondary Antibody Superparamagnetic Beads," Journal of Proteome 2006, 6, 34-43.
Zhao et al., "Methylated DNA Immunoprecipitation and High-Throughput Sequencing (MeDIP-seq) Using Low Amounts of Genomic DNA," Cellular Reprogramming 2014, 16(3), in 20 pages.
10X Genomics, Inc., 2019, User Guide: Visium Spatial Gene Expression Reagent Kits, www.10xGenomics.com, 76 pp.
2018 Top 10 Innovations, The Scientist Magazine® (2018). Available at: https://thescientist.com/features/2018-top-10-innovations-65140, 16 pp.
Achim et al., "High-throughput spatial mapping of single-cell RNA-seq data to tissue of origin," Nature Biotechnology 2015, 33(5), 503-511.
Advisory Action dated Nov. 29, 2019 in U.S. Appl. No. 15/084,307.
Advisory Action dated Dec. 2, 2019 in U.S. Appl. No. 15/055,407.
Advisory Action dated Aug. 25, 2020 in U.S. Appl. No. 15/084,307.
Agasti et al., "Photocleavable DNA barcode-antibody conjugates allow sensitive and multiplexed protein analysis in single cell," J Am Chem Soc. 2012, 134(45), 18499-18502.
Alexandra M. Ewing of Richards, Layton and Finger, P.A., Entry of Appearance dated Jan. 18, 2019 in the USDC District of Delaware, C.A. No. 18-1800-RGA, 1 pp.
Alkan et al., "Personalized copy number and segmental duplication maps using next-generation sequencing," Nat Genet. 2009, 41(10):1061-1067.
Anderson, "Study Describes RNA Sequencing Applications for Molecular Indexing Methods," GenomeWeb 2014, 5 pp.
Ansorge, "Next-generation DNA sequencing techniques," New Biotechnology 2009, 25(4), 195-203.
Applied Biosystems, Apr. 2008, SOLID™ System Barcoding, Application Note, 4 pp.
Argrawal et al., "Counting Single Native Biomolecules and Intact Viruses with Color-Coded Nanoparticles," Analytical Chemistry 2006, 78, 1061-1070.
Arslan et al., "An efficient algorithm for the stochastic simulation of the hybridization of DNA to microarrays," BMC Bioinformatics 2009, 10(411), 1-17.
Atanur et al., "The genome sequence of the spontaneously hypertensive rat: Analysis and functional significance." Genome Res. 2010, 20(6), 791-803.
Audic et al., "The Significance of Digital Gene Expression Profiles," Genome Res. 1997, 7, 986-995.

Baek et al., "Development of Hydrogel TentaGel Shell-Core Beads for Ultra-high Throughput Solution Phase Screening of Encoded OBOC Combinatorial Small Molecule Libraries," J. Comb Chem. 2009, 11(1), 91-102.
BD Life Sciences, 2018, BD AbSeq antibody-oligo conjugates, bd.com/genomics, 2 pp.
BD Life Sciences, 2018, BD AbSeq on the BD Rhapsody system: Exploration of single-cell gene regulation by simultaneous digital mRNA and protein quantification, bd.com/genomics, 7 pp.
Bendall et al., "Single-Cell Mass Cytometry of Differential Immune and Drug Responses Across a Human Hematopoietic Continuum," Science 2011, 332(6030), 687-696.
Bionumbers, Aug. 21, 2010, "Useful fundamental numbers in molecular biology," http://bionumbers.hms.harvard.edu/KeyNumbers/aspx, 1-4.
Biosciences Product Catalogue, Dynal® Catalog 1999, Oslo, Norway, 49-51.
Bioscribe "Massively parallel sequencing technology for single-cell gene expression published" (press release), PhysOrg 2015, 1-2.
Blainey, "The future is now: single-cell genomics of bacteria and archaea," FEMS Microbiol Rev. 2013, 37(3), 407-427.
Bogdanova et al., "Normalization of full-length enriched cDNA," Molecular Biosystems 2008, 4(3), 205-212.
Bonaldo et al., "Normalization and Subtraction: Two Approaches to facilitate Gene Discovery," Genome Res. 1996, 6, 791-806.
Bontoux et al., "Integrating whole transcriptome assays on a lab-on-a-chip for single cell gene profiling", Lab on a Chip 2008, 8(3), 443-450.
Bose et al., "Scalable microfluidics for single-cell RNA printing and sequencing," Genome Biology 2015, 16(120), 1-16.
Brady et al., "Construction of cDNA libraries form single cells", Methods in Enzymology 1993, (225), 611-623.
Braha et al., "Simultaneous stochastic sensing of divalent metal ions," Nature Biotechnology 2000, 18, 1005-1007.
Bratke et al., "Differential expression of human granzymes A, B, and K in natural killer cells and during CD8+ T cell differentiation in peripheral blood," Eur J Immunol. 2005, 35, 2608-2616.
Brenner et al., "Gene expression analysis by massively parallel signature sequencing (MPSS) on microbead arrays," Nature Biotechnology 2000, 18, 630-634.
Brenner et al., "In vitro cloning of complex mixtures of DNA on microbeads: Physical separation of differentially expressed cDNAs," PNAS 2000, 97(4), 1665-1670.
Brinza et al., "Detection of somatic mutations at 0.1% frequency from cfDNA in peripheral blood with a multiplex next-generation sequencing assay," Conference Poster, AACR 107th Annual Meeting, Apr. 16-20, 2016, 1 p.
Brisco et al., "Quantification of RNA integrity and its use for measurement of transcript number," Nucleic Acids Research 2012, 40(18), e144, 1-9.
Brodin et al., "Challenges with Using Primer IDs to Improve Accuracy of Next Generation Sequencing," PLoS One 2015, 19(3), 1-12.
Buggenum et al., "A covalent and cleavable antibody DNA conjugation strategy for sensitive protein detection via immunoPCR," Scientific Reports 2016, 6(22675), 1-12.
Buschmann et al., Enhancing the detection of barcoded reads in high throughput DNA sequencing DNA by controlling the false discovery rate, BMC Bioinformatics, 15(1), 264, 1-16.
Bustin, "Absolute quantification of mRNA using real-time reverse transcription polymerase chain reaction assays," Journal of Molecular Endocrinology 2000, 25, 169-193.
Butkus, "Cellular research set to launch first gene expression platform using 'molecular indexing' technology," GenomeWeb 2014, 1-5.
Cai, "Turning single cells in microarrays by super-resolution barcoding," Briefings in Functional Genomics 2012, 12(2), 75-80.
Cao et al., "Comprehensive single-cell transcriptional profiling of a multicellular organism," Science 2017, 357, 661-667.
Carr et al., "Inferring relative proportions of DNA variants from sequencing electropherograms," Bioinformatics 2009, 25(24), 3244-3250.

(56) References Cited

OTHER PUBLICATIONS

Caruccio et al., "Nextera (TM) Technology for NGS DNA Library Preparation: Simultaneous Fragmentation and Tagging by in Vitro Transposition," EpiBio 2009, 16(3), 4-6.
Casbon et al., "A method for counting PCR template molecules with application to next-generation sequencing," Nucleic Acids Res. 2011, 39(12), e81, 1-8.
Castellarnau et al., "Stochastic particle barcoding for single-cell tracking and multiparametric analysis," Small 2015, 11(4), 489-498.
Castle et al., "DNA copy number, including telomeres and mitochondria, assayed using next-generation sequencing," BMC Genomics 2010, 11(244), 1-11.
Chamberlain et al., "Deletion screening of the Duchenne muscular dystrophy locus via multiplex DNA amplification," Nucleic Acids Res. 1988, 16(23), 11141-11156.
Chang et al., "Detection of Allelic Imbalance in Ascitic Supernatant by Digital Single Nucleotide Polymorphism Analysis," Clinical Cancer Research, 8, 2580-2585.
Chapin et al., "Rapid microRNA Profiling on Encoded Gel Microparticles," Angew Chem Int Ed Engl. 2011, 50(10), 2289-2293.
Chee et al., "Accessing genetic information with high-density DNA arrays," Science 1996, 274, 610-614.
Chee, "Enzymatic multiplex DNA sequencing," Nucleic Acids Research 1991, 19(12), 3301-3305.
Chen et al., "Spatially resolved, highly multiplexed RNA profiling in single cells," Science Express 2015, 348(6233), aaa6090, 1-36.
Church et al., "Multiplex DNA sequencing," Science 1988, 240(4849), 185-188.
Civil Cover Sheet filed Nov. 15, 2018 in the USDC for the District of Delaware, C.A. 18-1800-RGA, 1 pp.
Clontech Laboratories, Inc., "SMART™ PCR cDNA Synthesis Kit User Manual," Clontech 2007, 1-39.
Cloonan et al., "Stem cell transcriptome profiling via massive-scale mRNA sequencing", Nature Methods 2008, 5(7), 613-619.
Combined Search and Examination Report dated Aug. 6, 2014 in UK Patent Application No. 1408829.8.
Combined Search and Examination Report dated Feb. 21, 2017 in UK Patent Application No. 1609740.4.
Communication of a Notice of Opposition dated Jul. 21, 2016 in European Patent Application No. EP 10762102.1.
Complaint filed in *Becton, Dickinson and Company and Cellular Research Inc.* v. *10X Genomics, Inc.* dated Nov. 15, 2018 in the USDC for the District of Delaware, C.A. 18-1800-RGA, 141 pp.
Costa et al., "Single-Tube Nested Real-Time PCR as a New Highly Sensitive Approach to Trace Hazelnut," Journal of Agricultural and Food Chemistry 2012, 60, 8103-8110.
Costello et al., "Discovery and characterization of artefactual mutations in deep coverage targeted capture sequencing data due to oxidative DNA damage during sample preparation," Nucleic Acids Res 2013, 41(6), e67, 1-12.
Cotten et al., "Selection of proteins with desired properties from natural proteome libraries using mRNA display," Nature Protocols 2011, 6, 1163-1182.
Cox, "Bar coding objects with DNA," Analyst 2001, 126, 545-547.
Craig et al., "Identification of genetic variants using bar-coded multiplexed sequencing," Nat Methods 2008, 5(10), 887-893.
Cusanovich et al., "Multiplex single-cell profiling of chromatin accessibility by combinatorial cellular indexing," Science 2015, 348(6237), 910-914.
Custom Antibody Services, Precision Antibody, accessed Apr. 16, 2014, 2 pp.
Daines et al., "High-throughput multiplex sequencing to discover copy number variants in *Drosophila*," Genetics 2009, 182(4), 182, 935-941.
Dalerba et al., "Single-cell dissection of transcriptional heterogeneity in human colon tumors," Nat Biotechnol. 2011, 29(12), 1120-1127.
D'Antoni et al., "Rapid quantitative analysis using a single molecule counting approach," Anal Biochem. 2006, 352, 97-109.
Daser et al., "Interrogation of genomes by molecular copy-number counting (MCC)," Nature Methods 2006, 3(6), 447-453.
Day et al., "Immobilization of polynucleotides on magnetic particles," Biochem. J. 1991, 278, 735-740.
Decision of Refusal dated Aug. 21, 2017 in Japanese Patent Application No. 2014-558975.
Defendant 10X Genomics, Inc.'s Letter to Judge Andrews in Response to Plaintiff's Letter of Supplemental Authority, dated Jul. 11, 2019 in the USDC for the District of Delaware, C.A. 18-1800-RGA, 2 pp.
Defendant 10X Genomics Motion for Admission Pro Hac Vice of Paul Ehrlich, Azra Hadzimehmedovic and Aaron Nathan, Pursuant to Local Rule 83.5, dated May 1, 2019 in the USDC for the District of Delaware, C.A. 18-1800-RGA, 5 pp.
Defendant 10X Genomics, Inc.'s Motion for Admission Pro Hac Vice Pursuant to Local Rule 83.5, dated Jan. 18, 2019 in the USDC District of Delaware, C.A. No. 18-1800-RGA, 5 pp.
Defendant 10X Genomics, Inc.'s Motion to Dismiss Pursuant to Federal Rule of Civil Procedure 12(b)(6), dated Jan. 18, 2019 in the USDC for the District of Delaware, C.A. 18-1800-RGA, 1 pp.
Defendant 10X Genomics, Inc.'s Motion to Dismiss the First Amended Complaint Pursuant to Federal Rule of Civil Procedure 12(b)(6), dated Mar. 1, 2019 in the USDC for the District of Delaware, C.A. 18-1800-RGA, 1 pp.
Defendant 10X Genomics Notice of Service for Initial Disclosures served to Opposing Counsel, dated Jun. 7, 2019 in the USDC for the District of Delaware, C.A. 18-1800-RGA, 2 pp.
Defendan 10X Genomic Inc.'s Notice of Service for Initial Requests for Production and Interrogatories Served to Becton, Dickinson, and Company and Cellular Research, Inc., dated May 31, 2019 in the USDC for the District of Delaware, C.A. 18-1800-RGA, 2 pp.
Defendant 10X Genomics Inc's, Notice of Service of Technical Documents, dated Jul. 8, 2019 in the USDC for the District of Delaware, C.A. 18-1800-RGA, 2 pp.
Defendant 10X Genomics, Inc.'s Opening Brief in Support of Its Motion to Dismiss Pursuant to Federal Rule of Civil Procedure 12(b)(6), dated Jan. 18, 2019 in the USDC District of Delaware, C.A. No. 1:18-cv-01800-RGA, 25 pp.
Defendant 10X Genomics, Inc.'s Opening Brief in Support of Its Motion to Dismiss Pursuant to Federal Rule of Civil Procedure 12(b)(6), dated Mar. 1, 2019 in the USDC District of Delaware, C.A. No. 18-1800 RGA, 26 pp.
Defendant 10X Genomics, Inc.'s [Proposed] Order for Partial Dismissal Pursuant to Federal Rules of Civil Procedure 12(b)(6), dated Jan. 18, 2019 in the USDC District of Delaware, C.A. No. 18-1800-RGA, 1 pp.
Defendant 10X Genomics, Inc's Proposed Order for Dismissal pursuant to Federal Rules of Civil Procedure 12(b)(6), filed Mar. 1, 2019 in the USDC for the District of Delaware, C.A. 18-1800-RGA, 1 pp.
Defendant 10X Genomics Reply Brief in Support of its Motion to Dismiss Pursuant to Federal Rule of Civil Procedure 12(b)(6), dated Apr. 12, 2019 in the USDC for the District of Delaware, C.A. No. 18-1800-RGA, 15 pp.
Defendant 10X Genomics Request for Oral Argument Under D. Del. LR 7.1.4, dated Apr. 18, 2019 in the USDC for the District of Delaware, C.A. 18-1800-RGA 2 pp.
Defendant 10X Genomics Response Letter to Judge Richard G. Andrews re Request for a Rule 16, dated Apr. 16, 2019 in the USDC for the District of Delaware, C.A. 18-1800-RGA, 2 pp.
Defendant 10X Genomics, Inc.'s Rule 7.1 Disclosure Statement, dated Jan. 18, 2019 in the USDC District of Delaware, C.A. No. 18-1800-RGA, 1 pp. 1.
Delley et al., "Combined aptamer and transcriptome sequencing of single cells," bioRxiv 2017, 1-10.
De Saizieu et al., "Bacterial transcript imaging by hybridization of total RNA to oligonucleotide arrays," Nature Biotechnology 1988, 16, 45-48.
Di Carlo et al., "Dynamic single-cell analysis for quantitative biology," Analytical Chemistry 2006, 78(23), 7918-7925.
Dirks et al., Triggered amplification by hybridization chain reaction., Proc Natl Acad Sci 2014, 101(43), 15275-15278.

(56) References Cited

OTHER PUBLICATIONS

Dube et al., "Mathematical Analysis of Copy Number Variation in a DNA Sample Using Digital PCR on a Nanofluidic Device," PLoS One 2008, 3(8) e2876.
Eberwine et al., "Analysis of gene expression in single live neurons," Proc. Natl. Acad. Sci. 1992, 89, 3010-3014.
Evanko et al., "Hybridization chain reaction," Nature Methods 2004, 1(3), 186-187.
Examination Report dated Oct. 24, 2017 in Australian Patent Application No. 2013226081.
Examination Report dated Jul. 20, 2018 in Australian Patent Application No. 2014312208.
Examination Report dated May 12, 2020 in Australian Patent Application No. 2018220004.
Examination Report dated Jul. 12, 2016 in European Patent Application No. 13755319.4.
Examination Report dated Apr. 10, 2017 in European Patent Application No. 14761937.3.
Examination Report dated Oct. 10, 2017 in European Patent Application No. 14761937.3.
Examination Report dated Mar. 16, 2018 in European Patent Application No. 13754428.4.
Examination Report dated Sep. 5, 2018 in European Patent Application No. 16710357.1.
Examination Report dated Sep. 26, 2018 in European Patent Application No. 16714081.3.
Examination Report dated Dec. 12, 2018 in European Patent Application No. 16719706.0.
Examination Report dated Jan. 2, 2019 in European Patent Application No. 16757986.1.
Examination Report dated Feb. 6, 2019 in European Patent Application No. 13754428.4.
Examination Report dated Apr. 26, 2019 in European Patent Application No. 16710357.1.
Examination Report dated Jun. 18, 2019 in European Patent Application No. 16710551.9.
Examination Report dated Jul. 24, 2019 in European Patent Application No. 16714081.3.
Examination Report dated Aug. 2, 2019 in European Patent Application No. 17202409.3.
Examination Report dated Oct. 11, 2019 in European Patent Application No. 16757986.1.
Examination Report dated Dec. 4, 2019 in European Patent Application No. 16719706.0.
Examination Report dated Feb. 19, 2020 in European Patent Application No. 16710551.9.
Examination Report dated Mar. 18, 2020 in European Patent Application No. 17202409.3.
Examination Report dated Jul. 6, 2020 in European Patent Application No. 17781265.8.
Examination Report dated Sep. 21, 2020 in European Patent Application No. 18703156.2.
Examination Report dated Mar. 18, 2019 in Singapore Patent Application No. 11201405274W.
Examination Report dated Jan. 27, 2016 in United Kingdom Patent Application No. 1408829.8.
Examination Report dated Feb. 19, 2016 in United Kingdom Patent Application No. GB1511591.8.
Examination Report dated Jun. 8, 2016 in United Kingdom Patent Application No. 1408829.8.
Examination Report dated Jun. 15, 2016 in United Kingdom Patent Application No. GB1511591.8.
Examination Report dated Jan. 3, 2018 in United Kingdom Patent Application No. 1609740.4.
Exhibit A filed Jul. 10, 2019 in the USDC for the District of Delaware, C.A. 18-1800-RGA, 25 pp.
Exhibits 12-32 filed Feb. 8, 2019 in the USDC for the District of Delaware, C.A. 18-1800-RGA, 795 pp.
Exhibits A-D filed Jan. 18, 2019 in the USDC District of Delaware, C.A. No. 1:18-cv-01800-RGA, 47 pp.
Exhibits A-E filed Mar. 1, 2019 in the USDC District of Delaware, C.A. No. 18-1800 RGA, 75 pp.
Extended European Search Report dated Jul. 17, 2015 in European Patent Application No. 13755319.4.
Extended European Search Report dated Dec. 14, 2015 in European Patent Application No. 13754428.4.
Extended European Search Report dated Feb. 8, 2018 in European Patent Application No. 17202409.3.
Extended European Search Report dated Jun. 11, 2018 in European Patent Application No. 16740872.3.
Extended European Search Report dated Mar. 22, 2019 in European Patent Application No. 18195513.9.
Fan et al., "Parallel Genotyping of Human SNPs Using Generic High-density Oligonucleotide Tag Arrays," Genome Research 2000, 10, 853-860.
Fan et al., "Microfluidic digital PCR enables rapid prenatal diagnosis of fetal aneuploidy," Am Obstet Gynecol. 2009, 200, 543e1-543e7.
Fan, "Molecular counting: from noninvasive prenatal diagnostics to whole-genome haplotyping," Doctoral Dissertation, Stanford University 2010, 1-185.
Fan et al., "Non-invasive Prenatal Measurement of the Fetal Genome," Nature 2012, 487(7407), 320-324.
Fan et al., "Combinatorial labeling of single cells for gene expression cytometry," Science 2015, 347(6222), 1258366-1258369.
Feldhaus et al., "Oligonucleotide-conjugated beads for transdominant genetic experiments," Nucleic Acids Res. 2000, 28(2), 534-543.
Final Office Action dated Sep. 1, 2015 for U.S. Appl. No. 14/540,029.
Final Office Action dated Sep. 24, 2015 for U.S. Appl. No. 14/540,007.
Final Office Action dated Oct. 6, 2015 in U.S. Appl. No. 14/540,018.
Final Office Action dated Apr. 11, 2016 for U.S. Appl. No. 14/800,526.
Final Office Action dated Jul. 20, 2016 for U.S. Appl. No. 14/281,706.
Final Office Action dated Aug. 12, 2016 in U.S. Appl. No. 14/381,488.
Final Office Action dated Feb. 13, 2017 in U.S. Appl. No. 14/381,488.
Final Office Action dated May 8, 2017 in U.S. Appl. No. 15/224,460.
Final Office Action dated Oct. 16, 2017 in U.S. Appl. No. 15/409,355.
Final Office Action dated Nov. 16, 2017 in U.S. Appl. No. 14/381,488.
Final Office Action dated Jan. 25, 2018 in U.S. Appl. No. 14/381,526.
Final Office Action dated May 3, 2018 in U.S. Appl. No. 15/046,225.
Final Office Action dated May 10, 2018 in U.S. Appl. No. 14/381,488.
Final Office Action dated Jul. 5, 2018 in U.S. Appl. No. 15/004,618.
Final Office Action dated Jul. 20, 2018 in U.S. Appl. No. 15/217,886.
Final Office Action dated Nov. 16, 2018 in U.S. Appl. No. 15/134,967.
Final Office Action dated Feb. 19, 2019 in U.S. Appl. No. 14/381,526.
Final Office Action dated Mar. 1, 2019 in U.S. Appl. No. 16/012,584.
Final Office Action dated Apr. 22, 2019 in U.S. Appl. No. 15/987,851.
Final Office Action dated May 2, 2019 in U.S. Appl. No. 16/012,635.
Final Office Action dated May 3, 2019 in U.S. Appl. No. 15/937,713.
Final Office Action dated Sep. 18, 2019 in U.S. Appl. No. 15/055,407.
Final Office Action dated Oct. 2, 2019 in U.S. Appl. No. 15/084,307.
Final Office Action dated Dec. 4, 2019 in U.S. Appl. No. 15/596,364.
Final Office Action dated Jan. 8, 2020 in U.S. Appl. No. 15/459,977.
Final Office Action dated Jan. 16, 2020 in U.S. Appl. No. 16/012,584.
Final Office Action dated Jan. 29, 2020 in U.S. Appl. No. 14/381,488.
Final Office Action dated Feb. 4, 2020 in U.S. Appl. No. 15/715,028.
Final Office Action dated Mar. 9, 2020 in U.S. Appl. No. 15/987,851.
Final Office Action dated Apr. 28, 2020 in U.S. Appl. No. 15/134,967.
Final Office Action dated Jun. 5, 2020 in U.S. Appl. No. 15/084,307.
Final Office Action dated Aug. 19, 2020 in U.S. Appl. No. 15/875,816.
Final Office Action dated Sep. 14, 2020 in U.S. Appl. No. 16/789,358.
Final Office Action dated Sep. 22, 2020 in U.S. Appl. No. 16/789,311.
Final Office Action dated Sep. 25, 2020 in U.S. Appl. No. 15/055,407.
Final Office Action dated Dec. 7, 2020 in U.S. Appl. No. 16/012,584.
First Action Interview Pilot Program Pre-Interview Communication dated Oct. 15, 2018 in U.S. Appl. No. 15/987,851.
First Action Interview Office Action Summary dated Jan. 25, 2019 in U.S. Appl. No. 15/987,851.
Flanigon et al., "Multiplex protein detection with DNA readout via mass spectrometry," N Biotechnol. 2013, 30(2), 153-158.
Forster et al., "A human gut bacterial genome and culture collection for improved metagenomic analyses," Nature Biotechnology 2019, 37, 186-192.

(56) References Cited

OTHER PUBLICATIONS

Fox-Walsh et al., "A multiplex RNA-seq strategy to profile poly(A+) RNA: application to analysis of transcription response and 3' end formation," Genomics 2011, 98, 266-721.
Fu et al., "Counting individual DNA molecules by the stochastic attachment of diverse labels," Proc Natl Acad Sci 2011, 108(22), 9026-9031.
Fu et al., Digital Encoding of Cellular mRNAs Enabling Precise and Absolute Gene Expression Measurement by Single-Molecule Counting. Anal Chem. 2014, 86, 2867-2870.
Fu et al., "Molecular indexing enables quantitative targeted RNA sequencing and reveals poor efficiencies in standard library preparation," PNAS 2014, 111(5), 1891-1896.
Gerry et al., "Universal DNA Microarray Method for Multiplex Detection of Low Abundance Point Mutations," Journal of Molecular Biology 1999, 292, 251-262.
Gillespie, "Exact Stochastic Simulation of Coupled Chemical Reactions," Journal of Physical Chemistry 1977, 81(25), 2340-2361.
Gong et al., "Massively parallel detection of gene expression in single cells using subnanolitre wells," Lab Chip 2010, 10, 2334-2337.
Gong et al., "Simple Method Prepare Oligonucleotide-Conjugated Antibodies and Its Application in Multiplex Protein Detection in Single Cells," Bioconjugate Chem. 2016, 27, 217-225.
Grant et al., "SNP genotyping on a genome-wide amplified DOP-PCR template," Nucleic Acids Res 2002, 30(22), e25, 1-6.
Gu et al., "Complete workflow for detection of low frequency somatic mutations from cell-free DNA using Ion Torrent™ platforms," Conference Poster, AACR 107th Annual Meeting, Apr. 16-20, 2016, 1 p.
Gu et al., "Depletion of abundant sequences by hybridization (DSH): using Cas9 to remove unwanted high-abundance species in sequencing libraries and molecular counting applications," Genome Biology 2016, 17(41) 1-13.
Gunderson et al., "Decoding Randomly Ordered DNA Arrays," Genome Research 2004, 14, 870-877.
Gundry et al., "Direct, genome-wide assessment of DNA mutations in single cells," Nucleic Acids Research 2011, 40(5), 2032-2040.
Gundry et al., "Direct mutation analysis by high-throughput sequencing: from germline to low-abundant, somatic variants," Mutat Res. 2012, 729(1-2), 1-15.
Hacia et al., "Determination of ancestral alleles for human single-nucleotide polymorphisms using high-density oligonucleotide arrays," Nature Genetics 1999, 22, 164-167.
Haff, "Improved Quantitative PCR Using Nested Primers," PCR Methods and Applications 1994, 3, 332-337.
Hamady et al., "Error-correcting barcoded primers for pyrosequencing hundreds of samples in multiplex," Nat Methods 2008, 5(3), 235-237.
Han et al., "An approach to multiplexing an immunosorbent assay with antibody-oligonucleotide conjugates," Bioconjug Chem. 2010, 21(12), 2190-2196.
Harbers, "The current status of cDNA cloning," Genomics 2008, 91, 232-242.
Harrington et al., Cross-sectional characterization of HIV-1 env compartmentalization in cerebrospinal fluid over the full disease course, AIDS 2009, 23(8), 907-915.
Hartmann, "Gene expression profiling of single cells on large-scale oligonucleotide arrays", Nucleic Acids Research, (Oct. 2006) vol. 34, No. 21, p. e143, 1-12.
Hashimshony et al., "CEL-Seq: Single-Cell RNA-Seq by Multiplexed Linear Amplification," Cell Rep. 2012, 2(3), 666-673.
Hensel et al., "Simultaneous identification of bacterial virulence genes by negative selection," Science 1995, 269(5222), 400-403.
Hiatt et al., "Parallel, tag-directed assembly of locally derived short sequence reads," Nat Methods 2010, 7(2), 119-122.
Hiatt et al., "Single molecule molecular inversion probes for targeted, high-accuracy detection of low-frequency variation," Genome Res. 2013, 23(5), 843-854.

Holcomb et al., "Abstract 1853: Single-cell multiplexed profiling of protein-level changes induced by EGFR inhibitor gefitinib," Cancer Res 2016, 76(14 Suppl), Abstract 1853.
Hollas et al., "A stochastic approach to count RNA molecules using DNA sequencing methods," Algorithms in Bioinformatics. WABI 2003, Lecture Notes in Computer Science, 2812, 55-62.
How many species of bacteria are there? Wisegeek.org, accessed Jan. 21, 2014, 2 pp.
Hu et al., "Dissecting Cell-Type Composition and Activity-Dependent Transcriptional State in Mammalian Brains by Massively Parallel Single-Nucleus RNA-Seq," Molecular Cell 2017, 68, 1006-1015.
Hu et al., "Single Cell Multi-Omics Technology: Methodology and Application," Frontiers in Cell and Developmental Biology 2018, 6(28), 1-13.
Hug et al., Measure of the Number of Molecular of a Single mRNA Species in a Complex mRNA Preparation, Journal of Theoretical Biology 2003, 221, 615-624.
Ingolia et al., Genome-Wide Analysis in Vivo of Translation with Nucleotide Resolution Using Ribosome Profiling, Science 2009, 324(5924), 218-223.
International Preliminary Report on Patentability dated Mar. 26, 2019 in PCT Application No. PCT/US2017/053331.
International Preliminary Report on Patentability dated Aug. 6, 2019 in PCT Application No. PCT/US2018/014385.
International Preliminary Report on Patentability dated Nov. 3, 2020 in PCT Application No. PCT/US2019/030175.
International Preliminary Report on Patentability dated Nov. 3, 2020 in PCT Application No. PCT/US2019/030245.
International Search Report and Written Opinion dated May 7, 2012 for PCT Application No. PCT/IB2011/003160.
International Search Report and Written Opinion dated Jun. 6, 2012 in PCT Application No. PCT/US2011/065291.
International Search Report and Written Opinion dated Jun. 14, 2013 in PCT Application No. PCT/US2013/028103.
International Search Report and Written Opinion dated Aug. 16, 2013 for PCT Application No. PCT/US2013/027891.
International Search Report and Written Opinion dated Dec. 19, 2014 in PCT Application No. PCT/US2014/059542.
International Search Report and Written Opinion dated Feb. 3, 2015 in PCT Application No. PCT/US2014/053301.
International Search Report and Written Opinion dated May 3, 2016 in PCT Application No. PCT/US2016/018354.
International Search Report and Written Opinion dated Jun. 9, 2016 in PCT Application No. PCT/US2016/022712.
International Search Report and Written Opinion dated Jun. 17, 2016 in PCT Application No. PCT/US2016/019962.
International Search Report and Written Opinion dated Jun. 20, 2016 in PCT Application No. PCT/US2016/014612.
International Search Report and Written Opinion dated Aug. 9, 2016 in PCT Application No. PCT/US2016/019971.
International Search Report and Written Opinion dated Sep. 27, 2016 in PCT Application No. PCT/US2016/034473.
International Search Report and Written Opinion dated Sep. 28, 2016 in PCT Application No. PCT/US2016/028694.
International Search Report and Written Opinion dated Dec. 5, 2016 in PCT Application No. PCT/US2016/024783.
International Search Report and Written Opinion dated Jan. 31, 2017 in PCT Application No. PCT/US2016/050694.
International Search Report and Written Opinion dated Aug. 7, 2017 in PCT Application No. PCT/US2017/034576.
International Search Report and Written Opinion dated Sep. 8, 2017 in PCT Application No. PCT/US2017/030097.
International Search Report and Written Opinion dated Mar. 20, 2018 in PCT Application No. PCT/US2017/053331.
International Search Report and Written Opinion dated Mar. 28, 2018 in PCT Application No. PCT/US2018/014385.
International Search Report and Written Opinion dated Jul. 16, 2018 in PCT Application No. PCT/US2018/024602.
International Search Report and Written Opinion dated Jun. 24, 2019 in PCT Application No. PCT/US2019/030175.
International Search Report and Written Opinion dated Oct. 8, 2019 in PCT Application No. PCT/US2019/043949.

(56) References Cited

OTHER PUBLICATIONS

International Search Report and Written Opinion dated Oct. 16, 2019 in PCT Application No. PCT/US2019/030245.
International Search Report and Written Opinion dated Nov. 27, 2019 in PCT Application No. PCT/US2019/046549.
International Search Report and Written Opinion dated Dec. 4, 2019 in PCT Application No. PCT/US2019/053868.
International Search Report and Written Opinion dated Jan. 27, 2020 in PCT Application No. PCT/US2019/048179.
International Search Report and Written Opinion dated Mar. 30, 2020 in PCT Application No. PCT/US2019/060243.
International Search Report and Written Opinion dated Mar. 30, 2020 in PCT Application No. PCT/US2019/065237.
International Search Report and Written Opinion dated May 18, 2020 in PCT Application No. PCT/US2020/014339.
International Search Report and Written Opinion dated Jun. 30, 2020 in PCT Application No. PCT/US2020/017890.
International Search Report and Written Opinion dated Nov. 12, 2020 in PCT Application No. PCT/US2020/042880.
Invitation to Pay Fees dated Mar. 16, 2016 in PCT Application No. PCT/US2016/019971.
Invitation to Pay Fees dated May 16, 2018 in PCT Application No. PCT/US2018/024602.
Invitation to Pay Fees dated Nov. 26, 2019 in PCT Application No. PCT/US2019/048179.
Invitation to Pay Additional Search Fees dated May 7, 2020 in PCT Application No. PCT/US2020/017890.
Invitation to Respond to Written Opinion dated May 26, 2017 in Singapore Patent Application No. 11201405274W.
Islam et al., "Characterization of the single-cell transcriptional landscape by highly multiplex RNA-seq," Genome Research 2011, 21, 1160-1167.
Islam et al., "Highly multiplexed and strand specific single-cell RNA 5' end sequencing," Nature Protocols 2012, 7(5), 813-828.
Islam et al., "Quantitative single-cell RNA-seq with unique molecular identifiers," Nature Methods 2014, 11(2), 163-168.
Jabara, "Capturing the cloud: High throughput sequencing of multiple individual genomes from a retroviral population," Biology Lunch Bunch Series, Training Initiatives in Biomedical & Biological Sciences of the University of North Carolina at Chapel Hill 2010.
Jabara et al., "Accurate sampling and deep sequencing of the HIV-1 protease gene using a Primer ID," PNAS 2011, 108(50), 20166-20171.
Jason J. Rawnsley of Richards, Layton and Finger, P.A., Entry of Appearance dated Jan. 18, 2019 in the USDC District of Delaware, C.A. No. 18-1800-RGA, 1 pp.
Jiang et al., "Synthetic spike-in standards for RNA-seq experiments," Genome Res. 2011, 21, 1543-1551.
Joint Stipulation and Order to Extend Time to Respond to Plaintiff's First Amended Complaint, dated Feb. 21, 2019 in the USDC for the District of Delaware, C.A. 18-1800-RGA, 2 pp.
Joint Stipulation and Order to Request Extended Time to File Opposition to Defendant's Motion to Dismiss dated, Mar. 8, 2019 in the USDC District of Delaware, C.A. No. 18-1800 RGA, 2 pp.
Joint Stipulation and Order to Request Extended Time to Submit a proposed Protective Order, dated Jun. 7, 2019 in the USDC for the District of Delaware, C.A. 18-1800-RGA, 1 pp.
Joint Stipulation and Order to Extended Time to Submit Agreed Document Production Protocol, filed Jun. 28, 2019 in the USDC for the District of Delaware, C.A. 18-1800 (RGA), 1 pp.
Joint Stipulation and Order to Request Extended Time to Submit Agreed Document Production Protocol, dated Jul. 11, 2019 in the USDC for the District of Delaware, C.A. 18-1800 (RGA), 1 pp.
Junker et al., "Single-Cell Transcriptomics Enters the Age of Mass Production," Molecular Cell 2015, 58, 563-564.
Kanagawa, "Bias and artifacts in multi-template polymerase chain reactions (PCR)," Journal of Bioscience and Bioengineering 2003, 96(4), 317-323.
Kang et al., "Targeted sequencing with enrichment PCR: a novel diagnostic method for the detection of EGFR mutations," Oncotarget 2015, 6(15), 13742-13749.
Kang et al., "Application of multi-omics in single cells," Ann Biotechnol. 2018, 2(1007), 1-8.
Karrer et al., "In situ isolation of mRNA from individual plant cells: creation of cell-specific cDNA libraries," Proc. Natl. Acad. Sci. USA 1995, 92, 3814-3818.
Kausch et al., "Organelle Isolation by Magnetic Immunoabsorption," BioTechniques 1999, 26(2), 336-343.
Kebschull et al., "Sources of PCR-induced distortions in high-throughput sequencing data sets," Nucleic Acids Research 2015, 1-15.
Keys et al., Primer ID Informs Next-Generation Sequencing Platforms and Reveals Preexisting Drug Resistance Mutations in the HIV-1 Reverse Transcriptase Coding Domain, AIDS Research and Human Retroviruses 2015, 31(6), 658-668.
Kim et al., Polony Multiplex Analysis of Gene Expression (PMAGE) in Mouse Hypertrophic Cardiomyopathy, Science 2007, 316(5830), 1481-1484.
Kinde et al., "Detection and quantification of rare mutations with massively parallel sequencing," Proc. Natl Acad Sci 2011, 108(23), 9530-0535.
Kirsebom et al., "Stimuli-Responsive Polymers in the 21st Century: Elaborated Architecture to Achieve High Sensitivity, Fast Response, and Robust Behavior," Journal of Polymer Science: Part B: Polymer Physics 2011, 49, 173-178.
Kivioja et al., "Counting absolute Nos. of molecules using unique molecular identifiers," Nature Proceedings 2011, 1-18.
Klein et al., Droplet Barcoding for Single-Cell Transcriptomics Applied to Embryonic Stem Cells, Cell 2015, 161, 1187-1201.
Ko et al., "RNA-conjugated template-switching RT-PCR method for generating an *Escherichia coli* cDNA library for small RNAs," Journal of Microbiological Methods 2006, 64, 297-304.
Koboldt et al., VarScan: variant detection in massively parallel sequencing of individual and pooled samples, Bioinformatics 2009, 25(17), 2283-2285.
Kolodziejczyk et al., The Technology and Biology of Single-Cell RNA Sequencing, Molecular Cell 2015, 58, 610-620.
Konig et al., "iCLIP reveals the function of hnRNAP particles in splicing at individual nucleotide resolution," Nature Structural & Molecular Biology 2010, 17(7), 909-916.
Kooiker & Xue, "cDNA Library Preparation," Cereal Genomics 2013, 1099, 29-40.
Kotake et al., "A simple nested RT-PCR method for quantitation of the relative amounts of multiple cytokine mRNAs in small tissue samples," Journal of Immunological Methods 1996, 199, 193-203.
Kozarewa & Turner, "96-Plex Molecular Barcoding for the Illumina Genome Analyzer," High-Throughput Next Generation Sequencing. Methods in Molecular Biology (Methods and Applications) 2011, 733, 24 pp. DOI: 10.1007/978-1-61779-089-8_20.
Kozlov et al., "A high-complexity, multiplexed solution-phase assay for profiling protease activity on microarrays," Comb Chem High Throughput Screen 2008, 11(1), 24-35.
Kurimoto et al., "An improved single-cell cDNA amplification method for efficient high-density oligonucleotide microarray analysis," Nucleic Acids Res. 2006, 34(5), e42, 1-17.
Kurimoto et al., "Global single-cell cDNA amplification to provide a template for representative high-density oligonucleotide microarray analysis," Nature Protocols 2007, 2(3), 739-752.
Lamble et al., "Improved workflows for high throughput library preparation using the transposome-based nextera system," BMC Biotechnology 2013, 13, 104, 1-10.
Larson et al., "A single molecule view of gene expression," Trends Cell Biol. 2009, 19(11), 630-637.
Lass-Napiorkowska et al., "Detection methodology based on target molecule-induced sequence-specific binding to a single-stranded oligonucleotide," Anal Chem. 2012, 84(7), 3382-3389.
Leamon et al., A massively parallel PicoTiterPlate based platform for discrete picoliter-scale polymerase chain reactions, Electrophoresis 2003, 24, 3769-3777.
Lee et al., "Large-scale arrays of picolitre chambers for single-cell analysis of large cell populations," Lab Chip 2010, 10, 2952-2958.

(56) References Cited

OTHER PUBLICATIONS

Lee et al., "Highly Multiplexed Subcellular RNA Sequencing in Situ," Science 2014, 343, 1360-1363.

Lee et al., "Universal process-inert encoding architecture for polymer microparticles," Nature Materials 2014, 13(5), 524-529.

Letter regarding the opposition procedure dated Jul. 22, 2015 for European Patent Application No. 11810645.9.

Letter to Judge Richard G. Andrews Requesting a Rule 16 Conference, dated Apr. 15, 2019 in the USDC for the District of Delaware, C.A. 18-1800 (RGA), 1 pp.

Letter to Judge Andrews regarding Agreement on Proposed Scheduling Order, dated May 7, 2019 in the USDC for the District of Delaware, C.A. 18-1800-RGA, 1 pp.

Letter to Judge Andrews regarding Notice of Supplemental Authority, dated Jul. 10, 2019 in the USDC for the District of Delaware, C.A. 18-1800(RGA), 2pp.

Lin et al., "Self-Assembled Combinatorial Encoding Nanoarrays for Multiplexed Biosensin," Nano Lett. 2007, 7 (2), 507-512.

Liu et al., "Single-cell transcriptome sequencing: recent advances and remaining challenges," F1000Research 2016, 5(F1000 Faculty Rev)(182), 1-9.

Lizardi et al., "Mutation detection and single-molecule counting using isothermal rolling-circle amplification," Nat Genet. 1998, 19, 225-232.

Lockhart et al., "Expression monitoring by hybridization to high-density oligonucleotide arrays," Nature Biotechnology 1996, 14, 1675-1680.

Lovatt et al., "Transcriptome in vivo analysis (TIVA) of spatially defined single cells in live tissue," Nat Methods 2014, 11(2), 190-196.

Loy et al., "A rapid library preparation method with custom assay designs for detection of variants at 0.1% allelic frequency in liquid biopsy samples," Oct. 2, 2018, 1 p.

Lucito et al., "Representational Oligonucleotide Microarray Analysis: A High-Resolution Method to Detect Genome Copy Number Variation," Genome Research 2003, 13, 2291-2305.

Lundberg et al., "Practical innovations for high-throughput amplicon sequencing," Nature Methods 2013, 10(10), 999-1007.

Lundberg et al., "Supplementary Information for: Practical innovations for high-throughput amplicon sequencing," Nature Methods 2013, 1-24.

Maamar et al., "Noise in Gene Expression Determines Cell Fate in Bacillus subtilis," Science 2007, 317, 526-529.

Macaulay et al., "Single Cell Genomics: Advances and Future Perspectives," PLoS Genetics 2014, 10(1), 1-9.

Macaulay et al., "G&T-seq: parallel sequencing of single-cell genomes and transcriptomes," Nature Methods 2015, 1-7.

Macosko et al., "Highly parallel genome-wide expression profiling of individual cells using nanoliter droplets," Cell 2015, 161, 1202-1214.

Maeda et al., "Development of a DNA barcode tagging method for monitoring dynamic changes in gene expression by using an ultra high-throughput sequencer," BioTechniques 2008, 45(1), 95-97.

Makrigiorgos et al., "A PCR-Based amplification method retaining quantities difference between two complex genomes," Nature Biotech 2002, 20(9), 936-939.

Marcus et al., "Microfluidic single-cell mRNA isolation and analysis," Anal Chem. 2006, 78, 3084-3089.

Mardis, "Next-generation DNA sequencing methods", Annu. Rev. Genomics Hum. Genet. 2008, 9, 387-402.

Marguerat et al., "Next-generation sequencing: applications beyond genomes," Biochem. Soc. Trans. 2008, 36(5), 1091-1096.

Marguiles et al., Genome sequencing in microfabricated high-density picolitre reactors, Nature 2005, 437, 376-380.

Martinez et al., "A microfluidic approach to encapsulate living cells in uniform alginate hydrogel microparticles," Macromol. Biosci 2012, 12, 946-951.

Massachusetts General Hospital, Overview of Illumina Chemistry, http://nextgen.mgh.harvard.edu/IlluminaChemistry.html, downloaded Jan. 28, 2020, 2 pp.

McCloskey et al., "Encoding PCR products with batch-stamps and barcodes," Biochem Genet. 2007, 45(11-12), 761-767.

Medvedev et al., "Detecting copy number variation with mated short reads," Genome Res. 2010, 20, 1613-1622.

Mei et al., "Identification of recurrent regions of Copy-Number Variants across multiple individuals," BMC Bioinformatics 2010, 11, 147, 1-14.

Merriam-Webster, definition of associate: http://merriam-webster.com/dictionary/associate, accessed Apr. 5, 2016.

Meyer et al., "Parallel tagged sequencing on the 454 platform," Nature Protocols 2008, 3(2), 267-278.

Miller et al., Directed evolution by in vitro compartmentalization, Nature Methods 2006, 3(7), 561-570.

Miner et al., "Molecular barcodes detect redundancy and contamination in hairpin-bisulfite PCR," Nucleic Acids Research 2004, 32(17), e135, 1-4.

Mortazavi et al., "Mapping and quantifying mammalian transcriptomes by RNA-Seq," Nat. Methods 2008, 5(7), 621-628.

Motion and Order for Admission Pro Hac Vice Pursuant to Local Rule 83.5, dated Jan. 24, 2019 in the USDC District of Delaware, C.A. No. 18-1800-RGA, 7 pp.

Nadai et al., Protocol for nearly full-length sequencing of HIV-1 RNA from plasma, PLoS One 2008, 3(1), e1420, 1-6.

Nagai et al., "Development of a microchamber array for picoleter PCR," Anal. Chem. 2001, 73, 1043-1047.

Navin et al., "The first five years of single-cell cancer genomics and beyond," Genome Research 2015, 25, 1499-1507.

Newell et al., Cytometry by time-of-flight shows combinatorial cytokine expression and virus-specific cell niches within a continuum of CD8+ T cell phenotypes. Immunity 2012, 36(1), 142-152.

Non-Final Office Action dated Oct. 3, 2013 in U.S. Appl. No. 12/969,581.

Non-Final Office Action dated Feb. 18, 2015 for U.S. Appl. No. 14/540,007.

Non-Final Office Action dated Feb. 26, 2015 for U.S. Appl. No. 14/540,029.

Non-Final Office Action dated Mar. 19, 2015 in U.S. Appl. No. 14/540,018.

Non-Final Office Action dated May 7, 2015 for U.S. Appl. No. 13/327,526.

Non-Final Office Action dated Dec. 3, 2015 for U.S. Appl. No. 14/281,706.

Non-Final Office Action dated Dec. 31, 2015 for U.S. Appl. No. 14/800,526.

Non-Final Office Action dated Apr. 11, 2016 in U.S. Appl. No. 14/472,363.

Non-Final Office Action dated May 10, 2016 in U.S. Appl. No. 14/381,488.

Non-Final Office Action dated May 13, 2016 in U.S. Appl. No. 14/508,911.

Non-Final Office Action dated Aug. 17, 2016 for U.S. Appl. No. 14/800,526.

Non-Final Office Action dated Sep. 26, 2016 in U.S. Appl. No. 15/167,807.

Non-Final Office Action dated Oct. 11, 2016 in U.S. Appl. No. 15/224,460.

Non-Final Office Action dated Jan. 19, 2017 in U.S. Appl. No. 15/055,445.

Non-Final Office Action dated Mar. 24, 2017 in U.S. Appl. No. 15/409,355.

Non-Final Office Action dated Jun. 2, 2017 in U.S. Appl. No. 14/381,526.

Non-Final Office Action dated Jun. 7, 2017 in U.S. Appl. No. 14/381,488.

Non-Final Office Action dated Jul. 28, 2017 in U.S. Appl. No. 14/975,441.

Non-Final Office Action dated Sep. 8, 2017 in U.S. Appl. No. 15/046,225.

Non-Final Office Action dated Sep. 8, 2017 in U.S. Appl. No. 15/134,967.

Non-Final Office Action dated Nov. 1, 2017 in U.S. Appl. No. 15/667,125.

(56) References Cited

OTHER PUBLICATIONS

Non-Final Office Action dated Nov. 9, 2017 in U.S. Appl. No. 15/004,618.
Non-Final Office Action dated Jan. 9, 2018 in U.S. Appl. No. 15/217,896.
Non-Final Office Action dated Jan. 12, 2018 in U.S. Appl. No. 15/217,886.
Non-Final Office Action dated Mar. 8, 2018 in U.S. Appl. No. 15/608,780.
Non-Final Office Action dated Apr. 6, 2018 in U.S. Appl. No. 15/603,239.
Non-Final Office Action dated Jul. 25, 2018 in U.S. Appl. No. 15/108,268.
Non-Final Office Action dated Oct. 4, 2018 in U.S. Appl. No. 15/260, 106.
Non-Final Office Action dated Oct. 25, 2018 in U.S. Appl. No. 16/012,584.
Non-Final Office Action dated Nov. 5, 2018 in U.S. Appl. No. 16/038,790.
Non-Final Office Action dated Nov. 26, 2018 in U.S. Appl. No. 15/937,713.
Non-Final Office Action dated Jan. 7, 2019 in U.S. Appl. No. 15/055,407.
Non-Final Office Action dated Jan. 14, 2019 in U.S. Appl. No. 16/219,553.
Non-Final Office Action dated Mar. 19, 2019 in U.S. Appl. No. 15/046,225.
Non-Final Office Action dated May 15, 2019 in U.S. Appl. No. 15/084,307.
Non-Final Office Action dated May 23, 2019 in U.S. Appl. No. 15/459,977.
Non-Final Office Action dated Jun. 17, 2019 in U.S. Appl. No. 14/381,488.
Non-Final Office Action dated Jul. 9, 2019 in U.S. Appl. No. 15/596,364.
Non-Final Office Action dated Aug. 20, 2019 for U.S. Appl. No. 15/715,028.
Non-Final Office Action dated Sep. 18, 2019 in U.S. Appl. No. 16/194,819.
Non-Final Office Action dated Nov. 29, 2019 in U.S. Appl. No. 15/937,713.
Non-Final Office Action dated Jan. 17, 2020 in U.S. Appl. No. 15/084,307.
Non-Final Office Action dated Feb. 5, 2020 in U.S. Appl. No. 15/875,816.
Non-Final Office Action dated Mar. 12, 2020 in U.S. Appl. No. 16/789,358.
Non-Final Office Action dated Mar. 17, 2020 in U.S. Appl. No. 15/055,407.
Non-Final Office Action dated Mar. 26, 2020 in U.S. Appl. No. 16/012,635.
Non-Final Office Action dated Mar. 26, 2020 in U.S. Appl. No. 16/789,311.
Non-Final Office Action dated Jun. 8, 2020 in U.S. Appl. No. 15/715,028.
Non-Final Office Action dated Aug. 4, 2020 in U.S. Appl. No. 15/459,977.
Non-Final Office Action dated Aug. 19, 2020 in U.S. Appl. No. 16/374,626.
Non-Final Office Action dated Aug. 25, 2020 in U.S. Appl. No. 14/381,488.
Non-Final Office Action dated Dec. 4, 2020 in U.S. Appl. No. 16/677,012.
Non-Final Office Action dated Dec. 9, 2020 in U.S. Appl. No. 16/788,743.
Notice of Allowability dated Jun. 19, 2014 for U.S. Appl. No. 12/969,581.
Notice of Allowance dated Mar. 21, 2014 for U.S. Appl. No. 12/969,581.
Notice of Allowance dated Aug. 22, 2014 for U.S. Appl. No. 12/969,581.
Notice of Allowance dated Dec. 15, 2015 for U.S. Appl. No. 14/540,007.
Notice of Allowance dated Dec. 21, 2015 in U.S. Appl. No. 14/540,018.
Notice of Allowance dated Jan. 21, 2016 for U.S. Appl. No. 13/327,526.
Notice of Allowance dated Jan. 9, 2019 in U.S. Appl. No. 15/603,239.
Notice of Allowance dated Mar. 20, 2019 in U.S. Appl. No. 16/219,553.
Notice of Allowance dated Mar. 21, 2019 in U.S. Appl. No. 15/993,468.
Notice of Allowance dated May 28, 2019 in U.S. Appl. No. 16/219,553.
Notice of Allowance dated Sep. 24, 2019 in U.S. Appl. No. 15/217,886.
Notice of Allowance dated Nov. 11, 2019 in Japanese Patent Application No. 2017-245295.
Notice of Allowance dated Nov. 29, 2019 in U.S. Appl. No. 16/012,635.
Notice of Allowance dated Dec. 27, 2019 in U.S. Patent Application No. 15/260, 106.
Notice of Allowance dated Mar. 5, 2020 in U.S. Appl. No. 15/217,886.
Notice of Allowance dated Mar. 27, 2020 in U.S. Appl. No. 15/596,364.
Notice of Allowance dated Mar. 30, 2020 in U.S. Appl. No. 15/937,713.
Notice of Allowance dated Apr. 15, 2020 in U.S. Appl. No. 16/012,635.
Notice of Allowance dated Sep. 23, 2020 in Korean Patent Application No. 10-2016-7008144.
Notice of Allowance dated Oct. 29, 2020 in U.S. Appl. No. 15/987,851.
Notice, Consent, and Reference of a Civil Action to a Magistrate Judge (Rule 73.1), filed Nov. 15, 2018 in the USDC for the District of Delaware, C.A. 18-1800-RGA, 3 pp.
Notice of Opposition dated Jul. 9, 2015 for European Patent Application No. 11810645.9.
Notice of Opposition dated Jul. 27, 2016 for European Patent Application No. 10762102.1.
Notice of Reasons for Rejection dated Dec. 28, 2016 in Japanese Patent Application No. 2014-558975.
Notice of Reasons for Rejection dated Apr. 2, 2018 in Japanese Patent Application No. 2014-558975.
Notice of Reasons for Rejection dated Jul. 30, 2018 in Japanese Patent Application No. 2016-537867.
Notice of Reasons for Rejection dated Aug. 31, 2018 in Japanese Patent Application No. 2016-520632.
Notice of Reasons for Rejection dated Dec. 5, 2018 in Japanese Patent Application No. 2017-245295.
Notice of Reason for Rejection dated Nov. 21, 2019 in Korean Patent Application No. 10-2016-7008144.
Notice of Reasons for Rejection dated Feb. 25, 2020 in Japanese Patent Application No. 2019-014564.
Notice of Reasons for Rejection dated May 11, 2020 in Japanese Patent Application No. 2017-549390.
Notice of Service of Disclosures to Opposing Counsel, dated Jun. 10, 2019 in the USDC for the District of Delaware, C.A. 18-1800 (RGA), 3 pp.
Notice of Service of Interrogatories and First Request of Documents and Things to Defendant 10X Genomics, Inc., dated Jul. 5, 2019 in the USDC for the District of Delaware, C.A. 18-1800 (RGA), 3 pp.
Notification Prior to Examination dated Nov. 27, 2019 in Israeli Patent Application No. 265478.
Novak et al., "Single-Cell Multiplex Gene Detection and Sequencing with Microfluidically Generated Agarose Emulsions," Angew. Chem. Int. Ed. 2011, 50, 390-395.
Office Action dated Jun. 6, 2016 in Chinese Patent Application No. 201380022187.9.
Office Action dated Dec. 27, 2016 in Chinese Patent Application No. 201380022187.9.

(56) References Cited

OTHER PUBLICATIONS

Office Action dated Feb. 17, 2017 in Canadian Patent Application No. 2,865,575.
Office Action dated Jul. 14, 2017 in Chinese Patent Application No. 201380022187.9.
Office Action dated Dec. 19, 2017 in Chinese Patent Application No. 201480061859.1.
Office Action dated Feb. 15, 2018 in Canadian Patent Application No. 2,865,575.
Office Action dated Sep. 7, 2018 in Chinese Patent Application No. 201480061859.1.
Office Action dated Dec. 13, 2018 in Canadian Patent Application No. 2,865,575.
Office Action dated Jan. 2, 2019 in Chinese Patent Application No. 201480059505.3.
Office Action dated Mar. 4, 2020 in Canadian Patent Application No. 2,865,575.
Office Action dated Jun. 22, 2020 in Chinese Patent Application No. 201680007351.2.
Office Action dated Jun. 22, 2020 in Chinese Patent Application No. 201680007652.5.
Office Action dated Jun. 23, 2020 in Chinese Patent Application No. 2016800157452.
Office Action dated Jul. 20, 2020 in Japanese Patent Application No. 2018-512152.
Office Action dated Oct. 29, 2020 in Chinese Patent Application No. 2018800377201.
Office Action dated Nov. 12, 2020 in European Patent Application No. 18716877.8.
Office Action dated Dec. 3, 2020 in European Patent Application No. 16719706.0.
Office Action dated Jan. 4, 2021 in Japanese Patent Application No. 2017-549390.
Ogino et al., "Quantification of PCR bias caused by a single nucleotide polymorphism in SMN gene dosage analysis," J Mol Diagn. 2002, 4(4), 185-190.
Opposition to Defendant's Motion to Dismiss Pursuant to Federal Rule of Civil Procedure 12(b)(6) dated Feb. 15, 2019, in the USDC for the District of Delaware, C.A. 18-800-RGA, 3 pp.
Oral Order by Judge Andrews Canceling Scheduling Conference set for May 8, 2019.
Order Setting Rule 16(b) Conference as Ordered by Judge Andrews Pursuant to Fed. R. Civ. P. 16(b), ruling dated Apr. 17, 2019 in the USDC District of Delaware, C.A. 18-1800-RGA, 1 pp.
Order Scheduling ADR Mediation Teleconference, filed May 13, 2019 in the USDC for the District of Delaware, C.A. 18-1800-RGA, 4pp.
Ozkumur et al., "Inertial Focusing for Tumor Antigen-Dependent and —Independent Sorting of Rare Circulating Tumor Cells," Science Translational Medicine 2013, 5(179), 1-20.
Parameswaran et al., "A pyrosequencing-tailored nucleotide barcode design unveils opportunities for large-scale sample multiplexing," Nucleic Acids Res. 2007, 35(19), e130, 1-9.
Park et al., "Discovery of common Asian copy number variants using integrated high-resolution array CGH and massively parallel DNA sequencing," Nat Genet. 2010, 42(5), 400-405.
Patanjali et al., "Construction of a uniform-abundance (normalized) CNDA library," Proceedings of the National Academy of Sciences 1991, 88(5), 1943-1947.
Peng et al., "Reducing amplification artifacts in high multiplex amplicon sequencing by using molecular barcodes," BMC Genomics 2015, 16(589), 1-12.
PéRez-Rentero et al., "Synthesis of Oligonucleotides Carrying Thiol Groups Using a Simple Reagent Derived from Threoninol," Molecules 2012, 17, 10026-10045.
Peterson et al., "Multiplexed quantification of proteins and transcripts in single cells," Nature Biotechnology 2017, 35, 936-939.

Pfaffl et al., "Determination of stable housekeeping genes, differentially regulated target genes and sample integrity: BestKeeper—Excel-based tool using pair-wise correlations," Biotechnology Letters, 26(6), 505-515.
Picelli et al., "Tn5 transposase and tagmentation procedures for massively scaled sequencing projects," Genome Research 2014, 24(12), 2033-2040.
Picelli et al., "Single-cell RNA-sequencing: The future of genome biology is now," RNA Biology 2017, 14(5), 637-650.
Pihlak et al., "Rapid genome sequencing with short universal tiling probes," Nature Biotechnology 2008, 26, 1-9.
Pinkel et al., "Comparative Genomic Hybridization," Annual Review of Genomics and Human Genetics 2005, 6, 331-354.
Plaintiff's Brief in Opposition to Defendant's Motion to Dismiss Pursuant to Fed. R. Civ. P. 12(b)(6), filed Mar. 29, 2019 in the USDC District of Delaware, C.A. No. 18-1800 (RGA), 27 pp.
Plaintiff's First Amended Complaint filed on Feb. 8, 2019, in the USDC for the District of Delaware, C.A. 18-1800-RGA, 178 pp.
Pleasance et al., "A small-cell lung cancer genome with complex signatures of tobacco exposure," Nature 2010, 463(7278), 184-190.
Plessy et al., "Population transcriptomics with single-cell resolution: a new field made possible by microfluidics: a technology for high throughput transcript counting and data-driven definition of cell types," Bioessays 2012, 35, 131-140.
Pre-interview communication dated Nov. 27, 2018 in U.S. Appl. No. 16/012,635.
Preissl et al., "Single-nucleus analysis of accessible chromatin in developing mouse forebrain reveals cell-type-specific transcriptional regulation," Nature Neuroscience 2018, 21(3), 432-439.
Proposed Stipulated Protective Order Pursuant to Rule 26(c) of the Federal Rules of Civil Procedure, filed Jun. 20, 2019 In the USDC for the District of Delaware, C.A. 18-1800 (RGA), 26 pp.
Qiu et al., "DNA Sequence-Based "Bar Codes" for Tracking the Origins of Expressed Sequence Tags from a Maize cDNA Library Constructed Using Multiple mRNA Sources," Plant Physiol. 2003, 133, 475-481.
Raj et al., "Stochastic mRNA synthesis in mammalian cells," PLoS Biol. 2006, 4(10) 1707-1719.
Raj et al., "Imaging individual mRNA molecules using multiple singly labeled probes," Nature Methods 2008, 5(10), 877-879.
Raj et al., "Single-Molecule Approaches to Stochastic Gene Expression," Annu Rev Biophys 2009, 38, 255-270.
Rajeevan et al., "Global amplification of sense RNA: a novel method to replicate and archive mRNA for gene expression analysis," Genomics 2003, 82, 491-497.
Report on the Filing or Determination of an Action Regarding a Patent or Trademark filed Nov. 15, 2018 in the USDC for the District of Delaware, C.A. 18-1800-RGA, 2 pp.
Restriction Requirement dated Mar. 15, 2016 in U.S. Appl. No. 14/381,488.
Restriction Requirement dated Mar. 17, 2016 in U.S. Appl. No. 14/472,363.
Restriction Requirement dated Mar. 29, 2019 in U.S. Appl. No. 15/715,028.
Restriction Requirement dated Jun. 19, 2019 in U.S. Appl. No. 15/596,364.
Restriction Requirement dated Sep. 20, 2019 in U.S. Appl. No. 15/875,816.
Rhee et al., "Simultaneous detection of mRNA and protein stem cell markers in live cells," BMC Biotechnology 2009, 9(30), 1-10.
Roche Diagnostics GmbH, "Genome Sequencer 20 System: First to the Finish," 2006, 1-40.
Rule 7.1 Disclosure Statement dated Nov. 15, 2018 in the USDC for the District of Delaware, C.A. 18-1800-RGA, 1 pp.
Sah et al., "Complete Genome Sequence of a 2019 Novel Coronavirus (SARS-COV-2) Strain Isolated in Nepal," Microbiol Resour Announc. 2020, 9(11), e00169-20, 3 pp.
Sano et al., "Immuno-PCR: Very Sensitive Antigen Detection by Means of Specific Antibody-DNA Conjugates," Science 1992, 258, 120-122.
Sasagawa et al., "Quartz-Seq: a highly reproducible and sensitive single-cell RNA sequencing method, reveals non-genetic gene-expression heterogeneity," Genome Biology 2013, 14, R31.

(56) References Cited

OTHER PUBLICATIONS

Sasuga et al., Single-cell chemical lysis method for analyses of intracellular molecules using an array of picoliter-scale microwells, Anal Chem 2008, 80(23), 9141-9149.
Satija et al., Spatial reconstruction of single-cell gene expression data, Nature Biotechnology 2015, 33(5), 495-508.
Scheduling Order pursuant to Local Rule 16.1(b), filed May 7, 2019 in the USDC for the District of Delaware, C.A. 18-1800-RGA, 10 pp.
Scheduling Order Signed by Judge Andrews, dated May 8, 2019 in the USDC for the District of Delaware, C.A. 18-1800-RGA, 10 pp.
Schmitt et al., "Detection of ultra-rare mutations by next-generation sequencing," Proc Natl Acad Sci 2012, 109(36), 1-6.
Search and Examination Report dated Aug. 26, 2015 in United Kingdom Patent Application No. 1511591.8.
Search Report and Written Opinion dated Jan. 26, 2016 in Singapore Patent Application No. 1120140527W.
Search Report and Written Opinion dated Aug. 26, 2020 in Singapore Patent Application No. 10201806890V.
Sebat et al., "Large-Scale Copy No. Polymorphism in the Human Genome," Science 2004, 305, 525-528.
Shahi et al., "Abseq: ultrahigh-throughput single cell protein profiling with droplet microfluidic barcoding," Scientific Reports 2017, 7(44447), 1-10.
Shalek et al., "Single-cell transcriptomics reveals bimodality in expression and splicing in immune cells," Nature 2013, 498(7453), 236-240.
Shendure et al., "Next-generation DNA sequencing," Nature Biotechnology 2008, 26(10), 1135-1145.
Shiroguchi et al., "Digital RNA sequencing minimizes sequence-dependent bias and amplification noise with optimized single-molecule barcodes," Proc Natl Acad Sci 2012, 109(4): 1347-1352.
S.H.KO, "An 'equalized cDNA library' by the reassociation of short double-stranded cDNAs," Nucleic Acids Res. 1990, 18(19), 5705-5711.
Shoemaker et al., "Quantitative phenotypic analysis of yeast deletion mutants using a highly parallel molecular bar-coding strategy," Nature Genetics 1996, 14, 450-456.
Shortreed et al., "A thermodynamic approach to designing structure-free combinatorial DNA word sets," Nucleic Acids Res. 2005, 33(15), 4965-4977.
Shum et al., "Quantitation of mRNA Transcripts and Proteins Using the BD Rhapsody™ Single-Cell Analysis System," Adv Exp Med Biol. 2019, 1129, 63-79.
Simpson et al., "Copy number variant detection in inbred strains from short read sequence data," Bioinformatics 2010, 26(4), 565-567.
Smith et al., "Highly-multiplexed barcode sequencing: an efficient method for parallel analysis of pooled samples," Nucleic Acids Research 2010, 38(13), e142, 1-7.
Soares et al., "Construction and characterization of a normalized cDNA library," Proc. Natl., Acad. Sci. 1994, 91, 9228-9232.
Sogin et al., "Microbial diversity in the deep sea and the underexplored "rare biosphere"," PNAS 2008, 103(32), 12115-12120.
Sommer et al., "Minimal homology requirements for PCR primers," Nucleic Acids Research 1989, 17(16), 6749.
Song et al., "Design rules for size-based cell sorting and sheathless cell focusing by hydrophoresis," Journal of Chromatography A 2013, 1302, 191-196.
Soumillon et al., "Characterization of directed differentiation by high-throughput single-cell RNA-Seq," bioRxiv 2014, 1-13.
Speicher et al., "The new cytogenetics: blurring the boundaries with molecular biology," Nature Reviews Genetics 2005, 6(10), 782-792.
Statement of Opposition of Strawman Limited filed against European Patent No. EP2414548B1 on Jul. 19, 2016.
Statement of Opposition dated Jul. 21, 2016 filed against European Patent No. EP2414548B1.
Statement of Opposition filed against European Patent No. EP2414548B1 on Jul. 26, 2016.
Statement regarding Third-Party Submission filed on Jun. 6, 2018 for U.S. Appl. No. 15/847,752.
Stipulated Protective Order Pursuant to Rule 26(c) of the Federal Rules of Civil Procedure, dated Jun. 21, 2019 in the USDC for the District of Delaware, C.A. 18-1800 (RGA), 26 pp.
Stipulation and Order to Extend Time to File Opposition to Motion to Dismiss, and Reply in Support of the Motion, dated Jan. 28, 2019 in the USDC for the District of Delaware, C.A. 18-1800-RGA, 2 pp.
Stoeckius et al., "Large-scale simultaneous measurement of epitopes and transcriptomes in single cells," Nature Methods 2017, 14(9), 865-868.
Stratagene 1988 Catalog, Gene Characterization Kits, 39.
Subkhankulova et al., "Comparative evaluation of linear and exponential amplification techniques for expression profiling at the single cell level," Genome Biology 2006, 7(3), 1-16.
Submission dated Jan. 15, 2018 in preparation for upcoming oral proceedings in opposition against European Patent No. EP2414548B1.
Summons in a Civil Action to Defendant 10X Genomics, Inc. filed Nov. 16, 2018 in the USDC for the District of Delaware, Civil Action No. 18-1800, 2 pp.
Summons to Attend Oral Proceedings dated Nov. 16, 2020 in European Patent Application No. 17202409.3.
Sun et al., "Ultra-deep profiling of alternatively spliced *Drosophila* Dscam isoforms by circularization-assisted multi-segment sequencing," EMBO J. 2013, 32(14), 2029-2038.
Takahashi et al., "Novel technique of quantitative nested real-time PCR assay for *mycobacterium tuberculosis* DNA," Journal of Clinical Microbiology 2006, 44, 1029-1039.
Tan et al., "Genome-wide comparison of DNA hydroxymethylation in mouse embryonic stem cells andneural progenitor cells by a new comparative hMeDIP-seq method," Nucleic Acids Res. 2013, 41(7), e84, 1-12.
Tang et al., "RNA-Seq analysis to capture the transcriptome landscape of a single cell," Nature Protocols 2010, 5(3), 516-535.
Taudien et al., "Haplotyping and copy number estimation of the highly polymorphic human beta-defensin locus on 8p23 by 454 amplicon sequencing," BMC Genomics 2010, 11, 252, 1-14.
The Tibbs Times, UNC bioscience newsletter, Apr. 2010, 1-17.
Third-Party Submission filed on May 21, 2018 for U.S. Appl. No. 15/847,752.
Tomaz et al., "Differential methylation as a cause of allele dropout at the imprinted GNAS locus," Genet Test Mol Biomarkers 2010, 14(4), 455-460.
Treutlein et al., Reconstructing lineage hierarchies of the distal lung epithelium using single-cell RNA-seq, Nature 2014, 509, 371-375.
Ullal et al., "Cancer cell profiling by barcoding allows multiplexed protein analysis in fine needle aspirates," Sci Transl Med. 2014, 6(219), 22 pp.
Unopposed Motion to Extend Time for Defendant's Response, dated Dec. 4, 2018 in the USDC for the District of Delaware, C.A. 18-1800-(RGA), 2 pp.
Vandesompele et al., "Accurate normalization of real-time quantitative RT-PCR data by geometric averaging of multiple internal control genes," Genome Biology 2002, 3(7), 1-12.
Velculescu et al., "Serial Analysis of Gene Expression," Science 1995, 270(5235), 484-487.
Velculescu et al., "Characterization of the Yeast Transcriptome," Cell 1997, 88, 243-251.
Vogelstein et al., "Digital PCR," Proc. Natl. Acad. Sci. 1999, 96, 9236-9241.
Vollbrecht et al., "Validation and comparison of two NGS assays for the detection of EGFR T790M resistance mutation in liquid biopsies of NSCLC patients," Oncotarget 2018, 9(26), 18529-18539.
Walker et al., "Isothermal in vitro amplification of DNA by a restriction enzyme/DNA polymerase system," Proc Natl Acad Sci 1992, 89, 392-396.
Walsh et al., "Detection of inherited mutations for breast and ovarian cancer using genomic capture and massively parallel sequencing," Proc Natl Acad Sci 2010, 107(28), 12629-12633.
Wang et al., "Combining Gold Nanoparticles with Real-Time Immuno-PCR for Analysis of HIV p24 Antigens," Proceedings of ICBBE 2007, 1198-1201.

(56) References Cited

OTHER PUBLICATIONS

Wang et al., "RNA-Seq: a revolutionary tool for transcriptomics," Nature Reviews Genetics 2009, 10(1), 57-63.
Wang et al., "iCLIP predicts the dual splicing effects of TIA-RNA interactions," PLoS Biol 2010, 8(10), e1000530, 1-16.
Wang et al., "Advances and applications of single-cell sequencing technologies," Molecular Cell 2015, 58, 598-609.
Warren et al., "Transcription factor profiling in individual hematopoietic progenitors by digital RT-PCR," PNAS 2006, 103(47), 17807-17812.
Weber et al., "A real-time polymerase chain reaction assay for quantification of allele ratios and correction of amplification bias," Anal Biochem. 2003, 320, 252-258.
Weibrecht et al., "Proximity ligation assays: a recent addition to the proteomics toolbox," Expert Rev. Proteomics 2010, 7(3), 401-409.
Weiner et al., "Kits and their unique role in molecular biology: a brief retrospective," BioTechniques 2008, 44(5), 701-704.
White et al., "High-throughput microfluidic single-cell RT-qPCR," PNAS 2011, 108(34), 13999-14004.
Wittes et al., "Searching for Evidence of Altered Gene Expression: a Comment on Statistical Analysis of Microarray Data," Journal of the National Cancer Institute 1999, 91(5), 400-401.
Wodicka et al., "Genome-wide expression monitoring in *Saccharomyces cerevisiae*," Nature Biotechnology 1997, 15, 1359-1367.
Wojdacz et al., "Primer design versus PCR bias in methylation independent PCR amplifications," Epigenetics 2009, 4(4), 231-234.
Wood et al., "Using next-generation sequencing for high resolution multiplex analysis of copy number variation from nanogram quantities of DNA from formalin-fixed paraffin-embedded specimens," Nucleic Acids Res. 2010, 38(14), 1-14.
Written Submission of Publications dated Jun. 14, 2018 in Japanese Patent Application No. 2016-537867.
Wu et al., "Quantitative assessment of single-cell RNA-sequencing methods," Nat Methods 2014, 11(1), 41-46.
Yandell et al., "A probabilistic disease-gene finder for personal genomes," Genome Res. 2011, 21(9), 1529-1542.
Ye et al., Fluorescent microsphere-based readout technology for multiplexed human single nucleotide polymorphism analysis and bacterial identification, Human Mutation 2001, 17(4), 305-316.
Yoon et al., Sensitive and accurate detection of copy number variants using read depth of coverage, Genome Res. 2009, 19, 1586-1592.
Zagordi et al., "Error correction of next-generation sequencing data and reliable estimation of HIV quasispecies," Nucleic Acids Research 2010, 38(21), 7400-7409.
Zhang et al., "The impact of next-generation sequencing on genomics," J Genet Genomics 2011, 38(3), 95-109.
Zhang et al., "DNA-based hybridization chain reaction for amplified bioelectronic signal and ultrasensitive detection of proteins," Anal Chem. 2012, 84, 5392-5399.
Zhao et al., "Homozygous Deletions and Chromosome Amplifications in Human Lung Carcinomas Revealed by Single Nucleotide Polymorphism Array Analysis," Cancer Research 2005, 65(13), 5561-5570.
Zheng et al., "Haplotyping germline and cancer genomes with high-throughput linked-read sequencing," Nature Biotechnology 2016, 34(3), 303-311.
Zhou et al., "Counting alleles reveals a connection between chromosome 18q loss and vascular invasion," Nature Biotechnology 2001, 19, 78-81.
Zhou et al., "Photocleavable Peptide-Oligonucleotide Conjugates for Protein Kinase Assays by MALDI-TOF MS," Mol. BioSyst. 2012, 8, 2395-2404.
Zhu et al., "Reverse Transcriptase Template Switching: A SMART Approach for Full-Length cDNA Library Construction," BioTechniques 2001, 30(4), 892-897.
Lee et al., "Comparison of Surface Markers between Human and Rabbit Mesenchymal Stem Cells," PLos ONE 2014, 9(11), in 10 pages.
10X Genomics, Inc., 2022, "Chromium Fixed RNA Profiling Reagent Kits," 10xGenomics.com, User Guide, in 95 pages.
Advisory Action dated May 31, 2023 in U.S. Appl. No. 16/789,311.
Arguel et al., "A cost effective 5' selective single cell transcriptome profiling approach with improved UMI design," Nucleic Acids Research 2017, 45(7), e48, in 11 pages.
De Simone et al., "Single Cell T Cell Receptor Sequencing: Techniques and Future Challenges," Frontiers in Immunology 2018, 9(1638), 1-7.
Delebecque et al. "Designing and using RNA scaffolds to assemble proteins in vivo". Nature protocols, 2012, 7(10), 1797-1807.
Dickey and Giangrande. "Oligonucleotide Aptamers: A Next-Generation Technology for the Capture and Detection of Circulating Tumor Cells." Methods, 2016 97:94-103.
Dovgan et al., "Antibody-Oligonucleotide Conjugates as Therapeutic, Imaging, and Detection Agents," Bioconjugate Chem. 2019, 30, 2483-2501.
Dua, et al. "Patents on SELEX and therapeutic aptamers. Recent patents on DNA & gene sequences," 2008, 2( 3), 172-186.
Erickson et al., "AbSeq Protocol Using the Nano-Well Cartridge-Based Rhapsody Platform to Generate Protein and Transcript Expression Data on the Single-Cell Level," STAR Protocols 2020, in 31 pages.
Eulberg, et al. "Development of an automated in vitro selection protocol to obtain RNA-based aptamers: identification of a biostable substance P antagonist," Nucleic acids research, 2005, 33(4), e45. https://doi.org/ 10.1093/nar/gni044.
Fathi,, P. Design and Characterization of SSDNA Aptamer Candidates to Bind Bacteroides Fragilis Toxin Subtypes BFT-1 and BFT-2 (Johns Hopkins University).2017, Master thesis.
Final Office Action dated Jan. 25, 2023 in U.S. Appl. No. 16/789,311.
Final Office Action dated Jan. 26, 2023 in U.S. Appl. No. 16/459,444.
Final Office Action dated Feb. 21, 2023 in U.S. Appl. No. 16/551,620.
Final Office Action dated Apr. 25, 2023 in U.S. Appl. No. 16/525,054.
Final Office Action dated May 15, 2023 in U.S. Appl. No. 16/551,638.
Final Office Action dated May 19, 2023 in U.S. Patent Application No. 17/163, 177.
Final Office Action dated Jun. 8, 2023 in U.S. Appl. No. 17/147,283.
Hoinka and Przytycka. "AptaPLEX-A Dedicated, Multithreaded Demultiplexer for HT-SE LEX Data." Methods, 2016, 106:82-85 . . . .
International Search Report and Written Opinion dated Dec. 5, 2022, in PCT Application No. PCT/US2022/075774.
International Search Report and Written Opinion dated Dec. 15, 2022, in PCT Application No. PCT/US2022/075655.
International Search Report and Written Opinion dated Dec. 20, 2022, in PCT Application No. PCT/US2022/075661.
International Search Report and Written Opinion dated Dec. 22, 2022, in PCT Application No. PCT/US2022/075577.
International Search Report and Written Opinion dated Jan. 9, 2023, in PCT Application No. PCT/US2022/076366.
International Search Report and Written Opinion dated Jan. 17, 2023, in PCT Application No. PCT/US2022/076056.
International Search Report and Written Opinion dated Feb. 13, 2023, in PCT Application No. PCT/US2022/075656.
International Search Report and Written Opinion dated Jun. 5, 2023, in PCT Application No. PCT/US2023/061980.
Ku, et al. "Nucleic Acid Aptamers: An Emerging Tool for Biotechnology and Biomedical Sensing." Sensors, 2015, 15, 16281-16313.
Mairal et al. "Aptamers: Molecular Tools for Analytical Applications." Analytical and bioanalytical chemistry 2008,390: 989-1007.
Mayer et al., "Obtaining deeper insights into microbiome diversity using a simple method to block host and nontargets in amplicon sequencing," Molecular Ecology Resources 2021, 21 (6), 1952-1965.
Non-Final Office Action dated Dec. 8, 2022 in U.S. Appl. No. 16/934,530.
Non-Final Office Action dated Dec. 21, 2022 in U.S. Appl. No. 15/055,407.
Non-Final Office Action dated Jan. 10, 2023 in U.S. Appl. No. 17/163,177.
Non-Final Office Action dated Jan. 19, 2023 in U.S. Appl. No. 17/091,639.

(56) References Cited

OTHER PUBLICATIONS

Non-Final Office Action dated Jan. 23, 2023 in U.S. Appl. No. 17/183,840.
Non-Final Office Action dated Jan. 24, 2023 in U.S. Appl. No. 17/157,872.
Non-Final Office Action dated Feb. 10, 2023 in U.S. Appl. No. 17/390,640.
Non-Final Office Action dated Feb. 23, 2023 in U.S. Appl. No. 17/408,374.
Non-Final Office Action dated Mar. 13, 2023 in U.S. Appl. No. 17/151,050.
Non-Final Office Action dated Apr. 26, 2023 in U.S. Appl. No. 16/540,971.
Non-Final Office Action dated Apr. 26, 2023 in U.S. Appl. No. 16/374,626.
Non-Final Office Action dated Jun. 14, 2023 In U.S. Appl. No. 17/174,249.
Non-Final Office Action dated Jun. 30, 2023 In U.S. Appl. No. 17/684,289.
Notice of Allowance dated Jan. 10, 2023 in U.S. Appl. No. 16/588,405.
Notice of Allowance dated Jan. 19, 2023 in Korean Patent Application No. 10-2022-7004715.
Notice of Allowance dated Jan. 31, 2023 in U.S. Appl. No. 16/747,737.
Notice of Allowance dated Feb. 1, 2023 in U.S. Appl. No. 17/147,272.
Notice of Allowance dated Feb. 21, 2023 in Korean Patent Application No. 10-2022-7017261.
Notice of Allowance dated Mar. 1, 2023 in U.S. Appl. No. 17/192,814.
Notice of Allowance dated Mar. 10, 2023 in European Patent Application No. 19762517.1.
Notice of Allowance dated Mar. 10, 2023 in European Patent Application No. 20708266.0.
Notice of Allowance dated Mar. 10, 2023 in European Patent Application No. 19724003.9.
Notice of Allowance dated Mar. 13, 2023 in European Patent Application No. 17781265.8.
Notice of Allowance dated Apr. 4, 2023 in Australian Patent Application No. 2017331459.
Notice of Allowance dated Jun. 8, 2023 in U.S. Appl. No. 16/459,444.
Office Action dated Sep. 21, 2022 in Israel Patent Application No. 265478.
Office Action dated Jan. 30, 2023 in European Patent Application No. 19752792.2.
Office Action dated Feb. 8, 2023 in Australian Patent Application No. 2017331459.
Office Action dated Feb. 20, 2023 in European Patent Application No. 19723988.2.
Office Action dated Feb. 23, 2023 in European Patent Application No. 20816802.1.
Office Action dated Feb. 28, 2023 in Chinese Patent Application No. 2019111653930.
Office Action dated Nov. 24, 2022 in Chinese Patent Application No. 2018800147939.
Office Action dated Mar. 15, 2023 in European Patent Application No. 19787547.9.
Office Action dated Mar. 27, 2023 in European Patent Application No. 19836036.4.
Office Action dated Mar. 29, 2023 in Chinese Patent Application No. 2020800144092.
Office Action dated Apr. 10, 2023 in Japanese Patent Application No. 2022-030956.
Office Action dated Apr. 14, 2023 in Chinese Patent Application No. 201980082680.7.
Office Action dated Apr. 24, 2023 in Japanese Patent Application No. 2020-561800.
Office Action dated Apr. 24, 2023 in European Patent Application No. 21714995.4.
Office Action dated Apr. 26, 2023 in European Patent Application No. 18703156.2.
Office Action dated May 16, 2023 in European Patent Application No. 21707112.5.
Office Action dated May 26, 2023 in Chinese Patent Application No. 2019800373421.
Office Action dated May 27, 2023 in Chinese Patent Application No. 2019800656859.
Office Action dated Jun. 1, 2023 in Japanese Patent Application No. 2020-561807.
Office Action dated Jun. 16, 2023 in Chinese Patent Application No. 2019800708938.
Office Action dated Jun. 22, 2023 in Japanese Patent Application No. 2022-071002.
Office Action dated Jun. 28, 2023 in European Patent Application 19836239.4.
Office Action dated Jul. 12, 2023 in Chinese Patent Application No. 2020800212600.
Office Action dated Jul. 12, 2023 in Canadian Patent Application No. 3,059,559.
Office Action Dated Jul. 13, 2023 in Chinese Patent Application No. 202080077712.7.
Office Action dated Jul. 28, 2023 in Chinese Patent Application No. 201880014793.9.
Office Action dated Aug. 21, 2023 in Japanese Patent Application No. 2021-507836.
O'Shea et al., "Analysis of T Cell Receptor Beta Chain CDR3 Size Using RNA Extracted from Formalin Fixed Paraffin Wax Embedded Tissue," Journal of Clinical Pathology 1997, 50(10), 811-814.
Restriction Requirement dated Dec. 23, 2022 in U.S. Appl. No. 17/531,618.
Restriction Requirement dated Jan. 20, 2023 in U.S. Appl. No. 17/373,519.
Restriction Requirement dated Feb. 27, 2023 in U.S. Appl. No. 17/151,058.
Restriction Requirement dated Apr. 4, 2023 in U.S. Appl. No. 17/161,558.
Restriction Requirement dated Jun. 28, 2023 in U.S. Appl. No. 17/336,055.
Uellendahl-Werth et al., "A benchmark of hemoglobin blocking during library preparation for mRNA Sequencing of human blood samples," Scientific Reports 2020, 10(1), 5630.
Wangsanuwat et al., "Efficient and cost-effective bacterial mRNA sequencing from low input samples through ribosomal RNA depletion," BMC Genomics 2020, 21(1), 1-12.
Wu & Lambowitz, "Facile single-stranded DNA sequencing of human plasma DNA via thermostable group II intron reverse transcriptase template switching," Scientific Reports 2017, 7(8421), 1-14.
Zheng, et al. "Aptamer-Functionalized Barcode Particles for the Capture and Detection of Multiple Types of Circulating Tumor Cells." Advanced materials (Weinheim), 2014, 26, 7333-7338.
Zhou and Rossi. "Aptamers as Targeted Therapeutics: Current Potential and Challenges." Nature reviews. Drug discovery, 2017, 16:181-202.
Zhulidov et al., "Simple cDNA normalization using kamchatka crab duplex-specific nuclease," Nucleic Acids Research. 2004, 32(3)e37.

\* cited by examiner

SINGLE CELL CHROMATIN IMMUNOPRECIPITATION SEQUENCING ASSAY

RELATED APPLICATIONS

The present application claims priority under 35 U.S.C. § 119(e) to U.S. Provisional Application No. 62/876,922, filed Jul. 22, 2019; and U.S. Provisional Application No. 63/049,980, filed Jul. 9, 2020. The entire contents of these applications are hereby expressly incorporated by reference in their entireties.

REFERENCE TO SEQUENCE LISTING

The present application is being filed along with a Sequence Listing in electronic format. The Sequence Listing is provided as a file entitled Sequence_Listing_68EB_298713_US, created on Jul. 20, 2020, which is 4 kilobytes in size. The information in the electronic format of the Sequence Listing is incorporated herein by reference in its entirety.

BACKGROUND

Field

The present disclosure relates generally to the field of molecular biology, for example labeling a nuclear target associated with DNA in a single cell.

Description of the Related Art

Current technology allows measurement of gene expression of single cells in a massively parallel manner (e.g., >10000 cells) by attaching cell specific oligonucleotide barcodes to poly(A) mRNA molecules from individual cells as each of the cells is co-localized with a barcoded reagent bead in a compartment. There is a need for systems and methods for labeling nuclear target-associated DNA in single cells.

SUMMARY

Disclosed herein include methods of labeling nuclear target-associated DNA in a cell. In some embodiments, the method comprises: permeabilizing a cell comprising a nuclear target associated with double-stranded deoxyribonucleic acid (dsDNA). The dsDNA can be a genomic DNA (gDNA). The method can comprise: contacting the nuclear target with a digestion composition comprising a DNA digestion enzyme and a binding reagent capable of specifically binding to the nuclear target to generate a plurality of nuclear target-associated dsDNA fragments (e.g., nuclear target-associated gDNA fragments) each comprising a single-stranded overhang, wherein each binding reagent comprises a binding reagent specific oligonucleotide comprising a unique identifier sequence for the binding reagent. The method can comprise: barcoding the plurality of nuclear target-associated dsDNA fragments, or products thereof, using a first plurality of oligonucleotide barcodes to generate a plurality of barcoded nuclear target-associated DNA fragments each comprising a sequence complementary to at least a portion of the nuclear target-associated dsDNA fragment, wherein each oligonucleotide barcode of the first plurality of oligonucleotide barcodes comprises a first target-binding region capable of hybridizing to the plurality of nuclear target-associated dsDNA fragments, or products thereof. The barcoded nuclear target-associated DNA fragments can be, for example, single-stranded or double-stranded. The method can comprise: barcoding the binding reagent specific oligonucleotides, or products thereof, using a second plurality of oligonucleotide barcodes to generate a plurality of barcoded binding reagent specific oligonucleotides each comprising a sequence complementary to at least a portion of the unique identifier sequence, wherein each oligonucleotide barcode of the second plurality of oligonucleotide barcodes comprises a second target-binding region capable of hybridizing to the binding reagent specific oligonucleotides, or products thereof.

In some embodiments, contacting the nuclear target with the digestion composition comprises contacting the digestion composition with the permeabilized cell. In some embodiments, contacting the nuclear target with the composition comprises the binding reagent and the DNA digestion enzyme entering the permeabilized cell and the binding reagent binding to the nuclear target. In some embodiments, the digestion composition comprises a fusion protein comprising the binding reagent and the digestion enzyme, optionally wherein the fusion protein is sized to diffuse through a nuclear pore of the cell. In some embodiments, the digestion composition comprises a conjugate comprising the binding reagent and the digestion enzyme, optionally wherein the conjugate is sized to diffuse through a nuclear pore of the cell. In some embodiments, the DNA digestion enzyme comprises a domain that is capable of specifically binding to the binding reagent. In some embodiments, the domain of the DNA digestion enzyme comprises at least one of protein A, protein G, protein A/G, or protein L. In some embodiments, the binding reagent and the DNA digestion enzyme are separate from each other when contacted with the permeabilized cell, and wherein the binding reagent and the DNA digestion enzyme separately enter the cell. In some embodiments, the DNA digestion enzyme binds the binding reagent within the nucleus of the cell. In some embodiments, the DNA digestion enzyme binds the binding reagent before entering the nucleus of the cell, and wherein the DNA digestion enzyme bound to the binding reagent is sized to diffuse through a nuclear pore of the cell. In some embodiments, the DNA digestion enzyme binds the binding reagent before the binding reagent binds the nuclear target. In some embodiments, the conjugate, the fusion protein, and/or the DNA digestion enzyme bound to the binding reagent has a diameter of no more than 120 nm.

In some embodiments, the first target binding region is complementary to at least a portion of the single-stranded overhang of the nuclear target-associated dsDNA fragment. In some embodiments, contacting the nuclear target with the digestion composition generates a complex comprising the binding reagent, the DNA digestion enzyme, and a nuclear target-associated dsDNA fragment, and wherein barcoding the plurality of nuclear target-associated dsDNA fragments comprises contacting said complex with the first and second pluralities of oligonucleotide barcodes, optionally comprising digesting the complex with a proteinase after barcoding, further optionally the proteinase comprises proteinase K. In some embodiments, the DNA digestion enzyme comprises a restriction enzyme, Mnase I, a transposase, functional fragments thereof, or any combination thereof, optionally the transposase comprises a Tn5 transposase, further optionally the digestion composition comprises at least one of a first adaptor having a first 5' overhang and a second adaptor having a second 5' overhang. In some embodiments, barcoding the binding reagent specific oligonucleotides, or products thereof, comprises extending the second plurality of oligonucleotide barcodes hybridized to the binding reagent specific oligonucleotides, or products thereof, optionally the binding reagent oligonucleotide comprises a sequence complementary to the second target-binding region. The method can comprise obtaining sequence data of the plurality of barcoded binding reagent specific oligonucleotides, or products thereof, optionally wherein obtaining sequence information of the plurality of barcoded binding reagent specific oligonucleotides, or products thereof, comprises attaching sequencing adaptors and/or sequencing primers complementary sequences thereof, and/or portions thereof, to the plurality of barcoded binding reagent specific oligonucleotides, or products thereof.

Disclosed herein include methods of labeling nuclear target-associated DNA in a cell. In some embodiments, the method comprises: permeabilizing a cell comprising a nuclear target associated with double-stranded deoxyribonucleic acid (dsDNA). The dsDNA can be a genomic DNA (gDNA). The method can comprise: contacting the nuclear target with a conjugate comprising a transposome and a binding reagent capable of specifically binding to the nuclear target to generate a plurality of nuclear target-associated dsDNA fragments each comprising a first 5' overhang and a second 5' overhang, wherein the transposome comprises a transposase, a first adaptor having the first 5' overhang, and a second adaptor having the second 5' overhang; and barcoding the plurality of nuclear target-associated dsDNA fragments, or products thereof, using a first plurality of oligonucleotide barcodes to generate a plurality of barcoded nuclear target-associated DNA fragments, wherein each oligonucleotide barcode of the first plurality of oligonucleotide barcodes comprises a first target-binding region capable of hybridizing to the plurality of nuclear target-associated dsDNA fragments, or products thereof. The barcoded nuclear target-associated DNA fragments can be, for example, single-stranded or double-stranded.

In some embodiments, barcoding the plurality of nuclear target-associated dsDNA fragments, or products thereof, comprises ligating the nuclear target-associated dsDNA fragments, or products thereof, to the first plurality of oligonucleotide barcodes. In some embodiments, barcoding the plurality of nuclear target-associated dsDNA fragments, or products thereof, comprises extending the first plurality of oligonucleotide barcodes hybridized to the plurality of nuclear target-associated dsDNA fragments, or products thereof. In some embodiments, the first adaptor comprises a first barcode sequence and the second adaptor comprises a second barcode sequence. In some embodiments, the first barcode sequence and/or the second barcode sequence identify the nuclear target. In some embodiments, the first 5' overhang and/or the second 5' overhang comprise a poly (dA) region, a poly(dT) region, or any combination thereof. In some embodiments, the first 5' overhang and/or the second 5' overhang comprise a sequence complementary to the first target-binding region, or a complement thereof. In some embodiments, the first target-binding region comprises a sequence that is complementary to at least a portion of a 5' region, a 3' region, or an internal region of a nuclear target-associated dsDNA fragment. In some embodiments, the first adaptor and/or the second adaptor comprises a DNA end sequence of the transposon.

In some embodiments, the permeabilizing comprises chemical or physical permeabilization. In some embodiments, the permeabilizing comprises contacting the cell with a detergent and/or a surfactant. In some embodiments, the permeabilizing comprises permeabilizing the cell by sonification. The method can comprise: permeabilizing a nucleus in the cell to generate a permeabilized nucleus. The method can comprise: fixating the cell comprising the nucleus prior to permeabilizing the nucleus.

In some embodiments, the nuclear target comprises a methylated nucleotide, a DNA-associated protein, a chromatin-associated protein, or any combination thereof. In some embodiments, the nuclear target comprises ALC1, androgen receptor, Bmi-1, BRD4, Brg1, coREST, C-jun, c-Myc, CTCF, EED, EZH2, Fos, histone H, histone H3, histone H4, heterochromatin protein-1γ, heterochromatin protein-1, HMGN2/HMG-17, HP1α, HP1γ, hTERT, Jun, KLF4, K-Ras, Max, MeCP2, MLL/HRX, NPAT, p300, Nanog, NFAT-1, Oct4, P53, Pol II (8WG16), RNA Pol II Ser2P, RNA Pol II Ser5P, RNA Pol II Ser2+5P, RNA Pol II Ser7P, Rb, RNA polymerase II, SMCI, Sox2, STAT1, STAT2, STAT3, Suz12, Tip60, UTF1, or any combination thereof. In some embodiments, the binding reagent specifically binds to an epitope comprising a methylated (me), phosphorylated (ph), ubiquitylated (ub), sumoylated (su), biotinylated (bi), or acetylated (ac) histone residue, selected from the group consisting of H1S27ph, H1K25mel, H1K25me2, H1K25me3, H1K26me, H2(A)K4ac, H2(A) K5ac, H2(A)K7ac, H2(A)S1ph, H2(A)T119ph, H2(A) S122ph, H2(A)S129ph, H2(A)S139ph, H2(A)K119ub, H2(A)K126su, H2(A)K9bi, H2(A)K13bi, H2(B)K5ac, H2(B)K11ac, H2(B)K12ac, H2(B)K15ac, H2(B)K16ac, H2(B)K20ac, H2(B)S10ph, H2(B)S14ph, H2(B)33ph, H2(B)K120ub, H2(B)K123ub, H3K4ac, H3K9ac, H3K14ac, H3K18ac, H3K23ac, H3K27ac, H3K56ac, H3K4mel, H3K4me2, H3K4me3, H3R8me, H3K9mel, H3K9me2, H3K9me3, H3R17me, H3K27mel, H3K27me2, H3K27me3, H3K36me, H3K79mel, H3K79me2, H3K79me3, H3K122ac, H3T3ph, H3S10ph, H3T11ph, H3S28ph, H3K4bi, H3K9bi, H3K18bi, H4K5ac, H4K8ac, H4K12ac, H4K16ac, H4K91ac, H4R3me, H4K20me, H4K59me, H4S1ph, H4K12bi, and H4 n-terminal tail ubiquitylated, or any combination thereof.

In some embodiments, the binding reagent comprises a tetramer, an aptamer, a protein scaffold, or any a combination thereof. In some embodiments, the binding reagent comprises an antibody or fragment thereof. In some embodiments, the antibody or fragment thereof comprises a monoclonal antibody. In some embodiments, the antibody or fragment thereof comprises a Fab, a Fab', a F(ab')$_2$, a Fv, a scFv, a dsFv, a diabody, a triabody, a tetrabody, a multispecific antibody formed from antibody fragments, a single-domain antibody (sdAb), a single chain comprising complementary scFvs (tandem scFvs) or bispecific tandem scFvs, an Fv construct, a disulfide-linked Fv, a dual variable domain immunoglobulin (DVD-Ig) binding protein or a nanobody, an aptamer, an affibody, an affilin, an affitin, an affimer, an alphabody, an anticalin, an avimer, a DARPin, a Fynomer, a Kunitz domain peptide, a monobody, or any combination thereof. In some embodiments, the binding reagent is conjugated to the transposome via chemical coupling, genetic fusion, noncovalent association, or any combination thereof. In some embodiments, the conjugate is formed by a 1,3-dipolar cycloaddition reaction, a hetero-Diels-Alder reaction, a nucleophilic substitution reaction, a non-aldol type carbonyl reaction, an addition to carbon-carbon multiple bond, an oxidation reaction, a click reaction, or any combination thereof. In some embodiments, the conjugate is formed by a reaction between acetylene and azide. In some embodiments, the conjugate is formed by a reaction between an aldehyde or ketone group and a hydrazine or alkoxy amine. In some embodiments, the binding reagent is conjugated to the transposome via at least one of protein A, protein G, protein A/G, or protein L. In some embodiments, the transposase comprises a Tn5 transposase. In some embodiments, the transposome comprises a domain that specifically binds the binding reagent, wherein the binding reagent and the transposome are separate from each other when contacted with the permeabilized cell, and separately enter the cell, and wherein the transposome binds to the binding reagent within the nucleus of the cell. In some embodiments, the transposome is bound to the binding reagent before entering the permeabilized cell, and wherein the transposome bound to the binding reagent is sized to enter the nucleus of the cell through a nuclear pore. In some embodiments, the conjugate has a diameter of no more than 120 nm. In some embodiments, the binding reagent and the transposome are each sized to diffuse through a nuclear pore of the cell. In some embodiments, the permeabilized cell comprises an intact nucleus comprising chromatin that remains associated with genomic DNA at the time of the binding the binding reagent to the nuclear target. In some embodiments, the binding of the binding reagent to the nuclear target occurs in the nucleus of the permeabilized cell.

The method can comprise: obtaining sequence data of the plurality of barcoded nuclear target-associated DNA fragments, or products thereof. The method can comprise: determining information relating to the gDNA based on the sequences of the plurality of barcoded nuclear target-associated DNA fragments, or products thereof, in the sequencing data obtained. In some embodiments, determining the information relating to the gDNA comprises determining genome information of the gDNA based on the sequences of the plurality of barcoded nuclear target-associated DNA fragments in the sequencing data obtained. The method can comprise: digesting nucleosomes associated with the double-stranded gDNA. In some embodiments, determining the genome information of the gDNA comprises: determining at least a partial sequence of the gDNA by aligning the sequences of the plurality of barcoded nuclear target-associated DNA fragments to a reference sequence of the gDNA. In some embodiments, determining the information relating to the gDNA comprises determining methylome information of the gDNA based on the sequences of the plurality of barcoded nuclear target-associated DNA fragments in the sequencing data obtained. The method can comprise: digesting nucleosomes associated with the double-stranded gDNA. The method can comprise: performing chemical conversion and/or enzymatic conversion of cytosine bases of the plurality of nuclear target-associated dsDNA fragments, or products thereof, to generate a plurality of converted (e.g., bisulfite-converted) nuclear target-associated dsDNA fragments with uracil bases. In some embodiments, barcoding the plurality of nuclear target-associated dsDNA fragments, or products thereof, comprises barcoding the plurality of converted (e.g., bisulfite-converted) nuclear target-associated dsDNA fragments, or products thereof. Chemical conversion can comprise bisulfite treatment and enzymatic conversion can comprise APOBEC-mediated conversion. In some embodiments, determining the methylome information comprises: determining a position of the plurality of barcoded nuclear target-associated DNA fragments in the sequencing data has a thymine base and the corresponding position in a reference sequence of the gDNA has a cytosine base to determine the corresponding position in the gDNA has a 5-methylcytosine (5mC) base and/or 5-hydroxymethylcytosine (5hmC) base. The method can comprise: Hi-C, Chromatin Conformation Capture (3C), Circularized Chromatin Conformation Capture (4C), Carbon Copy Chromosome Conformation Capture (5C), Chromatin Immunoprecipitation (ChIP), ChIP-Loop, combined 3C-ChIP-cloning (6C), Capture-C, or any combination thereof. The method can comprise Hi-C/ChIP-seq. The method can comprise ChiP-seq.

In some embodiments, the cell comprises copies of a nucleic acid target. The method can comprise: contacting a second plurality of oligonucleotide barcodes with the copies of the nucleic acid target for hybridization; extending the second plurality of oligonucleotide barcodes hybridized to the copies of a nucleic acid target to generate a plurality of barcoded nucleic acid molecules each comprising a sequence complementary to at least a portion of the nucleic acid target and a molecular label; and obtaining sequence information of the plurality of barcoded nucleic acid molecules, or products thereof, to determine the copy number of the nucleic acid target in the cell. In some embodiments, extending the first and/or second plurality of oligonucleotide barcodes comprising extending the plurality of oligonucleotide barcodes using a reverse transcriptase and/or a DNA polymerase lacking at least one of 5' to 3' exonuclease activity and 3' to 5' exonuclease activity. In some embodiments, the DNA polymerase comprises a Klenow Fragment. In some embodiments, the reverse transcriptase comprises a viral reverse transcriptase, optionally wherein the viral reverse transcriptase is a murine leukemia virus (MLV) reverse transcriptase or a Moloney murine leukemia virus (MMLV) reverse transcriptase. In some embodiments, the nucleic acid target comprises a nucleic acid molecule. In some embodiments, the nucleic acid molecule comprises ribonucleic acid (RNA), messenger RNA (mRNA), microRNA, small interfering RNA (siRNA), RNA degradation product, RNA comprising a poly(A) tail, a sample indexing oligonucleotide, a cellular component-binding reagent specific oligonucleotide, or any combination thereof. In some embodiments, the first target-binding region and/or the second target-binding region comprises a poly(dA) region, a poly(dT) region, a random sequence, a gene-specific sequence, or any combination thereof.

In some embodiments, obtaining sequence information of the plurality of barcoded nuclear target-associated DNA fragments comprises attaching sequencing adaptors and/or sequencing primers complementary sequences thereof, and/or portions thereof, to the plurality of barcoded nuclear target-associated DNA fragments, or products thereof. In some embodiments, obtaining sequence information of the plurality of barcoded nucleic acid molecules comprises attaching sequencing adaptors and/or sequencing primers complementary sequences thereof, and/or portions thereof, to the plurality of barcoded nucleic acid molecules, or products thereof. In some embodiments, each oligonucleotide barcode of the first plurality of oligonucleotide barcodes comprises a first universal sequence, and wherein each oligonucleotide barcode of the second plurality of oligonucleotide barcodes comprises a second universal sequence. In some embodiments, the first universal sequence and the second universal sequence are the same. In some embodiments, the first universal sequence and the second universal sequence are different. In some embodiments, the first universal sequence and/or the second universal sequence comprise the binding sites of sequencing primers and/or sequencing adaptors, complementary sequences thereof, and/or portions thereof. In some embodiments, the sequencing adaptors comprise a P5 sequence, a P7 sequence, complementary sequences thereof, and/or portions thereof.

In some embodiments, the sequencing primers comprise a Read 1 sequencing primer, a Read 2 sequencing primer, complementary sequences thereof, and/or portions thereof. In some embodiments, the first and second pluralities of oligonucleotide barcodes each comprise a molecular label. In some embodiments, at least 10 of the first and second pluralities of oligonucleotide barcodes comprise different molecular label sequences. In some embodiments, each molecular label of the first and second pluralities of oligonucleotide barcodes comprises at least 6 nucleotides. In some embodiments, the first and second pluralities of oligonucleotide barcodes are associated with a solid support. In some embodiments, the first and second pluralities of oligonucleotide barcodes associated with the same solid support each comprise an identical sample label. In some embodiments, each sample label of the first and second pluralities of oligonucleotide barcodes comprises at least 6 nucleotides. In some embodiments, the first and second pluralities of oligonucleotide barcodes each comprise a cell label. In some embodiments, each cell label of the first and second pluralities of oligonucleotide barcodes comprises at least 6 nucleotides. In some embodiments, oligonucleotide barcodes of the first and second pluralities of oligonucleotide barcodes associated with the same solid support comprise the same cell label. In some embodiments, oligonucleotide barcodes of the first and second pluralities of oligonucleotide barcodes associated with different solid supports comprise different cell labels.

In some embodiments, the solid support comprises a synthetic particle, a planar surface, or a combination thereof. The method can comprise: associating a synthetic particle comprising the first and second pluralities of oligonucleotide barcodes with the cell. The method can comprise: lysing the cell after associating the synthetic particle with the cell, optionally lysing the cell comprises heating the cell, contacting the cell with a detergent, changing the pH of the cell, or any combination thereof. In some embodiments, the synthetic particle and the single cell are in the same partition, and optionally the partition is a well or a droplet. In some embodiments, at least one oligonucleotide barcode of the first and second pluralities of oligonucleotide barcodes is immobilized or partially immobilized on the synthetic particle, or at least one oligonucleotide barcode of the first and second pluralities of oligonucleotide barcodes is enclosed or partially enclosed in the synthetic particle. In some embodiments, the synthetic particle is disruptable, optionally a disruptable hydrogel particle. In some embodiments, the synthetic particle comprises a bead, optionally the bead comprises a sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. In some embodiments, the synthetic particle comprises a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, sepharose, cellulose, nylon, silicone, and any combination thereof. In some embodiments, each oligonucleotide barcode of the first and second pluralities of oligonucleotide barcodes comprises a linker functional group. In some embodiments, the synthetic particle comprises a solid support functional group. In some embodiments, the support functional group and the linker functional group are associated with each other, and optionally the linker functional group and the support functional group are individually selected from the group consisting of C6, biotin, streptavidin, primary amine(s), aldehyde(s), ketone(s), and any combination thereof.

Disclosed herein include kits. The kit can comprise a digestion composition comprising a DNA digestion enzyme and a binding reagent capable of specifically binding to the nuclear target, wherein the binding reagent comprises a binding reagent specific oligonucleotide comprising a unique identifier sequence for the binding reagent.

In some embodiments, the DNA digestion enzyme comprises a restriction enzyme, Mnase I, a transposase, functional fragments thereof, or any combination thereof, optionally the transposase comprises a Tn5 transposase, further optionally the digestion composition comprises at least one of a first adaptor having a first 5' overhang and a second adaptor having a second 5' overhang. In some embodiments, the digestion composition comprises a fusion protein comprising the binding reagent and the digestion enzyme, optionally wherein the fusion protein is sized to diffuse through a nuclear pore of a cell. In some embodiments, the digestion composition comprises a conjugate comprising the binding reagent and the digestion enzyme, optionally wherein the conjugate is sized to diffuse through a nuclear pore of a cell. In some embodiments, the DNA digestion enzyme comprises a domain that is capable of specifically binding to the binding reagent, optionally the domain of the DNA digestion enzyme comprises at least one of protein A, protein G, protein A/G, or protein L, further optionally the DNA digestion enzyme bound to the binding reagent is sized to diffuse through a nuclear pore of a cell. The kit can comprise: a proteinase (e.g., proteinase K).

Disclosed herein include kits. In some embodiments, the kit comprises: a conjugate comprising a transposome and a binding reagent capable of specifically binding to a nuclear target, wherein the transposome comprises a transposase, a first adaptor having a first 5' overhang, and a second adaptor having a second 5' overhang. The kit can comprise: a DNA polymerase lacking at least one of 5' to 3' exonuclease activity and 3' to 5' exonuclease activity, optionally wherein the DNA polymerase comprises a Klenow Fragment. The kit can comprise: a reverse transcriptase, optionally wherein the reverse transcriptase comprises a viral reverse transcriptase, and optionally the viral reverse transcriptase is a murine leukemia virus (MLV) reverse transcriptase or a Moloney murine leukemia virus (MMLV) reverse transcriptase. The kit can comprise: a ligase. The kit can comprise: a detergent and/or a surfactant. The kit can comprise: a buffer, a cartridge, or both. The kit can comprise: one or more reagents for a reverse transcription reaction and/or an amplification reaction.

In some embodiments, the nuclear target comprises a DNA-associated protein or chromatin-associated protein. In some embodiments, the nuclear target comprise a methylated nucleotide. In some embodiments, the nuclear target comprises ALC1, androgen receptor, Bmi-1, BRD4, Brg1, coREST, C-jun, c-Myc, CTCF, EED, EZH2, Fos, histone H1, histone H3, histone H4, heterochromatin protein-1γ, heterochromatin protein-1β, HMGN2/HMG-17, HP1α, HPγ, hTERT, Jun, KLF4, K-Ras, Max, MeCP2, MLL/HRX, NPAT, p300, Nanog, NFAT-1, Oct4, P53, Pol II (8WG16), RNA Pol II Ser2P, RNA Pol II Ser5P, RNA Pol II Ser2+5P, RNA Pol II Ser7P, Rb, RNA polymerase II, SMCI, Sox2, STAT1, STAT2, STAT3, Suz12, Tip60, UTF1, or any combination thereof. In some embodiments, the binding reagent specifically binds to an epitope comprising a methylated (me), phosphorylated (ph), ubiquitylated (ub), sumoylated (su), biotinylated (bi), or acetylated (ac) histone residue, selected from the group consisting of H1S27ph, H1K25me1, H1K25me2, H1K25me3, H1K26me, H2(A)K4ac, H2(A) K5ac, H2(A)K7ac, H2(A)S1ph, H2(A)T119ph, H2(A) S122ph, H2(A)S129ph, H2(A)S139ph, H2(A)K119ub, H2(A)K126su, H2(A)K9bi, H2(A)K13bi, H2(B)K5ac, H2(B)K11ac, H2(B)K12ac, H2(B)K15ac, H2(B)K16ac, H2(B)K20ac, H2(B)S10ph, H2(B)S14ph, H2(B)33ph, H2(B)K120ub, H2(B)K123ub, H3K4ac, H3K9ac, H3K14ac, H3K18ac, H3K23ac, H3K27ac, H3K56ac, H3K4me1, H3K4me2, H3K4me3, H3R8me, H3K9me1, H3K9me2, H3K9me3, H3R17me, H3K27me1, H3K27me2, H3K27me3, H3K36me, H3K79me1, H3K79me2, H3K79me3, H3K122ac, H3T3ph, H3S10ph, H3T11ph, H3S28ph, H3K4bi, H3K9bi, H3K18bi, H4K5ac, H4K8ac, H4K12ac, H4K16ac, H4K91ac, H4R3me, H4K20me, H4K59me, H4S1ph, H4K12bi, and H4 n-terminal tail ubiquitylated, or any combination thereof. In some embodiments, the binding reagent comprises a tetramer, an aptamer, a protein scaffold, or any a combination thereof. In some embodiments, the binding reagent comprises an antibody or fragment thereof. In some embodiments, the antibody or fragment thereof comprises a monoclonal antibody. In some embodiments, the antibody or fragment thereof comprises a Fab, a Fab', a F(ab')$_2$, a Fv, a scFv, a dsFv, a diabody, a triabody, a tetrabody, a multispecific antibody formed from antibody fragments, a single-domain antibody (sdAb), a single chain comprising complementary scFvs (tandem scFvs) or bispecific tandem scFvs, an Fv construct, a disulfide-linked Fv, a dual variable domain immunoglobulin (DVD-Ig) binding protein or a nanobody, an aptamer, an affibody, an affilin, an affitin, an affimer, an alphabody, an anticalin, an avimer, a DARPin, a Fynomer, a Kunitz domain peptide, a monobody, or any combination thereof. In some embodiments, the binding reagent is conjugated to the transposome via chemical coupling, genetic fusion, noncovalent association, or any combination thereof.

In some embodiments, the conjugate is formed by a 1,3-dipolar cycloaddition reaction, a hetero-Diels-Alder reaction, a nucleophilic substitution reaction, a non-aldol type carbonyl reaction, an addition to carbon-carbon multiple bond, an oxidation reaction, a click reaction, or any combination thereof. In some embodiments, the conjugate is formed by a reaction between acetylene and azide. In some embodiments, the conjugate is formed by a reaction between an aldehyde or ketone group and a hydrazine or alkoxy amine. In some embodiments, the binding reagent is conjugated to the transposome via at least one of protein A, protein G, protein A/G, or protein L. In some embodiments, the transposase comprises a Tn5 transposase. In some embodiments, the conjugate has a diameter of no more than 120 nm. In some embodiments, the binding reagent and the transposome are each sized to diffuse through a nuclear pore.

The kit can comprise: a plurality of oligonucleotide barcodes. In some embodiments, each of the plurality of oligonucleotide barcodes comprises a molecular label and a target-binding region. In some embodiments, at least 10 of the plurality of oligonucleotide barcodes comprise different molecular label sequences. In some embodiments, the target-binding region comprises a gene-specific sequence, an oligo(dT) sequence, a random multimer, or any combination thereof. Oligonucleotide barcodes of the first and/or second pluralities of oligonucleotide barcodes can comprise a target-binding region (e.g., a first target-binding region) capable of hybridizing (e.g., complementary to) the plurality of nuclear target-associated dsDNA fragments, or products thereof, such as, for example, 5' and/or 3' overhangs (e.g., a 5' overhang of a first adaptor, a 5' overhang of a second adaptor). In some embodiments, the oligonucleotide barcode comprises an identical sample label and/or an identical cell label. In some embodiments, each sample label and/or cell label of the plurality of oligonucleotide barcodes comprise at least 6 nucleotides. In some embodiments, each molecular label of the plurality of oligonucleotide barcodes comprises at least 6 nucleotides.

In some embodiments, at least one of the plurality of oligonucleotide barcodes is partially immobilized on the synthetic particle. In some embodiments, at least one of the plurality of oligonucleotide barcodes is immobilized or partially immobilized on the synthetic particle; and/or the at least one of the plurality of oligonucleotide barcodes is enclosed or partially enclosed in the synthetic particle. In some embodiments, the synthetic particle comprises a bead. In some embodiments, the bead comprises a sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. In some embodiments, the synthetic particle comprises a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, sepharose, cellulose, nylon, silicone, and any combination thereof. In some embodiments, each of the plurality of oligonucleotide barcodes comprises a linker functional group. In some embodiments, the synthetic particle comprises a solid support functional group. In some embodiments, the support functional group and the linker functional group are associated with each other. In some embodiments, the linker functional group and the support functional group are individually selected from the group consisting of C6, biotin, streptavidin, primary amine(s), aldehyde(s), ketone(s), and any combination thereof.

In some embodiments, a kit is described. The kit can comprise a binding reagent (e.g., protein binding reagent) associated with a reagent oligonucleotide comprising a unique identifier for the protein binding reagent, in which the protein binding reagent specifically binds a target protein. The kit can comprise a fusion protein comprising a DNA digestion enzyme, in which (i) the fusion protein comprises a domain that specifically binds the protein binding reagent, or (ii) the fusion protein is bound to the protein binding reagent. The kit can comprise a first oligonucleotide probe comprising a first target binding region and a sample identifier sequence, wherein the first target binding region is complementary to at least a portion of the reagent oligonucleotide associated with the protein binding reagent. The kit can comprise a second oligonucleotide probe comprising a second target binding region and a sample identifier sequence, wherein the second target binding region is complementary to at least a portion of the DNA. In some embodiments, for any of the kits described herein, the target protein comprises a DNA-associated protein or chromatin-associated protein. In some embodiments, for any of the kits described herein, the target protein is selected from the group consisting of: ALC1, androgen receptor, Bmi-1, BRD4, Brg1, coREST, C-jun, c-Myc, CTCF, EED, EZH2, Fos, histone H1, histone H3, histone H4, heterochromatin protein-1γ, heterochromatin protein-1, HMGN2/HMG-17, HP1α, HP1γ, hTERT, Jun, KLF4, K-Ras, Max, MeCP2, MLL/HRX, NPAT, p300, Nanog, NFAT-1, Oct4, P53, Pol II (8WG16), RNA Pol II Ser2P, RNA Pol II Ser5P, RNA Pol II Ser2+5P, RNA Pol II Ser7P, Rb, RNA polymerase II, SMCI, Sox2, STAT1, STAT2, STAT3, Suz12, Tip60, UTF1, H1S27ph, H1K25mel, H1K25me2, H1K25me3, H1K26me, H2(A)K4ac, H2(A)K5ac, H2(A)K7ac, H2(A)S1ph, H2(A) T119ph, H2(A)S122ph, H2(A)S129ph, H2(A)S139ph, H2(A)K119ub, H2(A)K126su, H2(A)K9bi, H2(A)K13bi, H2(B)K5ac, H2(B)K11ac, H2(B)K12ac, H2(B)K15ac, H2(B)K16ac, H2(B)K20ac, H2(B)S10ph, H2(B)S14ph, H2(B)33ph, H2(B)K120ub, H2(B)K123ub, H3K4ac, H3K9ac, H3K14ac, H3K18ac, H3K23ac, H3K27ac, H3K56ac, H3K4mel, H3K4me2, H3K4me3, H3R8me, H3K9mel, H3K9me2, H3K9me3, H3R17me, H3K27mel, H3K27me2, H3K27me3, H3K36me, H3K79mel, H3K79me2, H3K79me3, H3K122ac, H3T3ph, H3S10ph, H3T1ph, H3S28ph, H3K4bi, H3K9bi, H3K18bi, H4K5ac, H4K8ac, H4K12ac, H4K16ac, H4K91ac, H4R3me, H4K20me, H4K59me, H4S1ph, H4K12bi, and H4 n-terminal tail ubiquitylated, or a combination of two or more of the listed items. In some embodiments, for any of the kits described herein, the first and second oligonucleotide probe comprise the same sample identifier sequence. In some embodiments, for any of the kits described herein, the first and second oligonucleotide probe are immobilized on a substrate. In some embodiments, for any of the kits described herein, the substrate is a solid surface, a bead, a microarray, a plate, a tube, or a well. In some embodiments, for any of the kits described herein, the kit further comprises a composition comprising a reagent for generating a nucleic acid library, wherein the reagent comprises at least one of DNA restriction enzymes, nucleases (such as micrococcal nuclease), lysozyme, proteinase K, random hexamers, polymerase (Φ29 DNA polymerase, Taq polymerase, Bsu polymerase, Klenow polymerase), transposase (Tn5), primers (P5 and P7 adaptor sequences), ligase, catalyzing enzyme, deoxynucleotide triphosphates, buffers, or divalent cations.

In some embodiments, a method of labeling target-protein-associated DNA of a single cell is described. The method can comprise permeabilizing a cell comprising a target protein. The method can comprise contacting the permeabilized cell with a digestion composition comprising a binding reagent (e.g., protein binding reagent) associated with a reagent oligonucleotide comprising a unique identifier for the protein binding reagent in which the protein binding reagent specifically binds the target protein. The digestion composition can comprise a DNA digestion enzyme and a binding reagent capable of specifically binding to the nuclear target (e.g., nuclear protein). The composition can also comprise a fusion protein comprising a DNA digestion enzyme, in which (i) the fusion protein further comprises a domain that specifically binds the protein binding reagent or (ii) the fusion protein is bound to the protein binding reagent. The protein binding reagent and the fusion protein can enter the permeabilized cell. The method can comprise contacting the target protein of the permeabilized cell with the protein binding reagent and the fusion protein bound to the protein binding reagent. The method can comprise binding the binding reagent (e.g., protein binding reagent) to the target protein in the cell, wherein a DNA of the cell is associated with the target protein. The method can comprise digesting the DNA associated with the target protein with the DNA digestion enzyme of the fusion protein, the digested DNA comprising a single-stranded overhang, thus forming a complex comprising: the protein binding reagent; the fusion protein; and the digested DNA. The method can comprise contacting the complex with a first oligonucleotide probe comprising a first target binding region and a sample identifier sequence, wherein the first target binding region is complementary to at least a portion of the reagent oligonucleotide; and a second oligonucleotide probe comprising a second target binding region and the sample identifier sequence. The second target binding region can be complementary to at least a portion of the single-stranded overhang of the DNA. The first oligonucleotide probe and second oligonucleotide probe can comprise the same sample identifier sequence. The method can comprise extending the oligonucleotide probes to produce a plurality of labeled nucleic acids comprising the sample identifier sequence and the reverse-complement of at least a portion of the reagent oligonucleotide or at least a portion of the DNA. In some embodiments, for any method described herein, (i) the fusion protein comprises the domain that specifically binds the protein binding reagent, wherein the protein binding reagent and the fusion protein are separate from each other when contacted with the permeabilized cell, and separately enter the cell, and wherein the fusion protein binds to the protein binding reagent within the nucleus of the cell. In some embodiments, for any method described herein, the domain of the fusion protein comprises at least one of protein A, protein G, protein A/G, or protein L. In some embodiments, for any method described herein, (ii) the fusion protein is bound to the protein binding reagent, and the fusion protein bound to the protein binding reagent is sized to enter the nucleus of the cell through a nuclear pore. In some embodiments, for any method described herein, the method further comprises multiplex construction comprising the use of two or more different protein binding reagents that each have a specificity to a different target protein. In some embodiments, for any method described herein, the fusion protein bound to the protein binding reagent has a diameter of no more than 120 nm. In some embodiments, for any method described herein, the protein binding reagent and the fusion protein are each sized to diffuse through a nuclear pore of the cell. In some embodiments, for any method described herein, the first and second oligonucleotide probe are immobilized on a substrate. In some embodiments, for any method described herein, the substrate comprises at least one of a bead, a microarray, a plate, a tube, or a well. In some embodiments, for any method described herein, the method further comprises capturing the complex on the substrate. In some embodiments, for any method described herein, the first oligonucleotide probe comprises a first barcode sequence, and the second oligonucleotide probe comprises a second barcode sequence. The first and second barcode sequence each can be from a diverse set of unique barcode sequences. In some embodiments, for any method described herein, the permeabilized cell comprises an intact nucleus comprising chromatin that remains associated with genomic DNA at the time of binding the protein binding reagent to the target protein. In some embodiments, for any method described herein, the protein binding reagent comprises an antibody that specifically binds the target protein. In some embodiments, for any method described herein, binding the protein binding reagent to the target protein and digesting the DNA associated with the target protein occur in the nucleus of the cell. In some embodiments, for any method described herein, the target protein is selected from the group consisting of: ALC1, androgen receptor, Bmi-1, BRD4, Brg1, coREST, C-jun, c-Myc, CTCF, EED, EZH2, Fos, histone H1, histone H3, histone H4, heterochromatin protein-1γ, heterochromatin protein-1β, HMGN2/HMG-17, HP1α, HP1γ, hTERT, Jun, KLF4, K-Ras, Max, MeCP2, MLL/HRX, NPAT, p300, Nanog, NFAT-1, Oct4, P53, Pol II (8WG16), RNA Pol II Ser2P, RNA Pol II Ser5P, RNA Pol II Ser2+5P, RNA Pol II Ser7P, Rb, RNA polymerase II, SMCI, Sox2, STAT1, STAT2, STAT3, Suz12, Tip60, and UTF1, or a combination of two or more of the listed items. In some embodiments, for any method described herein, the protein binding reagent binds specifically to an epitope comprising, consisting essentially of, or consisting of a phosphorylated (ph), methylated (me), ubiquitylated (ub), sumoylated (su), biotinylated (bi), or acetylated (ac) histone residue selected from the group consisting of H1S27ph, H1K25mel, H1K25me2, H1K25me3, H1K26me, H2(A)K4ac, H2(A)K5ac, H2(A)K7ac, H2(A)S1ph, H2(A)T119ph, H2(A)S122ph, H2(A)K7ac, H2(A)S139ph, H2(A)K119ub, H2(A)K126su, H2(A)K9bi, H2(A)K13bi, H2(B)K5ac, H2(B)K11ac, H2(B)K12ac, H2(B)K15ac, H2(B)K16ac, H2(B)K20ac, H2(B)S10ph, H2(B)S14ph, H2(B)33ph, H2(B)K120ub, H2(B)K123ub, H3K4ac, H3K9ac, H3K14ac, H3K18ac, H3K23ac, H3K27ac, H3K56ac, H3K4mel, H3K4me2, H3K4me3, H3R8me, H3K9mel, H3K9me2, H3K9me3, H3R17me, H3K27mel, H3K27me2, H3K27me3, H3K36me, H3K79mel, H3K79me2, H3K79me3, H3K122ac, H3T3ph, H3S10ph, H3T11ph, H3S28ph, H3K4bi, H3K9bi, H3K18bi, H4K5ac, H4K8ac, H4K12ac, H4K16ac, H4K91ac, H4R3me, H4K20me, H4K59me, H4S1ph, H4K12bi, and H4 n-terminal tail ubiquitylated, or a combination of two or more of the listed items. In some embodiments, for any method described herein, permeabilizing comprises chemical or physical permeabilization. In some embodiments, for any method described herein, the method further comprises permeabilizing the cell by contacting the cell with a detergent or a surfactant, such as guanidine hydrochloride, Triton X, digitonin, or combinations thereof. In some embodiments, for any method described herein, the method further comprises permeabilizing the cell by sonification. In some embodiments, for any method described herein, the DNA digestion enzyme comprises a restriction enzyme, Mnase I, or a transposase (e.g., Tn5 transposase) or a functional fragment thereof. The transposase can be a Tn transposase (e.g., Tn3, Tn5, Tn7, Tn10, Tn552, Tn903), a MuA transposase, a Vibhar transposase (e.g., from *Vibrio harveyi*), Ac-Ds, Ascot-1, Bs1, Cin4, Copia, En/Spm, F element, hobo, Hsmarl, Hsmar2, IN (HIV), IS1, IS2, IS3, IS4, IS5, IS6, IS10, IS21, IS30, IS50, IS51, IS150, IS256, IS407, IS427, IS630, IS903, IS911, IS982, IS1031, ISL2, L1, Mariner, P element, Tam3, Tc, Tc3, Tel, THE-1, Tn/O, TnA, Tn3, Tn5, Tn7, Tn10, Tn552, Tn903, Toll, Tol2, Tn10, Ty1, any prokaryotic transposase, or any transposase related to and/or derived from those listed above. In some embodiments, a transposase related to and/or derived from a parent transposase can comprise a peptide fragment with at least about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% amino acid sequence homology to a corresponding peptide fragment of the parent transposase. The peptide fragment can be at least about 10, about 15, about 20, about 25, about 30, about 35, about 40, about 45, about 50, about 60, about 70, about 80, about 90, about 100, about 150, about 200, about 250, about 300, about 400, or about 500 amino acids in length. For example, a transposase derived from Tn5 can comprise a peptide fragment that is 50 amino acids in length and about 80% homologous to a corresponding fragment in a parent Tn5 transposase. In some cases, the insertion can be facilitated and/or triggered by addition of one or more cations. The cations can be divalent cations such as, for example, $Ca^{2+}$, $Mg^{2+}$ and $Mn^{2+}$. In some embodiments, for any method described herein, digesting the DNA is performed in the nucleus of the permeabilized cell. In some embodiments, for any method described herein, the first target binding region of the first oligonucleotide probe comprises a polyT sequence, and the reagent oligonucleotide comprises a polyA sequence. In some embodiments, for any method described herein, the first target binding region of the first oligonucleotide probe does not comprise five consecutive thymidines, and the reagent oligonucleotide comprises a sequence complementary to the first target binding region of the first oligonucleotide probe. In some embodiments, for any method described herein, the second target binding region of the second oligonucleotide probe comprises a sequence that is complementary to at least a portion of a 5' region, a 3' region, or an internal region of the DNA. In some embodiments, for any method described herein, the method further comprises ligating the second target binding region to the digested DNA. In some embodiments, for any method described herein, the method further comprises using reverse transcriptase to create a target-barcode conjugate, for example if the reagent oligonucleotide comprises single-stranded DNA, or an RNA. In some embodiments, for any method described herein, the method further comprises generating a nucleic acid library comprising labeled nucleic acids of the plurality. In some embodiments, for any method described herein, generating the nucleic acid library comprises contacting with a reagent comprising enzymes, chemicals, or primers. In some embodiments, for any method described herein, the reagent comprises at least one of DNA restriction enzymes, nucleases (such as micrococcal nuclease), lysozyme, proteinase K, random hexamers, polymerase (Φ29 DNA polymerase, Taq polymerase, Bsu polymerase, Klenow polymerase), transposase (Tn5), primers (P5 and P7 adaptor sequences), ligase, catalyzing enzyme, deoxynucleotide triphosphates, buffers, or divalent cations. In some embodiments, for any method described herein, the method further comprises digesting the protein binding reagent, the fusion protein, and the target protein with a proteinase after said extending. In some embodiments, for any method described herein, the proteinase comprises proteinase K. In some embodiments, for any method described herein, the method further comprises ligating a double stranded DNA (dsDNA) template to the second oligonucleotide probe. The dsDNA template can comprise a template strand and a complementary strand. In some embodiments, for any method described herein, the template strand comprises a template switching oligonucleotide and a unique capture sequence, and the complementary strand comprises a sequence complementary to the unique capture sequence. In some embodiments, for any method described herein, the unique capture sequence comprises a nucleic acid sequence of no more than 40 nucleotides in length. In some embodiments, for any method described herein, the dsDNA template further comprises a randomer. In some embodiments, for any method described herein, the method further comprises denaturing the dsDNA template, and removing the template strand, in which the complementary strand remains ligated to the second oligonucleotide probe. In some embodiments, for any method described herein, the dsDNA template is attached to biotin, and removing the template stand comprises contacting with streptavidin.

In some embodiments, a method of appending an oligonucleotide probe with a target binding region is described. The method can comprise providing an oligonucleotide probe, in which the oligonucleotide probe comprises a sample identifier sequence and a hybridization domain. The method can comprise contacting the oligonucleotide probe with a partially double stranded DNA (dsDNA) template comprising a template strand and a complementary strand. The template strand can comprise a single-stranded complementary hybridization domain that is complementary to at least a portion of the hybridization domain, a sequence complementary to the target binding region. The complementary strand can comprise a complementary strand comprising the target binding region, in which the target binding region of the complementary strand is hybridized to the sequence complementary to the target binding region of the template strand. The method can comprise ligating the dsDNA template to the oligonucleotide probe. The method can comprise denaturing the dsDNA template. The method can comprise removing the template strand. In some embodiments, for any method described herein, the oligonucleotide probe is associated with a substrate. In some embodiments, for any method described herein, the substrate comprises at least one of a bead, a microarray, a plate, a tube, or a well. In some embodiments, for any method described herein, the template strand is associated with biotin, and wherein removing the template strand comprises contacting the biotin with streptavidin. In some embodiments, for any method described herein, the hybridization domain of the oligonucleotide probe comprises a polyT sequence, and wherein the complementary hybridization domain comprises a polyA sequence. In some embodiments, for any method described herein, the target binding region does not comprise a polyT sequence. In some embodiments, for any method described herein, the method further comprises appending the first oligonucleotide probe with the first target binding region and/or appending the second oligonucleotide probe with the second target binding region according to the methods described herein.

In some embodiments, a kit is described. The kit can comprise an oligonucleotide probe comprising a sample identifier sequence and a hybridization domain. The kit can comprise a DNA template, comprising a template strand and a complementary strand. The template strand can comprise a single-stranded complementary hybridization domain that is complementary to at least a portion of the hybridization domain a sequence that is complementary to a target binding region. The complementary strand can comprise the target binding region. Optionally, in the kit, the target binding region is hybridized to the sequence that is complementary to the target binding region, so that the template strand is hybridized to the complementary strand. Thus, the template strand and complementary strand can form a partially double stranded DNA with at least part of the hybridization domain single-stranded. In some embodiments, for any kit described herein, the template strand sequence is associated with biotin, and wherein the kit further comprises a composition comprising streptavidin. In some embodiments, for any kit described herein, the oligonucleotide probe is associated with a substrate. In some embodiments, for any kit described herein, the substrate comprises at least one of a bead, a microarray, a plate, a tube, or a well. In some embodiments, for any kit described herein, the kit further comprises a denaturant. In some embodiments, for any kit described herein, the denaturant comprises dimethyl sulfoxide (DMSO), formamide, guanidine, propylene glycol, salt, sodium hydroxide, sodium salicylate, or urea. In some embodiments, for any kit or method or composition described herein, the protein binding reagent comprises an antibody.

In some embodiments, a composition is described. The composition can comprise a cell comprising a target protein associated with a DNA. The composition can comprise a complex bound to the target protein. The complex can comprise a protein binding reagent associated with a reagent oligonucleotide comprising a unique identifier for the protein binding reagent. The protein binding reagent can specifically bind the protein of interest. The complex can comprise a fusion protein comprising a DNA digestion enzyme bound to the protein binding reagent. In some embodiments, for any composition described herein, the fusion protein comprises a domain that specifically binds the protein binding reagent. In some embodiments, for any composition described herein, the complex binds the target protein within the nucleus of the cell. In some embodiments, for any composition described herein, the DNA digestion enzyme comprises a restriction enzyme, Mnase I, or Tn5 transposase or a functional fragment thereof.

BRIEF DESCRIPTION OF THE DRAWINGS

FIG. 5A is a schematic diagram illustrating capture of the complex of FIG. 3 with the substrate (e.g., bead) of FIG. 4, in accordance with some embodiments herein. FIG. 5B is a schematic diagram illustrating ligation and reverse transcription of the oligonucleotides of the captured complex of FIG. 5A, in accordance with some embodiments herein. FIG. 5C illustrates digestion of the protein binding reagent, the fusion protein, and the target protein to generate a bead associated only with oligonucleotides, in accordance with some embodiments herein. FIG. 5D illustrates denaturation, random priming and extension, and polymerase chain reaction to generate a library, in accordance with some embodiments herein.

FIG. 7A illustrates a bead having an oligonucleotide probe with a polyT hybridization domain, in accordance with some embodiments herein. FIG. 7B illustrates a double stranded DNA (dsDNA) having a template strand sequence that includes a polyA hybridization domain and a target nucleic acid sequence and a complementary strand sequence that includes a target binding region that is complementary to the target nucleic acid sequence, wherein the dsDNA is attached to biotin, in accordance with some embodiments herein. FIG. 7C illustrates hybridization of the oligonucleotide probe of FIG. 7A to the dsDNA of FIG. 7B, in accordance with some embodiments herein.

DETAILED DESCRIPTION

Figure 1:
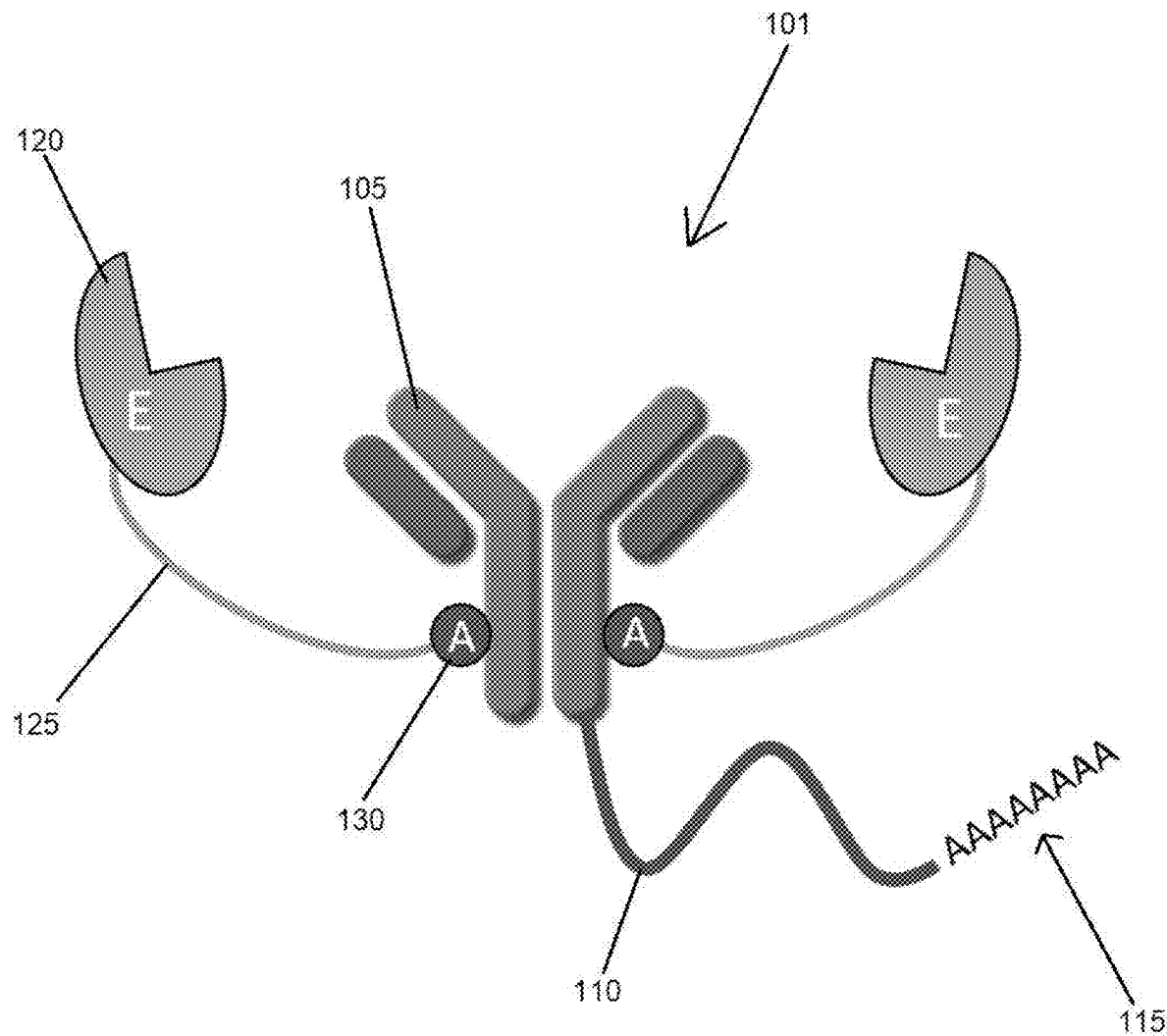
FIG. 1 is a schematic diagram illustrating a binding reagent (e.g., protein binding reagent) bound to a fusion protein that comprises a DNA digestion enzyme, in accordance with some embodiments herein.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Quantifying small numbers of nucleic acids, for example messenger ribonucleotide acid (mRNA) molecules, is clinically important for determining, for example, the genes that are expressed in a cell at different stages of development or under different environmental conditions. However, it can also be very challenging to determine the absolute number of nucleic acid molecules (e.g., mRNA molecules), especially when the number of molecules is very small. One method to determine the absolute number of molecules in a sample is digital polymerase chain reaction (PCR). Ideally, PCR produces an identical copy of a molecule at each cycle. However, PCR can have disadvantages such that each molecule replicates with a stochastic probability, and this probability varies by PCR cycle and gene sequence, resulting in amplification bias and inaccurate gene expression measurements. Stochastic barcodes with unique molecular labels (also referred to as molecular indexes (MIs)) can be used to count the number of molecules and correct for amplification bias. Stochastic barcoding, such as the Precise™ assay (Cellular Research, Inc. (Palo Alto, CA)) and Rhapsody™ assay (Becton, Dickinson and Company (Franklin Lakes, NJ)), can correct for bias induced by PCR and library preparation steps by using molecular labels (MLs) to label mRNAs during reverse transcription (RT).

The Precise™ assay can utilize a non-depleting pool of stochastic barcodes with large number, for example 6561 to 65536, unique molecular label sequences on poly(T) oligonucleotides to hybridize to all poly(A)-mRNAs in a sample during the RT step. A stochastic barcode can comprise a universal PCR priming site. During RT, target gene molecules react randomly with stochastic barcodes. Each target molecule can hybridize to a stochastic barcode resulting to generate stochastically barcoded complementary ribonucleotide acid (cDNA) molecules). After labeling, stochastically barcoded cDNA molecules from microwells of a microwell plate can be pooled into a single tube for PCR amplification and sequencing. Raw sequencing data can be analyzed to produce the number of reads, the number of stochastic barcodes with unique molecular label sequences, and the numbers of mRNA molecules.

In accordance with some embodiments herein, methods, kits, and compositions for labeling target-protein-associated DNA from a single cell are described. In methods, kits, and compositions of some embodiments, a first composition comprises, consists essentially of or consists of a binding reagent (e.g., protein binding reagent) that specifically binds to a target protein that is associated with DNA in a cell, for example chromatin, thus forming a complex. The binding reagent (e.g., protein binding reagent) can further comprise a unique identifier such as a nucleic acid barcode. A second composition can comprise, consist essentially of, or consist of a fusion protein that binds to the protein binding reagent. The fusion protein can comprise a DNA digestion enzyme that digests DNA associated with the target protein, yielding a complex comprising the protein binding reagent comprising the unique identifier, the fusion protein, and the digested DNA. Barcoding can then be performed so as to label particular digested DNAs that were associated with particular unique identifiers of protein binding regents. Thus, particular DNA sequences associated with particular target proteins can be identified at the single cell and single molecule level. For example, a bead comprising barcodes that each share a common sample identifier sequence can be contacted with the protein binding reagent complexed with the digested DNA, so that the digested DNA and unique identifier can each be associated with the same sample identifier sequence. Moreover, in order ascertain an accurate portrayal of intermolecular interaction in a cell, the complexes can form (and DNA can be digested) in situ in a permeabilized cell or cell nucleus. Without being limited by theory, it is contemplated that the formation of complexes in situ can avoid artifactual and false positive interactions that may arise from labeling cell extracts or fractions thereof. Optionally, a multiplex analysis can be performed to identify DNAs associated with two or more different types of target proteins in the same sample (e.g., in the same single cell). Some embodiments described herein relate to methods of using the kits and/or compositions described herein for target-protein-associated DNA labeling in a single cell. Some embodiments described herein relate to the kits and/or compositions.

Conventional methods for labeling target-protein-associated DNA can involve processes such as crosslinking target protein to the associated DNA, DNA fragmentation, immunoprecipitation, isolation of DNA, and sequencing. Such methods typically involve analysis of thousands or millions of cells in order to label and analyze the target-protein associated DNA. Thus, such methods have not been amenable to analysis of target-protein-associated DNA in a single cell. The kits, methods, and compositions of some embodiments described herein yield accurate and reproducible identification and analysis of target-protein-associated DNA in a single cell. In some embodiments, target protein associated with DNA in a single cell can be identified in situ (e.g., within the nucleus of a cell), thus identifying target protein-DNA interaction that are accurately portray interactions that occur in the cell itself.

Disclosed herein include methods of labeling nuclear target-associated DNA in a cell. In some embodiments, the method comprises: permeabilizing a cell comprising a nuclear target associated with double-stranded deoxyribonucleic acid (dsDNA). The dsDNA can be a genomic DNA (gDNA). The method can comprise: contacting the nuclear target with a conjugate comprising a transposome and a binding reagent capable of specifically binding to the nuclear target to generate a plurality of nuclear target-associated dsDNA fragments (e.g., nuclear target-associated gDNA fragments) each comprising a first 5' overhang and a second 5' overhang, wherein the transposome comprises a transposase, a first adaptor having the first 5' overhang, and a second adaptor having the second 5' overhang; and barcoding the plurality of nuclear target-associated dsDNA fragments, or products thereof, using a first plurality of oligonucleotide barcodes to generate a plurality of barcoded nuclear target-associated DNA fragments, wherein each oligonucleotide barcode of the first plurality of oligonucleotide barcodes comprises a first target-binding region capable of hybridizing to the plurality of nuclear target-associated dsDNA fragments, or products thereof. The barcoded nuclear target-associated DNA fragments can be single-stranded or double-stranded.

Disclosed herein include kits. In some embodiments, the kit comprises: a conjugate comprising a transposome and a binding reagent capable of specifically binding to a nuclear target, wherein the transposome comprises a transposase, a first adaptor having a first 5' overhang, and a second adaptor having a second 5' overhang. The kit can comprise: a DNA polymerase lacking at least one of 5' to 3' exonuclease activity and 3' to 5' exonuclease activity, optionally wherein the DNA polymerase comprises a Klenow Fragment. The kit can comprise: a reverse transcriptase, optionally wherein the reverse transcriptase comprises a viral reverse transcriptase, and optionally the viral reverse transcriptase is a murine leukemia virus (MLV) reverse transcriptase or a Moloney murine leukemia virus (MMLV) reverse transcriptase. The kit can comprise: a ligase. The kit can comprise: a detergent and/or a surfactant. The kit can comprise: a buffer, a cartridge, or both. The kit can comprise: one or more reagents for a reverse transcription reaction and/or an amplification reaction.

Disclosed herein include methods of labeling nuclear target-associated DNA in a cell. In some embodiments, the method comprises: permeabilizing a cell comprising a nuclear target associated with double-stranded deoxyribonucleic acid (dsDNA), wherein optionally the dsDNA is a genomic DNA (gDNA). The method can comprise: contacting the nuclear target with a digestion composition comprising a DNA digestion enzyme and a binding reagent capable of specifically binding to the nuclear target to generate a plurality of nuclear target-associated dsDNA fragments (e.g., nuclear target-associated gDNA fragments) each comprising a single-stranded overhang, wherein each binding reagent comprises a binding reagent specific oligonucleotide comprising a unique identifier sequence for the binding reagent. The method can comprise: barcoding the plurality of nuclear target-associated dsDNA fragments, or products thereof, using a first plurality of oligonucleotide barcodes to generate a plurality of barcoded nuclear target-associated DNA fragments each comprising a sequence complementary to at least a portion of the nuclear target-associated dsDNA fragment, wherein each oligonucleotide barcode of the first plurality of oligonucleotide barcodes comprises a first target-binding region capable of hybridizing to the plurality of nuclear target-associated dsDNA fragments, or products thereof. The barcoded nuclear target-associated DNA fragments can be single-stranded or double-stranded. The method can comprise: barcoding the binding reagent specific oligonucleotides, or products thereof, using a second plurality of oligonucleotide barcodes to generate a plurality of barcoded binding reagent specific oligonucleotides each comprising a sequence complementary to at least a portion of the unique identifier sequence, wherein each oligonucleotide barcode of the second plurality of oligonucleotide barcodes comprises a second target-binding region capable of hybridizing to the binding reagent specific oligonucleotides, or products thereof.

Disclosed herein include kits. The kit can comprise a digestion composition comprising a DNA digestion enzyme and a binding reagent capable of specifically binding to the nuclear target, wherein the binding reagent comprises a binding reagent specific oligonucleotide comprising a unique identifier sequence for the binding reagent.

DEFINITIONS

Unless defined otherwise, technical and scientific terms used herein have the same meaning as commonly understood by one of ordinary skill in the art to which the present disclosure belongs. See, e.g., Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, NY 1989). For purposes of the present disclosure, the following terms are defined below.

As used herein, the term "adaptor" can mean a sequence to facilitate amplification or sequencing of associated nucleic acids. The associated nucleic acids can comprise target nucleic acids. The associated nucleic acids can comprise one or more of spatial labels, target labels, sample labels, indexing label, or barcode sequences (e.g., molecular labels). The adaptors can be linear. The adaptors can be pre-adenylated adaptors. The adaptors can be double- or single-stranded. One or more adaptor can be located on the 5' or 3' end of a nucleic acid. When the adaptors comprise known sequences on the 5' and 3' ends, the known sequences can be the same or different sequences. An adaptor located on the 5' and/or 3' ends of a polynucleotide can be capable of hybridizing to one or more oligonucleotides immobilized on a surface. An adaptor can, in some embodiments, comprise a universal sequence. A universal sequence can be a region of nucleotide sequence that is common to two or more nucleic acid molecules. The two or more nucleic acid molecules can also have regions of different sequence. Thus, for example, the 5' adaptors can comprise identical and/or universal nucleic acid sequences and the 3' adaptors can comprise identical and/or universal sequences. A universal sequence that may be present in different members of a plurality of nucleic acid molecules can allow the replication or amplification of multiple different sequences using a single universal primer that is complementary to the universal sequence. Similarly, at least one, two (e.g., a pair) or more universal sequences that may be present in different members of a collection of nucleic acid molecules can allow the replication or amplification of multiple different sequences using at least one, two (e.g., a pair) or more single universal primers that are complementary to the universal sequences. Thus, a universal primer includes a sequence that can hybridize to such a universal sequence. The target nucleic acid sequence-bearing molecules may be modified to attach universal adaptors (e.g., non-target nucleic acid sequences) to one or both ends of the different target nucleic acid sequences. The one or more universal primers attached to the target nucleic acid can provide sites for hybridization of universal primers. The one or more universal primers attached to the target nucleic acid can be the same or different from each other.

As used herein the term "associated" or "associated with" can mean that two or more species are identifiable as being co-located at a point in time. An association can mean that two or more species are or were within a similar container. An association can be an informatics association. For example, digital information regarding two or more species can be stored and can be used to determine that one or more of the species were co-located at a point in time. An association can also be a physical association. In some embodiments, two or more associated species are "tethered", "attached", or "immobilized" to one another or to a common solid or semisolid surface. An association may refer to covalent or non-covalent means for attaching labels to solid or semi-solid supports such as beads. An association may be a covalent bond between a target and a label. An association can comprise hybridization between two molecules (such as a target molecule and a label).

As used herein, the term "complementary" can refer to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. A first nucleotide sequence can be said to be the "complement" of a second sequence if the first nucleotide sequence is complementary to the second nucleotide sequence. A first nucleotide sequence can be said to be the "reverse complement" of a second sequence, if the first nucleotide sequence is complementary to a sequence that is the reverse (i.e., the order of the nucleotides is reversed) of the second sequence. As used herein, a "complementary" sequence can refer to a "complement" or a "reverse complement" of a sequence. It is understood from the disclosure that if a molecule can hybridize to another molecule it may be complementary, or partially complementary, to the molecule that is hybridizing.

As used herein, the term "digital counting" can refer to a method for estimating a number of target molecules in a sample. Digital counting can include the step of determining a number of unique labels that have been associated with targets in a sample. This methodology, which can be stochastic in nature, transforms the problem of counting molecules from one of locating and identifying identical molecules to a series of yes/no digital questions regarding detection of a set of predefined labels.

As used herein, the term "label" or "labels" can refer to nucleic acid codes associated with a target within a sample. A label can be, for example, a nucleic acid label. A label can be an entirely or partially amplifiable label. A label can be entirely or partially sequencable label. A label can be a portion of a native nucleic acid that is identifiable as distinct. A label can be a known sequence. A label can comprise a junction of nucleic acid sequences, for example a junction of a native and non-native sequence. As used herein, the term "label" can be used interchangeably with the terms, "index", "tag," or "label-tag." Labels can convey information. For example, in various embodiments, labels can be used to determine an identity of a sample, a source of a sample, an identity of a cell, and/or a target.

As used herein, the term "non-depleting reservoirs" can refer to a pool of barcodes (e.g., stochastic barcodes) made up of many different labels. A non-depleting reservoir can comprise large numbers of different barcodes such that when the non-depleting reservoir is associated with a pool of targets each target is likely to be associated with a unique barcode. The uniqueness of each labeled target molecule can be determined by the statistics of random choice, and depends on the number of copies of identical target molecules in the collection compared to the diversity of labels. The size of the resulting set of labeled target molecules can be determined by the stochastic nature of the barcoding process, and analysis of the number of barcodes detected then allows calculation of the number of target molecules present in the original collection or sample. When the ratio of the number of copies of a target molecule present to the number of unique barcodes is low, the labeled target molecules are highly unique (i.e., there is a very low probability that more than one target molecule will have been labeled with a given label).

Various nucleic acids are described in accordance with some embodiments herein. For example, oligonucleotides, samples, and/or targets can comprise nucleic acids.

As used herein, the term "nucleic acid" refers to a polynucleotide sequence, or fragment thereof. A nucleic acid can comprise nucleotides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g., altered backbone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g., rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudouridine, dihydrouridine, queuosine, and wyosine. "Nucleic acid", "polynucleotide, "target polynucleotide", and "target nucleic acid" can be used interchangeably.

As used herein, "nucleoside" has its ordinary and customary meaning as understood by one of ordinary skill in the art in light of this specification, and may include natural nucleosides, such as 2'-deoxy and 2'-hydroxyl forms. "Analogs" in reference to nucleosides may include synthetic nucleosides comprising modified base moieties and/or modified sugar moieties, or the like. Analogs may be capable of hybridization. Analogs may include synthetic nucleosides designed to enhance binding properties, reduce complexity, increase specificity, and the like. Exemplary types of analogs may include oligonucleotide phosphoramidates (referred to herein as "amidates"), peptide nucleic acids (referred to herein as "PNAs"), oligo-2'-O-alkylribonucleotides, polynucleotides containing C-5 propynylpyrimidines, and locked nucleic acids (LNAs).

As used herein, "upstream" (and variations of this root term) has its ordinary and customary meaning as understood by one of ordinary skill in the art in light of this specification, and refers to a position that is relatively 5' on a nucleic acid (e.g., 5' in comparison to reference position). As used herein "downstream" (and variations of this root term) has its ordinary and customary meaning as understood by one of ordinary skill in the art in light of this specification, and refers to a position that is relatively 3' on a nucleic acid (e.g., 3' in comparison to reference position).

A nucleic acid can comprise one or more modifications (e.g., a base modification, a backbone modification), to provide the nucleic acid with a new or enhanced feature (e.g., improved stability). A nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within nucleic acids, the phosphate groups can commonly be referred to as forming the internucleoside backbone of the nucleic acid. The linkage or backbone can be a 3' to 5' phosphodiester linkage.

A nucleic acid can comprise a modified backbone and/or modified internucleoside linkages. Modified backbones can include those that retain a phosphorus atom in the backbone and those that do not have a phosphorus atom in the backbone. Suitable modified nucleic acid backbones containing a phosphorus atom therein can include, for example, phosphorothioates, chiral phosphorothioates, phosphorodithioates, phosphotriesters, aminoalkyl phosphotriesters, methyl and other alkyl phosphonate such as 3'-alkylene phosphonates, 5'-alkylene phosphonates, chiral phosphonates, phosphinates, phosphoramidates including 3'-amino phosphoramidate and aminoalkyl phosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage.

A nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

A nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can also be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A nucleic acid can comprise linked morpholino units (e.g., morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C, 4'-C-oxymethylene linkage thereby forming a bicyclic sugar moiety. The linkage can be a methylene (—$CH_2$), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A nucleic acid may also include nucleobase (often referred to simply as "base") modifications or substitutions. As used herein, "unmodified" or "natural" nucleobases can include the purine bases (e.g., adenine (A) and guanine (G)), and the pyrimidine bases (e.g., thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g., 9-(2-aminoethoxy)-H-pyrimido(5,4-(b) (1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g., 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2': 4,5)pyrrolo[2,3-d]pyrimidin-2-one).

As used herein, the term "sample" can refer to a composition comprising targets. Suitable samples for analysis by the disclosed methods, devices, and systems include cells, tissues, organs, or organisms. In some embodiments, a sample comprises raw or unprocessed samples, for example a whole cell, whole population of cells, or whole tissue. In some embodiments, a sample comprises an isolated cell or cell extract, or a nucleic-acid-containing fraction thereof, for example isolated nucleic acids, or a composition comprising enriched or isolated nucleic acids. In some embodiments, a sample comprises a fixed tissue, cell, or nucleic-acid-containing fraction thereof. In some embodiments, a sample comprises a frozen tissue, cell, or nucleic-acid-containing fraction thereof. In some embodiments, a sample comprises a solution comprising nucleic acids. In some embodiments, a sample comprises a solution comprising nucleic acids. In some embodiments, a sample comprises nucleic acids in a solid format, for example lyophilized nucleic acids and the like. In some embodiments, a sample identifier sequence is a sequence that is capable of providing a user with information related to the sample, such as identifying a particular sample or distinguishing one sample from another. A sample identifier sequence may be a unique nucleic acid sequence having 20 or fewer base pairs, such as 20, 18, 15, 12, 10, 9, 8, 7, 6, 5, 4, or 3 base pairs from a unique set of diverse sequences.

As used herein, the term "sampling device" or "device" can refer to a device which may take a section of a sample and/or place the section on a substrate. A sample device can refer to, for example, a fluorescence activated cell sorting (FACS) machine, a cell sorter machine, a biopsy needle, a biopsy device, a tissue sectioning device, a microfluidic device, a blade grid, and/or a microtome.

As used herein, the term "solid support" can refer to discrete solid or semi-solid surfaces to which a plurality of barcodes (e.g., stochastic barcodes) may be attached. A solid support may encompass any type of solid, porous, or hollow sphere, ball, bearing, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A bead can be non-spherical in shape. A plurality of solid supports spaced in an array may not comprise a substrate. A solid support may be used interchangeably with the term "bead."

As used herein, the term "stochastic barcode" can refer to a polynucleotide sequence comprising labels of the present disclosure. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "gene-specific stochastic barcode" can refer to a polynucleotide sequence comprising labels and a target-binding region that is gene-specific. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "stochastic barcoding" can refer to the random labeling (e.g., barcoding) of nucleic acids. Stochastic barcoding can utilize a recursive Poisson strategy to associate and quantify labels associated with targets. As used herein, the term "stochastic barcoding" can be used interchangeably with "stochastic labeling."

As used here, the term "target" can refer to a composition which can be associated with a barcode (e.g., a stochastic barcode). Exemplary suitable targets for analysis by the disclosed methods, devices, and systems include oligonucleotides, DNA, RNA, mRNA, microRNA, tRNA, and the like. Targets can be single or double stranded. In some embodiments, targets can be proteins, peptides, or polypeptides. In some embodiments, targets are lipids. As used herein, "target" can be used interchangeably with "species."

As used herein, the term "reverse transcriptase" refers to an enzyme having reverse transcriptase activity (i.e., that catalyze synthesis of DNA from an RNA template). In general, such enzymes include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants or derivatives thereof. Non-retroviral reverse transcriptases include non-LTR retrotransposon reverse transcriptases, retroplasmid reverse transcriptases, retron reverse transcriptases, and group II intron reverse transcriptases. Examples of group II intron reverse transcriptases include the *Lactococcus lactis* Ll.LtrB intron reverse transcriptase, the *Thermosynechococcus elongatus* TeI4c intron reverse transcriptase, or the *Geobacillus stearothermophilus* GsI-IIC intron reverse transcriptase. Other classes of reverse transcriptases can include many classes of non-retroviral reverse transcriptases (i.e., retrons, group II introns, and diversity-generating retroelements among others).

The terms "universal adaptor primer," "universal primer adaptor" or "universal adaptor sequence" are used interchangeably to refer to a nucleotide sequence that can be used to hybridize to barcodes (e.g., stochastic barcodes) to generate gene-specific barcodes. A universal adaptor sequence can, for example, be a known sequence that is universal across all barcodes used in methods of the disclosure. For example, when multiple targets are being labeled using the methods disclosed herein, each of the target-specific sequences may be linked to the same universal adaptor sequence. In some embodiments, more than one universal adaptor sequences may be used in the methods disclosed herein. For example, when multiple targets are being labeled using the methods disclosed herein, at least two of the target-specific sequences are linked to different universal adaptor sequences. A universal adaptor primer and its complement may be included in two oligonucleotides, one of which comprises a target-specific sequence and the other comprises a barcode. For example, a universal adaptor sequence may be part of an oligonucleotide comprising a target-specific sequence to generate a nucleotide sequence that is complementary to a target nucleic acid. A second oligonucleotide comprising a barcode and a complementary sequence of the universal adaptor sequence may hybridize with the nucleotide sequence and generate a target-specific barcode (e.g., a target-specific stochastic barcode). In some embodiments, a universal adaptor primer has a sequence that is different from a universal PCR primer used in the methods of this disclosure.

As used herein, the term "cell" has its ordinary and customary meaning as understood by one of ordinary skill in the art in light of this specification. It can refer to one or more cells. In some embodiments, the cells are normal cells, for example, human cells in different stages of development, or human cells from different organs or tissue types. In some embodiments, the cells are non-human cells, for example, other types of mammalian cells (e.g., mouse, rat, pig, dog, cow, and horse). In some embodiments, the cells are other types of animal or plant cells. In other embodiments, the cells can be any prokaryotic or eukaryotic cells. A permeabilized cell is a cell comprising openings in the cell membrane and nuclease of sufficient size for a protein binding reagent and fusion protein (separately, or optionally, associated with each other) to diffuse though the openings in order to enter the nucleus.

Barcodes

Barcoding, such as stochastic barcoding, has been described in, for example, Fu et al., *Proc Natl Acad Sci U.S.A.*, 2011 May 31, 108(22):9026-31; U.S. Patent Application Publication No. US2011/0160078; Fan et al., *Science*, 2015 Feb. 6, 347(6222):1258367; US Patent Application Publication No. US2015/0299784; and PCT Application Publication No. WO2015/031691; the content of each of these, including any supporting or supplemental information or material, is incorporated herein by reference in its entirety. In some embodiments, the barcode disclosed herein can be a stochastic barcode which can be a polynucleotide sequence that may be used to stochastically label (e.g., barcode, tag) a target. Barcodes can be referred to stochastic barcodes if the ratio of the number of different barcode sequences of the stochastic barcodes and the number of occurrence of any of the targets to be labeled can be, or be about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be an mRNA species comprising mRNA molecules with identical or nearly identical sequences. Barcodes can be referred to as stochastic barcodes if the ratio of the number of different barcode sequences of the stochastic barcodes and the number of occurrence of any of the targets to be labeled is at least, or is at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1. Barcode sequences of stochastic barcodes can be referred to as molecular labels.

Figure 11:
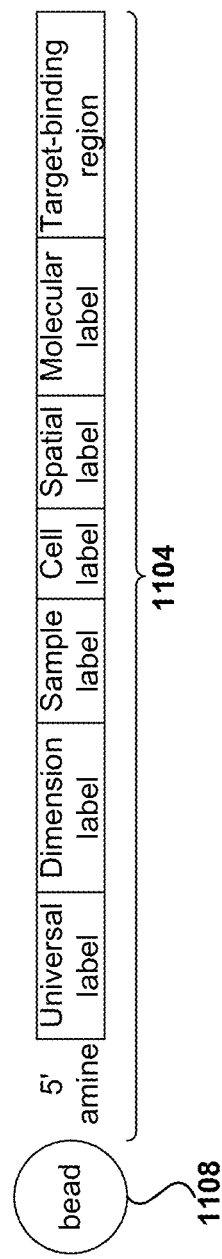
FIG. 11 illustrates a non-limiting exemplary barcode.

A barcode, for example a stochastic barcode, can comprise one or more labels. Exemplary labels can include a universal label, a cell label, a barcode sequence (e.g., a molecular label), a sample label, a plate label, a spatial label, and/or a pre-spatial label. FIG. 11 illustrates an exemplary barcode 1104 with a spatial label. The barcode 1104 can comprise a 5'amine that may link the barcode to a solid support 1105. The barcode can comprise a universal label, a dimension label, a spatial label, a cell label, and/or a molecular label. The order of different labels (including but not limited to the universal label, the dimension label, the spatial label, the cell label, and the molecule label) in the barcode can vary. For example, as shown in FIG. 11, the universal label may be the 5'-most label, and the molecular label may be the 3'-most label. The spatial label, dimension label, and the cell label may be in any order. In some embodiments, the universal label, the spatial label, the dimension label, the cell label, and the molecular label are in any order. The barcode can comprise a target-binding region. The target-binding region can interact with a target (e.g., target nucleic acid, RNA, mRNA, DNA) in a sample. For example, a target-binding region can comprise an oligo (dT) sequence which can interact with poly(A) tails of mRNAs. In some instances, the labels of the barcode (e.g., universal label, dimension label, spatial label, cell label, and barcode sequence) may be separated by 1, 2, 3, 4, 5, 6, 7, 8, 9, 10, 11, 12, 13, 14, 15, 16, 17, 18, 19, or 20 or more nucleotides.

A label, for example the cell label, can comprise a unique set of nucleic acid sub-sequences of defined length, e.g., seven nucleotides each (equivalent to the number of bits used in some Hamming error correction codes), which can be designed to provide error correction capability. The set of error correction sub-sequences comprise seven nucleotide sequences can be designed such that any pairwise combination of sequences in the set exhibits a defined "genetic distance" (or number of mismatched bases), for example, a set of error correction sub-sequences can be designed to exhibit a genetic distance of three nucleotides. In this case, review of the error correction sequences in the set of sequence data for labeled target nucleic acid molecules (described more fully below) can allow one to detect or correct amplification or sequencing errors. In some embodiments, the length of the nucleic acid sub-sequences used for creating error correction codes can vary, for example, they can be, or be about 1, 2, 3, 4, 5, 6, 7, 8, 9, 10, 15, 20, 30, 31, 40, 50, or a number or a range between any two of these values, nucleotides in length. In some embodiments, nucleic acid sub-sequences of other lengths can be used for creating error correction codes.

The barcode can comprise a target-binding region. The target-binding region can interact with a target in a sample. The target can be, or comprise, ribonucleic acids (RNAs), messenger RNAs (mRNAs), microRNAs, small interfering RNAs (siRNAs), RNA degradation products, RNAs each comprising a poly(A) tail, or any combination thereof. In some embodiments, the plurality of targets can include deoxyribonucleic acids (DNAs).

In some embodiments, a target-binding region can comprise an oligo(dT) sequence which can interact with poly(A) tails of mRNAs. One or more of the labels of the barcode (e.g., the universal label, the dimension label, the spatial label, the cell label, and the barcode sequences (e.g., molecular label)) can be separated by a spacer from another one or two of the remaining labels of the barcode. The spacer can be, for example, 1, 2, 3, 4, 5, 6, 7, 8, 9, 10, 11, 12, 13, 14, 15, 16, 17, 18, 19, or 20, or more nucleotides. In some embodiments, none of the labels of the barcode is separated by spacer.

Universal Labels

A barcode can comprise one or more universal labels. In some embodiments, the one or more universal labels can be the same for all barcodes in the set of barcodes attached to a given solid support. In some embodiments, the one or more universal labels can be the same for all barcodes attached to a plurality of beads. In some embodiments, a universal label can comprise a nucleic acid sequence that is capable of hybridizing to a sequencing primer. Sequencing primers can be used for sequencing barcodes comprising a universal label. Sequencing primers (e.g., universal sequencing primers) can comprise sequencing primers associated with high-throughput sequencing platforms. In some embodiments, a universal label can comprise a nucleic acid sequence that is capable of hybridizing to a PCR primer. In some embodiments, the universal label can comprise a nucleic acid sequence that is capable of hybridizing to a sequencing primer and a PCR primer. The nucleic acid sequence of the universal label that is capable of hybridizing to a sequencing or PCR primer can be referred to as a primer binding site. A universal label can comprise a sequence that can be used to initiate transcription of the barcode. A universal label can comprise a sequence that can be used for extension of the barcode or a region within the barcode. A universal label can be, or be about, 1, 2, 3, 4, 5, 10, 15, 20, 25, 30, 35, 40, 45, 50, or a number or a range between any two of these values, nucleotides in length. For example, a universal label can comprise at least about 10 nucleotides. A universal label can be at least, or be at most, 1, 2, 3, 4, 5, 10, 15, 20, 25, 30, 35, 40, 45, 50, 100, 200, or 300 nucleotides in length. In some embodiments, a cleavable linker or modified nucleotide can be part of the universal label sequence to enable the barcode to be cleaved off from the support.

Dimension Labels

A barcode can comprise one or more dimension labels. In some embodiments, a dimension label can comprise a nucleic acid sequence that provides information about a dimension in which the labeling (e.g., stochastic labeling) occurred. For example, a dimension label can provide information about the time at which a target was barcoded. A dimension label can be associated with a time of barcoding (e.g., stochastic barcoding) in a sample. A dimension label can be activated at the time of labeling. Different dimension labels can be activated at different times. The dimension label provides information about the order in which targets, groups of targets, and/or samples were barcoded. For example, a population of cells can be barcoded at the G0 phase of the cell cycle. The cells can be pulsed again with barcodes (e.g., stochastic barcodes) at the G1 phase of the cell cycle. The cells can be pulsed again with barcodes at the S phase of the cell cycle, and so on. Barcodes at each pulse (e.g., each phase of the cell cycle), can comprise different dimension labels. In this way, the dimension label provides information about which targets were labelled at which phase of the cell cycle. Dimension labels can interrogate many different biological times. Exemplary biological times can include, but are not limited to, the cell cycle, transcription (e.g., transcription initiation), and transcript degradation. In another example, a sample (e.g., a cell, a population of cells) can be labeled before and/or after treatment with a drug and/or therapy. The changes in the number of copies of distinct targets can be indicative of the sample's response to the drug and/or therapy.

A dimension label can be activatable. An activatable dimension label can be activated at a specific time point. The activatable label can be, for example, constitutively activated (e.g., not turned off). The activatable dimension label can be, for example, reversibly activated (e.g., the activatable dimension label can be turned on and turned off). The dimension label can be, for example, reversibly activatable at least 1, 2, 3, 4, 5, 6, 7, 8, 9, 10, or more times. The dimension label can be reversibly activatable, for example, at least 1, 2, 3, 4, 5, 6, 7, 8, 9, 10 or more times. In some embodiments, the dimension label can be activated with fluorescence, light, a chemical event (e.g., cleavage, ligation of another molecule, addition of modifications (e.g., pegylated, sumoylated, acetylated, methylated, deacetylated, demethylated), a photochemical event (e.g., photocaging), and introduction of a non-natural nucleotide.

The dimension label can, in some embodiments, be identical for all barcodes (e.g., stochastic barcodes) attached to a given solid support (e.g., a bead), but different for different solid supports (e.g., beads). In some embodiments, at least 60%, 70%, 80%, 85%, 90%, 95%, 97%, 99% or 100%, of barcodes on the same solid support can comprise the same dimension label. In some embodiments, at least 60% of barcodes on the same solid support can comprise the same dimension label. In some embodiments, at least 95% of barcodes on the same solid support can comprise the same dimension label.

There can be as many as $10^6$ or more unique dimension label sequences represented in a plurality of solid supports (e.g., beads). A dimension label can be, or be about 1, 2, 3, 4, 5, 10, 15, 20, 25, 30, 35, 40, 45, 50, or a number or a range between any two of these values, nucleotides in length. A dimension label can be at least, or be at most, 1, 2, 3, 4, 5, 10, 15, 20, 25, 30, 35, 40, 45, 50, 100, 200, or 300, nucleotides in length. A dimension label can comprise between about 5 to about 200 nucleotides. A dimension label can comprise between about 10 to about 150 nucleotides. A dimension label can comprise between about 20 to about 125 nucleotides in length.

Spatial Labels

A barcode can comprise one or more spatial labels. In some embodiments, a spatial label can comprise a nucleic acid sequence that provides information about the spatial orientation of a target molecule which is associated with the barcode. A spatial label can be associated with a coordinate in a sample. The coordinate can be a fixed coordinate. For example, a coordinate can be fixed in reference to a substrate. A spatial label can be in reference to a two or three-dimensional grid. A coordinate can be fixed in reference to a landmark. The landmark can be identifiable in space. A landmark can be a structure which can be imaged. A landmark can be a biological structure, for example an anatomical landmark. A landmark can be a cellular landmark, for instance an organelle. A landmark can be a non-natural landmark such as a structure with an identifiable identifier such as a color code, bar code, magnetic property, fluorescents, radioactivity, or a unique size or shape. A spatial label can be associated with a physical partition (e.g., A well, a container, or a droplet). In some embodiments, multiple spatial labels are used together to encode one or more positions in space.

The spatial label can be identical for all barcodes attached to a given solid support (e.g., a bead), but different for different solid supports (e.g., beads). In some embodiments, the percentage of barcodes on the same solid support comprising the same spatial label can be, or be about, 60%, 70%, 80%, 85%, 90%, 95%, 97%, 99%, 100%, or a number or a range between any two of these values. In some embodiments, the percentage of barcodes on the same solid support comprising the same spatial label can be at least, or be at most, 60%, 70%, 80%, 85%, 90%, 95%, 97%, 99%, or 100%. In some embodiments, at least 60% of barcodes on the same solid support can comprise the same spatial label. In some embodiments, at least 95% of barcodes on the same solid support can comprise the same spatial label.

There can be as many as $10^6$ or more unique spatial label sequences represented in a plurality of solid supports (e.g., beads). A spatial label can be, or be about, 1, 2, 3, 4, 5, 10, 15, 20, 25, 30, 35, 40, 45, 50, or a number or a range between any two of these values, nucleotides in length. A spatial label can be at least or at most 1, 2, 3, 4, 5, 10, 15, 20, 25, 30, 35, 40, 45, 50, 100, 200, or 300 nucleotides in length. A spatial label can comprise between about 5 to about 200 nucleotides. A spatial label can comprise between about 10 to about 150 nucleotides. A spatial label can comprise between about 20 to about 125 nucleotides in length.

Cell Labels

A barcode (e.g., a stochastic barcode) can comprise one or more cell labels. In some embodiments, a cell label can comprise a nucleic acid sequence that provides information for determining which target nucleic acid originated from which cell. In some embodiments, the cell label is identical for all barcodes attached to a given solid support (e.g., a bead), but different for different solid supports (e.g., beads). In some embodiments, the percentage of barcodes on the same solid support comprising the same cell label can be, or be about 60%, 70%, 80%, 85%, 90%, 95%, 97%, 99%, 100%, or a number or a range between any two of these values. In some embodiments, the percentage of barcodes on the same solid support comprising the same cell label can be, or be about 60%, 70%, 80%, 85%, 90%, 95%, 97%, 99%, or 100%. For example, at least 60% of barcodes on the same solid support can comprise the same cell label. As another example, at least 95% of barcodes on the same solid support can comprise the same cell label.

There can be as many as $10^6$ or more unique cell label sequences represented in a plurality of solid supports (e.g., beads). A cell label can be, or be about, 1, 2, 3, 4, 5, 10, 15, 20, 25, 30, 35, 40, 45, 50, or a number or a range between any two of these values, nucleotides in length. A cell label can be at least, or be at most, 1, 2, 3, 4, 5, 10, 15, 20, 25, 30, 35, 40, 45, 50, 100, 200, or 300 nucleotides in length. For example, a cell label can comprise between about 5 to about 200 nucleotides. As another example, a cell label can comprise between about 10 to about 150 nucleotides. As yet another example, a cell label can comprise between about 20 to about 125 nucleotides in length.

Barcode Sequences

A barcode can comprise one or more barcode sequences. In some embodiments, a barcode sequence can comprise a nucleic acid sequence that provides identifying information for the specific type of target nucleic acid species hybridized to the barcode. A barcode sequence can comprise a nucleic acid sequence that provides a counter (e.g., that provides a rough approximation) for the specific occurrence of the target nucleic acid species hybridized to the barcode (e.g., target-binding region).

In some embodiments, a diverse set of barcode sequences are attached to a given solid support (e.g., a bead). In some embodiments, there can be, or be about, $10^2$, $10^3$, $10^4$, $10^5$, $10^6$, $10^7$, $10^8$, $10^9$, or a number or a range between any two of these values, unique molecular label sequences. For example, a plurality of barcodes can comprise about 6561 barcodes sequences with distinct sequences. As another example, a plurality of barcodes can comprise about 65536 barcode sequences with distinct sequences. In some embodiments, there can be at least, or be at most, $10^2$, $10^3$, $10^4$, $10^5$, $10^6$, $10^7$, $10^8$, or $10^9$, unique barcode sequences. The unique molecular label sequences can be attached to a given solid support (e.g., a bead). In some embodiments, the unique molecular label sequence is partially or entirely encompassed by a particle (e.g., a hydrogel bead).

The length of a barcode can be different in different implementations. For example, a barcode can be, or be about, 1, 2, 3, 4, 5, 10, 15, 20, 25, 30, 35, 40, 45, 50, or a number or a range between any two of these values, nucleotides in length. As another example, a barcode can be at least, or be at most, 1, 2, 3, 4, 5, 10, 15, 20, 25, 30, 35, 40, 45, 50, 100, 200, or 300 nucleotides in length.

Molecular Labels

A barcode (e.g., a stochastic barcode) can comprise one or more molecular labels. Molecular labels can include barcode sequences. In some embodiments, a molecular label can comprise a nucleic acid sequence that provides identifying information for the specific type of target nucleic acid species hybridized to the barcode. A molecular label can comprise a nucleic acid sequence that provides a counter for the specific occurrence of the target nucleic acid species hybridized to the barcode (e.g., target-binding region).

In some embodiments, a diverse set of molecular labels are attached to a given solid support (e.g., a bead). In some embodiments, there can be, or be about, $10^2$, $10^3$, $10^4$, $10^5$, $10^6$, $10^7$, $10^8$, $10^9$, or a number or a range between any two of these values, of unique molecular label sequences. For example, a plurality of barcodes can comprise about 6561 molecular labels with distinct sequences. As another example, a plurality of barcodes can comprise about 65536 molecular labels with distinct sequences. In some embodiments, there can be at least, or be at most, $10^2$, $10^3$, $10^4$, $10^5$, $10^6$, $10^7$, $10^8$, or $10^9$, unique molecular label sequences. Barcodes with unique molecular label sequences can be attached to a given solid support (e.g., a bead).

For barcoding (e.g., stochastic barcoding) using a plurality of stochastic barcodes, the ratio of the number of different molecular label sequences and the number of occurrence of any of the targets can be, or be about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be an mRNA species comprising mRNA molecules with identical or nearly identical sequences. In some embodiments, the ratio of the number of different molecular label sequences and the number of occurrence of any of the targets is at least, or is at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1.

A molecular label can be, or be about, 1, 2, 3, 4, 5, 10, 15, 20, 25, 30, 35, 40, 45, 50, or a number or a range between any two of these values, nucleotides in length. A molecular label can be at least, or be at most, 1, 2, 3, 4, 5, 10, 15, 20, 25, 30, 35, 40, 45, 50, 100, 200, or 300 nucleotides in length.

Target-Binding Region

A barcode can comprise one or more target binding regions, such as capture probes. In some embodiments, a target-binding region can hybridize with a target of interest. In some embodiments, the target binding regions can comprise a nucleic acid sequence that hybridizes specifically to a target (e.g., target nucleic acid, target molecule, e.g., a cellular nucleic acid to be analyzed), for example to a specific gene sequence. In some embodiments, a target binding region can comprise a nucleic acid sequence that can attach (e.g., hybridize) to a specific location of a specific target nucleic acid. In some embodiments, the target binding region can comprise a nucleic acid sequence that is capable of specific hybridization to a restriction enzyme site overhang (e.g., an EcoRI sticky-end overhang). The barcode can then ligate to any nucleic acid molecule comprising a sequence complementary to the restriction site overhang.

In some embodiments, a target binding region can comprise a non-specific target nucleic acid sequence. A non-specific target nucleic acid sequence can refer to a sequence that can bind to multiple target nucleic acids, independent of the specific sequence of the target nucleic acid. For example, target binding region can comprise a random multimer sequence, a poly(dA) sequence, a poly(dT) sequence, a poly(dG) sequence, a poly(dC) sequence, or a combination thereof. For example, the target binding region can be an oligo(dT) sequence that hybridizes to the poly(A) tail on mRNA molecules. A random multimer sequence can be, for example, a random dimer, trimer, quatramer, pentamer, hexamer, septamer, octamer, nonamer, decamer, or higher multimer sequence of any length. In some embodiments, the target binding region is the same for all barcodes attached to a given bead. In some embodiments, the target binding regions for the plurality of barcodes attached to a given bead can comprise two or more different target binding sequences. A target binding region can be, or be about, 5, 10, 15, 20, 25, 30, 35, 40, 45, 50, or a number or a range between any two of these values, nucleotides in length. A target binding region can be at most about 5, 10, 15, 20, 25, 30, 35, 40, 45, 50 or more nucleotides in length. For example, an mRNA molecule can be reverse transcribed using a reverse transcriptase, such as Moloney murine leukemia virus (MMLV) reverse transcriptase, to generate a cDNA molecule with a poly(dC) tail. A barcode can include a target binding region with a poly(dG) tail. Upon base pairing between the poly(dG) tail of the barcode and the poly(dC) tail of the cDNA molecule, the reverse transcriptase switches template strands, from cellular RNA molecule to the barcode, and continues replication to the 5' end of the barcode. By doing so, the resulting cDNA molecule contains the sequence of the barcode (such as the molecular label) on the 3' end of the cDNA molecule.

In some embodiments, a target-binding region can comprise an oligo(dT) which can hybridize with mRNAs comprising polyadenylated ends. A target-binding region can be gene-specific. For example, a target-binding region can be configured to hybridize to a specific region of a target. A target-binding region can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these values, nucleotides in length. A target-binding region can be at least, or be at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30, nucleotides in length. A target-binding region can be about 5-30 nucleotides in length. When a barcode comprises a gene-specific target-binding region, the barcode can be referred to herein as a gene-specific barcode.

Orientation Property

A stochastic barcode (e.g., a stochastic barcode) can comprise one or more orientation properties which can be used to orient (e.g., align) the barcodes. A barcode can comprise a moiety for isoelectric focusing. Different barcodes can comprise different isoelectric focusing points. When these barcodes are introduced to a sample, the sample can undergo isoelectric focusing in order to orient the barcodes into a known way. In this way, the orientation property can be used to develop a known map of barcodes in a sample. Exemplary orientation properties can include, electrophoretic mobility (e.g., based on size of the barcode), isoelectric point, spin, conductivity, and/or self-assembly. For example, barcodes with an orientation property of self-assembly, can self-assemble into a specific orientation (e.g., nucleic acid nanostructure) upon activation.

Affinity Property

A barcode (e.g., a stochastic barcode) can comprise one or more affinity properties. For example, a spatial label can comprise an affinity property. An affinity property can include a chemical and/or biological moiety that can facilitate binding of the barcode to another entity (e.g., cell receptor). For example, an affinity property can comprise an antibody, for example, an antibody specific for a specific moiety (e.g., receptor) on a sample. In some embodiments, the antibody can guide the barcode to a specific cell type or molecule. Targets at and/or near the specific cell type or molecule can be labeled (e.g., stochastically labeled). The affinity property can, in some embodiments, provide spatial information in addition to the nucleotide sequence of the spatial label because the antibody can guide the barcode to a specific location. The antibody can be a therapeutic antibody, for example a monoclonal antibody or a polyclonal antibody. The antibody can be humanized or chimeric. The antibody can be a naked antibody or a fusion antibody.

The antibody can be a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

The antibody fragment can be, for example, a portion of an antibody such as F(ab')2, Fab', Fab, Fv, sFv and the like. In some embodiments, the antibody fragment can bind with the same antigen that is recognized by the full-length antibody. The antibody fragment can include isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins"). Exemplary antibodies can include, but are not limited to, antibodies for cancer cells, antibodies for viruses, antibodies that bind to cell surface receptors (CD8, CD34, CD45), and therapeutic antibodies.

Universal Adaptor Primer

A barcode can comprise one or more universal adaptor primers. For example, a gene-specific barcode, such as a gene-specific stochastic barcode, can comprise a universal adaptor primer. A universal adaptor primer can refer to a nucleotide sequence that is universal across all barcodes. A universal adaptor primer can be used for building gene-specific barcodes. A universal adaptor primer can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these nucleotides in length. A universal adaptor primer can be at least, or be at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30 nucleotides in length. A universal adaptor primer can be from 5-30 nucleotides in length.

Linker

When a barcode comprises more than one of a type of label (e.g., more than one cell label or more than one barcode sequence, such as one molecular label), the labels may be interspersed with a linker label sequence. A linker label sequence can be at least about 5, 10, 15, 20, 25, 30, 35, 40, 45, 50 or more nucleotides in length. A linker label sequence can be at most about 5, 10, 15, 20, 25, 30, 35, 40, 45, 50 or more nucleotides in length. In some instances, a linker label sequence is 12 nucleotides in length. A linker label sequence can be used to facilitate the synthesis of the barcode. The linker label can comprise an error-correcting (e.g., Hamming) code.

Solid Supports

Barcodes, such as stochastic barcodes, disclosed herein can, in some embodiments, be associated with a solid support. The solid support can be, for example, a synthetic particle. In some embodiments, some or all of the barcode sequences, such as molecular labels for stochastic barcodes (e.g., the first barcode sequences) of a plurality of barcodes (e.g., the first plurality of barcodes) on a solid support differ by at least one nucleotide. The cell labels of the barcodes on the same solid support can be the same. The cell labels of the barcodes on different solid supports can differ by at least one nucleotide. For example, first cell labels of a first plurality of barcodes on a first solid support can have the same sequence, and second cell labels of a second plurality of barcodes on a second solid support can have the same sequence. The first cell labels of the first plurality of barcodes on the first solid support and the second cell labels of the second plurality of barcodes on the second solid support can differ by at least one nucleotide. A cell label can be, for example, about 5-20 nucleotides long. A barcode sequence can be, for example, about 5-20 nucleotides long. The synthetic particle can be, for example, a bead.

The bead can be, for example, a silica gel bead, a controlled pore glass bead, a magnetic bead, a Dynabead, a Sephadex/Sepharose bead, a cellulose bead, a polystyrene bead, or any combination thereof. The bead can comprise a material such as polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, or any combination thereof.

In some embodiments, the bead can be a polymeric bead, for example a deformable bead or a gel bead, functionalized with barcodes or stochastic barcodes (such as gel beads from 1× Genomics (San Francisco, CA). In some implementation, a gel bead can comprise a polymer based gels. Gel beads can be generated, for example, by encapsulating one or more polymeric precursors into droplets. Upon exposure of the polymeric precursors to an accelerator (e.g., tetramethylethylenediamine (TEMED)), a gel bead may be generated.

In some embodiments, the particle can be disruptable (e.g., dissolvable, degradable). For example, the polymeric bead can dissolve, melt, or degrade, for example, under a desired condition. The desired condition can include an environmental condition. The desired condition may result in the polymeric bead dissolving, melting, or degrading in a controlled manner. A gel bead may dissolve, melt, or degrade due to a chemical stimulus, a physical stimulus, a biological stimulus, a thermal stimulus, a magnetic stimulus, an electric stimulus, a light stimulus, or any combination thereof.

Analytes and/or reagents, such as oligonucleotide barcodes, for example, may be coupled/immobilized to the interior surface of a gel bead (e.g., the interior accessible via diffusion of an oligonucleotide barcode and/or materials used to generate an oligonucleotide barcode) and/or the outer surface of a gel bead or any other microcapsule described herein. Coupling/immobilization may be via any form of chemical bonding (e.g., covalent bond, ionic bond) or physical phenomena (e.g., Van der Waals forces, dipole-dipole interactions, etc.). In some embodiments, coupling/immobilization of a reagent to a gel bead or any other microcapsule described herein may be reversible, such as, for example, via a labile moiety (e.g., via a chemical cross-linker, including chemical cross-linkers described herein). Upon application of a stimulus, the labile moiety may be cleaved and the immobilized reagent set free. In some embodiments, the labile moiety is a disulfide bond. For example, in the case where an oligonucleotide barcode is immobilized to a gel bead via a disulfide bond, exposure of the disulfide bond to a reducing agent can cleave the disulfide bond and free the oligonucleotide barcode from the bead. The labile moiety may be included as part of a gel bead or microcapsule, as part of a chemical linker that links a reagent or analyte to a gel bead or microcapsule, and/or as part of a reagent or analyte. In some embodiments, at least one barcode of the plurality of barcodes can be immobilized on the particle, partially immobilized on the particle, enclosed in the particle, partially enclosed in the particle, or any combination thereof.

In some embodiments, a gel bead can comprise a wide range of different polymers including but not limited to: polymers, heat sensitive polymers, photosensitive polymers, magnetic polymers, pH sensitive polymers, salt-sensitive polymers, chemically sensitive polymers, polyelectrolytes, polysaccharides, peptides, proteins, and/or plastics. Polymers may include but are not limited to materials such as poly(N-isopropylacrylamide) (PNIPAAm), poly(styrene sulfonate) (PSS), poly(allyl amine) (PAAm), poly(acrylic acid) (PAA), poly(ethylene imine) (PEI), poly(diallyldimethyl-ammonium chloride) (PDADMAC), poly(pyrolle) (PPy), poly(vinylpyrrolidone) (PVPON), poly(vinyl pyridine) (PVP), poly(methacrylic acid) (PMAA), poly(methyl methacrylate) (PMMA), polystyrene (PS), poly(tetrahydrofuran) (PTHF), poly(phthaladehyde) (PTHF), poly(hexyl viologen) (PHV), poly(L-lysine) (PLL), poly(L-arginine) (PARG), poly(lactic-co-glycolic acid) (PLGA).

Numerous chemical stimuli can be used to trigger the disruption, dissolution, or degradation of the beads. Examples of these chemical changes may include, but are not limited to pH-mediated changes to the bead wall, disintegration of the bead wall via chemical cleavage of cross-link bonds, triggered depolymerization of the bead wall, and bead wall switching reactions. Bulk changes may also be used to trigger disruption of the beads.

Bulk or physical changes to the microcapsule through various stimuli also offer many advantages in designing capsules to release reagents. Bulk or physical changes occur on a macroscopic scale, in which bead rupture is the result of mechano-physical forces induced by a stimulus. These processes may include, but are not limited to pressure induced rupture, bead wall melting, or changes in the porosity of the bead wall.

Biological stimuli may also be used to trigger disruption, dissolution, or degradation of beads. Generally, biological triggers resemble chemical triggers, but many examples use biomolecules, or molecules commonly found in living systems such as enzymes, peptides, saccharides, fatty acids, nucleic acids and the like. For example, beads may comprise polymers with peptide cross-links that are sensitive to cleavage by specific proteases. More specifically, one example may comprise a microcapsule comprising GFLGK peptide cross links. Upon addition of a biological trigger such as the protease Cathepsin B, the peptide cross links of the shell well are cleaved and the contents of the beads are released. In other cases, the proteases may be heat-activated. In another example, beads comprise a shell wall comprising cellulose. Addition of the hydrolytic enzyme chitosan serves as biologic trigger for cleavage of cellulosic bonds, depolymerization of the shell wall, and release of its inner contents.

The beads may also be induced to release their contents upon the application of a thermal stimulus. A change in temperature can cause a variety changes to the beads. A change in heat may cause melting of a bead such that the bead wall disintegrates. In other cases, the heat may increase the internal pressure of the inner components of the bead such that the bead ruptures or explodes. In still other cases, the heat may transform the bead into a shrunken dehydrated state. The heat may also act upon heat-sensitive polymers within the wall of a bead to cause disruption of the bead.

Inclusion of magnetic nanoparticles to the bead wall of microcapsules may allow triggered rupture of the beads as well as guide the beads in an array. A device of this disclosure may comprise magnetic beads for either purpose. In one example, incorporation of $Fe_3O_4$ nanoparticles into polyelectrolyte containing beads triggers rupture in the presence of an oscillating magnetic field stimulus.

A bead may also be disrupted, dissolved, or degraded as the result of electrical stimulation. Similar to magnetic particles described in the previous section, electrically sensitive beads can allow for both triggered rupture of the beads as well as other functions such as alignment in an electric field, electrical conductivity or redox reactions. In one example, beads containing electrically sensitive material are aligned in an electric field such that release of inner reagents can be controlled. In other examples, electrical fields may induce redox reactions within the bead wall itself that may increase porosity.

A light stimulus may also be used to disrupt the beads. Numerous light triggers are possible and may include systems that use various molecules such as nanoparticles and chromophores capable of absorbing photons of specific ranges of wavelengths. For example, metal oxide coatings can be used as capsule triggers. UV irradiation of polyelectrolyte capsules coated with $SiO_2$ may result in disintegration of the bead wall. In yet another example, photo switchable materials such as azobenzene groups may be incorporated in the bead wall. Upon the application of UV or visible light, chemicals such as these undergo a reversible cis-to-trans isomerization upon absorption of photons. In this aspect, incorporation of photon switches result in a bead wall that may disintegrate or become more porous upon the application of a light trigger.

Figure 12:
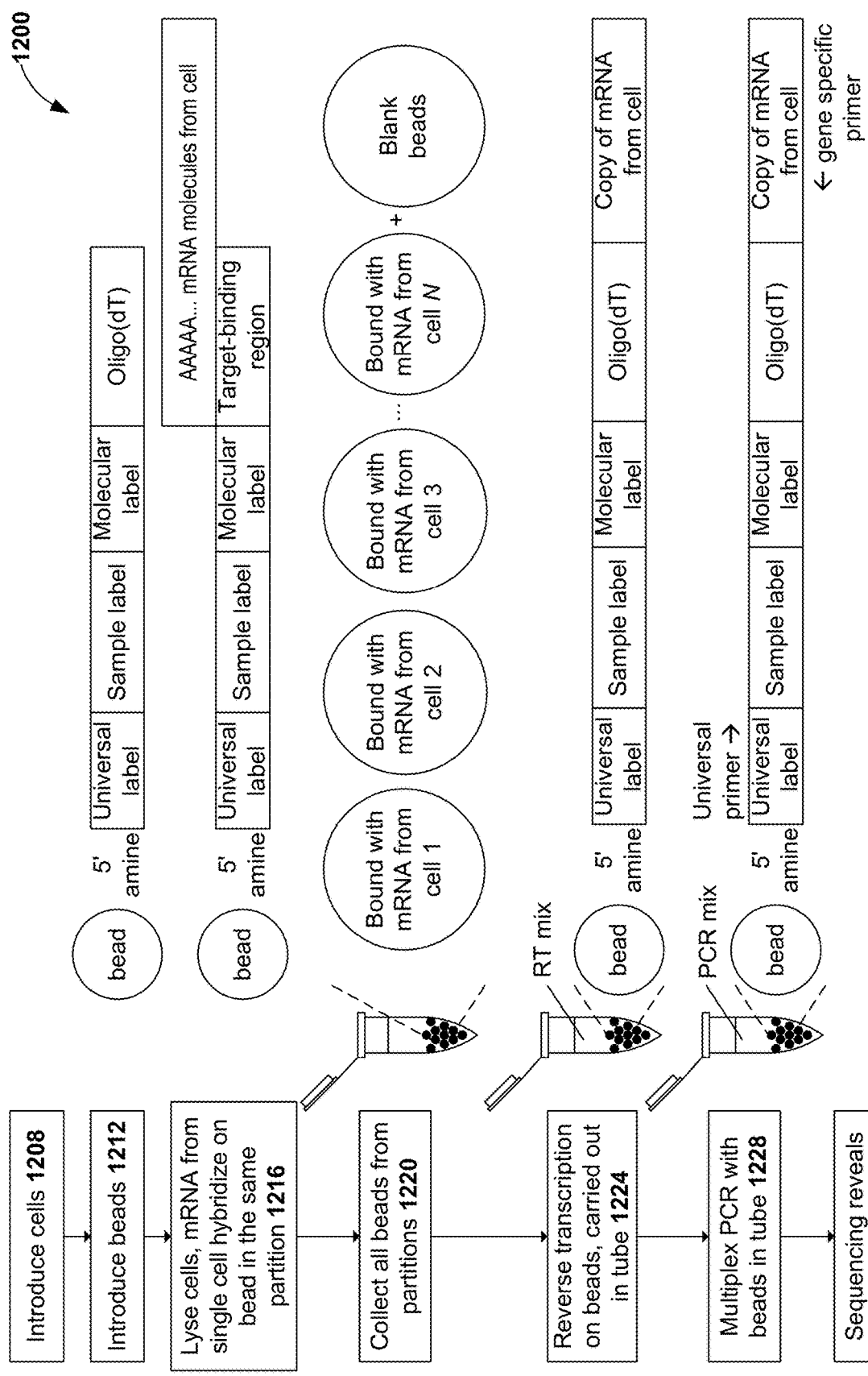
FIG. 12 shows a non-limiting exemplary workflow of barcoding and digital counting.

For example, in a non-limiting example of barcoding (e.g., stochastic barcoding) illustrated in FIG. 12, after introducing cells such as single cells onto a plurality of microwells of a microwell array at block 1208, beads can be introduced onto the plurality of microwells of the microwell array at block 1212. Each microwell can comprise one bead. The beads can comprise a plurality of barcodes. A barcode can comprise a 5' amine region attached to a bead. The barcode can comprise a universal label, a barcode sequence (e.g., a molecular label), a target-binding region, or any combination thereof.

The barcodes disclosed herein can be associated with (e.g., attached to) a solid support (e.g., a bead). The barcodes associated with a solid support can each comprise a barcode sequence selected from a group comprising at least 100 or 1000 barcode sequences with unique sequences. In some embodiments, different barcodes associated with a solid support can comprise barcode with different sequences. In some embodiments, a percentage of barcodes associated with a solid support comprises the same cell label. For example, the percentage can be, or be about 60%, 70%, 80%, 85%, 90%, 95%, 97%, 99%, 100%, or a number or a range between any two of these values. As another example, the percentage can be at least, or be at most 60%, 70%, 80%, 85%, 90%, 95%, 97%, 99%, or 100%. In some embodiments, barcodes associated with a solid support can have the same cell label. The barcodes associated with different solid supports can have different cell labels selected from a group comprising at least 100 or 1000 cell labels with unique sequences.

The barcodes disclosed herein can be associated to (e.g., attached to) a solid support (e.g., a bead). In some embodiments, barcoding the plurality of targets in the sample can be performed with a solid support including a plurality of synthetic particles associated with the plurality of barcodes. In some embodiments, the solid support can include a plurality of synthetic particles associated with the plurality of barcodes. The spatial labels of the plurality of barcodes on different solid supports can differ by at least one nucleotide. The solid support can, for example, include the plurality of barcodes in two dimensions or three dimensions. The synthetic particles can be beads. The beads can be silica gel beads, controlled pore glass beads, magnetic beads, Dynabeads, Sephadex/Sepharose beads, cellulose beads, polystyrene beads, or any combination thereof. The solid support can include a polymer, a matrix, a hydrogel, a needle array device, an antibody, or any combination thereof. In some embodiments, the solid supports can be free floating. In some embodiments, the solid supports can be embedded in a semi-solid or solid array. The barcodes may not be associated with solid supports. The barcodes can be individual nucleotides. The barcodes can be associated with a substrate.

As used herein, the terms "tethered," "attached," and "immobilized," are used interchangeably, and can refer to covalent or non-covalent means for attaching barcodes to a solid support. Any of a variety of different solid supports can be used as solid supports for attaching pre-synthesized barcodes or for in situ solid-phase synthesis of barcode.

In some embodiments, the solid support is a bead. The bead can comprise one or more types of solid, porous, or hollow sphere, ball, bearing, cylinder, or other similar configuration which a nucleic acid can be immobilized (e.g., covalently or non-covalently). The bead can be, for example, composed of plastic, ceramic, metal, polymeric material, or any combination thereof. A bead can be, or comprise, a discrete particle that is spherical (e.g., microspheres) or have a non-spherical or irregular shape, such as cubic, cuboid, pyramidal, cylindrical, conical, oblong, or disc-shaped, and the like. In some embodiments, a bead can be non-spherical in shape.

Beads can comprise a variety of materials including, but not limited to, paramagnetic materials (e.g., magnesium, molybdenum, lithium, and tantalum), superparamagnetic materials (e.g., ferrite ($Fe_3O_4$; magnetite) nanoparticles), ferromagnetic materials (e.g., iron, nickel, cobalt, some alloys thereof, and some rare earth metal compounds), ceramic, plastic, glass, polystyrene, silica, methylstyrene, acrylic polymers, titanium, latex, Sepharose, agarose, hydrogel, polymer, cellulose, nylon, or any combination thereof.

In some embodiments, the bead (e.g., the bead to which the labels are attached) is a hydrogel bead. In some embodiments, the bead comprises hydrogel.

Some embodiments disclosed herein include one or more particles (for example, beads). Each of the particles can comprise a plurality of oligonucleotides (e.g., barcodes). Each of the plurality of oligonucleotides can comprise a barcode sequence (e.g., a molecular label sequence), a cell label, and a target-binding region (e.g., an oligo(dT) sequence, a gene-specific sequence, a random multimer, or a combination thereof). The cell label sequence of each of the plurality of oligonucleotides can be the same. The cell label sequences of oligonucleotides on different particles can be different such that the oligonucleotides on different particles can be identified. The number of different cell label sequences can be different in different implementations. In some embodiments, the number of cell label sequences can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, a number or a range between any two of these values, or more. In some embodiments, the number of cell label sequences can be at least, or be at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. In some embodiments, no more than 1, 2, 3, 4, 5, 6, 7, 8, 9, 10, 20, 30, 40, 50, 60, 70, 80, 90, 100, 200, 300, 400, 500, 600, 700, 800, 900, 1000, or more of the plurality of the particles include oligonucleotides with the same cell sequence. In some embodiment, the plurality of particles that include oligonucleotides with the same cell sequence can be at most 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, or more. In some embodiments, none of the plurality of the particles has the same cell label sequence.

The plurality of oligonucleotides on each particle can comprise different barcode sequences (e.g., molecular labels). In some embodiments, the number of barcode sequences can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, or a number or a range between any two of these values. In some embodiments, the number of barcode sequences can be at least, or be at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. For example, at least 100 of the plurality of oligonucleotides comprise different barcode sequences. As another example, in a single particle, at least 100, 500, 1000, 5000, 10000, 15000, 20000, 50000, a number or a range between any two of these values, or more of the plurality of oligonucleotides comprise different barcode sequences. Some embodiments provide a plurality of the particles comprising barcodes. In some embodiments, the ratio of an occurrence (or a copy or a number) of a target to be labeled and the different barcode sequences can be at least 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90, or more. In some embodiments, each of the plurality of oligonucleotides further comprises a sample label, a universal label, or both. The particle can be, for example, a nanoparticle or microparticle.

The size of the beads can vary. For example, the diameter of the bead can range from 0.1 micrometer to 50 micrometer. In some embodiments, the diameter of the bead can be, or be about, 0.1, 0.5, 1, 2, 3, 4, 5, 6, 7, 8, 9, 10, 20, 30, 40, 50 micrometer, or a number or a range between any two of these values.

The diameter of the bead can be related to the diameter of the wells of the substrate. In some embodiments, the diameter of the bead can be, or be about, 10%, 20%, 30%, 40%, 50%, 60%, 70%, 80%, 90%, 100%, or a number or a range between any two of these values, longer or shorter than the diameter of the well. The diameter of the beads can be related to the diameter of a cell (e.g., a single cell entrapped by a well of the substrate). In some embodiments, the diameter of the bead can be at least, or be at most, 10%, 20%, 30%, 40%, 50%, 60%, 70%, 80%, 90%, or 100% longer or shorter than the diameter of the well. The diameter of the beads can be related to the diameter of a cell (e.g., a single cell entrapped by a well of the substrate). In some embodiments, the diameter of the bead can be, or be about, 10%, 20%, 30%, 40%, 50%, 60%, 70%, 80%, 90%, 100%, 150%, 200%, 250%, 300%, or a number or a range between any two of these values, longer or shorter than the diameter of the cell. In some embodiments, the diameter of the beads can be at least, or be at most, 10%, 20%, 30%, 40%, 50%, 60%, 70%, 80%, 90%, 100%, 150%, 200%, 250%, or 300% longer or shorter than the diameter of the cell.

A bead can be attached to and/or embedded in a substrate. A bead can be attached to and/or embedded in a gel, hydrogel, polymer and/or matrix. The spatial position of a bead within a substrate (e.g., gel, matrix, scaffold, or polymer) can be identified using the spatial label present on the barcode on the bead which can serve as a location address.

Examples of beads can include, but are not limited to, streptavidin beads, agarose beads, magnetic beads, Dynabeads®, MACS® microbeads, antibody conjugated beads (e.g., anti-immunoglobulin microbeads), protein A conjugated beads, protein G conjugated beads, protein A/G conjugated beads, protein L conjugated beads, oligo(dT) conjugated beads, silica beads, silica-like beads, anti-biotin microbeads, anti-fluorochrome microbeads, and BcMag™ Carboxyl-Terminated Magnetic Beads.

A bead can be associated with (e.g., impregnated with) quantum dots or fluorescent dyes to make it fluorescent in one fluorescence optical channel or multiple optical channels. A bead can be associated with iron oxide or chromium oxide to make it paramagnetic or ferromagnetic. Beads can be identifiable. For example, a bead can be imaged using a camera. A bead can have a detectable code associated with the bead. For example, a bead can comprise a barcode. A bead can change size, for example, due to swelling in an organic or inorganic solution. A bead can be hydrophobic. A bead can be hydrophilic. A bead can be biocompatible.

A solid support (e.g., a bead) can be visualized. The solid support can comprise a visualizing tag (e.g., fluorescent dye). A solid support (e.g., a bead) can be etched with an identifier (e.g., a number). The identifier can be visualized through imaging the beads.

A solid support can comprise an insoluble, semi-soluble, or insoluble material. A solid support can be referred to as "functionalized" when it includes a linker, a scaffold, a building block, or other reactive moiety attached thereto, whereas a solid support may be "nonfunctionalized" when it lacks such a reactive moiety attached thereto. The solid support can be employed free in solution, such as in a microtiter well format; in a flow-through format, such as in a column; or in a dipstick.

The solid support can comprise a membrane, paper, plastic, coated surface, flat surface, glass, slide, chip, or any combination thereof. A solid support can take the form of resins, gels, microspheres, or other geometric configurations. A solid support can comprise silica chips, microparticles, nanoparticles, plates, arrays, capillaries, flat supports such as glass fiber filters, glass surfaces, metal surfaces (steel, gold silver, aluminum, silicon and copper), glass supports, plastic supports, silicon supports, chips, filters, membranes, microwell plates, slides, plastic materials including multiwell plates or membranes (e.g., formed of polyethylene, polypropylene, polyamide, polyvinylidenedifluoride), and/or wafers, combs, pins or needles (e.g., arrays of pins suitable for combinatorial synthesis or analysis) or beads in an array of pits or nanoliter wells of flat surfaces such as wafers (e.g., silicon wafers), wafers with pits with or without filter bottoms.

The solid support can comprise a polymer matrix (e.g., gel, hydrogel). The polymer matrix may be able to permeate intracellular space (e.g., around organelles). The polymer matrix may able to be pumped throughout the circulatory system.

Substrates and Microwell Array

As used herein, a substrate can refer to a type of solid support. A substrate can refer to a solid support that can comprise barcodes or stochastic barcodes of the disclosure. A substrate can, for example, comprise a plurality of microwells. For example, a substrate can be a well array comprising two or more microwells. In some embodiments, a microwell can comprise a small reaction chamber of defined volume. In some embodiments, a microwell can entrap one or more cells. In some embodiments, a microwell can entrap only one cell. In some embodiments, a microwell can entrap one or more solid supports. In some embodiments, a microwell can entrap only one solid support. In some embodiments, a microwell entraps a single cell and a single solid support (e.g., a bead). A microwell can comprise barcode reagents of the disclosure.

Methods of Barcoding

The disclosure provides for methods for estimating the number of distinct targets at distinct locations in a physical sample (e.g., tissue, organ, tumor, cell). The methods can comprise placing barcodes (e.g., stochastic barcodes) in close proximity with the sample, lysing the sample, associating distinct targets with the barcodes, amplifying the targets and/or digitally counting the targets. The method can further comprise analyzing and/or visualizing the information obtained from the spatial labels on the barcodes. In some embodiments, a method comprises visualizing the plurality of targets in the sample. Mapping the plurality of targets onto the map of the sample can include generating a two dimensional map or a three dimensional map of the sample. The two dimensional map and the three dimensional map can be generated prior to or after barcoding (e.g., stochastically barcoding) the plurality of targets in the sample. Visualizing the plurality of targets in the sample can include mapping the plurality of targets onto a map of the sample. Mapping the plurality of targets onto the map of the sample can include generating a two dimensional map or a three dimensional map of the sample. The two dimensional map and the three dimensional map can be generated prior to or after barcoding the plurality of targets in the sample. in some embodiments, the two dimensional map and the three dimensional map can be generated before or after lysing the sample. Lysing the sample before or after generating the two dimensional map or the three dimensional map can include heating the sample, contacting the sample with a detergent, changing the pH of the sample, or any combination thereof.

In some embodiments, barcoding the plurality of targets comprises hybridizing a plurality of barcodes with a plurality of targets to create barcoded targets (e.g., stochastically barcoded targets). Barcoding the plurality of targets can comprise generating an indexed library of the barcoded targets. Generating an indexed library of the barcoded targets can be performed with a solid support comprising the plurality of barcodes (e.g., stochastic barcodes).

Contacting a Sample and a Barcode

The disclosure provides for methods for contacting a sample (e.g., cells) to a substrate of the disclosure. A sample comprising, for example, a cell, organ, or tissue thin section, can be contacted to barcodes (e.g., stochastic barcodes). The cells can be contacted, for example, by gravity flow wherein the cells can settle and create a monolayer. The sample can be a tissue thin section. The thin section can be placed on the substrate. The sample can be one-dimensional (e.g., forms a planar surface). The sample (e.g., cells) can be spread across the substrate, for example, by growing/culturing the cells on the substrate.

When barcodes are in close proximity to targets, the targets can hybridize to the barcode. The barcodes can be contacted at a non-depletable ratio such that each distinct target can associate with a distinct barcode of the disclosure. To ensure efficient association between the target and the barcode, the targets can be cross-linked to barcode.

Cell Lysis

Following the distribution of cells and barcodes, the cells can be lysed to liberate the target molecules. Cell lysis can be accomplished by any of a variety of means, for example, by chemical or biochemical means, by osmotic shock, or by means of thermal lysis, mechanical lysis, or optical lysis. Cells can be lysed by addition of a cell lysis buffer comprising a detergent (e.g., SDS, Li dodecyl sulfate, Triton X-100, Tween-20, or NP-40), an organic solvent (e.g., methanol or acetone), or digestive enzymes (e.g., proteinase K, pepsin, or trypsin), or any combination thereof. To increase the association of a target and a barcode, the rate of the diffusion of the target molecules can be altered by for example, reducing the temperature and/or increasing the viscosity of the lysate.

In some embodiments, the sample can be lysed using a filter paper. The filter paper can be soaked with a lysis buffer on top of the filter paper. The filter paper can be applied to the sample with pressure which can facilitate lysis of the sample and hybridization of the targets of the sample to the substrate.

In some embodiments, lysis can be performed by mechanical lysis, heat lysis, optical lysis, and/or chemical lysis. Chemical lysis can include the use of digestive enzymes such as proteinase K, pepsin, and trypsin. Lysis can be performed by the addition of a lysis buffer to the substrate. A lysis buffer can comprise Tris HCl. A lysis buffer can comprise at least about 0.01, 0.05, 0.1, 0.5, or 1 M or more Tris HCl. A lysis buffer can comprise at most about 0.01, 0.05, 0.1, 0.5, or 1 M or more Tris HCL. A lysis buffer can comprise about 0.1 M Tris HCl. The pH of the lysis buffer can be at least about 1, 2, 3, 4, 5, 6, 7, 8, 9, 10, or more. The pH of the lysis buffer can be at most about 1, 2, 3, 4, 5, 6, 7, 8, 9,10, or more. In some embodiments, the pH of the lysis buffer is about 7.5. The lysis buffer can comprise a salt (e.g., LiCl). The concentration of salt in the lysis buffer can be at least about 0.1, 0.5, or 1 M or more. The concentration of salt in the lysis buffer can be at most about 0.1, 0.5, or 1 M or more. In some embodiments, the concentration of salt in the lysis buffer is about 0.5M. The lysis buffer can comprise a detergent (e.g., SDS, Li dodecyl sulfate, triton X, tween, NP-40). The concentration of the detergent in the lysis buffer can be at least about 0.0001%, 0.0005%, 0.001%, 0.005%, 0.01%, 0.05%, 0.1%, 0.5%, 1%, 2%, 3%, 4%, 5%, 6%, or 7%, or more. The concentration of the detergent in the lysis buffer can be at most about 0.0001%, 0.0005%, 0.001%, 0.005%, 0.01%, 0.05%, 0.1%, 0.5%, 1%, 2%, 3%, 4%, 5%, 6%, or 7%, or more. In some embodiments, the concentration of the detergent in the lysis buffer is about 1% Li dodecyl sulfate. The time used in the method for lysis can be dependent on the amount of detergent used. In some embodiments, the more detergent used, the less time needed for lysis. The lysis buffer can comprise a chelating agent (e.g., EDTA, EGTA). The concentration of a chelating agent in the lysis buffer can be at least about 1, 5, 10, 15, 20, 25, or 30 mM or more. The concentration of a chelating agent in the lysis buffer can be at most about 1, 5, 10, 15, 20, 25, or 30 mM or more. In some embodiments, the concentration of chelating agent in the lysis buffer is about 10 mM. The lysis buffer can comprise a reducing reagent (e.g., beta-mercaptoethanol, DTT). The concentration of the reducing reagent in the lysis buffer can be at least about 1, 5, 10, 15, or 20 mM or more. The concentration of the reducing reagent in the lysis buffer can be at most about 1, 5, 10, 15, or 20 mM or more. In some embodiments, the concentration of reducing reagent in the lysis buffer is about 5 mM. In some embodiments, a lysis buffer can comprise about 0.1M TrisHCl, about pH 7.5, about 0.5M LiCl, about 1% lithium dodecyl sulfate, about 10 mM EDTA, and about 5 mM DTT.

Lysis can be performed at a temperature of about 4, 10, 15, 20, 25, or 30° C. Lysis can be performed for about 1, 5, 10, 15, or 20 or more minutes. A lysed cell can comprise at least about 100000, 200000, 300000, 400000, 500000, 600000, or 700000 or more target nucleic acid molecules. A lysed cell can comprise at most about 100000, 200000, 300000, 400000, 500000, 600000, or 700000 or more target nucleic acid molecules.

Attachment of Barcodes to Target Nucleic Acid Molecules

Following lysis of the cells and release of nucleic acid molecules therefrom, the nucleic acid molecules can randomly associate with the barcodes of the co-localized solid support. Association can comprise hybridization of a barcode's target recognition region to a complementary portion of the target nucleic acid molecule (e.g., oligo(dT) of the barcode can interact with a poly(A) tail of a target). The assay conditions used for hybridization (e.g., buffer pH, ionic strength, temperature, etc.) can be chosen to promote formation of specific, stable hybrids. In some embodiments, the nucleic acid molecules released from the lysed cells can associate with the plurality of probes on the substrate (e.g., hybridize with the probes on the substrate). When the probes comprise oligo(dT), mRNA molecules can hybridize to the probes and be reverse transcribed. The oligo(dT) portion of the oligonucleotide can act as a primer for first strand synthesis of the cDNA molecule. For example, in a non-limiting example of barcoding illustrated in FIG. 12, at block 1216, mRNA molecules can hybridize to barcodes on beads. For example, single-stranded nucleotide fragments can hybridize to the target-binding regions of barcodes.

Attachment can further comprise ligation of a barcode's target recognition region and a portion of the target nucleic acid molecule. For example, the target binding region can comprise a nucleic acid sequence that can be capable of specific hybridization to a restriction site overhang (e.g., an EcoRI sticky-end overhang). The assay procedure can further comprise treating the target nucleic acids with a restriction enzyme (e.g., EcoRI) to create a restriction site overhang. The barcode can then be ligated to any nucleic acid molecule comprising a sequence complementary to the restriction site overhang. A ligase (e.g., T4 DNA ligase) can be used to join the two fragments. In some embodiments provided herein, the assay procedure can comprise treating the target nucleic acids with a transposase (e.g., Tn5) to generate tagmentation products. Tagmentation products can comprise overhangs. Tagmentation products can be captured by the oligonucleotide barcodes provided herein (e.g., by binding said overhangs). Tagmentation products can comprise gaps. A DNA polymerase (e.g., Klenow) can be employed to fill in said gaps before a ligation reaction.

For example, in a non-limiting example of barcoding illustrated in FIG. 12, at block 1220, the labeled targets from a plurality of cells (or a plurality of samples) (e.g., target-barcode molecules) can be subsequently pooled, for example, into a tube. The labeled targets can be pooled by, for example, retrieving the barcodes and/or the beads to which the target-barcode molecules are attached.

The retrieval of solid support-based collections of attached target-barcode molecules can be implemented by use of magnetic beads and an externally-applied magnetic field. Once the target-barcode molecules have been pooled, all further processing can proceed in a single reaction vessel. Further processing can include, for example, reverse transcription reactions, amplification reactions, cleavage reactions, dissociation reactions, and/or nucleic acid extension reactions. Further processing reactions can be performed within the microwells, that is, without first pooling the labeled target nucleic acid molecules from a plurality of cells.

Reverse Transcription or Nucleic Acid Extension

The disclosure provides for a method to create a target-barcode conjugate using reverse transcription (e.g., at block 1224 of FIG. 12) or nucleic acid extension. The target-barcode conjugate can comprise the barcode and a complementary sequence of all or a portion of the target nucleic acid (i.e., a barcoded cDNA molecule, such as a stochastically barcoded cDNA molecule). Reverse transcription of the associated RNA molecule can occur by the addition of a reverse transcription primer along with the reverse transcriptase. The reverse transcription primer can be an oligo (dT) primer, a random hexanucleotide primer, or a target-specific oligonucleotide primer. Oligo(dT) primers can be, or can be about, 12-18 nucleotides in length and bind to the endogenous poly(A) tail at the 3' end of mammalian mRNA. Random hexanucleotide primers can bind to mRNA at a variety of complementary sites. Target-specific oligonucleotide primers typically selectively prime the mRNA of interest.

In some embodiments, reverse transcription of an mRNA molecule to a labeled-RNA molecule can occur by the addition of a reverse transcription primer. In some embodiments, the reverse transcription primer is an oligo(dT) primer, random hexanucleotide primer, or a target-specific oligonucleotide primer. Generally, oligo(dT) primers are 12-18 nucleotides in length and bind to the endogenous poly(A) tail at the 3' end of mammalian mRNA. Random hexanucleotide primers can bind to mRNA at a variety of complementary sites. Target-specific oligonucleotide primers typically selectively prime the mRNA of interest.

In some embodiments, a target is a cDNA molecule. For example, an mRNA molecule can be reverse transcribed using a reverse transcriptase, such as Moloney murine leukemia virus (MMLV) reverse transcriptase, to generate a cDNA molecule with a poly(dC) tail. A barcode can include a target binding region with a poly(dG) tail. Upon base pairing between the poly(dG) tail of the barcode and the poly(dC) tail of the cDNA molecule, the reverse transcriptase switches template strands, from cellular RNA molecule to the barcode, and continues replication to the 5' end of the barcode. By doing so, the resulting cDNA molecule contains the sequence of the barcode (such as the molecular label) on the 3' end of the cDNA molecule.

Reverse transcription can occur repeatedly to produce multiple labeled-cDNA molecules. The methods disclosed herein can comprise conducting at least about 1, 2, 3, 4, 5, 6, 7, 8, 9, 10, 11, 12, 13, 14, 15, 16, 17, 18, 19, or 20 reverse transcription reactions. The method can comprise conducting at least about 25, 30, 35, 40, 45, 50, 55, 60, 65, 70, 75, 80, 85, 90, 95, or 100 reverse transcription reactions.

Amplification

One or more nucleic acid amplification reactions (e.g., at block 1228 of FIG. 12) can be performed to create multiple copies of the labeled target nucleic acid molecules. Amplification can be performed in a multiplexed manner, wherein multiple target nucleic acid sequences are amplified simultaneously. The amplification reaction can be used to add sequencing adaptors to the nucleic acid molecules. The amplification reactions can comprise amplifying at least a portion of a sample label, if present. The amplification reactions can comprise amplifying at least a portion of the cellular label and/or barcode sequence (e.g., a molecular label). The amplification reactions can comprise amplifying at least a portion of a sample tag, a cell label, a spatial label, a barcode sequence (e.g., a molecular label), a target nucleic acid, or a combination thereof. The amplification reactions can comprise amplifying 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 100%, or a range or a number between any two of these values, of the plurality of nucleic acids. The method can further comprise conducting one or more cDNA synthesis reactions to produce one or more cDNA copies of target-barcode molecules comprising a sample label, a cell label, a spatial label, and/or a barcode sequence (e.g., a molecular label).

In some embodiments, amplification can be performed using a polymerase chain reaction (PCR). As used herein, PCR can refer to a reaction for the in vitro amplification of specific DNA sequences by the simultaneous primer extension of complementary strands of DNA. As used herein, PCR can encompass derivative forms of the reaction, including but not limited to, RT-PCR, real-time PCR, nested PCR, quantitative PCR, multiplexed PCR, digital PCR, and assembly PCR.

Amplification of the labeled nucleic acids can comprise non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), and a Qβ replicase (Qβ) method, use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and ramification extension amplification (RAM). In some embodiments, the amplification does not produce circularized transcripts.

In some embodiments, the methods disclosed herein further comprise conducting a polymerase chain reaction on the labeled nucleic acid (e.g., labeled-RNA, labeled-DNA, labeled-cDNA) to produce a labeled amplicon (e.g., a stochastically labeled amplicon). The labeled amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample label, a spatial label, a cell label, and/or a barcode sequence (e.g., a molecular label). The labeled amplicon can be a single-stranded molecule. The single-stranded molecule can comprise DNA, RNA, or a combination thereof. The nucleic acids of the disclosure can comprise synthetic or altered nucleic acids.

Amplification can comprise use of one or more non-natural nucleotides. Non-natural nucleotides can comprise photolabile or triggerable nucleotides. Examples of non-natural nucleotides can include, but are not limited to, peptide nucleic acid (PNA), morpholino and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise, for example, 1, 2, 3, 4, 5, 6, 7, 8, 9, 10, 11, 12, 13, 14, or 15 or more nucleotides. The one or more primers can comprise at least 1, 2, 3, 4, 5, 6, 7, 8, 9, 10, 11, 12, 13, 14, or 15 or more nucleotides. The one or more primers can comprise less than 12-15 nucleotides. The one or more primers can anneal to at least a portion of the plurality of labeled targets (e.g., stochastically labeled targets). The one or more primers can anneal to the 3' end or 5' end of the plurality of labeled targets. The one or more primers can anneal to an internal region of the plurality of labeled targets. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled targets. The one or more primers can comprise a fixed panel of primers. The one or more primers can comprise at least one or more custom primers. The one or more primers can comprise at least one or more control primers. The one or more primers can comprise at least one or more gene-specific primers.

The one or more primers can comprise a universal primer. The universal primer can anneal to a universal primer binding site. The one or more custom primers can anneal to a first sample label, a second sample label, a spatial label, a cell label, a barcode sequence (e.g., a molecular label), a target, or any combination thereof. The one or more primers can comprise a universal primer and a custom primer. The custom primer can be designed to amplify one or more targets. The targets can comprise a subset of the total nucleic acids in one or more samples. The targets can comprise a subset of the total labeled targets in one or more samples. The one or more primers can comprise at least 96 or more custom primers. The one or more primers can comprise at least 960 or more custom primers. The one or more primers can comprise at least 9600 or more custom primers. The one or more custom primers can anneal to two or more different labeled nucleic acids. The two or more different labeled nucleic acids can correspond to one or more genes.

Any amplification scheme can be used in the methods of the present disclosure. For example, in one scheme, the first round PCR can amplify molecules attached to the bead using a gene specific primer and a primer against the universal Illumina sequencing primer 1 sequence. The second round of PCR can amplify the first PCR products using a nested gene specific primer flanked by Illumina sequencing primer 2 sequence, and a primer against the universal Illumina sequencing primer 1 sequence. The third round of PCR adds P5 and P7 and sample index to turn PCR products into an Illumina sequencing library. Sequencing using 150 bp×2 sequencing can reveal the cell label and barcode sequence (e.g., molecular label) on read 1, the gene on read 2, and the sample index on index 1 read.

In some embodiments, nucleic acids can be removed from the substrate using chemical cleavage. For example, a chemical group or a modified base present in a nucleic acid can be used to facilitate its removal from a solid support. For example, an enzyme can be used to remove a nucleic acid from a substrate. For example, a nucleic acid can be removed from a substrate through a restriction endonuclease digestion. For example, treatment of a nucleic acid containing a dUTP or ddUTP with uracil-d-glycosylase (UDG) can be used to remove a nucleic acid from a substrate. For example, a nucleic acid can be removed from a substrate using an enzyme that performs nucleotide excision, such as a base excision repair enzyme, such as an apurinic/apyrimidinic (AP) endonuclease. In some embodiments, a nucleic acid can be removed from a substrate using a photocleavable group and light. In some embodiments, a cleavable linker can be used to remove a nucleic acid from the substrate. For example, the cleavable linker can comprise at least one of biotin/avidin, biotin/streptavidin, biotin/neutravidin, Ig-protein A, a photo-labile linker, acid or base labile linker group, or an aptamer.

When the probes are gene-specific, the molecules can hybridize to the probes and be reverse transcribed and/or amplified. In some embodiments, after the nucleic acid has been synthesized (e.g., reverse transcribed), it can be amplified. Amplification can be performed in a multiplex manner, wherein multiple target nucleic acid sequences are amplified simultaneously. Amplification can add sequencing adaptors to the nucleic acid.

In some embodiments, amplification can be performed on the substrate, for example, with bridge amplification. cDNAs can be homopolymer tailed in order to generate a compatible end for bridge amplification using oligo(dT) probes on the substrate. In bridge amplification, the primer that is complementary to the 3' end of the template nucleic acid can be the first primer of each pair that is covalently attached to the solid particle. When a sample containing the template nucleic acid is contacted with the particle and a single thermal cycle is performed, the template molecule can be annealed to the first primer and the first primer is elongated in the forward direction by addition of nucleotides to form a duplex molecule consisting of the template molecule and a newly formed DNA strand that is complementary to the template. In the heating step of the next cycle, the duplex molecule can be denatured, releasing the template molecule from the particle and leaving the complementary DNA strand attached to the particle through the first primer. In the annealing stage of the annealing and elongation step that follows, the complementary strand can hybridize to the second primer, which is complementary to a segment of the complementary strand at a location removed from the first primer. This hybridization can cause the complementary strand to form a bridge between the first and second primers secured to the first primer by a covalent bond and to the second primer by hybridization. In the elongation stage, the second primer can be elongated in the reverse direction by the addition of nucleotides in the same reaction mixture, thereby converting the bridge to a double-stranded bridge. The next cycle then begins, and the double-stranded bridge can be denatured to yield two single-stranded nucleic acid molecules, each having one end attached to the particle surface via the first and second primers, respectively, with the other end of each unattached. In the annealing and elongation step of this second cycle, each strand can hybridize to a further complementary primer, previously unused, on the same particle, to form new single-strand bridges. The two previously unused primers that are now hybridized elongate to convert the two new bridges to double-strand bridges.

The amplification reactions can comprise amplifying at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the plurality of nucleic acids.

Amplification of the labeled nucleic acids can comprise PCR-based methods or non-PCR based methods. Amplification of the labeled nucleic acids can comprise exponential amplification of the labeled nucleic acids. Amplification of the labeled nucleic acids can comprise linear amplification of the labeled nucleic acids. Amplification can be performed by polymerase chain reaction (PCR). PCR can refer to a reaction for the in vitro amplification of specific DNA sequences by the simultaneous primer extension of complementary strands of DNA. PCR can encompass derivative forms of the reaction, including but not limited to, RT-PCR, real-time PCR, nested PCR, quantitative PCR, multiplexed PCR, digital PCR, suppression PCR, semi-suppressive PCR and assembly PCR.

In some embodiments, amplification of the labeled nucleic acids comprises non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), a Qβ replicase (Qβ), use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and/or ramification extension amplification (RAM).

In some embodiments, the methods disclosed herein further comprise conducting a nested polymerase chain reaction on the amplified amplicon (e.g., target). The amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample tag or molecular identifier label. Alternatively, the amplicon can be a single-stranded molecule. The single-stranded molecule can comprise DNA, RNA, or a combination thereof. The nucleic acids of the present invention can comprise synthetic or altered nucleic acids.

In some embodiments, the method comprises repeatedly amplifying the labeled nucleic acid to produce multiple amplicons. The methods disclosed herein can comprise conducting at least about 1, 2, 3, 4, 5, 6, 7, 8, 9, 10, 11, 12, 13, 14, 15, 16, 17, 18, 19, or 20 amplification reactions. Alternatively, the method comprises conducting at least about 25, 30, 35, 40, 45, 50, 55, 60, 65, 70, 75, 80, 85, 90, 95, or 100 amplification reactions.

Amplification can further comprise adding one or more control nucleic acids to one or more samples comprising a plurality of nucleic acids. Amplification can further comprise adding one or more control nucleic acids to a plurality of nucleic acids. The control nucleic acids can comprise a control label.

Amplification can comprise use of one or more non-natural nucleotides. Non-natural nucleotides can comprise photolabile and/or triggerable nucleotides. Examples of non-natural nucleotides include, but are not limited to, peptide nucleic acid (PNA), morpholino and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise one or more oligonucleotides. The one or more oligonucleotides can comprise at least about 7-9 nucleotides. The one or more oligonucleotides can comprise less than 12-15 nucleotides. The one or more primers can anneal to at least a portion of the plurality of labeled nucleic acids. The one or more primers can anneal to the 3' end and/or 5' end of the plurality of labeled nucleic acids. The one or more primers can anneal to an internal region of the plurality of labeled nucleic acids. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled nucleic acids. The one or more primers can comprise a fixed panel of primers. The one or more primers can comprise at least one or more custom primers. The one or more primers can comprise at least one or more control primers. The one or more primers can comprise at least one or more housekeeping gene primers. The one or more primers can comprise a universal primer. The universal primer can anneal to a universal primer binding site. The one or more custom primers can anneal to the first sample tag, the second sample tag, the molecular identifier label, the nucleic acid or a product thereof. The one or more primers can comprise a universal primer and a custom primer. The custom primer can be designed to amplify one or more target nucleic acids. The target nucleic acids can comprise a subset of the total nucleic acids in one or more samples. In some embodiments, the primers are the probes attached to the array of the disclosure.

In some embodiments, barcoding (e.g., stochastically barcoding) the plurality of targets in the sample further comprises generating an indexed library of the barcoded targets (e.g., stochastically barcoded targets) or barcoded fragments of the targets. The barcode sequences of different barcodes (e.g., the molecular labels of different stochastic barcodes) can be different from one another. Generating an indexed library of the barcoded targets includes generating a plurality of indexed polynucleotides from the plurality of targets in the sample. For example, for an indexed library of the barcoded targets comprising a first indexed target and a second indexed target, the label region of the first indexed polynucleotide can differ from the label region of the second indexed polynucleotide by, by about, by at least, or by at most, 1, 2, 3, 4, 5, 6, 7, 8, 9, 10, 20, 30, 40, 50, or a number or a range between any two of these values, nucleotides. In some embodiments, generating an indexed library of the barcoded targets includes contacting a plurality of targets, for example mRNA molecules, with a plurality of oligonucleotides including a poly(T) region and a label region; and conducting a first strand synthesis using a reverse transcriptase to produce single-strand labeled cDNA molecules each comprising a cDNA region and a label region, wherein the plurality of targets includes at least two mRNA molecules of different sequences and the plurality of oligonucleotides includes at least two oligonucleotides of different sequences. Generating an indexed library of the barcoded targets can further comprise amplifying the single-strand labeled cDNA molecules to produce double-strand labeled cDNA molecules; and conducting nested PCR on the double-strand labeled cDNA molecules to produce labeled amplicons. In some embodiments, the method can include generating an adaptor-labeled amplicon.

Barcoding (e.g., stochastic barcoding) can include using nucleic acid barcodes or tags to label individual nucleic acid (e.g., DNA or RNA) molecules. In some embodiments, it involves adding DNA barcodes or tags to cDNA molecules as they are generated from mRNA. Nested PCR can be performed to minimize PCR amplification bias. Adaptors can be added for sequencing using, for example, next generation sequencing (NGS). The sequencing results can be used to determine cell labels, molecular labels, and sequences of nucleotide fragments of the one or more copies of the targets, for example at block 1232 of FIG. 12.

Figure 13:
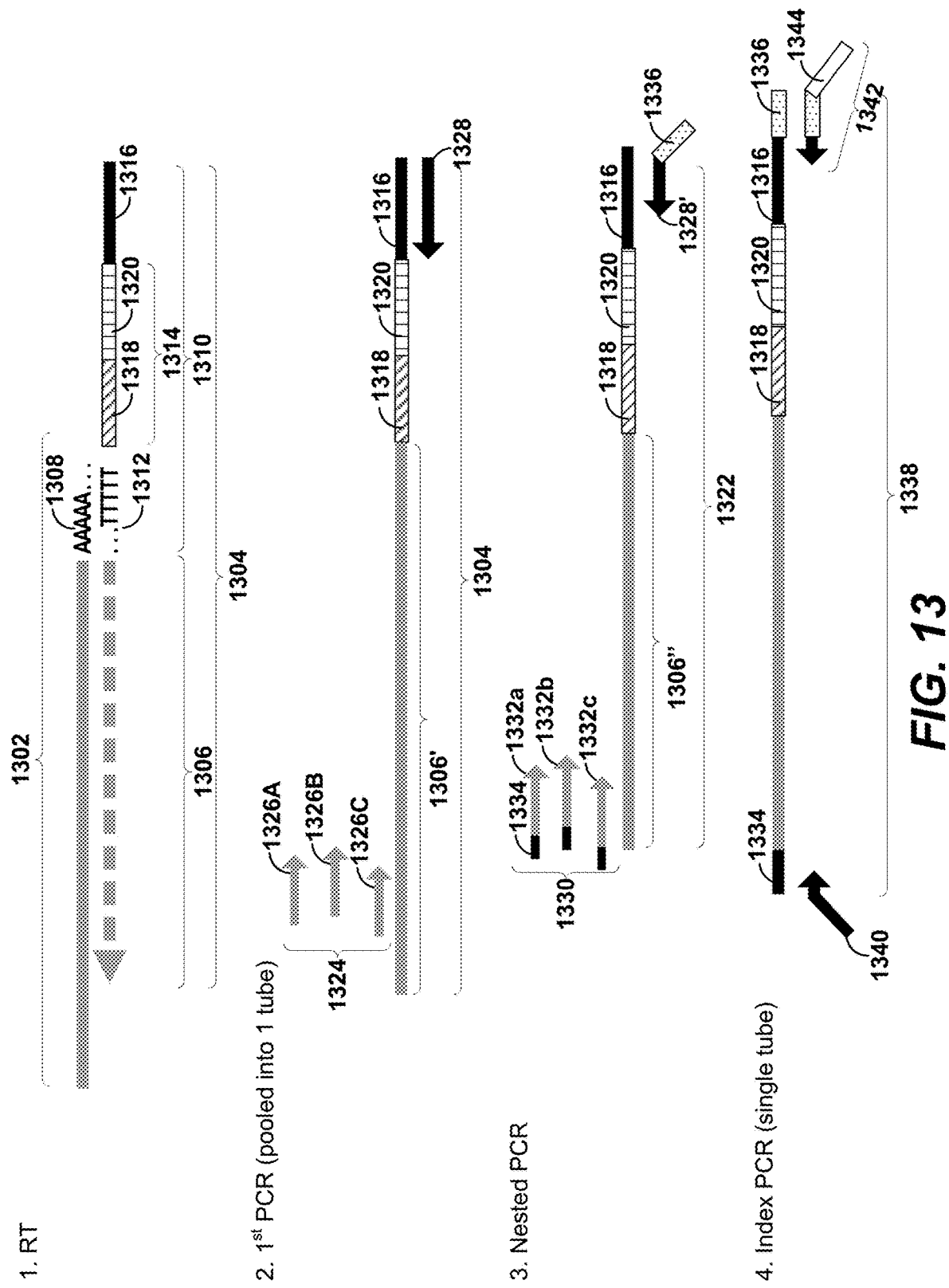
FIG. 13 is a schematic illustration showing a non-limiting exemplary process for generating an indexed library of targets barcoded at the 3'-ends from a plurality of targets.

FIG. 13 is a schematic illustration showing a non-limiting exemplary process of generating an indexed library of the barcoded targets (e.g., stochastically barcoded targets), such as barcoded mRNAs or fragments thereof. As shown in step 1, the reverse transcription process can encode each mRNA molecule with a unique molecular label sequence, a cell label sequence, and a universal PCR site. In particular, RNA molecules 1302 can be reverse transcribed to produce labeled cDNA molecules 1304, including a cDNA region 1306, by hybridization (e.g., stochastic hybridization) of a set of barcodes (e.g., stochastic barcodes) 1310 to the poly(A) tail region 1308 of the RNA molecules 1302. Each of the barcodes 1310 can comprise a target-binding region, for example a poly(dT) region 1312, a label region 1314 (e.g., a barcode sequence or a molecule), and a universal PCR region 1316.

In some embodiments, the cell label sequence can include 3 to 20 nucleotides. In some embodiments, the molecular label sequence can include 3 to 20 nucleotides. In some embodiments, each of the plurality of stochastic barcodes further comprises one or more of a universal label and a cell label, wherein universal labels are the same for the plurality of stochastic barcodes on the solid support and cell labels are the same for the plurality of stochastic barcodes on the solid support. In some embodiments, the universal label can include 3 to 20 nucleotides. In some embodiments, the cell label comprises 3 to 20 nucleotides.

In some embodiments, the label region 1314 can include a barcode sequence or a molecular label 1318 and a cell label 1320. In some embodiments, the label region 1314 can include one or more of a universal label, a dimension label, and a cell label. The barcode sequence or molecular label 1318 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The cell label 1320 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The universal label can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. Universal labels can be the same for the plurality of stochastic barcodes on the solid support and cell labels are the same for the plurality of stochastic barcodes on the solid support. The dimension label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length.

In some embodiments, the label region 1314 can comprise, comprise about, comprise at least, or comprise at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different labels, such as a barcode sequence or a molecular label 1318 and a cell label 1320. Each label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length. A set of barcodes or stochastic barcodes 1310 can contain, contain about, contain at least, or can be at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, barcodes or stochastic barcodes 1310. And the set of barcodes or stochastic barcodes 1310 can, for example, each contain a unique label region 1314. The labeled cDNA molecules 1304 can be purified to remove excess barcodes or stochastic barcodes 1310. Purification can comprise Ampure bead purification.

As shown in step 2, products from the reverse transcription process in step 1 can be pooled into 1 tube and PCR amplified with a $1^{st}$ PCR primer pool and a $1^{st}$ universal PCR primer. Pooling is possible because of the unique label region 1314. In particular, the labeled cDNA molecules 1304 can be amplified to produce nested PCR labeled amplicons 1322. Amplification can comprise multiplex PCR amplification. Amplification can comprise a multiplex PCR amplification with 96 multiplex primers in a single reaction volume. In some embodiments, multiplex PCR amplification can utilize, utilize about, utilize at least, or utilize at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, multiplex primers in a single reaction volume. Amplification can comprise using a $1^{st}$ PCR primer pool 1324 comprising custom primers 1326A-C targeting specific genes and a universal primer 1328. The custom primers 1326 can hybridize to a region within the cDNA portion 1306' of the labeled cDNA molecule 1304. The universal primer 1328 can hybridize to the universal PCR region 1316 of the labeled cDNA molecule 1304.

As shown in step 3 of FIG. 13, products from PCR amplification in step 2 can be amplified with a nested PCR primers pool and a $2^{nd}$ universal PCR primer. Nested PCR can minimize PCR amplification bias. In particular, the nested PCR labeled amplicons 1322 can be further amplified by nested PCR. The nested PCR can comprise multiplex PCR with nested PCR primers pool 1330 of nested PCR primers 1332a-c and a $2^{nd}$ universal PCR primer 1328' in a single reaction volume. The nested PCR primer pool 1328 can contain, contain about, contain at least, or contain at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different nested PCR primers 1330. The nested PCR primers 1332 can contain an adaptor 1334 and hybridize to a region within the cDNA portion 1306" of the labeled amplicon 1322. The universal primer 1328' can contain an adaptor 1336 and hybridize to the universal PCR region 1316 of the labeled amplicon 1322. Thus, step 3 produces adaptor-labeled amplicon 1338. In some embodiments, nested PCR primers 1332 and the $2^{nd}$ universal PCR primer 1328' may not contain the adaptors 1334 and 1336. The adaptors 1334 and 1336 can instead be ligated to the products of nested PCR to produce adaptor-labeled amplicon 1338.

As shown in step 4, PCR products from step 3 can be PCR amplified for sequencing using library amplification primers. In particular, the adaptors 1334 and 1336 can be used to conduct one or more additional assays on the adaptor-labeled amplicon 1338. The adaptors 1334 and 1336 can be hybridized to primers 1340 and 1342. The one or more primers 1340 and 1342 can be PCR amplification primers. The one or more primers 1340 and 1342 can be sequencing primers. The one or more adaptors 1334 and 1336 can be used for further amplification of the adaptor-labeled amplicons 1338. The one or more adaptors 1334 and 1336 can be used for sequencing the adaptor-labeled amplicon 1338. The primer 1342 can contain a plate index 1344 so that amplicons generated using the same set of barcodes or stochastic barcodes 1310 can be sequenced in one sequencing reaction using next generation sequencing (NGS).

Binding Reagents

Binding reagents disclosed herein include protein binding reagents. As used herein, a "protein binding reagent" has its ordinary and customary meaning as understood by one of ordinary skill in the art in light of this specification, and refers to an agent that specifically binds a protein. By way of example, a protein binding reagent can comprise an antibody or fragment thereof. Examples of suitable protein binding reagents include any protein binding reagent described in U.S. Patent Pub. Nos. 2018/0088112 or 2018/0346970, each of which is incorporated by reference in its entirety and for the specific disclosure referenced herein. In some embodiments, the binding reagent (e.g., protein binding reagent) specifically binds a target protein. In some embodiments, the protein binding reagent comprises an antibody that specifically binds the target protein. As used herein, the term "antibody" has its ordinary and customary meaning as understood by one of ordinary skill in the art in light of this specification, and refers to monoclonal antibodies, polyclonal antibodies, multivalent antibodies, or multi-specific antibodies. Antibodies can include full-length antibodies, or a binding fragment thereof, for example, a Fab, Fab', F(ab')$_2$, Fab'-SH, Fd, single chain Fvs (scFv), single chain antibodies, disulfide-linked Fvs (sdFv), or fragments comprising a V$_L$ or V$_H$ domain. The antibody or binding fragment thereof can specifically bind to the target protein.

Example binding reagents (e.g., protein binding reagents) suitable for methods, kits, and compositions as described herein can include, for example, an antibody that specifically binds to CTCF (such as an antibody available by way of Millipore catalog #07-729), H3K27me3 (such as an antibody available by way of Millipore catalog #07-449, EpiGentek catalog #A4039, or Cell Signaling catalog #9733), c-Myc (such as an antibody available by way of Cell Signaling catalog #D3N8F), Max (such as an antibody available by way of Santa Cruz catalog #sc-197), Pol II (8WG16; such as an antibody available by way of Abcam catalog #ab817), H3K4me1 (such as an antibody available by way of Abcam catalog #ab8895 or EpiGentek catalog #A4031), H3K4me2 (such as an antibody available by way of Upstate catalog #07-330 or EpiGentek catalog #A4032), H3K4me3 (such as an antibody available by way of Millipore catalog #05-745, EpiGentek catalog #A4033 or #68393, or Active Motif catalog #39159), H3K27ac (such as an antibody as available by way of Abcam catalog #ab4729, EpiGentek catalog #A4708, or Millipore catalog #MABE647), Oct4 (such as an antibody available by way of Thermo catalog #701756), Sox2 (such as an antibody available by way of Active Motif catalog #39843, or Abcam catalog #ab92494), Nanog (such as an antibody available by way of Active Motif catalog #61419), Brg1 (such as an antibody available by way of Bethyl Laboratories catalog #A300-813), Suz12 (such as an antibody available by way of Bethyl Laboratories catalog #A302-407A), IgG (such as a mouse IgG available by way of Millipore catalog #06-371), RNA Pol II Ser2P, RNA Pol II Ser5P, RNA Pol II Ser2+5P, RNA Pol II Ser7P (such as an antibody available by way of Cell Signaling catalog #54020), NPAT (such as an antibody available by way of Thermo catalog #PA5-66839), STAT1 (such as an antibody available by way of Becton Dickinson catalog #610115), NFAT-1 (such as an antibody available by way of Becton Dickinson catalog #610702), STAT1 (pY701, clone 14/P-STAT1) (such as an antibody available by way of Becton Dickinson catalog #612132), STAT1 (pY701, clone 4A) (such as an antibody available by way of Becton Dickinson catalog #612232), Jun (such as an antibody available by way of Becton Dickinson catalog #610326), p53 (such as clone PAb240, available by way of Becton Dickinson catalog #554166), p53 (such as clone 80/p53, available by way of Becton Dickinson catalog #610183), Rb (such as an antibody available by way of Becton Dickinson catalog #554162), STAT3 (such as an antibody available by way of Becton Dickinson catalog #610189), STAT2 (such as an antibody available by way of Becton Dickinson catalog #610187), Fos (such as an antibody available by way of Becton Dickinson catalog #554156), androgen receptor (such as clone G122-434, available by way of Becton Dickinson catalog #554225), androgen receptor (such as antibody clone G122-25, available by way of Becton Dickinson catalog #554224), H1K25me1 (such as an antibody available by way of EpiGentek catalog #A68342), H1K25me2 (such as an antibody available by way of EpiGentek catalog #A68343), H1K25me3 (such as an antibody available by way of EpiGentek catalog #A68370), H2(A)K4ac (such as an antibody available by way of EpiGentek catalog #A68365), H2(A)K5ac (such as an antibody available by way of EpiGentek catalog #A68350 or A4300), H2(A)K7ac (such as an antibody available by way of EpiGentek catalog #A683512), H2(B)K5ac (such as an antibody available by way of EpiGentek catalog #A68366), H2(B)K12ac (such as an antibody available by way of EpiGentek catalog #A68352), H2(B)K15ac (such as an antibody available by way of EpiGentek catalog #A68353), H2(B)K20ac (such as an antibody available by way of EpiGentek catalog #A68434), H3K4ac (such as an antibody available by way of EpiGentek catalog #A69361), H3K9ac (such as an antibody available by way of EpiGentek catalog #A4054, 4022, or A4021), H3K14ac (such as an antibody available by way of EpiGentek catalog #A4021), H3K18ac (such as an antibody available by way of EpiGentek catalog #A4024), H3K23ac (such as an antibody available by way of EpiGentek catalog #A4025), H3K56ac (such as an antibody available by way of EpiGentek catalog #A68431), H3K9me1 (such as an antibody available by way of EpiGentek catalog #A68435), H3K9me2 (such as an antibody available by way of EpiGentek catalog #A68435), H3K9me3 (such as an antibody available by way of EpiGentek catalog #A68435), H3K27me1 (such as an antibody available by way of EpiGentek catalog #A4037), H3K27me2 (such as an antibody available by way of EpiGentek catalog #A68392 or A4038), H3K36me (such as an antibody available by way of EpiGentek catalog #A4040, A68396, A4041, A4042, or A68388), H3K79me1 (such as an antibody available by way of EpiGentek catalog #A68419), H3K79me2 (such as an antibody available by way of EpiGentek catalog #A68419), H3K79me3 (such as an antibody available by way of EpiGentek catalog #A68419), H4K5ac (such as an antibody available by way of EpiGentek catalog #A68408, A68356, or A4027), H4K8ac (such as an antibody available by way of EpiGentek catalog #A4028), H4K12ac (such as an antibody available by way of EpiGentek catalog #A4029 or A68357), H4K16ac (such as an antibody available by way of EpiGentek catalog #A68404 pr A68398), H4K91ac (such as an antibody available by way of EpiGentek catalog #A68367), H4K20me (such as an antibody available by way of EpiGentek catalog #A4046, A4047, A68422, or A4048), or H4K59me (such as an antibody available by way of EpiGentek catalog #A68337 or A68338), or a combination of two or more of the listed items.

As used herein, the term "specific," "specifically," or "specificity" with relation to specific binding of a reagent to a target has its ordinary and customary meaning as understood by one of ordinary skill in the art in light of this specification, and refers to a binding affinity of the reagent to a target that is higher than, or increased, compared to binding affinity of the reagent to a non-target. Thus, specific binding refers to preferential binding to the noted target over a non-target. However, it will be appreciated that specific binding does not necessarily exclude some minor or trivial (e.g., background) interaction with substances other than the target. By way of example, specific binding can refer to binding with a dissociation constant ($K_D$) that is numerically smaller (indicating tighter binding) than $10^{-5}$ M, for example, a $K_D$ less than $10^{-5}$ M, $10^{-6}$ M, $10^{-7}$ M, $10^{-8}$ M, or $10^{-9}$ M. For example, specific binding can refer to a binding affinity of a reagent to a target that is at least 1.5 fold, 2 fold, 2.5 fold, 3 fold, 4 fold, 5 fold, 6 fold, 7 fold, 8 fold, 9 fold, or 10 fold or higher than a binding affinity of the reagent to a non-target. Specific binding may also refer to binding of the reagent to the target to a detectably greater degree, such as at least 1.5 fold, 2 fold, 2.5 fold, 3 fold, 4 fold, 5 fold, 6 fold, 7 fold, 8 fold, 9 fold, or 10 fold or higher than a binding affinity of the reagent to a non-target.

In some embodiments, the binding reagent (e.g., protein binding reagent) is associated with a reagent oligonucleotide. In some embodiments, the reagent oligonucleotide includes a unique identifier for the binding reagent (e.g., protein binding reagent). As used herein the term "associated" has its ordinary and customary meaning as understood by one of ordinary skill in the art in light of this specification, and refers to an interaction between two or more components, and may include covalent or non-covalent bonding. The chemical nature of covalent bonds (two atoms sharing one or more pairs of valence electrons) are known in the art and include, for example, disulfide bonds or peptide bonds. A non-covalent bond is a chemical bond between atoms or molecules that does not involve the sharing of pairs of valence electrons. For example, non-covalent interactions include, for example, hydrophobic interactions, hydrogen-bonding interactions, ionic bonding, Van der Waals bonding, or dipole-dipole interactions.

As used herein, the term "fusion protein" has its ordinary and customary meaning as understood by one of ordinary skill in the art in light of this specification. It refers to all or part of a polypeptide or compound associated with a DNA digestion enzyme. The association can be covalent or non-covalent as described herein. In some embodiments, the DNA digestion enzyme comprises, consists essentially of, or consists of any enzyme or functional fragment thereof that is capable of digesting a nucleic acid. In some embodiments, the DNA digestion enzyme comprises a restriction enzyme, Mnase I, or Tn5 transposase, or a function fragment thereof. In some embodiments, the fusion protein comprises a domain that specifically binds the binding reagent (e.g., protein binding reagent). In some embodiments, the domain comprises any polypeptide of binding portion thereof that is capable of specifically binding to the protein binding reagent, such as at least one of protein A, protein G, protein A/G, or protein L. In some embodiments, the fusion protein is bound to the protein binding reagent. In one embodiment, the protein binding reagent and the fusion protein are associated as a single complex prior to use. In another embodiment, the protein binding reagent and the fusion protein are not associated as a single complex, but are separate complexes that become associated after use, for example upon entry of the compositions within a nucleus of a cell. In some embodiments, whether the protein binding reagent and fusion protein are associated together or separate prior to use, the size of the protein binding reagent, the fusion protein, or the complex that includes the protein binding reagent associated with the fusion protein is of sufficient size to enter a permeabilized cell and/or of sufficient size to enter a nuclear pore of a cell nucleus.

Restriction enzymes suitable for DNA digestion enzymes of methods, kits, and compositions of some embodiments include, for example, type I (e.g., EcoAI, EcoK, or EcoB), type II (e.g., HhaI, Hind II, HindIII, BamHI, NotI, NdeI, PacI, PvuI, EcoRI, EcoRII, Sau3AI, SmaI, or TaqI), type III (e.g., EcoP15, PstII, PhaBI, or HinfIII), type IV (e.g., McrBC or Mrr), and/or type V (e.g., the cas9-gRNA complex from CRISPRs) restriction enzymes. In some instances, Type I enzymes are complex, multi-subunit, combination restriction-and-modification enzymes that cut DNA at random far from their recognition sequences. Generally, type II enzymes cut DNA at defined positions close to or within their recognition sequences. They may produce discrete restriction fragments and distinct gel banding patterns. Type III enzymes are also large combination restriction-and-modification enzymes. They often cleave outside of their recognition sequences and may require two such sequences in opposite orientations within the same DNA molecule to accomplish cleavage; they rarely give complete digests. In some instances, type IV enzymes recognize modified, typically methylated DNA and may be exemplified by the McrBC and Mrr systems of $E.$ $coli.$ In some embodiments, the nuclear target is a target protein (e.g., a chromatin-associated protein). As used herein, a "target protein" has its ordinary and customary meaning as understood by one of ordinary skill in the art in light of this specification, and refers to a polypeptide of interest, and to which the binding reagent (e.g., protein binding reagent) specifically binds. In some embodiments, the target protein is associated with chromatin or DNA of a cell. In some embodiments, the target protein includes any protein that is known or discoverable to be associated with chromatin or DNA of a cell. In some embodiments, the target protein is a chromatin associated protein or a DNA associated protein. Target proteins associated with chromatin or DNA include, for example, ALC, androgen receptor, Bmi-1, BRD4, Brg1, coREST, C-jun, c-Myc, CTCF, EED, EZH2, Fos, histone H1, histone H2A, histone H2B, histone H3, histone H4, heterochromatin protein-1γ, heterochromatin protein-1, HMGN2/HMG-17, HP1α, HP1γ, hTERT, Jun, KLF4, K-Ras, Max, MeCP2, MLL/HRX, NPAT, p300, Nanog, NFAT-1, Oct4, p53, Pol II (8WG16), RNA Pol II Ser2P, RNA Pol II Ser5P, RNA Pol II Ser2+5P, RNA Pol II Ser7P, Rb, RNA polymerase II, SMCI, Sox2, STAT1, STAT2, STAT3, Suz12, Tip60, or UTF1. In some embodiments, the protein binding reagent binds specifically to an epitope that includes a methylated (me), phosphorylated (ph), ubiquitylated (ub), sumoylated (su), biotinylated (bi), or acetylated (ac) histone residue, including, for example, H1S27ph, H1K25me1, H1K25me2, H1K25me3, H1K26me, H2(A) K4ac, H2(A)K5ac, H2(A)K7ac, H2(A)S1ph, H2(A)T119ph, H2(A)S122ph, H2(A)S129ph, H2(A)S139ph, H2(A) K119ub, H2(A)K126su, H2(A)K9bi, H2(A)K13bi, H2(B) K5ac, H2(B)K11ac, H2(B)K12ac, H2(B)K15ac, H2(B) K16ac, H2(B)K20ac, H2(B)S10ph, H2(B)S14ph, H2(B) 33ph, H2(B)K120ub, H2(B)K123ub, H3K4ac, H3K9ac, H3K14ac, H3K18ac, H3K23ac, H3K27ac, H3K56ac, H3K4me1, H3K4me2, H3K4me3, H3R8me, H3K9me1, H3K9me2, H3K9me3, H3R17me, H3K27me1, H3K27me2, H3K27me3, H3K36me, H3K79me1, H3K79me2, H3K79me3, H3K122ac, H3T3ph, H3S10ph, H3T11ph, H3S28ph, H3K4bi, H3K9bi, H3K18bi, H4K5ac, H4K8ac, H4K12ac, H4K16ac, H4K91ac, H4R3me, H4K20me, H4K59me, H4S1ph, H4K12bi, or H4 n-terminal tail ubiquitylated. Thus in some embodiments, the target protein comprises any of the listed proteins, or a combination or two or more of the listed proteins.

Some embodiments described herein comprise a first composition that comprises a binding reagent (e.g., protein binding reagent) and a fusion protein as described herein.

Oligonucleotide Probes

In accordance with methods, kits, and compositions of some embodiments herein, oligonucleotide probes (e.g., oligonucleotide barcodes) are described. In some embodiments, the oligonucleotide probes include any oligonucleotide probe as described in U.S. Patent Pub. Nos. 2015/0299784 or 2018/0276332, each of which is incorporated by reference herein in its entirety and for the specific disclosure referenced herein. In methods, kits, and compositions of some embodiments, a second composition comprises a first oligonucleotide probe and a second oligonucleotide probe As used herein, the term "oligonucleotide probe" has its ordinary and customary meaning as understood by one of ordinary skill in the art in light of this specification, and refers to an oligonucleotide comprising a nucleotide sequence complementary to at least a portion of a target sequence. By way of example, the nucleotide sequence complementary to at least a portion of the target sequence can comprise a "capture sequence" or "target binding region" as described herein. As used herein, "complementary" has its ordinary and customary meaning as understood by one of ordinary skill in the art in light of this specification, and refers to a property of at least a portion of an oligonucleotide that are capable of hydrogen bonding with a target sequence when the oligonucleotide and the target sequence are aligned in opposite directions. Thus, complementary can refer to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. A first nucleotide sequence can be said to be the "complement" of a second sequence if the first nucleotide sequence is complementary to the second nucleotide sequence. A first nucleotide sequence can be said to be the "reverse complement" of a second sequence, if the first nucleotide sequence is complementary to a sequence that is the reverse (i.e., the order of the nucleotides is reversed) of the second sequence. As used herein, the terms "complement", "complementary", and "reverse complement" can be used interchangeably. It is understood from the disclosure that if a molecule can hybridize to another molecule it may be the complement of the molecule that is hybridizing.

Complementary nucleobase pairs include adenine (A) and thymine (T), adenine (A) and uracil (U), cytosine (C) and guanine (G), 5-methyl cytosine (mC) and guanine (G). Complementary oligonucleotides and/or nucleic acids need not have nucleobase complementarity at each nucleoside. Rather, some mismatches are tolerated. As used herein, "fully complementary" or "100% complementary" in reference to oligonucleotides means that such oligonucleotides are complementary to another oligonucleotide or nucleic acid at each nucleoside of the oligonucleotide. Complementary to at least a portion of the target sequence may include full complementarity, such as 100% complementary, or less than 100% complementary, such as 95%, 90%, 80%, 70%, 60%, 50%, 40%, or 30% complementary, so long as the complementarity is sufficient such that the oligonucleotide probe is capable of binding to a target sequence.

In some embodiments, the first oligonucleotide probe comprises a first target binding region (which may also be referred to as a "capture sequence") and a sample identifier sequence. By way of example, the first target binding region can be disposed 3' of the sample identifier sequence. Accordingly, upon hybridization and 5'→3' extension of the first target binding region along the target, a strand complementary to the target can be barcoded with the sample identifier sequence. In some embodiments, the first target binding region is complementary to at least a portion of the reagent oligonucleotide that is associated with the protein binding reagent. In some embodiments, contacting the first oligonucleotide probe and the protein binding reagent results in hybridization of the first target binding region to the reagent oligonucleotide, which can associate the first oligonucleotide probe with the protein binding reagent. It is contemplated that the first target binding region can comprise any suitable sequence that is complementary to, and thus capable of hybridizing to the protein binding reagent or a portion thereof at the temperature of the reaction. For example, the first target binding region can comprise at least 2, 3, 4, 5, 6, 7, 8, 9, or 10 consecutive nucleotides that are complementary to a sequence of the reagent oligonucleotide. In some embodiments, the first target binding region (which may also be referred to as a "capture sequence") comprises, consists essentially of, or consists of a polyT sequence and the reagent oligonucleotide includes a polyA sequence. A polyT sequence may include a sequence having consecutive thymidines of more than 2, 3, 4, 5, 6, 7, 8, 9, or 10 thymidines, and a polyA sequence has a complementary number of consecutive adenines or more than 2, 3, 4, 5, 6, 7, 8, 9, or 10 adenines. It is also contemplated that in some embodiments, the reagent oligonucleotide does not comprise a polyA sequence, and as such, the first target binding region does not comprise a polyT sequence. In some embodiments, the first target binding region does not include two, three, four, or five consecutive thymidines.

As used herein, "hybridization" has its ordinary and customary meaning as understood by one of ordinary skill in the art in light of this specification, and refers to the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

In the compositions and/or methods of some embodiments, the second oligonucleotide probe includes a second target binding region and a sample identifier sequence. In some embodiments, the second target binding region is complementary to at least a portion of a single stranded overhang of DNA associated with the target protein as described herein. The single stranded overhang of DNA associated with the target protein may be generated from a DNA digestion enzyme, such as a restriction enzyme, Mnase I, or Tn5 transposase that is capable of creating a restriction site overhang.

In some embodiments, the compositions and methods include one or more second oligonucleotide probe. For example, the second oligonucleotide probe can comprise, consist essentially of, or consist of multiple oligonucleotide probes, particularly for a multiplex comprising more than one antibody. In such embodiments, a Tn5 transposase may include a different adaptor loaded antibody so that each antibody bound DNA bind to a different adaptor. A different oligonucleotide probe complementary for each adaptor may be attached to the substrate, such that one substrate will include more than two different types of oligonucleotide probes to capture different adaptor added DNA fragments.

As used herein, the term "sample identifier sequence" has its ordinary and customary meaning as understood by one of ordinary skill in the art in light of this specification and refers to a sequence of the first or second oligonucleotide probe that is used to identify the oligonucleotide probe. A sample identifier sequence can be any sequence that may be used to specifically identify the oligonucleotide probe. In some embodiments, the first and second oligonucleotide probes include the same sample identifier sequence. In some embodiments, the first oligonucleotide probe includes a first sample identifier sequence and the second oligonucleotide probes includes a second sample identifier sequence. In some embodiments, the first and second sample identifier sequences are each from a diverse set of unique sample identifier sequences. The length of a sample identifier sequence can depend on the number (or estimated number) of samples. For example, there can be as many as $10^6$ or more unique sample identifier sequences represented in a plurality of solid supports (e.g., beads). It will be appreciated that in some embodiments, for example if all of the cells undergoing labeling are from the same sample, the sample identifier sequence may be a cell label as described herein. Accordingly, wherever a "sample identifier sequence" (or variation of this root term) is mentioned herein, it will be appreciated that in some embodiments, the sample identifier sequence can be a cell label. It will further be appreciated that in some embodiments, a nucleic acid can be labeled with both a sample identifier sequence and a cell label (for example, if cells from two or more different samples are being labeled). Accordingly, it will also be appreciated that a probe or labeled nucleic acid of some embodiments comprising a "sample label" may optionally further comprise a cell label as described herein.

A barcode sequence comprises or consists of a nucleic acid sequence that is useful in identifying a nucleic acid, for example a target-protein-associated DNA from a cell, or an amplicon or reverse-transcript derived from a target-protein-associated DNA from a cell. By way of example, a barcode sequence can comprise at least 4, 5, 6, 7, 8, 9, 10, 11, 12, 13, 14, 15, 16, 17, 18, 19, 20, 25, 30, 35, 40, 45, or 50 nucleotides, including ranges between any two of the listed values, for example, 4-10, 4-15, 4-20, 4-30, 4-50, 6-10, 6-15, 6-20, 6-30, 6-50, 8-10, 8-15, 8-20, 8-30, or 8-50. In some embodiments, a barcode sequence comprises a random sequence. In some embodiments, there can be at least, or at most, $10^2$, $10^3$, $10^4$, $10^5$, $10^6$, $10^7$, $10^8$, or $10^9$, unique barcode sequences.

In some embodiments, the first and second oligonucleotide probes are immobilized on a substrate. In some embodiments, the substrate includes any substrate to which an oligonucleotide sequence may be immobilized, such as a bead, a microarray, a plate, a tube, or a well. In some embodiments, the first and second oligonucleotide probes are both immobilized to the same substrate. The substrate may consist essentially of or consist of a bead, a microarray, a plate, a tube, or a well.

As used herein, the terms "tethered," "attached," and "immobilized" are used interchangeably, and can refer to covalent or non-covalent means for attaching barcodes to a solid support. Any of a variety of different solid supports can be used as solid supports for immobilizing oligonucleotide probes.

A substrate can comprise a type of solid support. A substrate can refer to a continuous solid or semi-solid surface on which the methods of the disclosure may be performed. A substrate can refer to an array, a cartridge, a chip, a device, and a slide, for example. As such, "solid support" and "substrate" can be used interchangeably.

The substrate may comprise or consist essentially of a bead, membrane, paper, plastic, coated surface, flat surface, glass, slide, chip, or any combination thereof. In some embodiments, at least one surface of the support may be substantially flat, although in some embodiments, it may be desirable to physically separate synthesis regions for different compounds with, for example, wells, raised regions, pins, etched trenches, or the like. According to some embodiments, the substrate may comprise, consist essentially of, or consist of resins, gels, microspheres, or other geometric configurations. According to some embodiments, the substrate comprises silica chips, microparticles, nanoparticles, plates, and arrays. Solid supports may include beads (e.g., silica gel, controlled pore glass, magnetic beads, Dynabeads, Wang resin; Merrifield resin, Sephadex/Sepharose beads, cellulose beads, polystyrene beads etc., capillaries, flat supports such as glass fiber filters, glass surfaces, metal surfaces (steel, gold silver, aluminum, silicon and copper), glass supports, plastic supports, silicon supports, chips, filters, membranes, microwell plates, slides, or the like. plastic materials including multiwell plates or membranes (e.g., formed of polyethylene, polypropylene, polyamide, polyvinylidenedifluoride), wafers, combs, pins or needles (e.g., arrays of pins suitable for combinatorial synthesis or analysis) or beads in an array of pits or nanoliter wells of flat surfaces such as wafers (e.g., silicon wafers), wafers with pits with or without filter bottoms.

A substrate or solid support in accordance with some embodiments herein can encompass any type of solid, porous, or hollow sphere, ball, bearing, cylinder, or other similar configuration composed of plastic, ceramic, metal, or polymeric material (e.g., hydrogel) onto which a nucleic acid may be immobilized (e.g., covalently or non-covalently). A substrate or solid support can comprise a discrete particle that may be spherical (e.g., microspheres) or have a non-spherical or irregular shape, such as cubic, cuboid, pyramidal, cylindrical, conical, oblong, or disc-shaped, and the like. A plurality of solid supports spaced in an array may not comprise a substrate. A solid support may be used interchangeably with the term "bead."

Substrates such as beads can comprise a variety of materials including, but not limited to, paramagnetic materials (e.g. magnesium, molybdenum, lithium, and tantalum), superparamagnetic materials (e.g. ferrite ($Fe_3O_4$; magnetite) nanoparticles), ferromagnetic materials (e.g. iron, nickel, cobalt, some alloys thereof, and some rare earth metal compounds), ceramic, plastic, glass, polystyrene, silica, methylstyrene, acrylic polymers, titanium, latex, Sepharose, agarose, hydrogel, polymer, cellulose, nylon, or any combination thereof.

Methods of Labeling Target-Protein-Associated DNA

Some embodiments described herein relate to methods of using the binding reagent (e.g., protein binding reagent), fusion protein, and oligonucleotides probes as described herein for labeling target-protein-associated DNA. By way of example, the method can comprise permeabilizing a cell comprising a target protein, contacting the permeabilized cell with a digestion composition, comprising, for example, a fusion protein and protein binding reagent associated with a reagent oligonucleotide so that the protein binding reagent, fusion protein form a complex. The method can comprise digesting target-protein associated DNA in the cell with the DNA digestion enzyme of the fusion protein, so as to form a single-stranded overhang of the DNA. The method can comprise contacting the cell with a first and second oligonucleotide probe that hybridize to the reagent oligonucleotide and single-stranded overhang of DNA, respectively. The method can comprise extending the first and second oligonucleotide probes. The binding of the binding reagent (e.g., protein binding reagent) to the target protein and the digesting may be performed in situ (e.g., in the nucleus of the cell). In some embodiments, the method may comprise labeling, sequencing, amplifying, or generating a library of target-protein associated DNA.

In some embodiments, the method comprises permeabilizing a cell. A cell may include any cell that includes a nucleic acid of interest, such as a target-protein-associated DNA. As used herein, "permeabilization" has its ordinary and customary meaning as understood by one of ordinary skill in the art in light of this specification, and refers to a process facilitating access to cellular cytoplasm or intracellular molecules, components, or structures of the cell. Permeabilization of a cell may comprises chemical or physical permeabilization, such as exposure of the cell to sonication, formaldehyde, ethanol, detergents, surfactants, guanidine hydrochloride, digitonin, or Triton X. In some embodiments, the permeabilized cell comprises an intact nucleus. In some embodiments, the permeabilized cell comprises chromatin that remains associated with genomic DNA. In some embodiments, the cell nucleus is isolated, and the kits and methods described herein include contacting the reagents described herein with an isolated nucleus. As such, it will be appreciated that wherever a cell comprising a nucleus is described herein, an isolated nucleus is also expressly contemplated. Thus, wherever a method, kit, composition, or use comprising a cell comprising a nucleus is described, an isolated nucleus can be substituted for the cell comprising the nucleus.

In some embodiments, the permeabilized cell is contacted with a composition as described herein that embodiments a binding reagent (e.g., protein binding reagent) and a fusion protein (including, for example, as part of a "first composition" as described herein). In some embodiments, the protein binding reagent and the fusion protein are sized to enter the permeabilized cell (for example by diffusion through permeabilization openings that have diameters larger than a largest diameter of the fusion protein) and are also sized to enter the nucleus of the cell (for example by diffusion through a nuclear pore).

In some embodiments, the binding reagent (e.g., protein binding reagent) and the fusion protein, are each sized to enter the permeabilized cell and the nucleus of the cell (or the isolated nucleus) individually, such that the protein binding reagent without the fusion protein is sized to enter the permeabilized cell and the nucleus of the cell, and such that the fusion protein without the protein binding reagent is of sufficient size to enter the permeabilized cell and the nucleus of the cell. In some embodiments the protein binding reagent and the fusion protein are each separately sized to diffuse through a nuclear pore of the cell. In some embodiments, upon contact of the permeabilized cell with the composition, the protein binding reagent and the fusion protein separately enter the permeabilized cell and the nucleus of the cell, and associate with one another after entering the nucleus of the cell. Thus, in some embodiments, the permeabilized cell is first contacted with the protein binding reagent (for example, by contacting the permeabilized cell with a composition that comprises, consists essentially of, or consists of the protein binding reagent), after which the permeabilized cell is contacted with the fusion protein (for example, by contacting the permeabilized cell with a composition that comprises the fusion protein. In some embodiments, a composition that comprises, consists essentially of, or consists of the fusion protein is contacted with the permeabilized cell prior to contacting the permeabilized cell with a composition that comprises the protein binding reagent. In any embodiment described herein, the protein binding reagent and fusion protein may be contacted with the permeabilized cell separately (e.g., sequentially) such that the protein binding reagent and the fusion protein separately enter the permeabilized cell and the nucleus of the cell.

In some embodiments, the binding reagent (e.g., protein binding reagent) and the fusion protein are associated with one another prior to contacting with the permeabilized cell. In such embodiments, the associated protein binding reagent and fusion protein is sized to enter the permeabilized cell and the nucleus of the cell in association with one another (for example, by diffusion through openings in the cell membrane of the permeabilized cell and/or through a nuclear pore). In some embodiments, the protein binding reagent associated with the fusion protein are collectively sized to diffuse through a nuclear pore of the cell. In some embodiments, the combination of the protein binding reagent associated with the fusion protein has a diameter of no more than 1 nm, no more than 2 nm, no more than 3 nm, no more than 4 nm, no more than 5 nm, no more than 10 nm, no more than 20 nm, no more than 30 nm, no more than 40 nm, no more than 50 nm, no more than 60 nm, no more than 70 nm, no more than 80 nm, no more than 90 nm, no more than 100 nm, no more than 110 nm, or no more than 120 nm, or a size within a range defined by any two of the aforementioned values. In some embodiments, a composition that includes the protein binding reagent is contacted with a composition that include the fusion protein, and the protein binding reagent and the fusion protein associate with one another, for example through the domain of the fusion protein that specifically bind the protein binding reagent. In some embodiments, the protein binding reagent and the fusion protein are bound to one another. In some embodiments, the associated protein binding reagent and the fusion protein are contacted with the permeabilized cell as a bound complex, which enters the permeabilized cell and diffuses through a nuclear pore of the cell to bind to target protein. As such, in any embodiment described herein, the protein binding reagent bound to the fusion protein may be contacted with the permeabilized cell, so that the protein binding reagent and the fusion protein enter the permeabilized cell bound together.

In some embodiments, the binding reagent (e.g., protein binding reagent) binds to a target protein of the permeabilized cell, in which the target protein is associated with a DNA of the cell. Binding of the protein binding reagent to target protein can comprise placing the fusion protein in proximity with the DNA that is associated with the target protein, such that the DNA digestion enzyme fusion protein is capable of interacting with, and catalyzing the digestion of DNA associated with the target protein. The DNA digestion enzyme of the fusion protein, can therefore brought within close proximity of the DNA for enzymatic digestion of the DNA. In some embodiments, the DNA digestion enzyme of the fusion protein digests the DNA associated with the target protein. In some embodiments, digestion of the DNA results in a single stranded overhang in the digested DNA. In some embodiments, digestion of the DNA associated with the target protein results in a complex that includes the fusion protein associated with the protein binding reagent bound to target protein, and associated with the digested DNA. The digestion reaction may be quenched or inactivated by subjecting the reaction to a chelating agent, including for example EDTA and/or EGTA. In some embodiments, the digestion reaction takes place in two steps, including cleavage and adapter integration.

In some embodiments, after antibody binding, single cells and beads with oligonucleotides are placed in a well (for example, a microliter-scale or nanoliter-scale well) such that digested DNA from a single cell becomes a unique label. In some embodiments, digestion is triggered by $Mg^{++}$, $Ca^{++}$, or enzyme buffer after the single cell is located in the well with beads to prevent digested DNA/fusion protein complex to mix with those from other cells.

In some embodiments, the formed complex that includes the fusion protein, the binding reagent (e.g., protein binding reagent), the target protein, and the digested DNA is contacted with a composition that includes the first oligonucleotide probe and the second oligonucleotide probe, as described herein. Optionally, the complex can be isolated from the permeabilized cell before being contacted with the first and second oligonucleotides probes. After the contacting, the first target binding region of the first oligonucleotide probe can hybridize with the reagent oligonucleotide of the protein binding reagent. The second target binding region of the second oligonucleotide probe can hybridize to the single-stranded overhang of the digested DNA. The hybridization of the first and second oligonucleotides probes with their respective complementary nucleic acid sequences thus results in associating these respective complementary sequences with the substrate. In some embodiments, polypeptide portions of the complex are removed (for example, by contacting with proteinase K), while nucleic acids remain. In some embodiments, unbound nucleic acids are removed (for example, by contacting with a nuclease, such as ExoI).

Some embodiments further include further manipulation of the digested DNA, including extending the oligonucleotide probes to produce a plurality of labeled nucleic acids, capturing the complex on a substrate, ligation, transcription, nucleic acid library construction, sequencing, immunoprecipitation, or other analyses. The methods, compositions, and kits disclosed herein may further comprise immunoprecipitation of a target-protein-associated DNA. Any or all of the methods described herein may be performed using an automated system, such as a thermocycler or thermomixer, wherein reverse transcription, ligation, digestion, incubation, and/or washing, and/or other steps are automated.

The methods disclosed herein may further comprise reverse transcription, for example if RNA or single stranded DNA is associated with the target protein. The reverse transcription can produce DNA complementary to the RNA or single stranded DNA. In some instances, at least a portion of an oligonucleotide probe comprises a primer for the reverse transcription reaction.

One or more nucleic acid amplification reactions can be performed to create multiple copies of the DNA associated with the target protein (a target nucleic acid sequence or a labeled nucleic acid), for example, to generate a nucleic acid library. Amplification can be performed in a multiplexed manner, in which multiple target nucleic acid sequences are amplified simultaneously. The amplification can be used to add sequencing adaptors to the nucleic acid molecules. The amplification reactions can comprise amplifying at least a portion of a sample label, if present. The amplification reactions can comprise amplifying at least a portion of the cellular and/or molecular label. The amplification reactions can comprise amplifying at least a portion of a sample tag, a cell label, a spatial label, a molecular label, a target nucleic acid, or a combination thereof. The amplification reactions can include amplifying at least 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 100%, or a range or a number between any two of these values, of a plurality of nucleic acids. The method can further include conducting one or more cDNA synthesis reactions to produce one or more cDNA copies of target-barcode molecules comprising a sample label, a cell label, a spatial label, and/or a molecular label.

An oligonucleotide probe as described herein may comprise a universal label (which may also be referred to herein as a universal primer site), a cellular label, a molecular label and a sample label, or any combination thereof. For example, the oligonucleotide probe may comprise a molecular label and a sample label. In combination, the sample label may distinguish target nucleic acids between samples, the cellular label may distinguish target nucleic acids from different cells in the sample, the molecular label may distinguish the different target nucleic acids in the cell (e.g., different copies of the same target nucleic acid), and the universal label may be used to amplify and sequence the target nucleic acids.

Any of a universal label, a molecular label, a cellular label, linker label and/or a sample label as described herein may comprise a random sequence of nucleotides. A random sequence of nucleotides may be computer generated. A random sequence of nucleotides may have no pattern associated with it. A universal label, a molecular label, a cellular label, linker label and/or a sample label may comprise a non-random (e.g., the nucleotides comprise a pattern) sequence of nucleotides. Sequences of the universal label, a molecular label, a cellular label, linker label and/or a sample label may be commercially available sequences. Sequences of the universal label, a molecular label, a cellular label, linker label and/or a sample label may be comprise randomer sequences. Randomer sequences may refer to oligonucleotide sequences composed of all possible sequences for a given length of the randomer. Alternatively, or additionally, a universal label, a molecular label, a cellular label, linker label and/or a sample label may comprise a predetermined sequence of nucleotides.

In some embodiments, amplification can be performed using a polymerase chain reaction (PCR). As used herein, PCR has its ordinary can refer to a reaction for the in vitro amplification of specific DNA sequences by the simultaneous primer extension of complementary strands of DNA. As used herein, PCR can encompass derivative forms of the reaction, including but not limited to, RT-PCR, real-time PCR, nested PCR, quantitative PCR, multiplexed PCR, digital PCR, and assembly PCR.

Amplification of the DNA associated with the target protein can comprise non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), and a Qβ replicase (Qβ) method, use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and ramification extension amplification (RAM). In some embodiments, the amplification does not produce circularized transcripts.

Amplification can include use of one or more non-natural nucleotides. Non-natural nucleotides can comprise photolabile or triggerable nucleotides. Examples of non-natural nucleotides can include, but are not limited to, peptide nucleic acid (PNA), morpholino and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Amplification as described herein can comprise the use of one or more primers. The primer(s) can each comprise, for example, at least 1, 2, 3, 4, 5, 6, 7, 8, 9, 10, 11, 12, 13, 14, 15, 20, 25 or more nucleotides, including ranges between any two of the listed values. The primers can each comprise at least 1, 2, 3, 4, 5, 6, 7, 8, 9, 10, 11, 12, 13, 14, 15, 20, 25, or more nucleotides, including ranges between any two of the listed values. The primers can comprise less than 12-15 nucleotides. The primers can each anneal to at least a portion of the plurality of stochastically labeled targets. The primers can each anneal to the 3' end or 5' end of a plurality of labeled targets (for example, a universal primer binding site as described herein). The primers can each anneal to a region of the plurality of labeled targets, for example, an internal region. The region can comprise at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled targets. The primers can be comprised by a fixed panel of primers. The primers can comprise at least one or more custom primers. By way of example, a 5' portion of an oligonucleotide probe hybridized to a target can act as a primer for amplifying the target. Optionally, the primers can comprise at least one or more control primers. The primers can comprise at least one or more gene-specific primers.

The one or more primers can comprise a universal primer and/or a custom primer. The universal primer can anneal to a universal primer binding site, such as a PCR handle as described herein. In accordance with some embodiments, one or more custom primers can anneal to a first sample label, a second sample label, a spatial label, a cell label, a molecular label, a target, or any combination thereof. The one or more primers can comprise a universal primer and a custom primer. The custom primer can be designed to specifically amplify one or more targets. The targets can comprise a subset of the total nucleic acids in one or more samples. The targets can comprise a subset of the total labeled targets in one or more samples. The one or more primers can comprise at least 96 or more unique custom primers. The one or more primers can comprise at least 960 or more custom primers. The one or more primers can comprise at least 9600 or more custom primers. The one or more custom primers can anneal to two or more different labeled nucleic acids. The two or more different labeled nucleic acids can correspond to one or more genes and/or intergenic nucleic acid.

Any amplification scheme can be used in the methods of the present disclosure. For example, in one scheme, the first round of PCR can amplify molecules immobilized on the bead through the use of a gene specific primer and a primer against the universal Illumina sequencing primer 1 sequence. The second round of PCR can amplify the first PCR products using a nested gene specific primer flanked by Illumina sequencing primer 2 sequence, and a primer against the universal Illumina sequencing primer 1 sequence. The third round of PCR can add P5 and P7 and sample index to turn PCR products into an Illumina sequencing library. Sequencing using 150 bp×2 sequencing can reveal the cell label and molecular label on read 1, the gene on read 2, and the sample index on index 1 read.

In some embodiments, nucleic acids can be removed from the substrate by way of chemical cleavage. For example, a chemical group or a modified base present in a nucleic acid can facilitate its removal from a solid support. For example, an enzyme can be used to remove a nucleic acid from a substrate. For example, a nucleic acid can be removed from a substrate through a restriction endonuclease digestion. For example, treatment of a nucleic acid containing a dUTP or ddUTP with uracil-d-glycosylase (UDG) can be used to remove a nucleic acid from a substrate. For example, a nucleic acid can be removed from a substrate using an enzyme that performs nucleotide excision, such as a base excision repair enzyme, such as an apurinic/apyrimidinic (AP) endonuclease. In some embodiments, a nucleic acid can be removed from a substrate using a photocleavable group and light. In some embodiments, a cleavable linker can be used to remove a nucleic acid from the substrate. For example, the cleavable linker can comprise at least one of biotin/avidin, biotin/streptavidin, biotin/neutravidin, Ig-protein A, a photo-labile linker, acid or base labile linker group, or an aptamer.

When the oligonucleotide probes are gene-specific, the target molecules can hybridize to the probes and can be reverse transcribed and/or amplified. In some embodiments, after the nucleic acid has been synthesized (e.g., reverse transcribed), it can be amplified. Amplification can be performed in a multiplex manner, wherein multiple target nucleic acid sequences are amplified simultaneously. Amplification can add sequencing adaptors to the nucleic acid.

In some embodiments, amplification can be performed on the substrate, for example, by way of bridge amplification. cDNAs can be homopolymer tailed in order to generate a compatible end for bridge amplification using oligo(dT) probes on the substrate. In bridge amplification, the primer that is complementary to the 3' end of the template nucleic acid can be the first primer of each pair that is covalently attached to the solid particle. When a sample containing the template nucleic acid is contacted with the particle and a single thermal cycle is performed, the template molecule can be annealed to the first primer and the first primer is elongated in the forward direction by addition of nucleotides to form a duplex molecule comprising or consisting of the template molecule and a newly formed DNA strand that is complementary to the template. In the heating step of the next cycle, the duplex molecule can be denatured, releasing the template molecule from the particle and leaving the complementary DNA strand attached to the particle through the first primer. In the annealing stage of the annealing and elongation step that follows, the complementary strand can hybridize to the second primer, which is complementary to a segment of the complementary strand at a location removed from the first primer. This hybridization can cause the complementary strand to form a bridge between the first and second primers secured to the first primer by a covalent bond and to the second primer by hybridization. In the elongation stage, the second primer can be elongated in the reverse direction by the addition of nucleotides in the same reaction mixture, thereby converting the bridge to a double-stranded bridge. The next cycle then begins, and the double-stranded bridge can be denatured to yield two single-stranded nucleic acid molecules, each having one end attached to the particle surface via the first and second primers, respectively, with the other end of each unattached. In the annealing and elongation step of this second cycle, each strand can hybridize to a further complementary primer, previously unused, on the same particle, to form new single-strand bridges. The two previously unused primers that are now hybridized elongate to convert the two new bridges to double-strand bridges.

In some embodiments, the method comprises repeatedly amplifying the labeled nucleic acid to produce multiple amplicons. The methods disclosed herein can comprise repeating the amplification for at least about 1, 2, 3, 4, 5, 6, 7, 8, 9, 10, 11, 12, 13, 14, 15, 16, 17, 18, 19, or 20 amplification reactions. Alternatively, the method comprises conducting at least about 25, 30, 35, 40, 45, 50, 55, 60, 65, 70, 75, 80, 85, 90, 95, or 100 amplification reactions.

Amplification can further comprise adding one or more control nucleic acids to one or more samples comprising a plurality of nucleic acids. Amplification can further comprise adding one or more control nucleic acids to a plurality of nucleic acids. The control nucleic acids can comprise a control label.

In some embodiments, the method further comprises sequencing. Sequencing a target nucleic acid, including a labeled target nucleic acid can comprise conducting a sequencing reaction to determine the sequence of at least a portion of the target nucleic acid, a complement thereof, a reverse complement thereof, or any combination thereof.

Determination of the sequence of a labeled target (e.g., amplified nucleic acid, labeled nucleic acid, cDNA copy of a labeled nucleic acid, etc.) can be performed using variety of sequencing methods including, but not limited to, sequencing by hybridization (SBH), sequencing by ligation (SBL), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads, wobble sequencing, multiplex sequencing, polymerized colony (POLONY) sequencing; nanogrid rolling circle sequencing (ROLONY), allele-specific oligo ligation assays (e.g., oligo ligation assay (OLA), single template molecule OLA using a ligated linear probe and a rolling circle amplification (RCA) readout, ligated padlock probes, or single template molecule OLA using a ligated circular padlock probe and a rolling circle amplification (RCA) readout), and the like.

In some embodiments, determining the sequence of the target nucleic acid or any product thereof comprises paired-end sequencing, nanopore sequencing, high-throughput sequencing, shotgun sequencing, dye-terminator sequencing, multiple-primer DNA sequencing, primer walking, Sanger dideoxy sequencing, Maxim-Gilbert sequencing, pyrosequencing, true single molecule sequencing, or any combination thereof. Alternatively, the sequence of the stochastically barcoded target or any product thereof can be determined by electron microscopy or a chemical-sensitive field effect transistor (chemFET) array.

High-throughput sequencing methods, such as cyclic array sequencing using platforms such as Roche 454, Illumina Solexa, ABI-SOLiD, ION Torrent, Complete Genomics, Pacific Bioscience, Helicos, or the Polonator platform, can be utilized. In some embodiments, sequencing can comprise MiSeq sequencing. In some embodiments, sequencing can comprise HiSeq sequencing.

Sequencing can include at least about 200, 300, 400, 500, 600, 700, 800, 900, 1,000 or more sequencing reads per run. In some embodiments, sequencing includes sequencing at least or at least about 1500, 2000, 3000, 4000, 5000, 6000, 7000, 8000, 9000, or 10000 or more sequencing reads per run. Sequencing can include less than or equal to about 1,600,000,000 sequencing reads per run. Sequencing can include less than or equal to about 200,000,000 reads per run.

Some embodiments of the description provided herein may be understood in light of the accompanying drawings. With reference to FIG. 1, provided is a binding reagent (e.g., protein binding reagent 105) associated with a fusion protein 125 that comprises a digestion enzyme 120 and a domain 130 that specifically binds the protein binding reagent 105. The protein binding reagent 105 comprises a reagent oligonucleotide 110. In some embodiments, the reagent oligonucleotide 110 includes a capture sequence, for example a polyA sequence 115. As discussed herein, it is noted that in some embodiments, the capture sequence can be a sequence other than a polyA sequence. In some embodiments, such as shown in FIG. 1, the protein binding reagent 105 is associated with to the fusion protein 125 to form an associated protein 101. For example, the protein binding reagent 105 can be non-covalently or covalently bound to the fusion protein 125 to form the associated protein 101.

Figure 2:
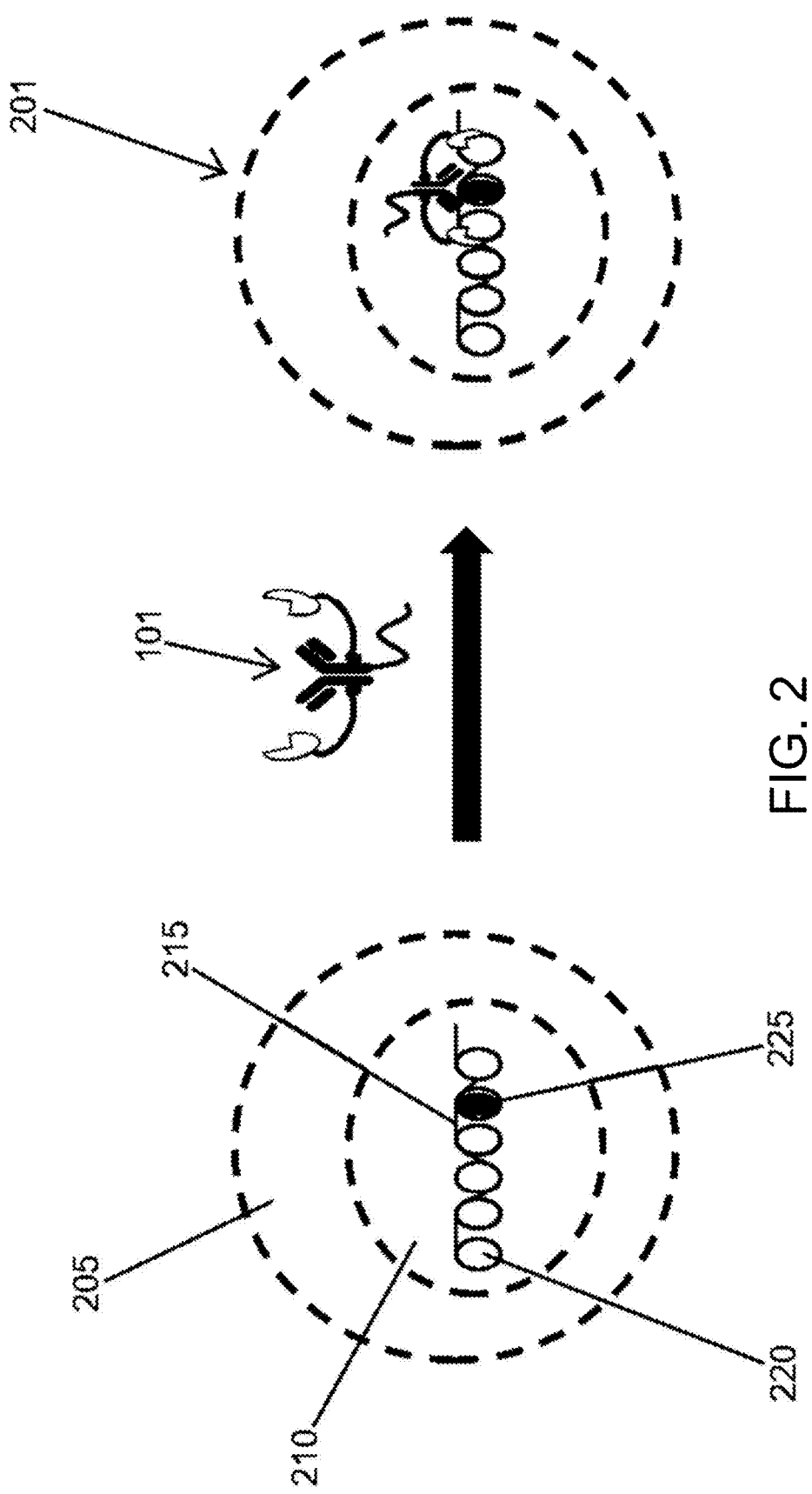
FIG. 2 is a schematic diagram illustrating contacting a permeabilized cell with the binding reagent (e.g., protein binding reagent) bound to the fusion protein of FIG. 1, such that the protein binding reagent bound to the fusion protein binds to a target protein associated with DNA in a nucleus of the cell, in accordance with some embodiments herein.

As shown in FIG. 2, a permeabilized cell 205 comprises a nuclear target (e.g., target protein 225) that is associated with a DNA 215 within a nucleus 210 of the permeabilized cell 205. Nuclear targets can comprise nuclear DNA (e.g., methylated DNA) or nuclear proteins (e.g., gDNA-associated proteins). In some embodiments, the DNA 215 may also be associated with other proteins, such as an off-target protein 220. In some embodiments the permeabilized cell 205 is contacted with the associated protein 101, which enters the permeabilized cell 205 and binds to target protein 225, forming a permeabilized cell 205 comprising associated protein 101 bound to the target protein 225. In some embodiments the permeabilized cell 205 is contacted with the protein binding reagent 105 and fusion protein 125, which enters the permeabilized cell 205 and form an associated protein 101. The associated protein can bind to target protein 225 in the nucleus 210 of the permeabilized cell 205, forming a permeabilized cell 205 comprising associated protein 101 bound to the target protein 225.

Figure 3:
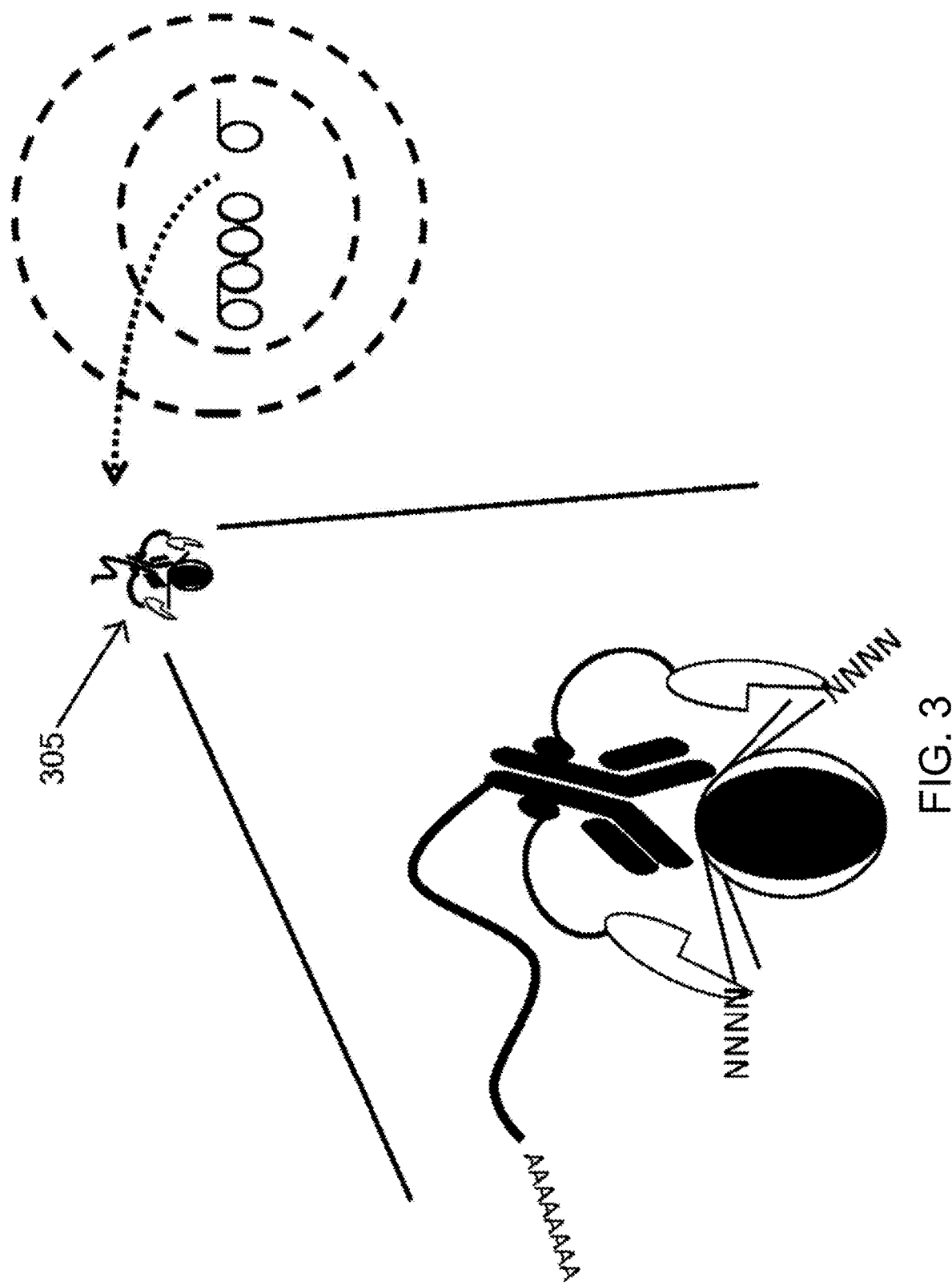
FIG. 3 is a schematic diagram illustrating digestion of the DNA with a DNA digestion enzyme, thus producing a complex that includes the binding reagent (e.g., protein binding reagent) bound to the fusion protein of FIG. 1 and digested DNA. The complex can isolated (e.g., removed) from the cell in accordance with some embodiments herein.

As shown in FIG. 3, the DNA digestion enzyme 120 of the fusion protein 125 digests the DNA 215, and the associated protein 101 forms a complex 305 that comprises the protein binding reagent 105, fusion protein 125, target protein 225, and digested DNA 215 having a single stranded overhang. FIG. 3 shows the complex 305 removed from the permeabilized cell 205. In some embodiments, the method comprises cell lysis (e.g., by chemical or biochemical means, by osmotic shock, or by means of thermal lysis, mechanical lysis, or optical lysis) to liberate the complex.

Figure 4:
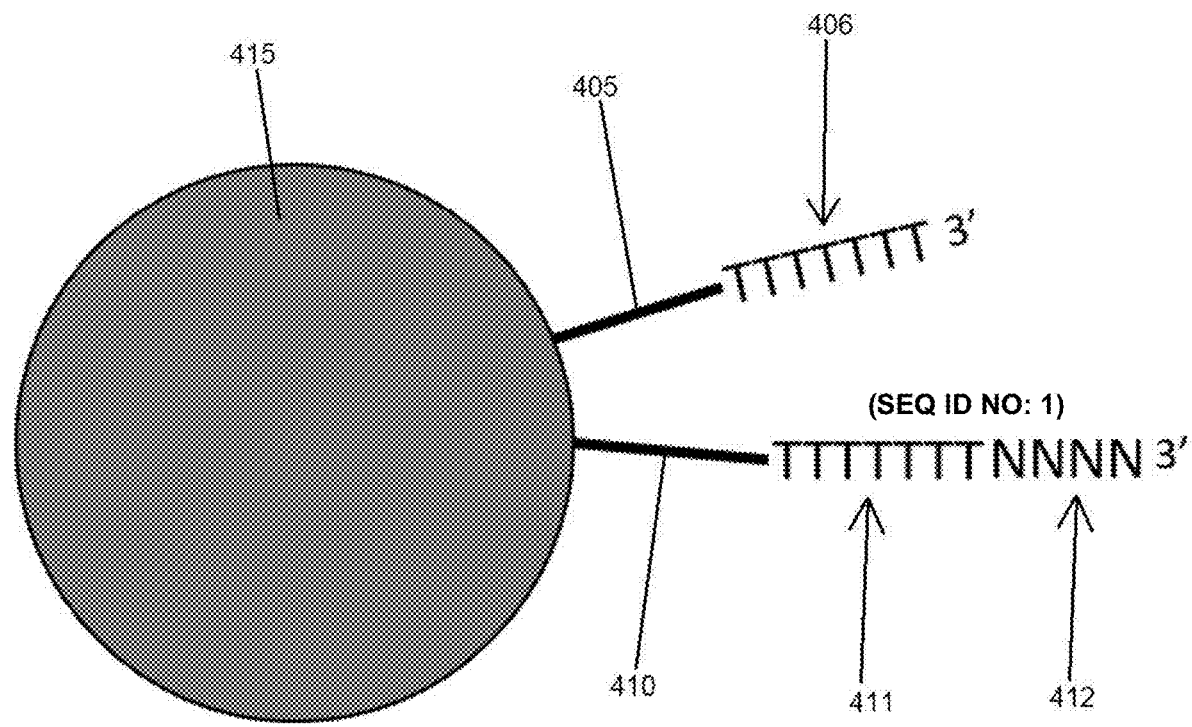
FIG. 4 is a schematic diagram illustrating a substrate (e.g., a bead) comprising first and second oligonucleotide probes immobilized on the substrate, in accordance with some embodiments herein.

FIG. 4 depicts a first oligonucleotide probe 405 and a second oligonucleotide probe 410, each immobilized to a bead 415. In some embodiments, the first oligonucleotide probe 405 includes a first target binding region 406. In some embodiments the first target binding region 406 comprises, consists essentially of, or consists of a polyT sequence. In some embodiments, the second oligonucleotide probe 410 includes a second target binding region 412. In some embodiments, the second oligonucleotide probe 410 comprises, consists essentially of, or consists of a second polyT sequence 411.

Figure 5A:
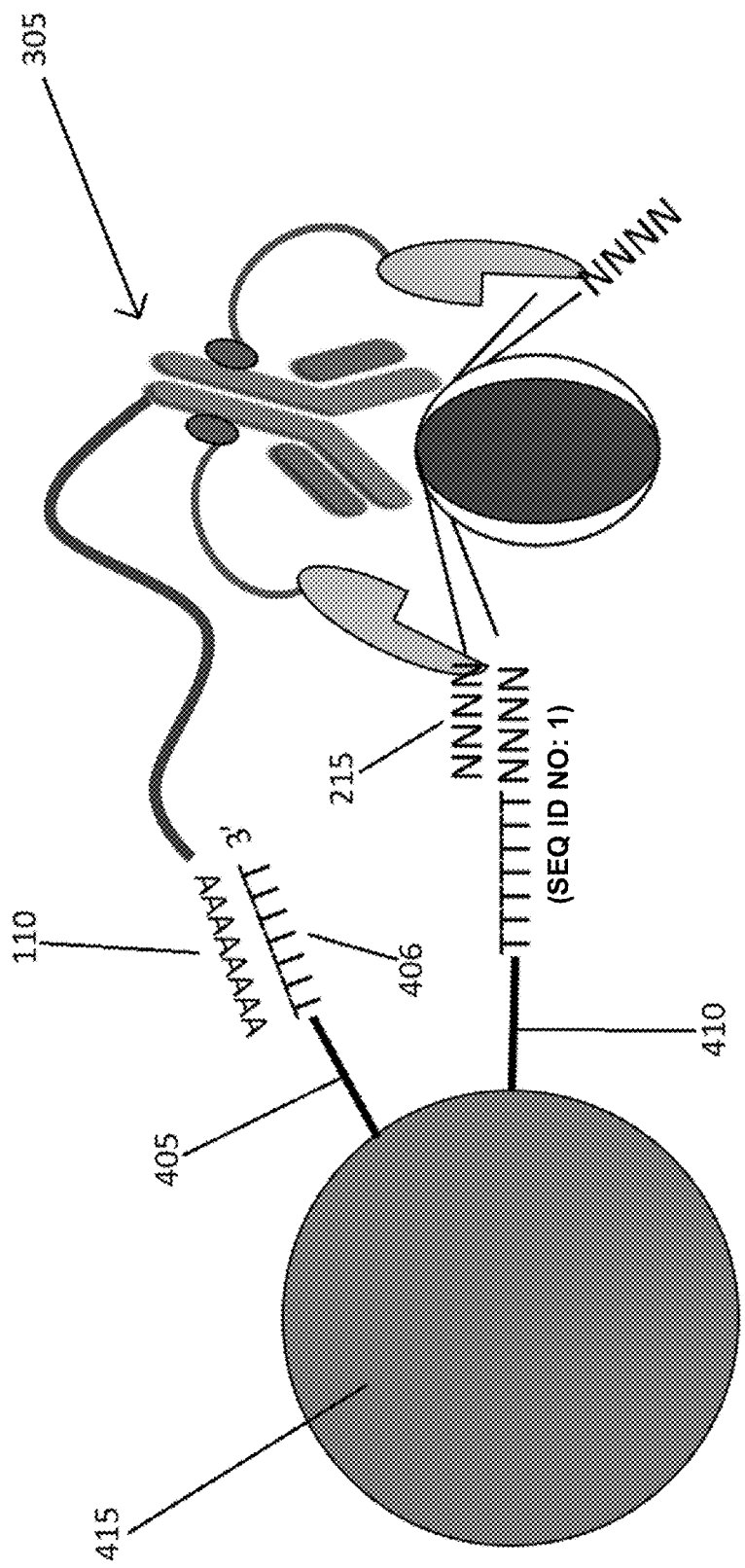
FIGS. 5A-5D are schematic diagrams illustrating capture and processing of DNA from a single cell.

As shown in FIG. 5A, contacting the complex 305, with the substrate 415 that includes the first oligonucleotide probe 405 and the second oligonucleotide probe 410 results in hybridization of the first target binding region 406 to the reagent oligonucleotide 110, and the second target binding region 410 to the single stranded overhang of the digested DNA 215. Thus, FIG. 5A shows capture of the complex 305 to the bead 415. In such embodiments, material not captured to the bead, including cells or components thereof, are removed, for example by washing.

Figure 5B:
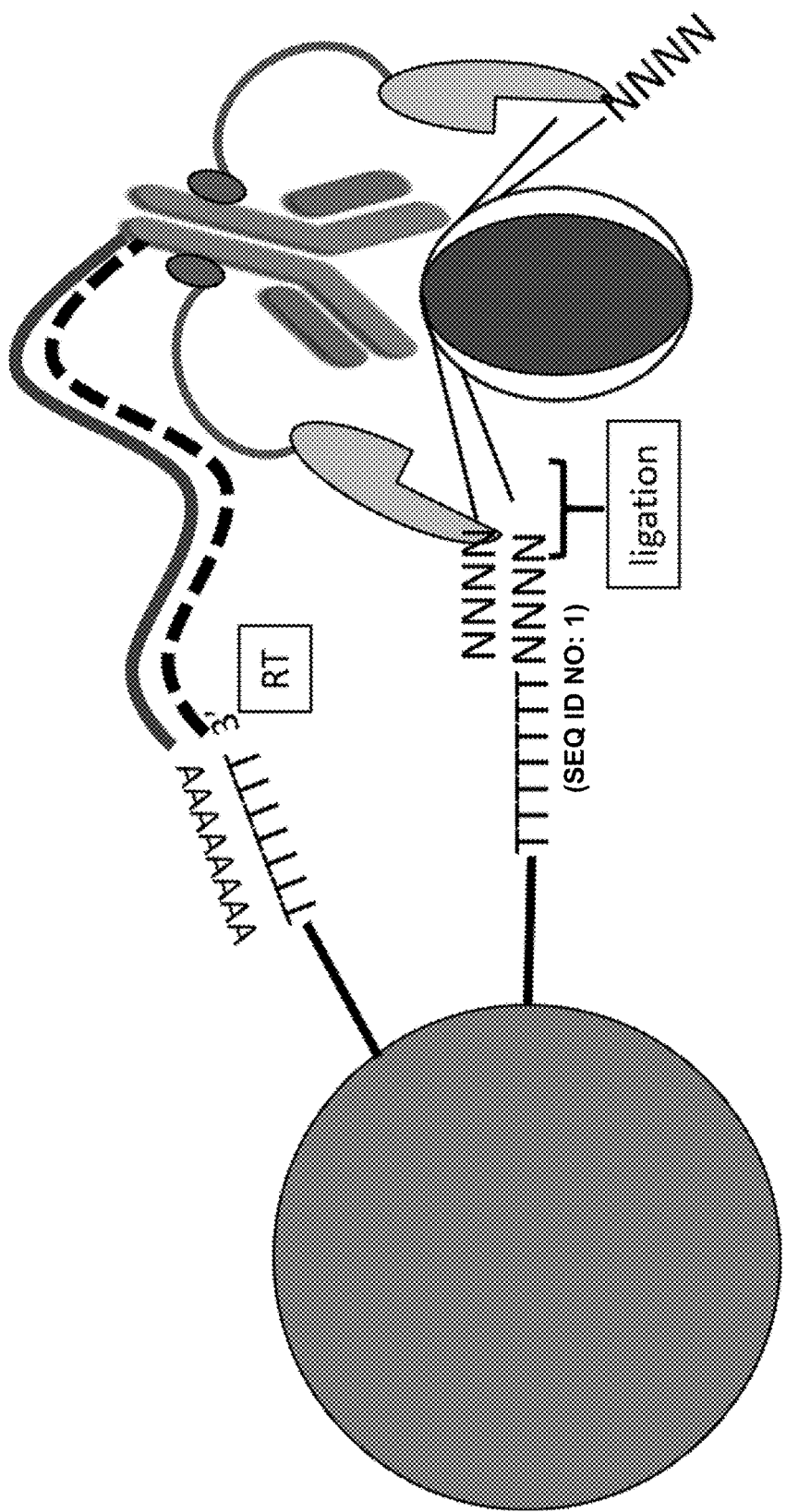
Figure 5C:
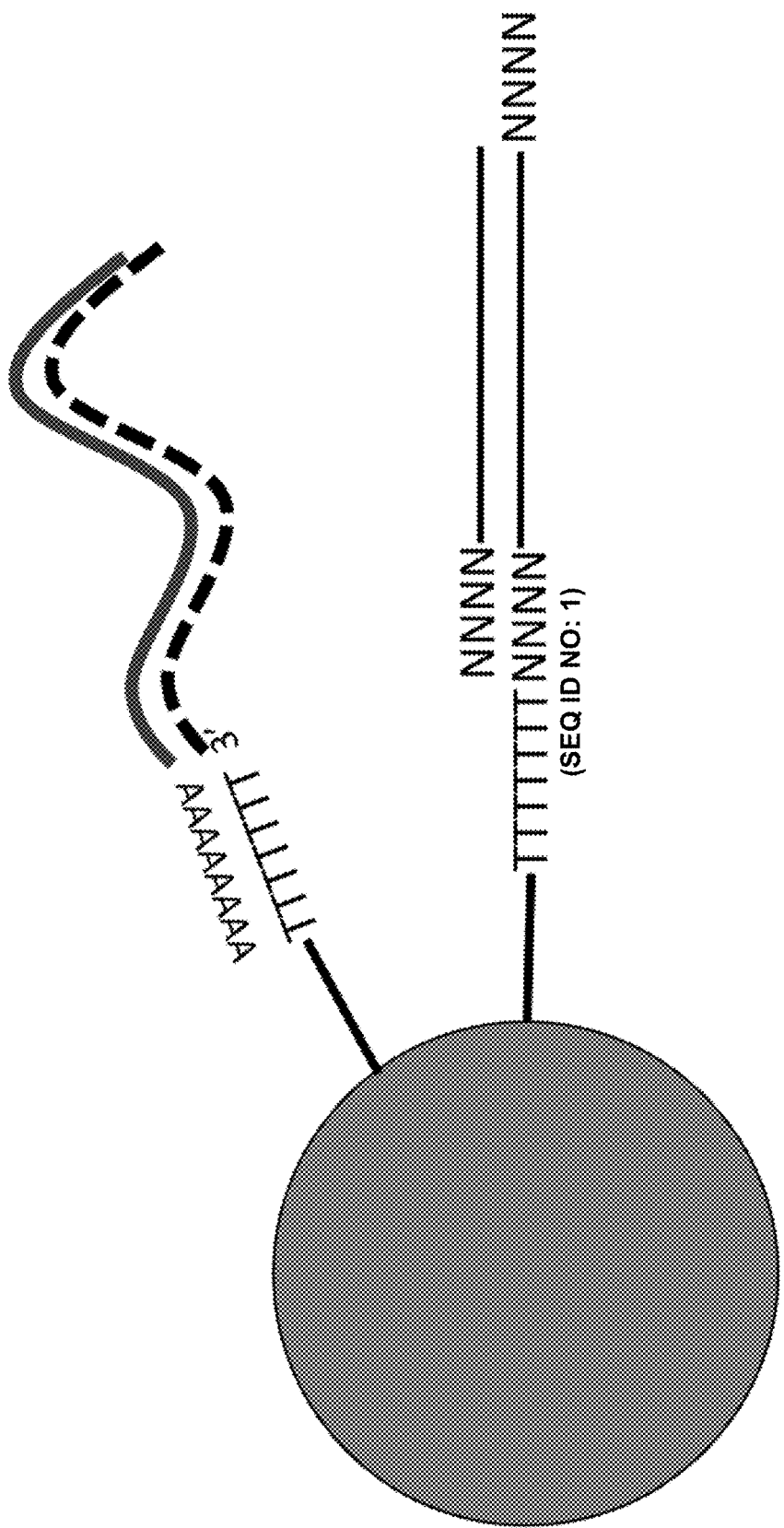
Figure 5D:
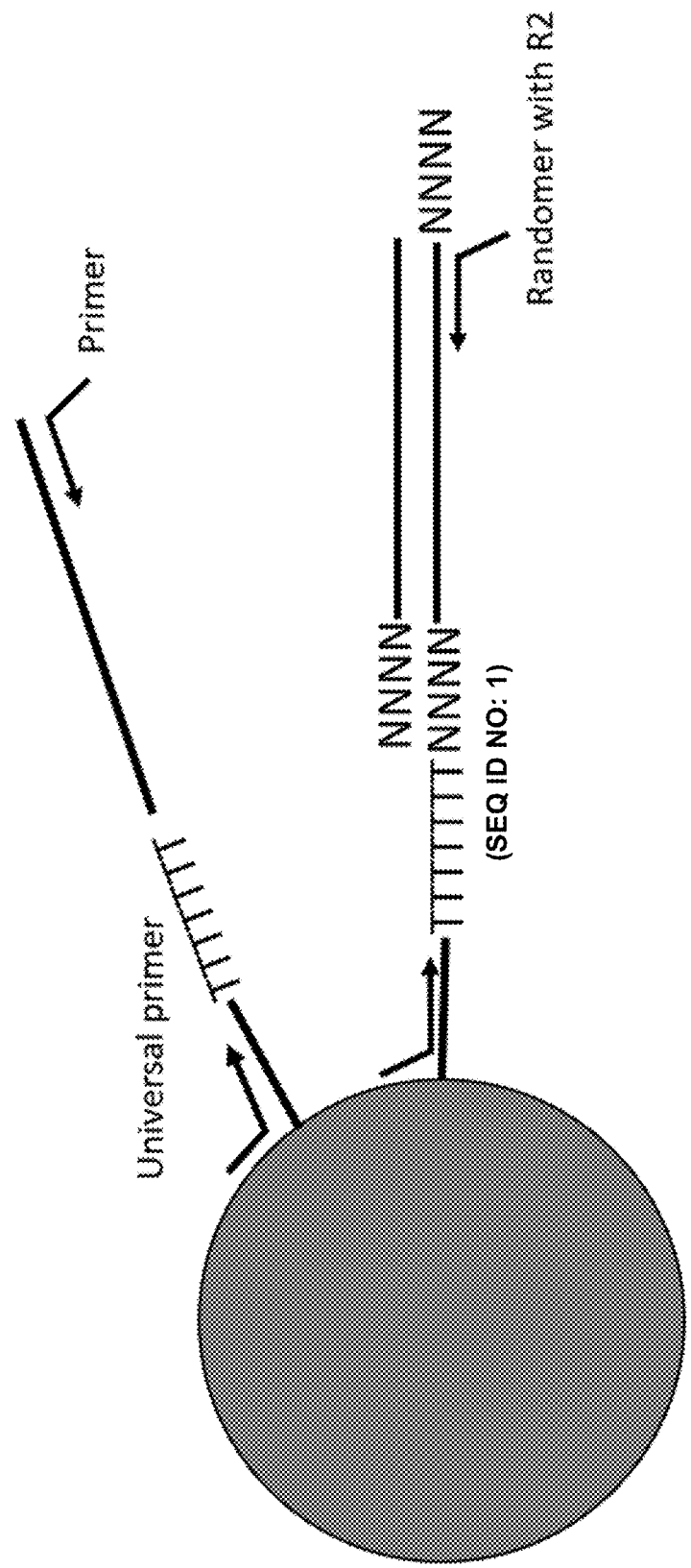
Figure 6:
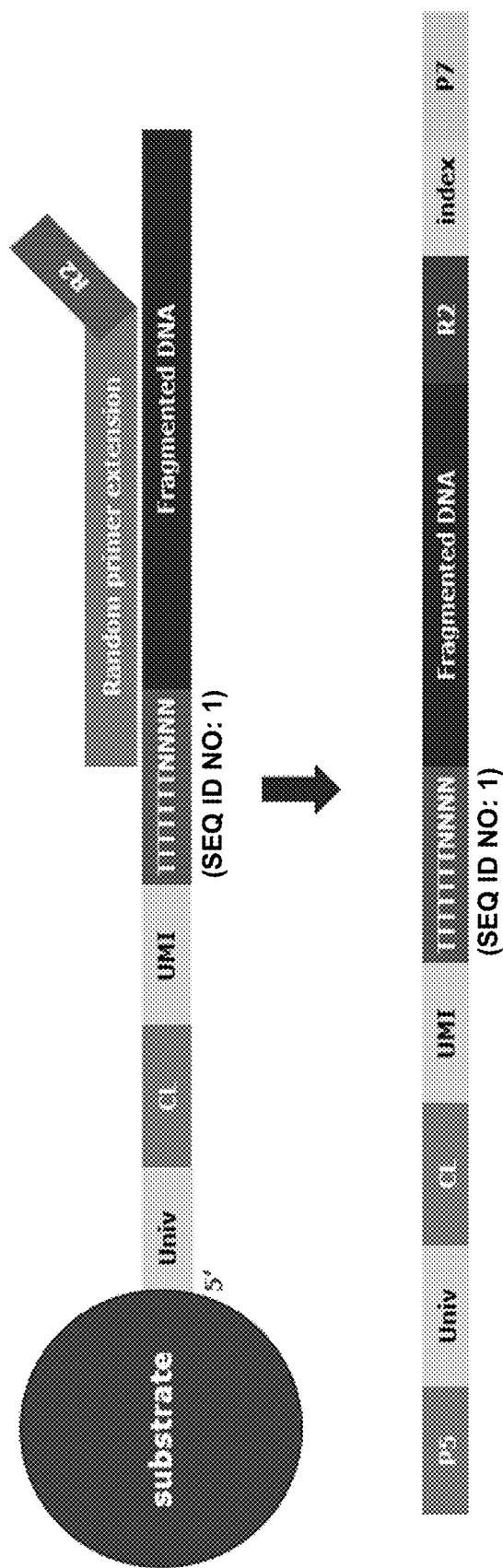
FIG. 6 is a schematic diagram illustrating library generation of a target protein-associated DNA, in accordance with some embodiments herein. Generating the library can comprise providing component parts of an oligonucleotide bound to a substrate.

As shown in FIG. 5B, in some embodiments, the captured complex may be subjected to ligation and reverse transcription. Such steps may be performed in an automated instrument, such as a thermomixer. A ligase (e.g., T4 DNA ligase)

may be used to join two fragments. Tagmentation products generated according to some of the embodiments provided herein can comprise gaps. Gaps between DNA fragments can be filled by a gap-filling enzyme, such as a DNA polymerase (e.g., Klenow). As shown in FIG. 5C, in some embodiments, proteins, including the protein binding reagent, the fusion protein, and the target protein are removed. Optionally, polypeptides may be removed, for example, by treatment of the captured complex with proteinase K. Furthermore, unbound nucleic acids may be removed, for example, by contacting with a nuclease, such as ExoI. As shown in FIG. 5D, in some embodiments, the hybridized nucleic acids may undergo further processing to barcode the nucleic acids of the captured complex (e.g., digested DNA and reagent oligonucleotide), including, for example, denaturation, random primer extension, and/or polymerase chain reaction. FIG. 6 depicts library generation, wherein a nucleic acid sequence immobilized on a substrate comprises a universal primer binding site (such as a PCR handle), a cell label (CL), a unique molecular identifier (UMI), a capture sequence (e.g., polyT) and target DNA sequence. Random primer extension may be performed to generate a library, which may include, in some embodiments a P5 and P7 primer adaptor sequences.

In some embodiments, the compositions and methods comprise multiplex construction, so that they are suitable for multiplex labeling and/or analysis. For example, a plurality of binding reagents (e.g., protein binding reagents) may be provided that specifically bind to different target proteins, and which each include a different reagent oligonucleotide. In multiplex construction, a plurality of first oligonucleotide probes are provided, each having a specificity to a different reagent oligonucleotide. Each of the plurality of first oligonucleotide probes can be capable of hybridizing to a different reagent oligonucleotide, such that a plurality of target proteins are captured. Each target protein can associated with a different DNA, each of which can be analyzed, labeled, or sequenced in multiplex. In multiplex embodiments, the plurality of binding reagent (e.g., protein binding reagents) may comprise at least 2, 3, 4, 5, 6, 7, 8, 9, 10, 20, 30, 40, 50, 60, 70, 80, 90, or 100 or more unique protein binding reagents, or an amount within a range defined by two or more of the above-mentioned values, that each specifically bind to a unique target protein. It is noted that in multiple embodiments, the cell may be contacted with target binding protein associated with (e.g., bound to) fusion protein, so that particular target binding proteins are associated with particular DNA digestion enzymes.

Methods of Appending Oligonucleotide Probe with a Target Binding Region

Some embodiments provided herein relate to methods of appending an oligonucleotide probe with a target binding region. The method can comprise providing an oligonucleotide probe that includes sample identifier sequence and a hybridization domain. By way of example, the oligonucleotide probe may be immobilized to a substrate, such as a bead, a well, an array, a plate, or a tube. The oligonucleotide probe can be contacted with a partially double-stranded DNA (dsDNA) template comprising (i) a template strand comprising a single-stranded complementary hybridization domain that is complementary to at least a portion of the hybridization domain and sequence complementary to the target binding region (e.g., a target nucleic acid sequence) and (ii) a complementary strand comprising the target binding region. The target binding region of the complementary strand can be hybridized to the target nucleic acid sequence of the template strand. The hybridization domain can hybridize to the complementary hybridization domain. The dsDNA template can be ligated to the oligonucleotide probe. The dsDNA can be denatured. The template strand can be removed. Thus, the strand that remains can comprise the oligonucleotide probe and the target binding region appended thereto. It is noted that any method of appending an oligonucleotide with a target binding region as described herein can be used in conjunction with any method of labeling a target-protein-associated DNA as described herein. For example, using the methods described herein, custom target binding regions can be appended to any oligonucleotide probe describe herein. For methods of labeling a target-protein-associated DNA that comprise multiple labeling for two or more different target proteins, custom target binding regions can be useful for differentiating between unique identifiers of different target binding proteins, so that particular target-binding proteins are immobilized on particular substrates (so that DNA sequences associated with the particular target proteins can be identified).

In some embodiments, the hybridization domain is a polyT sequence. In some embodiments, the oligonucleotide probe further includes a polymerase chain reaction (PCR) handle (such as a universal primer binding site), a cell label, and/or a unique molecular identifier. In some embodiments, the methods further comprise providing a double stranded DNA (dsDNA) template that include a template strand and a complementary strand. In some embodiments, the template strand comprises a sequence complementary to at least a portion of the hybridization domain of the oligonucleotide probe. Thus, when the hybridization domain of the oligonucleotide probe is a polyT sequence, the template strand comprises a polyA sequence. In some embodiments, the sequence complementary to the target binding region comprises a target nucleic acid sequence. A target nucleic acid sequence can include a sequence that is of interest, such as a target sequence of interest. In some embodiments, the complementary strand is complementary to the target binding region of the template strand. The complementary hybridization domain of the template strand is thus a single stranded overhang capable of hybridizing to the hybridization domain of the oligonucleotide probe. In some embodiments, the template strand is attached to biotin.

In some embodiments, the methods further include contacting the oligonucleotide probe with the dsDNA template under conditions in which the hybridization domain of the oligonucleotide probe hybridizes to the complementary hybridization domain of the template strand of the dsDNA template. In some embodiments, the methods include ligating the oligonucleotide probe to the dsDNA template. A ligase (e.g., T4 DNA ligase) may be used to join two fragments (for example, the oligonucleotide probe and the dsDNA template comprising the complementary strand). Upon ligation, the oligonucleotide probe can comprise the complementary strand appended thereto. In some embodiments, the methods include denaturing the dsDNA template. In some embodiments, the methods include removing the template strand of the dsDNA template. Removing the template strand may include contacting with streptavidin when the template strand is attached to biotin. The biotin can bind to the streptavidin, and the bound biotin-streptavidin-template strand can be removed. For example, the streptavidin can be immobilized on a substrate (for example a bead), and the substrate can be removed along with the biotin-streptavidin-template strand associated therewith.

Figure 7A:
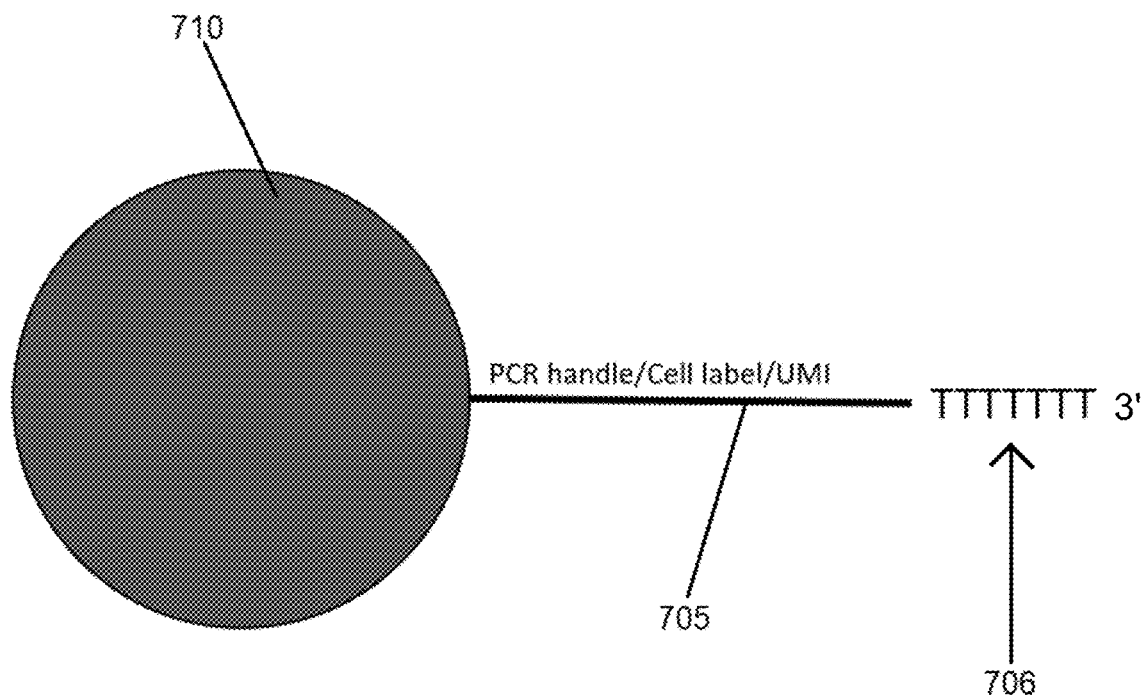
FIGS. 7A-7C are schematic illustrations of labeling an oligonucleotide probe with a target binding region nucleic acid sequence in accordance with some embodiments herein.
Figure 7B:
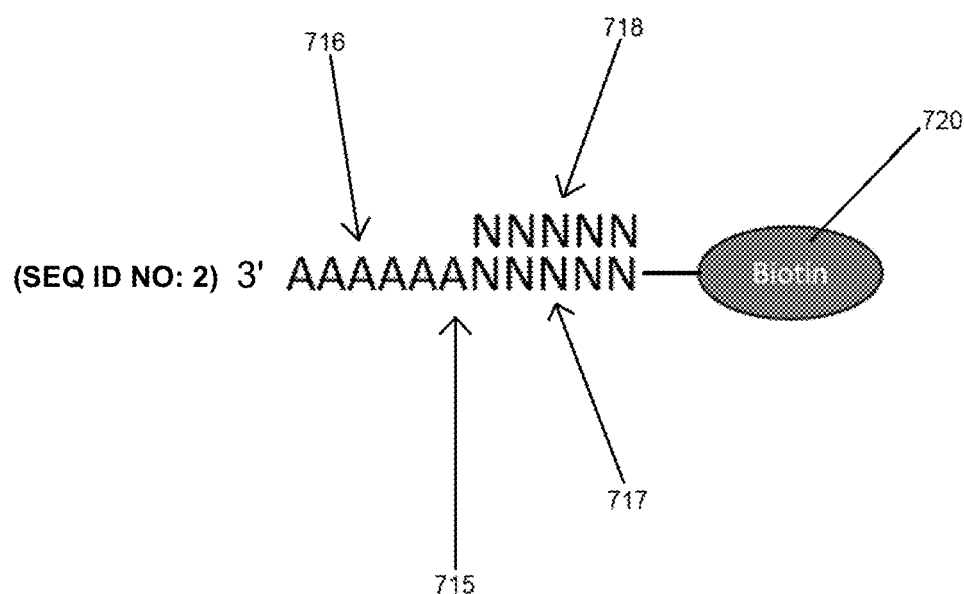
Figure 7C:
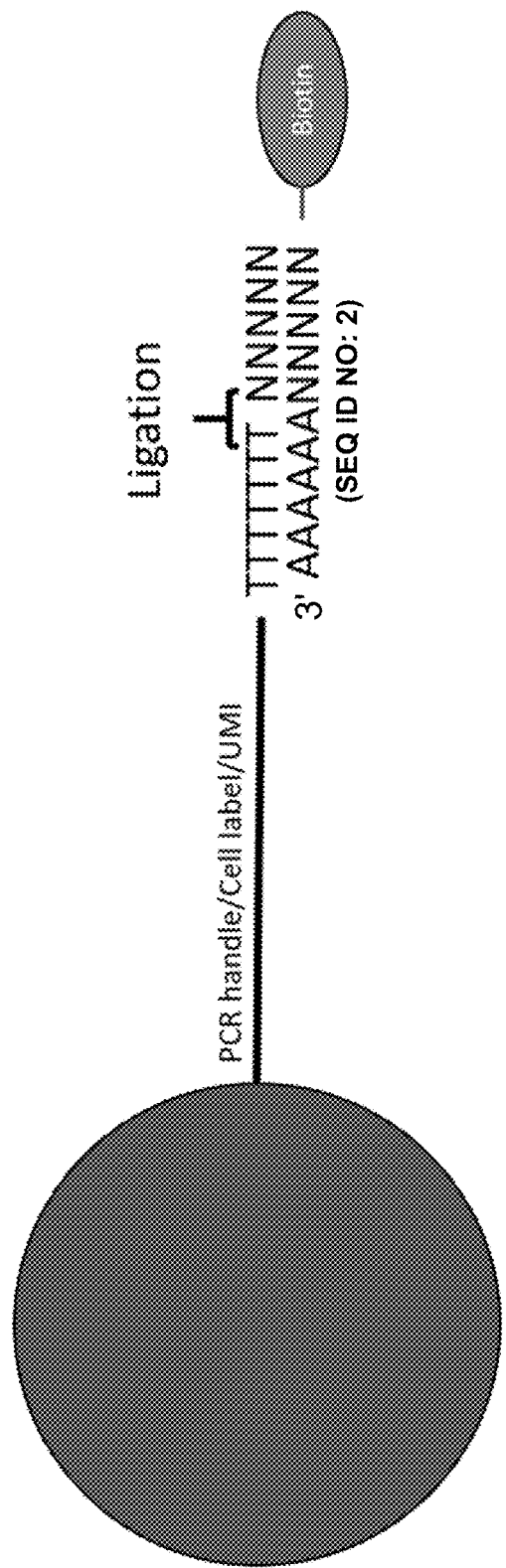
Figure 8:
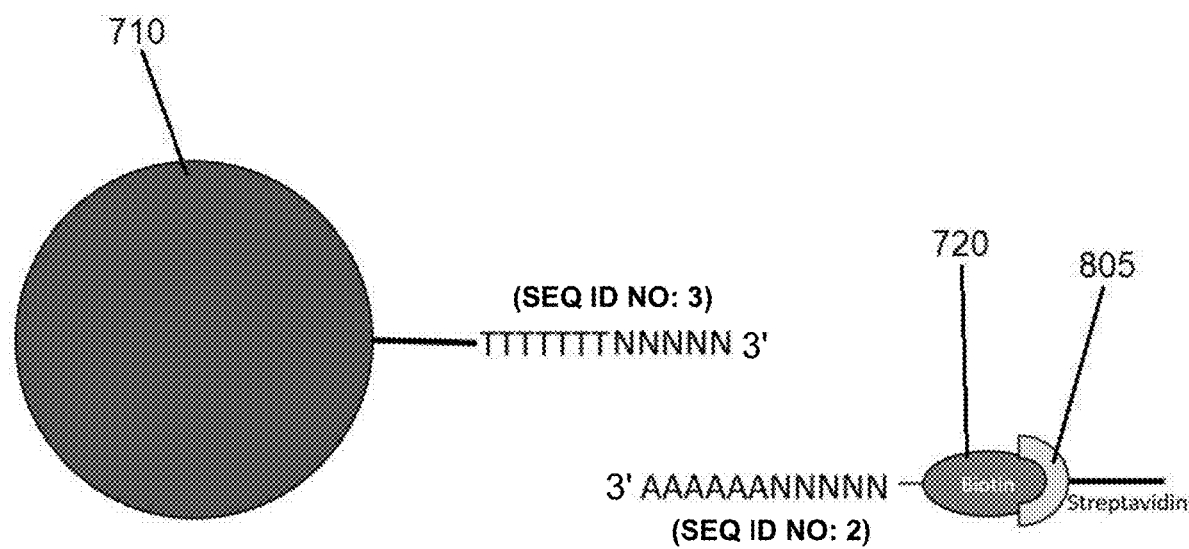
FIG. 8 schematically illustrates denaturing dsDNA after ligation of a complementary strand sequence of the dsDNA to the oligonucleotide probe, and removal of the template strand sequence by binding of biotin to streptavidin, in accordance with some embodiments herein.
Figure 9:
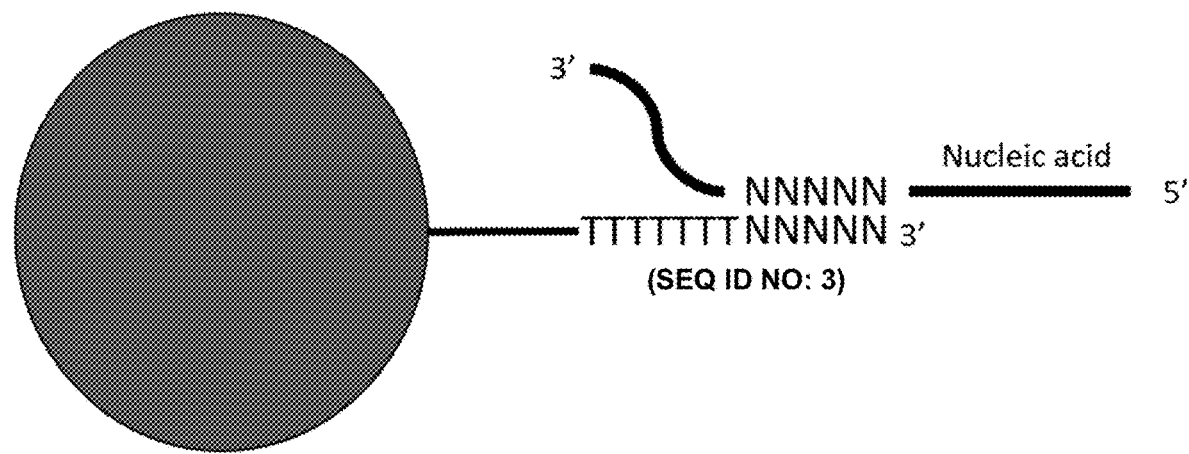
FIG. 9 schematically illustrates binding of an oligonucleotide probe having complementary target strand sequence as shown in FIG. 8 to a target nucleic acid sequence, in accordance with some embodiments herein.

As shown in FIGS. 7A-7C, a method of labeling an oligonucleotide probe with a target binding region is shown, according to some embodiments. As shown in FIG. 7A, a substrate (such as a bead) 710 is provided having an oligonucleotide probe 705 that comprises a hybridization domain 706. In this embodiment, the hybridization domain 706 comprises, consists essentially of, or consists of a polyT sequence. As shown in FIG. 7B, a dsDNA template is provided. The dsDNA template comprises a template strand 715 and a complementary strand 718. The template strand 715 comprises a complement of the hybridization domain 716. In this example, the complement of the hybridization domain 716 is a polyA sequence, though it will be appreciated that any suitable hybridization domain and complement can be used. The template strand 715 includes a target binding region 717, and is attached to biotin 720. Contacting the substrate 710 with the dsDNA template causes hybridization of the hybridization domain 706 to the complementary hybridization domain 716. The dsDNA template is then ligated to the oligonucleotide probe 705, as shown in FIG. 7C. A ligase (e.g., T4 DNA ligase) may be used to join two fragments. FIG. 8 depicts removal of the template strand of the dsDNA template by contacting with streptavidin 805, which binds to the biotin 720, so that the template strand is removed when the streptavidin 805 is removed. By way of example, the streptavidin 805 may be immobilized on a substrate, so that upon removal of the substrate, streptavidin 805 bound to biotin 720 and the template strand are removed. As shown in FIG. 9, the oligonucleotide probe that is labeled with target binding region may be used to bind to a target sequence of interest.

Any of the methods and compositions described herein may be implemented into a system or kit. Thus, some embodiments provided herein relate to a kit that comprises any binding reagent (e.g., protein binding reagent) as described herein, any fusion protein as described herein, any first oligonucleotide probe as described herein, and any second oligonucleotide probe as described herein. In some embodiments, the first and second oligonucleotide probe of the kit are immobilized on a substrate as described herein, such as a solid surface, a bead, a microarray, a plate, a tube, or a well. In some embodiments, the kit further includes a composition for carrying out a reaction, such as a reagent that includes a reagent for random priming (e.g., random primers and a polymerase), for sequencing (e.g., a universal primer), for cell permeabilization (e.g., a detergent), for DNA digestion (e.g., a DNAase), for ligation (e.g., a ligase), for reverse transcription (e.g., a reverse transcriptase), and/or for generating a nucleic acid library (e.g., a polymerase). Thus, such reagents may include, for example, DNA restriction enzymes, nucleases (such as micrococcal nuclease), lysozyme, proteinase K, random hexamers, polymerase (Φ29 DNA polymerase, Taq polymerase, Bsu polymerase, Klenow polymerase), transposase (Tn5), primers (P5 and P7 adaptor sequences), ligase, catalyzing enzyme, deoxynucleotide triphosphates, buffers, or divalent cations.

In some embodiments, the kit includes any oligonucleotide probe including a sample identifier sequence and a hybridization domain as described herein, and a dsDNA template. In some embodiments, the kit further includes reagents for labeling the oligonucleotide probe, including, for example, ligase and/or denaturants (for example, a base). In some embodiments, the oligonucleotide probe is immobilized on a substrate, such as a solid surface, a bead, a microarray, a plate, a tube, or a well.

Some embodiments described herein further relate to a cell composition. The cell composition may comprise a cell comprising target protein associated with DNA and a complex bound to the target DNA, in which the complex is any complex as described herein comprising any protein binding reagent as described herein and any fusion protein as described herein.

The methods and kits disclosed herein may include the use of one or more reagents. Examples of reagents include, but are not limited to, PCR reagents, ligation reagents, reverse transcription reagents, enzyme reagents, hybridization reagents, sample preparation reagents, permeabilization reagents (e.g., detergents), denaturing reagents, and reagents for nucleic acid purification and/or isolation.

The methods and kits disclosed herein may include the use of one or more buffers. Examples of buffers include, but are not limited to, wash buffers, ligation buffers, hybridization buffers, amplification buffers, and reverse transcription buffers. In some instances, the hybridization buffer is a commercially available buffer, such as TMAC Hyb solution, SSPE hybridization solution, and ECONO™ hybridization buffer. The buffers disclosed herein may comprise one or more detergents.

The methods and kits disclosed herein may comprise the use of one or more carriers. Carriers may enhance or improve the efficiency of one or more reactions disclosed herein (e.g., ligation reaction, reverse transcription, amplification, hybridization). Carriers may decrease or prevent non-specific loss of the molecules or any products thereof (e.g., labeled-molecule, labeled-cDNA molecule, labeled-amplicon). For example, the carrier may decrease non-specific loss of a labeled-molecule through absorption to surfaces. The carrier may decrease the affinity of the molecule, labeled-molecule, or any product thereof to a surface or substrate (e.g., container, Eppendorf tube, pipet tip). Alternatively, the carrier may increase the affinity of the molecule or any product thereof to a surface or substrate (e.g., bead, array, glass, slide, chip). Carriers may protect the molecule or any product thereof from degradation. For example, carriers may protect an RNA molecule or any product thereof from ribonucleases. Alternatively, carriers may protect a DNA molecule or any product thereof from a DNase. Examples of carriers include, but are not limited to, nucleic acid molecules such as DNA and/or RNA, or polypeptides. Examples of DNA carriers include plasmids, vectors, polyadenylated DNA, and DNA oligonucleotides. Examples of RNA carriers include polyadenylated RNA, phage RNA, phage MS2 RNA, *E. coli* RNA, yeast RNA, yeast tRNA, mammalian RNA, mammalian tRNA, short polyadenylated synthetic ribonucleotides and RNA oligonucleotides. The RNA carrier may be a polyadenylated RNA. Alternatively, the RNA carrier may be a non-polyadenylated RNA. In some instances, the carrier is from a bacteria, yeast, or virus. For example, the carrier may be a nucleic acid molecule or a polypeptide derived from a bacteria, yeast or virus. For example, the carrier is a protein from *Bacillus subtilis*. In another example, the carrier is a nucleic acid molecule from *Escherichia coli*. Alternatively, the carrier is a nucleic acid molecule or peptide from a mammal (e.g., human, mouse, goat, rat, cow, sheep, pig, dog, or rabbit), avian, amphibian, or reptile.

The methods and kits disclosed herein may comprise the use of one or more control agents. Control agents may include control oligonucleotides, inactive enzymes, non-specific competitors. Alternatively, the control agents comprise bright hybridization, bright probe controls, nucleic acid templates, spike-in controls, PCR amplification controls. The PCR amplification controls may be positive controls. In other instances, the PCR amplification controls are negative controls. The nucleic acid template controls may be of known concentrations. The control agents may comprise one or more labels.

Spike-in controls may be templates that are added to a reaction or sample. For example, a spike-in template may be added to an amplification reaction. The spike-in template may be added to the amplification reaction any time after the first amplification cycle. In some instances, the spike-in template is added to the amplification reaction after the 2nd, 3rd, 4th, 5th, 6th, 7th, 8th, 9th, 10th, 11th, 12th, 13th, 14th, 15th, 20th, 25th, 30th, 35th, 40th, 45th, or 50th amplification cycle. The spike-in template may be added to the amplification reaction any time before the last amplification cycle. The spike-in template may comprise one or more nucleotides or nucleic acid base pairs. The spike-in template may comprise DNA, RNA, or any combination thereof. The spike-in template may comprise one or more labels.

Compositions and Methods of Labeling Nuclear Target-Associated DNA

There are provided, in some embodiments, methods and compositions for labeling nuclear target-associated DNA in a cell. Disclosed herein include methods to perform modified antibody-mediated tagmentation. There are provided modified antibodies to be used in various epigenetics approaches provided herein. Currently Tn5 transposase is widely used to generate fragmented DNA with specific DNA tags (e.g., tagmentation). Disclosed herein include enzyme-conjugated antibodies to target specific regions of DNA for tagmentation which are associated with epigenetic marks of interest. By conjugating the Tn5 enzyme to the antibody specific to those epigenetic marks (e.g., histone modification, DNA methylation), DNA library associated to the epigenetic marks can be generated and sequenced. The DNA methylome has been studied through bisulfite sequencing using currently available methods, but to identify the methylome profile, the whole genome has to be sequenced, resulting in high sequencing costs. According to some embodiments provided herein, to target the region of interest, binding reagents (e.g., antibodies) detecting highly methylated region or methylated DNA binding protein can be used to generate a library of specific regions and bisulfite sequencing can then be performed to reduce sequencing costs. This dramatic cost reduction can improve the single cell methylome studies.

Without being bound by any particular theory, generating Tn5ase with direct conjugation with an antibody or a Fab version of antibody can increase accessibility to the cells and lead to improved assay efficiency. The compositions and methods provided herein can be extended to other applications and more diverse antibodies, including for methylome analysis, and Hi-C/ChIPseq can allow smaller sample size for each epigenetic technique and even at the single cell level (e.g., using the BD Rhapsody system). Tn5 and protein A fusion protein can be added after antibody bound to the protein in situ. However, in some embodiments, the multiple binding/washing step can generate background and inefficiencies for capturing all of antibody binding regions. By directly conjugating the enzyme to antibody, this problem can be solved. Moreover, by virtue of the methods and compositions provided herein, there is a potential to preserve mRNA in the cells that enables a user to analyze the epigenetic marks and transcriptome at the same time to enable multiomics approaches.

There are provided binding reagents (e.g., antibodies, or any protein binder specifically binds to protein of interest) directly conjugated with Tn5 enzyme for various assays, such as, for example methylome analysis, ChIP, HiC or any kind of assay using antibody to target region of interest on genome. The nuclear target can be any DNA binding protein or modified DNA (e.g., any antibody-recognizable entity). The nuclear target can be a chromatin binding protein. In some embodiments, the binding reagent (e.g., antibody) comprises a binding reagent oligonucleotide (e.g., MI oligonucleotide). In some embodiments the MI oligonucleotide on the antibody is optional (e.g., since the Tn5 enzyme also tags the excised DNA, it is possible to perform the single cell (e.g., Rhapsody) protocol in the absence of oligonucleotides bound to the antibody).

There are provided, in some embodiments, methods and compositions for antibody-mediated tagmentation. The binding reagent can be a modified antibody. There are provided binding reagents (e.g., antibodies) conjugated to Tn5 transposase. The binding reagent can be a Fab fragment with Tn5 transposase conjugation. Disclosed herein include antibodies specific for nuclear proteins or methylated nucleotides and protein G or A conjugated Tn5 transposase with DNA barcode. Disclosed herein include antibodies and fragments thereof (e.g., Fab fragments) specific for nuclear proteins or methylated nucleotides directly conjugated Tn5 transposase with DNA barcode. Applications of the methods and compositions provided herein include ChIP-Seq, Hi-C/ChIP-seq (e.g., address chromatin structure near specific protein or modified histones), determining methylome information (e.g., using methylated cysteine antibody to tagment the region and do bisulfide sequencing, which can reduce sequencing costs), and any sequencing technique using antibodies. Disclosed herein include generation of Fab-Tn5 conjugation with one or more DNA barcodes to enable easy access to cells for improved assay performance.

Figure 10A:
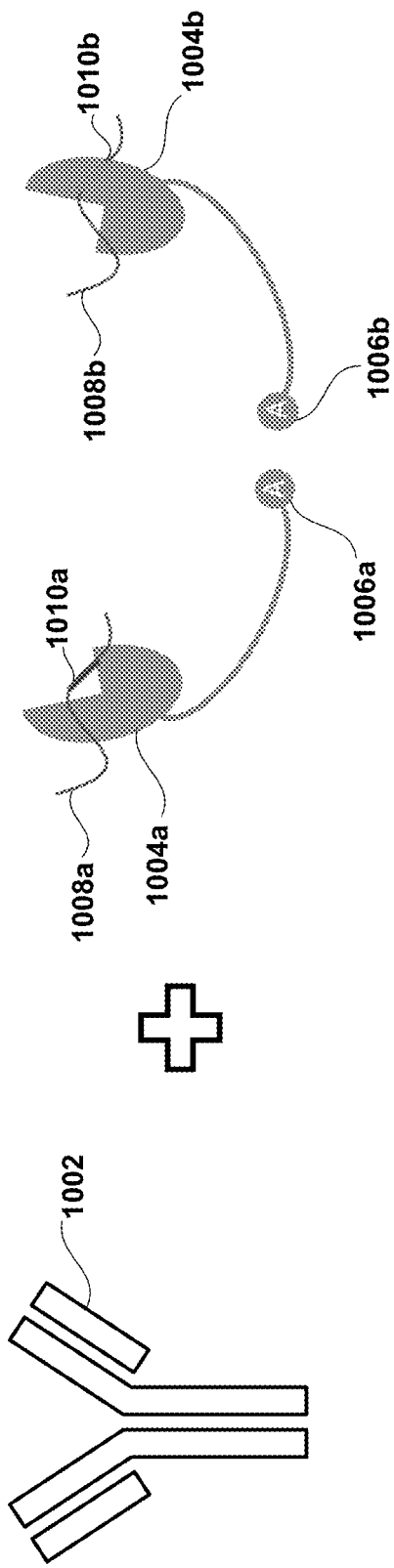
FIGS. 10A-B are non-limiting schematic illustrations of conjugates provided herein for labeling nuclear target-associated DNA from in a single cell.
Figure 10B:
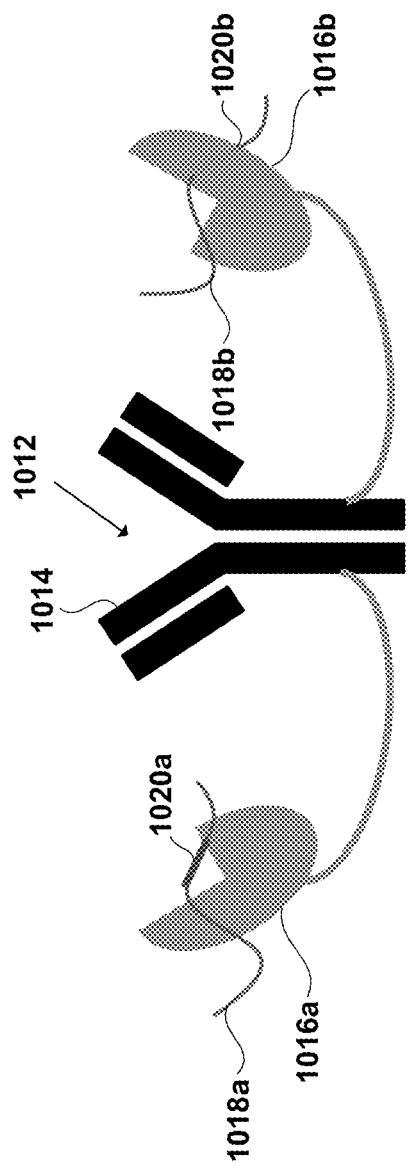

FIGS. 10A-B are non-limiting schematic illustrations of conjugates provided herein for labeling nuclear target-associated DNA in a single cell. In some embodiments, a binding reagent (e.g., antibody 1002) specific for a nuclear target (e.g., a nuclear protein or methylated nucleotide) is provided. In some embodiments a transposome is provided. The transposome can comprise a homodimer or a heterodimer. The transposome can comprise a transposase. The transposase can comprise Tn5 transposase. Tn5 transposase can comprise transposase monomers 1004a and 1004b. Tn5 transposase monomer 1004a can comprise a first adaptor 1008a and a domain 1006a that specifically binds the binding reagent (e.g., protein A or G). Tn5 transposase monomer 1004b can comprise a second adaptor 1008b and a domain 1006b that specifically binds the binding reagent (e.g., protein A or G). The first adaptor 1008a can comprise a first barcode 1010a (e.g., T5 barcode) and the second adaptor 1008b can comprise a second barcode 1010b (e.g., T7 barcode). The binding reagent and transposome can form a conjugate before being contacted with the cell, after being contacted with the cell, before entering the nucleus, after entering the nucleus, or any combination thereof. Disclosed herein include conjugates 1012 comprising a binding reagent (e.g., antibody 1002) specific for a nuclear target (e.g., nuclear protein or methylated nucleotide) directly conjugated to a transposome. The transposome can comprise a homodimer or a heterodimer. The transposome can comprise a transposase. The transposase can comprise Tn5 transposase. Tn5 transposase can comprise transposase monomers 1016a and 1016b. Tn5 transposase monomer 1016a can comprise a first adaptor 1018a and Tn5 transposase monomer 1016b can comprise a first adaptor 1018b. The first adaptor 1018a can comprise a first barcode 1020a (e.g., T5 barcode) and the second adaptor 1018b can comprise a second barcode 1020b (e.g., T7 barcode).

Disclosed herein include methods of labeling nuclear target-associated DNA in a cell. In some embodiments, the method comprises permeabilizing a cell comprising a nuclear target associated with double-stranded deoxyribonucleic acid (dsDNA). The dsDNA can be a genomic DNA (gDNA). The method can comprise: contacting the nuclear target with a digestion composition comprising a DNA digestion enzyme and a binding reagent capable of specifically binding to the nuclear target to generate a plurality of nuclear target-associated dsDNA fragments (e.g., nuclear target-associated gDNA fragments) each comprising a single-stranded overhang, wherein each binding reagent comprises a binding reagent specific oligonucleotide comprising a unique identifier sequence for the binding reagent. The method can comprise: barcoding the plurality of nuclear target-associated dsDNA fragments, or products thereof, using a first plurality of oligonucleotide barcodes to generate a plurality of barcoded nuclear target-associated DNA fragments each comprising a sequence complementary to at least a portion of the nuclear target-associated dsDNA fragment, wherein each oligonucleotide barcode of the first plurality of oligonucleotide barcodes comprises a first target-binding region capable of hybridizing to the plurality of nuclear target-associated dsDNA fragments, or products thereof. The barcoded nuclear target-associated DNA fragments can be single-stranded or double-stranded. The method can comprise: barcoding the binding reagent specific oligonucleotides, or products thereof, using a second plurality of oligonucleotide barcodes to generate a plurality of barcoded binding reagent specific oligonucleotides each comprising a sequence complementary to at least a portion of the unique identifier sequence, wherein each oligonucleotide barcode of the second plurality of oligonucleotide barcodes comprises a second target-binding region capable of hybridizing to the binding reagent specific oligonucleotides, or products thereof.

Contacting the nuclear target with the digestion composition can comprise contacting the digestion composition with the permeabilized cell. Contacting the nuclear target with the composition can comprise the binding reagent and the DNA digestion enzyme entering the permeabilized cell and the binding reagent binding to the nuclear target. The digestion composition can comprise a fusion protein comprising the binding reagent and the digestion enzyme. The fusion protein can be sized to diffuse through a nuclear pore of the cell. The digestion composition can comprise a conjugate comprising the binding reagent and the digestion enzyme. The conjugate can be sized to diffuse through a nuclear pore of the cell. The DNA digestion enzyme can comprise a domain that is capable of specifically binding to the binding reagent. The domain of the DNA digestion enzyme can comprise at least one of protein A, protein G, protein A/G, or protein L. The binding reagent and the DNA digestion enzyme can be separate from each other when contacted with the permeabilized cell. The binding reagent and the DNA digestion enzyme can separately enter the cell. The DNA digestion enzyme can bind the binding reagent within the nucleus of the cell. The DNA digestion enzyme can bind the binding reagent before entering the nucleus of the cell. The DNA digestion enzyme bound to the binding reagent can be sized to diffuse through a nuclear pore of the cell. The DNA digestion enzyme can bind the binding reagent before the binding reagent binds the nuclear target. The conjugate, the fusion protein, and/or the DNA digestion enzyme bound to the binding reagent can have a diameter of no more than 120 nm.

The first target binding region can be complementary to at least a portion of the single-stranded overhang of the nuclear target-associated dsDNA fragment. In some embodiments of the methods provided herein, contacting the nuclear target with the digestion composition generates a complex comprising the binding reagent, the DNA digestion enzyme, and a nuclear target-associated dsDNA fragment. Barcoding the plurality of nuclear target-associated dsDNA fragments can comprise contacting said complex with the first and second pluralities of oligonucleotide barcodes. The method can comprise digesting the complex with a proteinase (e.g., proteinase K). The DNA digestion enzyme can comprise a restriction enzyme, Mnase I, a transposase, functional fragments thereof, or any combination thereof. The transposase can comprise a Tn5 transposase. The digestion composition can comprise at least one of a first adaptor having a first 5' overhang and a second adaptor having a second 5' overhang. Barcoding the binding reagent specific oligonucleotides, or products thereof, can comprise extending the second plurality of oligonucleotide barcodes hybridized to the binding reagent specific oligonucleotides, or products thereof. The binding reagent oligonucleotide can comprise a sequence complementary to the second target-binding region. The method can comprise obtaining sequence data of the plurality of barcoded binding reagent specific oligonucleotides, or products thereof. Obtaining sequence information of the plurality of barcoded binding reagent specific oligonucleotides, or products thereof, can comprise attaching sequencing adaptors and/or sequencing primers complementary sequences thereof, and/or portions thereof, to the plurality of barcoded binding reagent specific oligonucleotides, or products thereof.

Disclosed herein include methods of labeling nuclear target-associated DNA in a cell. In some embodiments, the method comprises: permeabilizing a cell comprising a nuclear target associated with double-stranded deoxyribonucleic acid (dsDNA); contacting the nuclear target with a conjugate comprising a transposome and a binding reagent capable of specifically binding to the nuclear target to generate a plurality of nuclear target-associated dsDNA fragments (e.g., nuclear target-associated gDNA fragments) each comprising a first 5' overhang and a second 5' overhang, wherein the transposome comprises a transposase, a first adaptor having the first 5' overhang, and a second adaptor having the second 5' overhang; and barcoding the plurality of nuclear target-associated dsDNA fragments, or products thereof, using a first plurality of oligonucleotide barcodes to generate a plurality of barcoded nuclear target-associated DNA fragments, wherein each oligonucleotide barcode of the first plurality of oligonucleotide barcodes comprises a first target-binding region capable of hybridizing to the plurality of nuclear target-associated dsDNA fragments, or products thereof. The barcoded nuclear target-associated DNA fragments can be single-stranded or double-stranded. The cell can comprise a single cell derived from a sample. The sample can comprise a plurality of cells. The cell can be contacted with two or more conjugates (e.g., multiplexing). The two or more conjugates can comprise binding reagents directed to different nuclear targets. The two or more conjugates can comprise the same or different transposome. The transposome can comprise adaptors wherein a sequence identifies which of the nuclear targets is being bound.

Barcoding the plurality of nuclear target-associated dsDNA fragments (e.g., nuclear target-associated gDNA fragments), or products thereof, can comprise ligating the nuclear target-associated dsDNA fragments, or products thereof, to the first plurality of oligonucleotide barcodes. Barcoding the plurality of nuclear target-associated dsDNA fragments, or products thereof, can comprise extending the first plurality of oligonucleotide barcodes hybridized to the plurality of nuclear target-associated dsDNA fragments, or products thereof. The first adaptor can comprise a first barcode sequence and the second adaptor can comprise a second barcode sequence. In some embodiments, the first barcode sequence and/or the second barcode sequence identify the nuclear target. The first 5' overhang and/or the second 5' overhang can comprise a poly(dA) region, a poly(dT) region, or any combination thereof. The first 5' overhang and/or the second 5' overhang can comprise a sequence complementary to the first target-binding region, or a complement thereof. The first target-binding region can comprise a sequence that is complementary to at least a portion of a 5' region, a 3' region, or an internal region of a nuclear target-associated dsDNA fragment. The first adaptor and/or the second adaptor can comprise a DNA end sequence of the transposon.

The permeabilizing can comprise chemical or physical permeabilization. The permeabilizing can comprise contacting the cell with a detergent and/or a surfactant. The permeabilizing can comprise permeabilizing the cell by sonification. The method can comprise: permeabilizing a nucleus in the cell to generate a permeabilized nucleus. The method can comprise: fixating the cell comprising the nucleus prior to permeabilizing the nucleus.

The nuclear target can comprise a methylated nucleotide, a DNA-associated protein, a chromatin-associated protein, or any combination thereof. The nuclear target can comprise ALC1, androgen receptor, Bmi-1, BRD4, Brg1, coREST, C-jun, c-Myc, CTCF, EED, EZH2, Fos, histone H1, histone H3, histone H4, heterochromatin protein-1γ, heterochromatin protein-1, HMGN2/HMG-17, HP1α, HP1γ, hTERT, Jun, KLF4, K-Ras, Max, MeCP2, MLL/HRX, NPAT, p300, Nanog, NFAT-1, Oct4, P53, Pol II (8WG16), RNA Pol II Ser2P, RNA Pol II Ser5P, RNA Pol II Ser2+5P, RNA Pol II Ser7P, Rb, RNA polymerase II, SMCI, Sox2, STAT1, STAT2, STAT3, Suz12, Tip60, UTF1, or any combination thereof.

In some embodiments, the binding reagent specifically binds to an epitope comprising a methylated (me), phosphorylated (ph), ubiquitylated (ub), sumoylated (su), biotinylated (bi), or acetylated (ac) histone residue, selected from the group consisting of H1S27ph, H1K25me1, H1K25me2, H1K25me3, H1K26me, H2(A)K4ac, H2(A)K5ac, H2(A)K7ac, H2(A)S1ph, H2(A)T119ph, H2(A)S122ph, H2(A)S129ph, H2(A)S139ph, H2(A)K119ub, H2(A)K126su, H2(A)K9bi, H2(A)K13bi, H2(B)K5ac, H2(B)K11ac, H2(B)K12ac, H2(B)K15ac, H2(B)K16ac, H2(B)K20ac, H2(B)S10ph, H2(B)S14ph, H2(B)33ph, H2(B)K120ub, H2(B)K123ub, H3K4ac, H3K9ac, H3K14ac, H3K18ac, H3K23ac, H3K27ac, H3K56ac, H3K4me1, H3K4me2, H3K4me3, H3R8me, H3K9me1, H3K9me2, H3K9me3, H3R17me, H3K27me1, H3K27me2, H3K27me3, H3K36me, H3K79me1, H3K79me2, H3K79me3, H3K122ac, H3T3ph, H3S10ph, H3T11ph, H3S28ph, H3K4bi, H3K9bi, H3K18bi, H4K5ac, H4K8ac, H4K12ac, H4K16ac, H4K91ac, H4R3me, H4K20me, H4K59me, H4S1ph, H4K12bi, and H4 n-terminal tail ubiquitylated, or any combination thereof. The binding reagent can comprise a tetramer, an aptamer, a protein scaffold, or any a combination thereof. The binding reagent can comprise an antibody or fragment thereof (e.g., a monoclonal antibody). The antibody or fragment thereof can comprise a Fab, a Fab', a F(ab')$_2$, a Fv, a scFv, a dsFv, a diabody, a triabody, a tetrabody, a multispecific antibody formed from antibody fragments, a single-domain antibody (sdAb), a single chain comprising complementary scFvs (tandem scFvs) or bispecific tandem scFvs, an Fv construct, a disulfide-linked Fv, a dual variable domain immunoglobulin (DVD-Ig) binding protein or a nanobody, an aptamer, an affibody, an affilin, an affitin, an affimer, an alphabody, an anticalin, an avimer, a DARPin, a Fynomer, a Kunitz domain peptide, a monobody, or any combination thereof.

The binding reagent can be conjugated to the transposome via chemical coupling, genetic fusion, noncovalent association, or any combination thereof. The conjugate can be formed by a 1,3-dipolar cycloaddition reaction, a hetero-Diels-Alder reaction, a nucleophilic substitution reaction, a non-aldol type carbonyl reaction, an addition to carbon-carbon multiple bond, an oxidation reaction, a click reaction, or any combination thereof. The conjugate can be formed by a reaction between acetylene and azide. The conjugate can be formed by a reaction between an aldehyde or ketone group and a hydrazine or alkoxy amine. The binding reagent can be conjugated to the transposome via at least one of protein A, protein G, protein A/G, or protein L. The transposase can comprise a Tn5 transposase. In some embodiments, the transposome comprises a domain that specifically binds the binding reagent, wherein the binding reagent and the transposome are separate from each other when contacted with the permeabilized cell, and separately enter the cell, and wherein the transposome binds to the binding reagent within the nucleus of the cell. In some embodiments, the transposome is bound to the binding reagent before entering the permeabilized cell, and wherein the transposome bound to the binding reagent is sized to enter the nucleus of the cell through a nuclear pore. In some embodiments, the conjugate has a diameter of no more than 120 nm. The transposome, the binding reagent, and/or the conjugate can have a diameter that is at least, or is at most, 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 60 nm, 70 nm, 80 nm, 90 nm, 100 nm, 110 nm, 120 nm, 128 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, or a number or a range between any two of these values. The binding reagent and the transposome can be each sized to diffuse through a nuclear pore of the cell. The permeabilized cell can comprise an intact nucleus comprising chromatin that remains associated with genomic DNA at the time of the binding the binding reagent to the nuclear target. In some embodiments, the binding of the binding reagent to the nuclear target occurs in the nucleus of the permeabilized cell.

The method can comprise: obtaining sequence data of the plurality of barcoded nuclear target-associated DNA fragments (e.g., nuclear target-associated gDNA fragments), or products thereof. The method can comprise: determining information relating to the gDNA based on the sequences of the plurality of barcoded nuclear target-associated DNA fragments, or products thereof, in the sequencing data obtained. Determining the information relating to the gDNA can comprise determining genome information of the gDNA based on the sequences of the plurality of barcoded nuclear target-associated DNA fragments in the sequencing data obtained. The method can comprise: digesting nucleosomes associated with the double-stranded gDNA. Determining the genome information of the gDNA can comprise: determining at least a partial sequence of the gDNA by aligning the sequences of the plurality of barcoded nuclear target-associated DNA fragments to a reference sequence of the gDNA. Determining the information relating to the gDNA can comprise determining methylome information of the gDNA based on the sequences of the plurality of barcoded nuclear target-associated DNA fragments in the sequencing data obtained. The method can comprise: digesting nucleosomes associated with the double-stranded gDNA. The method can comprise: performing chemical conversion and/or enzymatic conversion of cytosine bases of the plurality of nuclear target-associated dsDNA fragments, or products thereof, to generate a plurality of converted nuclear target-associated dsDNA fragments with uracil bases. Chemical conversion can comprise bisulfite treatment and enzymatic conversion can comprise APOBEC-mediated conversion. Barcoding the plurality of nuclear target-associated dsDNA fragments, or products thereof, can comprise barcoding the plurality of converted nuclear target-associated dsDNA fragments, or products thereof. Determining the methylome information can comprise: determining a position of the plurality of barcoded nuclear target-associated DNA fragments in the sequencing data has a thymine base and the corresponding position in a reference sequence of the gDNA has a cytosine base to determine the corresponding position in the gDNA has a methylcytosine base, a 5-hydroxymethylcytosine (5hmC) base and/or a N6-methyladenine (m(6)A) base. The method can comprise: Hi-C/ChIP-seq, ChIP-seq, Hi-C, Chromatin Conformation Capture (3C), Circularized Chromatin Conformation Capture (4C), Carbon Copy Chromosome Conformation Capture (5C), Chromatin Immunoprecipitation (ChIP), ChIP-Loop, combined 3C-ChIP-cloning (6C), Capture-C, or any combination thereof.

The cell can comprise copies of a nucleic acid target. The method can comprise determining the copy number of the nucleic acid target in the cell. The method can comprise: contacting a second plurality of oligonucleotide barcodes with the copies of the nucleic acid target for hybridization; extending the second plurality of oligonucleotide barcodes hybridized to the copies of a nucleic acid target to generate a plurality of barcoded nucleic acid molecules each comprising a sequence complementary to at least a portion of the nucleic acid target and a molecular label; and obtaining sequence information of the plurality of barcoded nucleic acid molecules, or products thereof, to determine the copy number of the nucleic acid target in the cell. In some embodiments, extending the first and/or second plurality of oligonucleotide barcodes comprises extending the plurality of oligonucleotide barcodes using a reverse transcriptase and/or a DNA polymerase lacking at least one of 5' to 3' exonuclease activity and 3' to 5' exonuclease activity (e.g., a Klenow Fragment) The reverse transcriptase can comprise a viral reverse transcriptase (e.g., a viral reverse transcriptase such as murine leukemia virus (MLV) reverse transcriptase or a Moloney murine leukemia virus (MMLV) reverse transcriptase). The nucleic acid target can comprise a nucleic acid molecule (e.g., ribonucleic acid (RNA), messenger RNA (mRNA), microRNA, small interfering RNA (siRNA), RNA degradation product, RNA comprising a poly(A) tail, a sample indexing oligonucleotide, a cellular component-binding reagent specific oligonucleotide, or any combination thereof). The first target-binding region and/or the second target-binding region can comprise a poly(dA) region, a poly(dT) region, a random sequence, a gene-specific sequence, or any combination thereof. Obtaining sequence information of the plurality of barcoded nuclear target-associated DNA fragments (e.g., nuclear target-associated gDNA fragments) can comprise attaching sequencing adaptors and/or sequencing primers complementary sequences thereof, and/or portions thereof, to the plurality of barcoded nuclear target-associated DNA fragments, or products thereof. Obtaining sequence information of the plurality of barcoded nucleic acid molecules can comprise attaching sequencing adaptors and/or sequencing primers complementary sequences thereof, and/or portions thereof, to the plurality of barcoded nucleic acid molecules, or products thereof.

In some embodiments, each oligonucleotide barcode of the first plurality of oligonucleotide barcodes comprises a first universal sequence, and wherein each oligonucleotide barcode of the second plurality of oligonucleotide barcodes comprises a second universal sequence. In some embodiments, the first universal sequence and the second universal sequence can be the same or different. The first universal sequence and/or the second universal sequence can comprise the binding sites of sequencing primers and/or sequencing adaptors, complementary sequences thereof, and/or portions thereof. The sequencing adaptors can comprise a P5 sequence, a P7 sequence, complementary sequences thereof, and/or portions thereof. The sequencing primers can comprise a Read 1 sequencing primer, a Read 2 sequencing primer, complementary sequences thereof, and/or portions thereof. The first and second pluralities of oligonucleotide barcodes each can comprise a molecular label. At least 10 of the first and second pluralities of oligonucleotide barcodes can comprise different molecular label sequences. Each molecular label of the first and second pluralities of oligonucleotide barcodes can comprise at least 6 nucleotides.

The first and second pluralities of oligonucleotide barcodes can be associated with a solid support. The first and second pluralities of oligonucleotide barcodes associated with the same solid support each can comprise an identical sample label. Each sample label of the first and second pluralities of oligonucleotide barcodes can comprise at least 6 nucleotides. The first and second pluralities of oligonucleotide barcodes each can comprise a cell label. Each cell label of the first and second pluralities of oligonucleotide barcodes can comprise at least 6 nucleotides. Oligonucleotide barcodes of the first and second pluralities of oligonucleotide barcodes associated with the same solid support can comprise the same cell label. Oligonucleotide barcodes of the first and second pluralities of oligonucleotide barcodes associated with different solid supports can comprise different cell labels. The solid support can comprise a synthetic particle, a planar surface, or a combination thereof. The method can comprise: associating a synthetic particle comprising the first and second pluralities of oligonucleotide barcodes with the cell. The method can comprise: lysing the cell after associating the synthetic particle with the cell, Lysing the cell can comprise heating the cell, contacting the cell with a detergent, changing the pH of the cell, or any combination thereof. The synthetic particle and the single cell can be in the same partition (e.g., a well or a droplet). In some embodiments, at least one oligonucleotide barcode of the first and second pluralities of oligonucleotide barcodes is immobilized or partially immobilized on the synthetic particle, or at least one oligonucleotide barcode of the first and second pluralities of oligonucleotide barcodes is enclosed or partially enclosed in the synthetic particle.

The synthetic particle can be disruptable (e.g., a disruptable hydrogel particle). The synthetic particle can comprise a bead, optionally the bead comprises a sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The synthetic particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, sepharose, cellulose, nylon, silicone, and any combination thereof. Each oligonucleotide barcode of the first and second pluralities of oligonucleotide barcodes can comprise a linker functional group. The synthetic particle can comprise a solid support functional group. In some embodiments, the support functional group and the linker functional group are associated with each other, and optionally the linker functional group and the support functional group are individually selected from the group consisting of C6, biotin, streptavidin, primary amine(s), aldehyde(s), ketone(s), and any combination thereof.

Disclosed herein include kits. The kit can comprise a digestion composition comprising a DNA digestion enzyme and a binding reagent capable of specifically binding to the nuclear target, wherein the binding reagent comprises a binding reagent specific oligonucleotide comprising a unique identifier sequence for the binding reagent. The DNA digestion enzyme can comprise a restriction enzyme, Mnase I, a transposase (e.g., Tn5 transposase), functional fragments thereof, or any combination thereof. The digestion composition can comprise at least one of a first adaptor having a first 5' overhang and a second adaptor having a second 5' overhang. The digestion composition can comprise a fusion protein comprising the binding reagent and the digestion enzyme. The fusion protein can be sized to diffuse through a nuclear pore of a cell. The digestion composition can comprise a conjugate comprising the binding reagent and the digestion enzyme. The conjugate can be sized to diffuse through a nuclear pore of a cell. The DNA digestion enzyme can comprise a domain that is capable of specifically binding to the binding reagent. The domain of the DNA digestion enzyme can comprise at least one of protein A, protein G, protein A/G, or protein L. The DNA digestion enzyme bound to the binding reagent can be sized to diffuse through a nuclear pore of a cell. The kit can comprise a proteinase (e.g., proteinase K).

Disclosed herein include kits. In some embodiments, the kit comprises: a conjugate comprising a transposome and a binding reagent capable of specifically binding to a nuclear target, wherein the transposome comprises a transposase, a first adaptor having a first 5' overhang, and a second adaptor having a second 5' overhang. The kit can comprise: a DNA polymerase lacking at least one of 5' to 3' exonuclease activity and 3' to 5' exonuclease activity, (e.g., a Klenow Fragment). The kit can comprise: a reverse transcriptase, optionally wherein the reverse transcriptase comprises a viral reverse transcriptase, and optionally the viral reverse transcriptase is a murine leukemia virus (MLV) reverse transcriptase or a Moloney murine leukemia virus (MMLV) reverse transcriptase. The kit can comprise: a ligase. The kit can comprise: a detergent and/or a surfactant. The kit can comprise: a buffer, a cartridge, or both. The kit can comprise: one or more reagents for a reverse transcription reaction and/or an amplification reaction.

The nuclear target can comprise a DNA-associated protein or chromatin-associated protein. The nuclear target can comprise a methylated nucleotide. The nuclear target can comprise ALC, androgen receptor, Bmi-1, BRD4, Brg1, coREST, C-jun, c-Myc, CTCF, EED, EZH2, Fos, histone H1, histone H3, histone H4, heterochromatin protein-1γ, heterochromatin protein-1, HMGN2/HMG-17, HP1α, HP1γ, hTERT, Jun, KLF4, K-Ras, Max, MeCP2, MLL/HRX, NPAT, p300, Nanog, NFAT-1, Oct4, P53, Pol II (8WG16), RNA Pol II Ser2P, RNA Pol II Ser5P, RNA Pol II Ser2+5P, RNA Pol II Ser7P, Rb, RNA polymerase II, SMCI, Sox2, STAT1, STAT2, STAT3, Suz12, Tip60, UTF1, or any combination thereof. In some embodiments, the binding reagent specifically binds to an epitope comprising a methylated (me), phosphorylated (ph), ubiquitylated (ub), sumoylated (su), biotinylated (bi), or acetylated (ac) histone residue, selected from the group consisting of H1S27ph, H1K25me1, H1K25me2, H1K25me3, H1K26me, H2(A)K4ac, H2(A)K5ac, H2(A)K7ac, H2(A)S1ph, H2(A)T119ph, H2(A)S122ph, H2(A)S129ph, H2(A)S139ph, H2(A)K119ub, H2(A)K126su, H2(A)K9bi, H2(A)K13bi, H2(B)K5ac, H2(B)K11ac, H2(B)K12ac, H2(B)K15ac, H2(B)K16ac, H2(B)K20ac, H2(B)S10ph, H2(B)S14ph, H2(B)33ph, H2(B)K120ub, H2(B)K123ub, H3K4ac, H3K9ac, H3K14ac, H3K18ac, H3K23ac, H3K27ac, H3K56ac, H3K4me1, H3K4me2, H3K4me3, H3R8me, H3K9me1, H3K9me2, H3K9me3, H3R17me, H3K27me1, H3K27me2, H3K27me3, H3K36me, H3K79me1, H3K79me2, H3K79me3, H3K122ac, H3T3ph, H3S10ph, H3T11ph, H3S28ph, H3K4bi, H3K9bi, H3K18bi, H4K5ac, H4K8ac, H4K12ac, H4K16ac, H4K91ac, H4R3me, H4K20me, H4K59me, H4S1ph, H4K12bi, and H4 n-terminal tail ubiquitylated, or any combination thereof. The binding reagent can comprise a tetramer, an aptamer, a protein scaffold, or any a combination thereof. The binding reagent can comprise an antibody or fragment thereof (e.g., a monoclonal antibody). The antibody or fragment thereof can comprise a Fab, a Fab', a F(ab')$_2$, a Fv, a scFv, a dsFv, a diabody, a triabody, a tetrabody, a multispecific antibody formed from antibody fragments, a single-domain antibody (sdAb), a single chain comprising complementary scFvs (tandem scFvs) or bispecific tandem scFvs, an Fv construct, a disulfide-linked Fv, a dual variable domain immunoglobulin (DVD-Ig) binding protein or a nanobody, an aptamer, an affibody, an affilin, an affitin, an affimer, an alphabody, an anticalin, an avimer, a DARPin, a Fynomer, a Kunitz domain peptide, a monobody, or any combination thereof.

The binding reagent can be conjugated to the transposome via chemical coupling, genetic fusion, noncovalent association, or any combination thereof. The conjugate can be formed by a 1,3-dipolar cycloaddition reaction, a hetero-Diels-Alder reaction, a nucleophilic substitution reaction, a non-aldol type carbonyl reaction, an addition to carbon-carbon multiple bond, an oxidation reaction, a click reaction, or any combination thereof. The conjugate can be formed by a reaction between acetylene and azide. The conjugate can be formed by a reaction between an aldehyde or ketone group and a hydrazine or alkoxy amine. The binding reagent can be conjugated to the transposome via at least one of protein A, protein G, protein A/G, or protein L. The transposase can comprise a Tn5 transposase. In some embodiments, the conjugate has a diameter of no more than 120 nm. The transposome, the binding reagent, and/or the conjugate can have a diameter that is at least, or is at most, 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 60 nm, 70 nm, 80 nm, 90 nm, 100 nm, 110 nm, 120 nm, 128 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, or a number or a range between any two of these values. The binding reagent and the transposome can be each sized to diffuse through a nuclear pore.

The kit can comprise: a plurality of oligonucleotide barcodes. Each of the plurality of oligonucleotide barcodes can comprise a molecular label and a target-binding region. At least 10 of the plurality of oligonucleotide barcodes can comprise different molecular label sequences. The target-binding region can comprise a gene-specific sequence, an oligo(dT) sequence, a random multimer, or any combination thereof. The oligonucleotide barcode can comprise an identical sample label and/or an identical cell label In some embodiments, each sample label and/or cell label of the plurality of oligonucleotide barcodes comprise at least 6 nucleotides. Each molecular label of the plurality of oligonucleotide barcodes can comprise at least 6 nucleotides.

At least one of the plurality of oligonucleotide barcodes can be partially immobilized on the synthetic particle. At least one of the plurality of oligonucleotide barcodes can be immobilized or partially immobilized on the synthetic particle; and/or the at least one of the plurality of oligonucleotide barcodes can be enclosed or partially enclosed in the synthetic particle. The synthetic particle can comprise a bead. The bead can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The synthetic particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. Each of the plurality of oligonucleotide barcodes can comprise a linker functional group. The synthetic particle can comprise a solid support functional group. The support functional group and the linker functional group can be associated with each other. The linker functional group and the support functional group can be individually selected from the group consisting of C6, biotin, streptavidin, primary amine(s), aldehyde(s), ketone(s), and any combination thereof.

EXAMPLES

Some aspects of the embodiments described herein are disclosed in further detail in the following examples, which are not in any way intended to limit the scope of the present disclosure.

Example 1

Appending Oligonucleotide Probes with a Target Binding Region

This example describes appending an oligonucleotide prove with a target binding region in accordance with some embodiments described herein.

An oligonucleotide probe is provided, wherein the oligonucleotide probe includes a sample identifier sequence and a hybridization domain. The oligonucleotide probe includes a PCR handle (such as a universal primer binding site), a cell label, and a unique molecular identifier (UMI). The hybridization domain can be a polyT sequence having seven consecutive thymidines, as shown in FIG. 7A. The hybridization domain can comprise a poly(dT) region of varying length. The poly(dT) region can be, or be about 1, 2, 3, 4, 5, 6, 7, 8, 9, 10, 15, 18, 20, 30, 31, 40, 50, or a number or a range between any two of these values, nucleotides in length. The oligonucleotide probe is immobilized to a bead. The oligonucleotide probe does not include a target binding region. A target binding region is a sequence that specifically binds to (is complementary to) a target sequence.

A dsDNA template is provided, wherein the dsDNA template includes a template strand and a complementary strand. The template strand includes a complementary hybridization domain that is a polyA sequence, having seven consecutive adenines, as shown in FIG. 7B. The template strand further includes a sequence that was complementary to the target binding region, and is hybridized to the complementary strand, which includes a target binding region sequence of TCGCATGTG, identified in FIG. 7B as NNNNN, in which the target binding region sequence specifically binds to (is complementary to) a target sequence. It is to be understood that the target binding region sequence of the present example is exemplary, and that the sequence shown in FIG. 7B (NNNNN) can be any sequence that is about 1 to about 40 nucleotides in length. The template strand was attached to biotin.

The oligonucleotide probe is contacted with the dsDNA template, and the polyA sequence of the template strand hybridized to the complementary polyT sequence of the oligonucleotide probe. The oligonucleotide probe is ligated to the complementary strand, as shown in FIG. 7C, and complementary strand is denatured from the template strand by subjecting to denaturant. A ligase is used to join the fragments. The template strand is removed by contacting with streptavidin, which binds to the biotin, thereby removing the template strand, as shown in FIG. 8. The oligonucleotide probe is thus labeled with a target binding region.

Example 2

Labeling Target-Protein-Associated DNA of a Single Cell

This example describes a labeling target-protein-associated DNA of a single cell in accordance with some embodiments described herein.

A single cell is provided, wherein the single cell includes a target protein of interest that is associated with DNA. The single cell is subjected to permeabilization conditions (e.g., contact with 0.1% Triton X-100 for 10 minutes), wherein the single cell is permeabilized. The permeabilized cell is contacted with a binding reagent (e.g., protein binding reagent), anti-histone H3 antibody (as provided by Abcam listed as catalog #ab8895) and a fusion protein. The protein binding reagent specifically binds to the target protein of interest, in this case, histone H3. The protein binding reagent includes a reagent oligonucleotide, an oligonucleotide tag that includes a unique identifier sequence and a polyA tag. The fusion protein includes a DNA digestion enzyme, EcoRI and protein A, which is bound to the anti-histone H3 antibody, as shown in FIG. 1. Contacting the single cell with the antibody/digestion enzyme complex results in the complex entering the cell nucleus and binding to target protein, which is associated with DNA, as shown in FIG. 2. Alternatively, the antibody can be separately contacted with the permeabilized cell prior to or after contacting the cell with a digestion enzyme, such that each component of the complex separately enters the cell and such that the complex of the antibody/digestion enzyme is formed in situ within the cell nucleus.

The permeabilized cell having complex within the nucleus is subjected to enzyme digestion, such that the digestion enzyme cleaves the DNA, and releases a complex that includes the antibody, the digestion enzyme, the target protein, and the associated DNA, as shown in FIG. 3. The digested DNA includes a single stranded overhang, a result of the digestion enzyme generating a restriction site overhang. The complex shown in FIG. 3 is contacted with a bead having an oligonucleotide probe as prepared in Example 1, and as shown in FIG. 4. The bead includes a first oligonucleotide probe and a second oligonucleotide probe. The first oligonucleotide probe is a probe lacking a target binding region, but having a polyT sequence complementary to the polyA sequence attached to the antibody, thus hybridizing the reagent oligonucleotide on the antibody. The second oligonucleotide probe includes a target binding region, identified in FIG. 4 as NNNN, and which is complementary to a single stranded overhang on the digested DNA, resulting in hybridization to the digested DNA, as shown in FIG. 5A. The respective fragments are ligated and reverse transcribed, as shown in FIG. 5B.

All protein components, including the antibody, the digestion enzymes, the protein A, and the target protein are removed by subjecting the beads to proteinase K. Unbound nucleic acids are removed by contacting the beads with ExoI. A nucleic acid library is generated through random primer extension and PCR amplification, as shown in FIG. 5C.

Optionally, the cell nucleus can be isolated. Isolating the nucleus can be performed by hypotonic lysis the cell. The nucleus then can be centrifuged and washed in a buffer solution, and complexed with lectin-coated magnetic beads. The lectin-nucleus complex is resuspended with the antibody targeted at the protein of interest, which are incubated for 2 hours. The nuclei are washed in buffer to remove unbound antibodies. The nuclei are resuspended in the buffer with protein A/Mnase fusion protein, and incubated for 1 hour. The nuclei are then washed in buffer to remove unbound protein A/Mnase fusion protein. The nuclei are placed in a metal block and placed in ice water and $CaCl_2$ is added to initiate nuclease activity of Mnase to cleave the DNA around the DNA-binding protein. The digestion reaction is quenched by adding chelating agents, such as EDTA and/or EGTA. The components are then contacted with the beads as described in Example 1, and the isolated DNA is analyzed.

TERMINOLOGY

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method comprising:
permeabilizing a cell comprising a nuclear target associated with double-stranded deoxyribonucleic acid (dsDNA), wherein the dsDNA is a genomic DNA (gDNA), and wherein the nuclear target is a protein, wherein the nuclear target comprises a chromatin-associated protein and is attached to the dsDNA;
generating a plurality of nuclear target-associated dsDNA fragments by contacting the nuclear target associated with dsDNA with a digestion composition comprising a DNA digestion enzyme and a binding reagent capable of specifically binding to the nuclear target such that each of plurality of nuclear target-associated dsDNA fragments comprises a single-stranded overhang, wherein the binding reagent comprises a binding reagent specific oligonucleotide comprising a unique identifier sequence for the binding reagent, wherein the DNA digestion enzyme comprises a domain that is capable of specifically binding to the binding reagent, and wherein the DNA digestion enzyme is a restriction enzyme capable of creating a single-stranded restriction site overhang on the dsDNA of the nuclear target associated with dsDNA;
adding a synthetic particle comprising a first plurality of oligonucleotide barcodes and a second plurality of oligonucleotide barcodes to the permeabilized cell after the contacting step;
lysing the permeabilized cell after the adding step;
generating a plurality of barcoded nuclear target-associated DNA fragments by barcoding the plurality of nuclear target-associated dsDNA fragments using the first plurality of oligonucleotide barcodes, wherein each oligonucleotide barcode of the first plurality of oligonucleotide barcodes comprises a first target-binding region capable of hybridizing to the plurality of nuclear target-associated dsDNA fragments, wherein said barcoding the plurality of nuclear target-associated dsDNA fragments comprises:
hybridizing the first plurality of oligonucleotide barcodes to the plurality of nuclear target-associated dsDNA fragments,
extending the first plurality of oligonucleotide barcodes hybridized to the plurality of nuclear target-associated dsDNA fragments, and/or
ligating the nuclear target-associated dsDNA fragments to the first plurality of oligonucleotide barcodes hybridized to the plurality of nuclear target-associated dsDNA fragments; and
generating a plurality of barcoded binding reagent specific oligonucleotides by barcoding the binding reagent specific oligonucleotide using the second plurality of oligonucleotide barcodes after the lysing step, wherein each oligonucleotide barcode of the second plurality of oligonucleotide barcodes comprises a second target-binding region capable of hybridizing to the binding reagent specific oligonucleotide,
wherein said barcoding the binding reagent specific oligonucleotide comprises hybridizing the second plurality of oligonucleotide barcodes to the binding reagent specific oligonucleotide and extending the second plurality of oligonucleotide barcodes hybridized to the binding reagent specific oligonucleotide, and wherein the binding reagent specific oligonucleotide comprises a sequence complementary to the second target-binding region.

2. The method of claim 1, wherein said contacting the nuclear target with the digestion composition comprises contacting the digestion composition with the permeabilized cell, and wherein said contacting the nuclear target with the digestion composition comprises the binding reagent and the DNA digestion enzyme entering the permeabilized cell and the binding reagent binding to the nuclear target.

3. The method of claim 1, wherein the binding reagent and the DNA digestion enzyme forms a conjugate, and wherein the conjugate is sized to diffuse through a nuclear pore of the cell.

4. The method of claim 1, wherein each of the binding reagent and the DNA digestion enzyme separately contacts with the permeabilized cell, and wherein the binding reagent and the DNA digestion enzyme separately enter the cell, and wherein the DNA digestion enzyme binds the binding reagent within the nucleus of the cell and forms the digestion composition.

5. The method of claim 1, wherein each of the binding reagent and the DNA digestion enzyme separately contacts with the permeabilized cell, wherein the DNA digestion enzyme binds the binding reagent and forms a conjugate before it enters the nucleus of the cell, and wherein the conjugate is sized to diffuse through a nuclear pore of the cell.

6. The method of claim 1, wherein the first target binding region is complementary to at least a portion of the single-stranded overhang of the nuclear target-associated dsDNA fragments.

7. The method of claim 1, further comprising obtaining sequence data of the plurality of barcoded nuclear target-associated DNA fragments, and determining information relating to the gDNA based on the sequences of the plurality of barcoded nuclear target-associated DNA fragments from the sequencing data.

8. The method of claim 7, wherein said determining the information relating to the gDNA comprises determining genome information of the gDNA.

9. The method of claim 8, wherein said determining the genome information of the gDNA comprises:
determining at least a partial sequence of the gDNA by aligning the sequences of the plurality of barcoded nuclear target-associated DNA fragments to a reference sequence of the gDNA.

10. A method comprising:
permeabilizing a cell comprising a nuclear target associated with double-stranded deoxyribonucleic acid (dsDNA), wherein the dsDNA is a genomic DNA (gDNA), and wherein the nuclear target is a protein, wherein the nuclear target comprises a chromatin-associated protein and is attached to the dsDNA;
generating a plurality of nuclear target-associated dsDNA fragments by contacting the nuclear target associated with dsDNA with a conjugate comprising a transposome and a binding reagent capable of specifically binding to the nuclear target such that each of the plurality of nuclear target-associated dsDNA fragments comprising a first 5' overhang and a second 5' overhang, wherein the transposome comprises a transposase, a first adaptor having the first 5' overhang, and a second adaptor having the second 5' overhang, wherein the transposome comprises a domain that specifically binds the binding reagent and the transposase adds the first adaptor and the second adaptor to the dsDNA of the nuclear target associated with dsDNA, wherein the first adaptor comprises a first barcode sequence and the second adaptor comprises a second barcode sequence, and wherein the first barcode sequence and/or the second barcode sequence identify the nuclear target;

adding a synthetic particle comprising a first plurality of oligonucleotide barcodes to the permeabilized cell after the contacting step;

lysing the permeabilized cell after the adding step; and generating a plurality of barcoded nuclear target-associated DNA fragments by barcoding the plurality of nuclear target-associated dsDNA fragments using the first plurality of oligonucleotide barcodes after the lysing step, wherein each oligonucleotide barcode of the first plurality of oligonucleotide barcodes comprises a first target-binding region capable of hybridizing to the plurality of nuclear target-associated dsDNA fragments, wherein said barcoding the plurality of nuclear target-associated dsDNA fragments comprises:

hybridizing the first plurality of oligonucleotide barcodes to the plurality of nuclear target-associated dsDNA fragments, extending the first plurality of oligonucleotide barcodes hybridized to the plurality of nuclear target-associated dsDNA fragments, and/or ligating the nuclear target-associated dsDNA fragments to the first plurality of oligonucleotide barcodes hybridized to the plurality of nuclear target-associated dsDNA fragments.

11. The method of claim 10, wherein the first 5' overhang and/or the second 5' overhang comprise a sequence complementary to the first target-binding region, or a complement thereof.

12. The method of claim 10, wherein the binding reagent is conjugated to the transposome via protein A, protein G, protein A/G, protein L, a chemical coupling, a genetic fusion, a noncovalent association, or any combination thereof.

13. The method of claim 10, wherein each of the binding reagent and the transposome separately contacts with the permeabilized cell, and the binding reagent and the transposome separately enter the cell, and wherein the transposome binds to the binding reagent within the nucleus of the cell and forms the conjugate.

14. The method of claim 10, wherein the transposome is bound to the binding reagent and forms the conjugate before it enters the permeabilized cell, and wherein the conjugate is sized to enter the nucleus of the cell through a nuclear pore of the cell.

15. The method of claim 10, further comprising obtaining sequence data of the plurality of barcoded nuclear target-associated DNA fragments, and determining information relating to the gDNA based on the sequences of the plurality of barcoded nuclear target-associated DNA fragments from the sequencing data.

16. The method of claim 15, wherein said determining the information relating to the gDNA comprises determining genome information of the gDNA.

17. The method of claim 16, wherein said determining the genome information of the gDNA comprises:

determining at least a partial sequence of the gDNA by aligning the sequences of the plurality of barcoded nuclear target-associated DNA fragments to a reference sequence of the gDNA.

* * * * *

```
                        SEQUENCE LISTING

<160> NUMBER OF SEQ ID NOS: 3

<210> SEQ ID NO 1
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(11)
<223> OTHER INFORMATION: n is a, c, g, or t

<400> SEQUENCE: 1
ttttttnnnn n                                                          11

<210> SEQ ID NO 2
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(5)
<223> OTHER INFORMATION: n is a, c, g, or t

<400> SEQUENCE: 2
nnnnnaaaaa a                                                          11

<210> SEQ ID NO 3
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(12)
<223> OTHER INFORMATION: n is a, c, g, or t

<400> SEQUENCE: 3
tttttttnnn nn                                                         12
```